(12) United States Patent
Dang et al.

(10) Patent No.: US 9,982,309 B2
(45) Date of Patent: May 29, 2018

(54) METHOD FOR TREATING CELL PROLIFERATION RELATED DISORDERS

(71) Applicant: AGIOS PHARMACEUTICALS, INC., Cambridge, MA (US)

(72) Inventors: Leonard Luan C. Dang, Boston, MA (US); Stefan Gross, Brookline, MA (US); Hyun Gyung Jang, Waltham, MA (US); Shengfang Jin, Newton, MA (US); Shin-San Michael Su, Newton, MA (US); Craig Thompson, New York, NY (US)

(73) Assignee: AGIOS PHARMACEUTICALS, INC., Cambridge, MA (US)

( * ) Notice: Subject to any disclaimer, the term of this patent is extended or adjusted under 35 U.S.C. 154(b) by 0 days. days.

(21) Appl. No.: 15/238,161

(22) Filed: Aug. 16, 2016

(65) Prior Publication Data

US 2017/0044620 A1  Feb. 16, 2017

Related U.S. Application Data

(63) Continuation of application No. 14/504,983, filed on Oct. 2, 2014, which is a continuation of application No. 13/617,332, filed on Sep. 14, 2012, which is a continuation of application No. 13/452,136, filed on Apr. 20, 2012, now Pat. No. 9,434,979, which is a continuation of application No. PCT/US2010/053623, filed on Oct. 21, 2010.

(60) Provisional application No. 61/266,930, filed on Dec. 4, 2009, provisional application No. 61/253,821, filed on Oct. 21, 2009.

(51) Int. Cl.

| | |
|---|---|
| *A61K 31/225* | (2006.01) |
| *C12Q 1/68* | (2018.01) |
| *A61K 31/015* | (2006.01) |
| *A61K 31/05* | (2006.01) |
| *A61K 31/122* | (2006.01) |
| *A61K 31/355* | (2006.01) |
| *A61K 31/375* | (2006.01) |
| *A61K 31/381* | (2006.01) |
| *A61K 31/522* | (2006.01) |
| *A61K 31/7004* | (2006.01) |
| *A61K 31/713* | (2006.01) |
| *A61K 38/06* | (2006.01) |
| *A61K 38/44* | (2006.01) |
| *C12Q 1/32* | (2006.01) |
| *A61K 31/194* | (2006.01) |

(52) U.S. Cl.
CPC .......... *C12Q 1/6886* (2013.01); *A61K 31/015* (2013.01); *A61K 31/05* (2013.01); *A61K 31/122* (2013.01); *A61K 31/194* (2013.01); *A61K 31/225* (2013.01); *A61K 31/355* (2013.01); *A61K 31/375* (2013.01); *A61K 31/381* (2013.01); *A61K 31/522* (2013.01); *A61K 31/7004* (2013.01); *A61K 31/713* (2013.01); *A61K 38/063* (2013.01); *A61K 38/44* (2013.01); *C12Q 1/32* (2013.01); *C12Q 2600/106* (2013.01); *C12Q 2600/112* (2013.01); *C12Q 2600/118* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2,390,529 A | 12/1945 | Friedheim |
| 3,755,322 A | 8/1973 | Winter et al. |
| 3,867,383 A | 2/1975 | Winter |
| 4,084,053 A | 4/1978 | Desai et al. |
| 5,021,421 A | 6/1991 | Hino et al. |
| 5,489,591 A | 2/1996 | Kobayashi et al. |
| 5,807,876 A | 9/1998 | Armistead et al. |
| 5,834,485 A | 11/1998 | Dyke et al. |
| 5,965,559 A | 10/1999 | Faull et al. |
| 5,965,569 A | 10/1999 | Camps Garcia et al. |
| 5,984,882 A | 11/1999 | Rosenschein et al. |
| 6,262,113 B1 | 7/2001 | Widdowson et al. |
| 6,274,620 B1 | 8/2001 | Labrecque et al. |
| 6,313,127 B1 | 11/2001 | Waterson et al. |
| 6,399,358 B1 | 6/2002 | Williams et al. |
| 6,723,730 B2 | 4/2004 | Bakthavatchalam et al. |
| 6,979,675 B2 | 12/2005 | Tidmarsh |
| 7,173,025 B1 | 2/2007 | Stocker et al. |
| 7,858,782 B2 | 12/2010 | Tao et al. |
| 8,133,900 B2 | 3/2012 | Hood et al. |
| 8,465,673 B2 | 6/2013 | Yasuda et al. |
| 8,883,438 B2 * | 11/2014 | Cantley .............. A61K 31/4184 435/26 |

(Continued)

FOREIGN PATENT DOCUMENTS

| | | |
|---|---|---|
| CN | 101296909 A | 10/2008 |
| CN | 101575408 A | 11/2009 |

(Continued)

OTHER PUBLICATIONS

Yen, K. et al. AG-221, A First in Class Therapy Targeting Acute Myeloid Leukemia Harboring Oncogenic IDH2 Mutations. Cancer Discovery 7(5)478-493, May 2017.*
Dang L. et al. Isocitrate Dehydrogenase Mutation and (R)-2-Hydroxyglutarate. Annual Review of Biochemistry 86:305-331, Jun. 20, 2017.*
Dang L. et al. IDH Mutations in Cancer and Progress Toward Development of Targeted Therapeutics. Annals of Oncology 27(4)599-608, Apr. 2016.*
International Search Report and Written Opinion for International Application No. PCT/US15/020349 dated Jun. 15, 2015.
International Search Report and Written Opinion for International Application No. PCT/US2014/046202 dated Sep. 30, 2014.
International Search Report and Written Opinion for International Application No. PCT/US2014/049469 dated Jan. 22, 2015.

(Continued)

*Primary Examiner* — Ralph J Gitomer
(74) *Attorney, Agent, or Firm* — Goodwin Procter LLP

(57) ABSTRACT

Methods of treating and evaluating subjects having neoactive mutants of IDH (e.g., IDH1 or IDH2).

14 Claims, 49 Drawing Sheets

(56) References Cited

U.S. PATENT DOCUMENTS

| | | | |
|---|---|---|---|
| 9,434,979 B2* | 9/2016 | Su | |
| 2002/0188027 A1 | 12/2002 | Robinson et al. | |
| 2003/0095958 A1 | 5/2003 | Bhisetti et al. | |
| 2003/0109527 A1 | 6/2003 | Jin et al. | |
| 2003/0207882 A1 | 11/2003 | Stocker et al. | |
| 2003/0213405 A1 | 11/2003 | Harada et al. | |
| 2004/0067234 A1 | 4/2004 | Einat et al. | |
| 2004/0248221 A1 | 12/2004 | Stockwell | |
| 2006/0084645 A1 | 4/2006 | Pal et al. | |
| 2006/0281122 A1 | 12/2006 | Bryant et al. | |
| 2007/0244088 A1 | 10/2007 | Brickmann et al. | |
| 2008/0300208 A1 | 12/2008 | Einat et al. | |
| 2009/0093526 A1 | 4/2009 | Miller et al. | |
| 2009/0163508 A1 | 6/2009 | Kori et al. | |
| 2009/0163545 A1 | 6/2009 | Goldfarb | |
| 2010/0129350 A1 | 5/2010 | Zacharie et al. | |
| 2010/0144722 A1 | 6/2010 | Alexander et al. | |
| 2010/0273808 A1 | 10/2010 | Armitage et al. | |
| 2010/0331307 A1 | 12/2010 | Salituro et al. | |
| 2011/0073007 A1 | 3/2011 | Yasuda et al. | |
| 2011/0086088 A1 | 4/2011 | Berry | |
| 2011/0288065 A1 | 11/2011 | Fujihara et al. | |
| 2012/0121515 A1 | 5/2012 | Dang et al. | |
| 2012/0129865 A1 | 5/2012 | Wang et al. | |
| 2012/0164143 A1 | 6/2012 | Teeling et al. | |
| 2012/0202818 A1 | 8/2012 | Tao et al. | |
| 2012/0238576 A1 | 9/2012 | Tao et al. | |
| 2012/0277233 A1 | 11/2012 | Tao et al. | |
| 2013/0035329 A1 | 2/2013 | Saunders et al. | |
| 2013/0109643 A1 | 5/2013 | Riggins et al. | |
| 2013/0183281 A1 | 7/2013 | Su et al. | |
| 2013/0184222 A1 | 7/2013 | Popovici-Muller et al. | |
| 2013/0190249 A1 | 7/2013 | Lemieux et al. | |
| 2013/0190287 A1 | 7/2013 | Cianchetta et al. | |
| 2013/0197106 A1* | 8/2013 | Fantin | G01N 33/5011 514/789 |
| 2013/0288284 A1 | 10/2013 | Dang et al. | |
| 2014/0187435 A1 | 7/2014 | Dang et al. | |
| 2015/0018328 A1 | 1/2015 | Konteatis et al. | |
| 2015/0031627 A1 | 1/2015 | Lemieux et al. | |
| 2015/0044716 A1 | 2/2015 | Balss et al. | |
| 2015/0240286 A1 | 8/2015 | Dang et al. | |
| 2017/0157132 A1* | 6/2017 | Wu | A61K 31/53 |
| 2017/0174658 A1* | 6/2017 | Lin | C07D 401/12 |
| 2017/0325708 A1 | 11/2017 | Dang et al. | |

FOREIGN PATENT DOCUMENTS

| | | | |
|---|---|---|---|
| CN | 102659765 A | 9/2012 | |
| CN | 103097340 A | 5/2013 | |
| DE | 3314663 A1 | 10/1983 | |
| DE | 3512630 A1 | 10/1986 | |
| EP | 0022958 A1 | 1/1981 | |
| EP | 0384228 A1 | 8/1990 | |
| EP | 0385237 A2 | 9/1990 | |
| EP | 0945446 A1 | 9/1999 | |
| FR | 2735127 A1 | 12/1996 | |
| JP | 4099768 | 3/1992 | |
| JP | 9291034 A | 11/1997 | |
| JP | 11158073 | 6/1999 | |
| JP | 2004107220 A | 4/2004 | |
| JP | 2009237115 A | 10/2009 | |
| JP | 2010079130 A | 4/2010 | |
| JP | 2010181540 A | 8/2010 | |
| JP | 4753336 B2 | 8/2011 | |
| WO | 1996030343 A1 | 10/1996 | |
| WO | 97/28128 A1 | 8/1997 | |
| WO | 97/28129 A1 | 8/1997 | |
| WO | 1997044322 A1 | 11/1997 | |
| WO | 9932463 A1 | 7/1999 | |
| WO | 2001016097 A1 | 3/2001 | |
| WO | 2001019788 A2 | 3/2001 | |
| WO | 2001019798 A2 | 3/2001 | |
| WO | 2001064642 A2 | 9/2001 | |
| WO | 2001064643 A2 | 9/2001 | |
| WO | 2002100822 A1 | 12/2002 | |
| WO | 2002102313 A2 | 12/2002 | |
| WO | 030016289 A1 | 2/2003 | |
| WO | 2004009562 A1 | 1/2004 | |
| WO | 2004046120 A2 | 6/2004 | |
| WO | 2004050033 A2 | 6/2004 | |
| WO | 2004/073619 A2 | 9/2004 | |
| WO | 2004/074438 A2 | 9/2004 | |
| WO | 2004089470 A2 | 10/2004 | |
| WO | 2005035507 A2 | 4/2005 | |
| WO | 2005060956 A1 | 7/2005 | |
| WO | 2005065691 A1 | 7/2005 | |
| WO | 2005120474 A2 | 12/2005 | |
| WO | 2006034341 A2 | 3/2006 | |
| WO | 2006-038594 A1 | 4/2006 | |
| WO | 2006070198 A1 | 7/2006 | |
| WO | 2006079791 A1 | 8/2006 | |
| WO | 2007003934 A2 | 1/2007 | |
| WO | 2007023186 A1 | 3/2007 | |
| WO | 2008/050168 A1 | 5/2008 | |
| WO | 2008052190 A2 | 5/2008 | |
| WO | 2008070661 A1 | 6/2008 | |
| WO | 2008073670 A2 | 6/2008 | |
| WO | 2008076883 A2 | 6/2008 | |
| WO | 2008131547 A1 | 11/2008 | |
| WO | 2008154026 A1 | 12/2008 | |
| WO | 2009013126 A1 | 1/2009 | |
| WO | 2009016410 A2 | 2/2009 | |
| WO | 2009118567 A2 | 10/2009 | |
| WO | 2009126863 A2 | 10/2009 | |
| WO | 2009150248 A1 | 12/2009 | |
| WO | 2010007756 A1 | 1/2010 | |
| WO | 2010/028099 A1 | 3/2010 | |
| WO | 2010105243 A1 | 9/2010 | |
| WO | 2010/129596 A1 | 11/2010 | |
| WO | 2010130638 A1 | 11/2010 | |
| WO | 2010144338 A1 | 12/2010 | |
| WO | 2010144404 A1 | 12/2010 | |
| WO | 201105210 A1 | 1/2011 | |
| WO | 2011002817 A1 | 1/2011 | |
| WO | 2011032169 A2 | 3/2011 | |
| WO | 2011047432 A1 | 4/2011 | |
| WO | 2011050210 A1 | 4/2011 | |
| WO | 2011/072174 A1 | 6/2011 | |
| WO | 2012/009678 A1 | 1/2012 | |
| WO | 2012074999 A1 | 6/2012 | |
| WO | 2012/092442 A1 | 7/2012 | |
| WO | 2012151452 A1 | 11/2012 | |
| WO | 2012160034 A1 | 11/2012 | |
| WO | 2012171506 A1 | 12/2012 | |
| WO | 2013102431 A1 | 7/2013 | |
| WO | 2013107291 A1 | 7/2013 | |
| WO | 2013107405 A1 | 7/2013 | |
| WO | 2013133367 A1 | 9/2013 | |
| WO | 2014015422 A1 | 1/2014 | |

OTHER PUBLICATIONS

International Search Report and Written Opinion for International Application No. PCT/US2015/020346 dated Jun. 18, 2015.

International Search Report dated Mar. 5, 2012 for related international application No. PCT/US2011/067752.

International Search Report for International Application No. PCT/CN2013/079184 dated Jan. 12, 2015.

International Search Report for International Application No. PCT/CN2013/079200 dated Jan. 12, 2015.

International Search Report for International Application No. PCT/CN2014/082869 dated Sep. 30, 2014.

International Search Report for International Application No. PCT/US2014/046204 dated Oct. 1, 2014.

International Search Report for PCT/CN2012/000841 dated Sep. 27, 2012.

International Search Report for PCT/CN2012/077096 dated Oct. 4, 2012.

International Search Report for PCT/CN2013/000009 dated Apr. 18, 2013.

(56) References Cited

OTHER PUBLICATIONS

International Search Report for PCT/US201/030692 dated Jul. 27, 2011.
International Search Report for PCT/US2010/027253 dated Aug. 19, 2010.
International Search Report for PCT/US2010/059778 dated Mar. 17, 2011.
International Search Report for PCT/US2010/53623 dated Jan. 18, 2011.
International Search Report for PCT/US2011/067752 dated Feb. 22, 2012.
International Search Report for PCT/US2011044254 dated May 10, 2011.
International Search Report for PCT/US2013/064601 dated Feb. 24, 2014.
Irikura et al. "New s-Triazine Derivatives as Depressants for Reticuloendothelial Hyperfunction Induced by Bacterial Endotoxin" Journal of Medicinal Chemistry (2000) vol. 31, pp. 1081-1089.
Jennings et al. "Expression and mutagenesis of mammalian cytosolic NADP+-specific isocitrate dehydrogenase" Biochemistry (1997) vol. 36, pp. 13743-13747.
Kaila et al. "A convenient one-pot synthesis of trisubstituted 1,3,5-triazines through intermediary amidinothioureas" Tetrahedron Letters (2010) vol. 51, pp. 1486-1489.
Kelarev et al. "Synthesis and properties of sym-triazines. 10 Synthesis of 2,4-diamino-sym-triazines containing a sterically hindered phenol substituent" Chemistry of Heterocyclic Compounds (1992) vol. 28, No. 10, pp. 1189-1193.
Kim et al. "Identification and Functional Characterization of a Novel, Tissue-specific NAD+-dependent Isocitrate Dehydrogenase b Subunit Isoform" JBC (1999) vol. 274, No. 52, pp. 36866-36875.
Kim et al. "Ser95, Asn97, and Thr78 are important for the catalytic function of porcine NADP-dependent isocitrate dehydrogenase" Protein Science (2005) vol. 14, pp. 140-147.
Koshelev et al. "Synthesis of 1-3,7 N-substituted 2,4-diamino-1,3,5-triazines containing pyridyl groups" Russian Journal of Organic Chemistry (1995) vol. 31, No. 2, pp. 260-263.
Kranendijk et al. "IDH2 Mutations in Patients with D-2-Hydroxyglutaric Aciduria" Science (2010) vol. 330, p. 336.
Krell et al., "IDH mutations in tumorigenesis and their potential role as novel therapeutic targets" Future Oncology (2013) vol. 9, Iss 12, pp. 1923-1935.
Kusakabe et al. Chemical Abstracts vol. 152, No. 191956, Abstract for WO2010007756 (2010).
Lee et al. "Combinatorial Solid-Phase Synthesis of 6-Aryl-1,3,4-triazines via Suzuki Coupling" Aust. J. Chem. (2011) vol. 64, pp. 540-544.
Liu et al. "Inhibition of Cancer-Associated Mutant Isocitrate Dehydrogenases: Synthesis, Structure—Activity Relationship, and Selective Antitumor Activity" Journal of Medicinal Chemistry (2014) vol. 57, pp. 8307-8318.
Lou, "IDH1: function follows form" SciBX (2009) vol. 2, No. 48, pp. 1-2.
Lutker et al, "Crystal Polymorphism in a Carbamazepine Derivative: Oxcarbazepine". NIH Public Access. J Pharm Sci. Feb. 2010 ; 99(2): 794-803. doi: 10.1002/jps.21873.
Madsen-Duggan et al. "Lead optimization of 5.6-diarylpyridines as CB1 receptor inverse agonists" Bioorganic & Medicinal Chemistry Letters (2007) vol. 17, pp. 2031-2035.
May et al. "How many species are there on earth" Science (1988) vol. 241, p. 1441.
Moreno et al. "Identification of diamine linkers with differing reactivity and their applicationin the synthesis of melamine dendrimers" Tetrahedron Letters (2008) vol. 49, pp. 1152-1154.
Moreno et al. "Molecular recognition in dendrimers based on melamine" Polymer Preprints (2005) vol. 46, No. 2, pp. 1127.
Paronikyan et al. "Synthesis and biological activity of 3-piperazinylpyrano [3,4-C] pyridines" Armyanskii Khimicheskii Zhurnal (1990) vol. 43, No. 8, pp. 518-523.
Parsons et al. "An Integrated Genomic Analysis of Human Glioblastoma Multiforme" Science (2008) vol. 321, pp. 1807-1812 and Supplemental Data.
Pollard et al, "Cancer. Puzzling patterns of predisposition." Science (2009) vol. 324, pp. 192-194.
Popovici-Muller et al. "Discovery of the First Potent Inhibitors of Mutant IDH1 That Lower Tumor2-HG in Vivo" ACS Medicinal Chemistry Letters (2012) vol. 3, No. 10, pp. 850-855.
PUBCHEM CID 4078245 [online]; Sep. 13, 2005 [retrieved on Feb. 4, 2012]; retrieved from http://pubchem.ncbi.nim.nih.gov/; 2d-structure.
PUBCHEM CID 4854170 [online]; Sep. 17, 2005 [retrieved on Feb. 4, 2012]; retrieved from http://pubchem.ncbi.nim.nih.gov/; 2d-structure.
Rao et al., "Polymorphism in Drugs and its Significance in Therapeutics". Journal of Scientific & Industrial Research vol. 46 Oct. 1987 pp. 450-455.
Raynaud et al. "Absence of R140Q Mutation of Isocitrate Dehydrogenase 2 in Gliomas and Breast Cancers" Oncology Letters (2010) vol. 1, No. 5, pp. 883-884.
Registry (STN) [online], Aug. 23, 2006 [Retrieved on Jan. 29, 2016] CAS Registration No. 903862-76-0.
Registry (STN) [online], Aug. 23, 2006 [Retrieved on Jan. 29, 2016] CAS Registration No. 903869-26-1.
Registry (STN) [online], Apr. 13, 2007 [Retrieved on Jan. 29, 2016] CAS Registration No. 929819-92-1.
Registry (STN) [online], Apr. 13, 2007 [Retrieved on Jan. 29, 2016] CAS Registration No. 929971-43-7.
Registry (STN) [online], Apr. 19, 2009 [Retrieved on Jan. 29, 2016] CAS Registration No. 1136498-70-8.
Registry (STN) [online], Aug. 27, 2009 [Retrieved on Jan. 29, 2016] CAS Registration No. 1176756-98-1.
Reitman et al. "Isocitrate Dehydrogenase 1 and 2 Mutations in Cancer Alterations at a Crossroads of Cellular Metabolism" Journal of the National Cancer Institute (2010) vol. 102, No. 13, pp. 932-941.
Rohle et al. "An Inhibitor of Mutant IDH1 Delays Growth and Promotes Differentiation of Glioma Cells" Science (2013) vol. 340, No. 6132, pp. 626-630.
Scharn et al. "Spatially Addressed Synthesis of Amino- and Amino-Oxy-Substituted 1,3,5-Triazine Arrays on Polymeric Membranes" Journal of Combinatorial Chemistry (2000) vol. 2, No. 4, pp. 361-369.
Shih et al. "The Role of Mutations in Epigenetic Regulators in Myeloid Malignancies" Nature Reviews Cancer (2012) vol. 12, No. 9, pp. 599-612.
Sirkanyan et al "Synthesis of new derivatives of piperazine-substituted pyrano[3,4-c]pyridines" Hayastani Kimiakan Handes—Chemical Journal of Armenia (2009) vol. 62, No. 3-4 pp. 378-385. English Abstract Only.
Sonoda et al. "Analysis of IDH1 and IDH2 mutations in Japanese glioma patients" Cancer Science, vol. 100, No. 10, pp. 1996-1998.
Sosnovik et al. "Emerging concepts in molecular MRI" Current Opinions in Biotechnology (2007) vol. 18, pp. 4-10.
STN File CA, Registry No. 1023444-33-8, entered STN on May 29, 2008, Chemical Abstracts Index Name "Benzenesulfonamide, 3-[[4-(1,3-benzodioxol-5-ylmethyl)-1-piperazinyl]carbonyl]-N-(4-butylphenyl)-4-methyl-".
STN File CA, Registry No. 1090629-29-0, entered STN on Dec. 28, 2008, Chemical Abstracts Index Name "Benzenesulfonamide, 3-[[4-[(2,5-dimethoxyphenyl)methyl]-1-piperazinyl]carbonyl]-N-(4-methoxyphenyl)-4-methyl-".
STN File CA, Registry No. 134538-28-6, entered STN on Jun. 28, 1991, Chemical Abstracts Index Name "1H-Pyrano[3,4-c]pyridine-5-carbonitrile, 3,4-dihydro-3,3-dimethyl-6-[4-(1-oxobutyl)-1-piperazinyl]-8-phenyl-", disclosed in Paronikyan et al. Armyanskii Khimicheskii Zhurnal, 1990, vol. 43, No. 8.
STN File CA, Registry No. 134538-29-7, entered STN on Jun. 28, 1991, Chemical Abstracts Index Name "1H-Pyrano[3,4-c]pyridine-5-carbonitrile, 3,4-dihydro-3,3-dimethyl-6-[4-(2-methyl-1-oxopropyl)-1-piperazinyl]-8-phenyl-", disclosed in Paronikyan et al. Armyanskii Khimicheskii Zhurnal, 1990, vol. 43, No. 8.

(56) References Cited

OTHER PUBLICATIONS

STN File CA, Registry No. 134538-30-0, entered STN on Jun. 28, 1991, Chemical Abstracts Index Name "1H-Pyrano[3,4-c]pyridine-5-carbonitrile, 6-(4-benzoyl-1-piperazinyl)-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 134538-31-1, entered STN on Jun. 28, 1991, Chemical Abstracts Index Name "1H-pyrano[3,4-c]pyridine-5-carbonitrile, 6-[4-(2-furanylcarbonyl)-1-piperazinyl]-3,4-dihydro-3,3-dimethyl-8-phenyl-", disclosed in Paronikyan et al. Armyanskii Khimicheskii Zhurnal, 1990, vol. 43, No. 8.
STN File CA, Registry No. 380466-24-0 entered STN on Jan. 4, 2002, Chemical Abstracts Index Name "Benzenesulfonamide, N-methyl-N-phenyl-3-[[4-(2-pyridinyl)-1-piperazinyl]carbonyl]".
STN File CA, Registry No. 713505-78-3, entered STN on Jul. 21, 2004, Chemical Abstracts Index Name "1-Piperazinecarboxylic acid, 4-[4-methyl-3-[(phenylamino)sulfonyl]benzoyl]-, ethyl ester".
STN File CA, Registry No. 736168-79-9 entered STN on Aug. 31, 2004, Chemical Abstracts Index Name "Benzenesulfonamide, 3,4-difluoro-N-[3-334-(phenylmethyl0-1-piperazinyl]carbonyl]phenyl".
STN File CA, Registry No. 847757-57-7, entered STN on Apr. 1, 2005, Chemical Abstracts Index Name "Benzenesulfonamide, 3-[[4-(1,3-benzodioxol-5-ylmethyl)-1-piperazinyl]carbonyl]-N-(4-ethoxyphenyl)-N,4-dimethyl-" or "Piperazine, 1-(1,3-benzodioxol-5-ylmethyl)-4-[5-[[(4-ethoxyphenyl)methylamino]sulfonyl]-2-methylbenzoyl]-".
STN Registry, L23 Answer 2 of 3 (CAS No. 1032450-21-7), Database: ASINEX Ltd.,Entered STN: Jul. 3, 2008 (Jul. 3, 2008).
STN Registry. L23 Answer 1 of 3 (CAS No. 1038821-72-5),Database: ChemDB (University of California Irvine), Entered STN: Aug. 5, 2008 (Aug. 5, 2008).
Struys et al. "Investigations by mass isotopomer analysis of the formation of D-2-hydroxyglutarate by cultured lymphoblasts from two patients with D-2-hydroxyglutaric aciduria" FEBS Letters (2004) vol. 557, pp. 115-120.
Struys et al. "Mutations in the D-2-hydroxyglutarate dehydrogenase gene cause D-2-hydroxyglutaric aciduria" American Journal of Human Genetics (2005) vol. 76, pp. 358-360.
Struys, EA. et al. "Measurement of Urinary D- and L-2-Hydroxyglutarate Enantiomers by Stable-Isotope-Dilution LiquidChromatography-Tandem Mass Spectrometry after Derivatization with Diacetyi-L-Tartaric Anhydride." Clinical Chemistry (2004) 501391-1395.
Supplementary European Search Report for EP 10751525 dated Dec. 14, 2012.
Supplementary European Search Report for EP Application No. 10825707.2 dated Jun. 28, 2013.
Takagi et al. "Synthesis of poly(triazinylstyrene) containing nitrogen-bawed ligand and function as metal ion adsorbent and oxidation catalyst" Reactive & Functional Polymers (2006) vol. 31, pp. 1718-1724.
The radiation fact sheet published by the National Cancer Institute, http://www.cancer.gov/about-cancer/treatment/types/radiation-therapy/radiation-fact-sheet, reviewed Jun. 30, 2010.
Thompson, "Metabolic Enzymes as Oncogenes or Tumor Suppressors." The New England Journal of Medicine (2009) vol. 360, No. 8, pp. 813-815.
Van Schaftingen et al. "L-2-Hydroglutaric aciduria, a disorder of metabolite repair" J Inherit. Metab. Dis. (2009) vol. 32, pp. 135-142.
Wang et al "Facile Synthesis of 2,4-Dianiino-6-alkyi- or 6-Aryl-Pyrimidine Derivatives" Journal of Heterocyclic Chemistry (2010) vol. 47 pp. 1056-1061.
Wang et al. "A novel ligand N,N'-di(2-pyridyl)-2,4-diamino-6-phenyl-1,3,5-triazine (dpdapt) and its complexes: [Cu (dpdapt)Cl2] and [Cu(dpdapt)(NO3)(H2O)] • NO3 • H2O" Polyhedron (2006) vol. 25, No. 1, pp. 195-202.

Ward et al. "The Common Feature of Leukemia-Associated IDH1 and IDH2 Mutations is a Neomorphic Enzyme Activity Converting [alpha]-Ketoglutarate to 2-Hydroxyglutarate" Cancer Cell (2010) vol. 17, No. 3 pp. 225-234.
Watanabe et al., "IDH1 Mutations Are Early Events in the Development of Astrocytomas and Oligodendrogliomas". American Journal of Pathology (2009) vol. 174, No. 4, pp. 1149-1153.
Written Opinion for PCT/US2010/027253 dated Aug. 19, 2010.
Written Opinion of International Search Authority for PCT/CN2013/000009 dated Apr. 18, 2013.
Written Opinion of Search Authority for PCT/US2010/53623 dated Jan. 18, 2011.
Written Opinion of the International Searching Authority for PCT/US2011/067752 dated Mar. 5, 2012.
Yan et al., "IDH1 and IDH2 Mutations in Gliomas." The New England Journal of Medicine, 79 Feb. 18-22, 2009, vol. 360, No. 8, pp. 765-773.
Zhao et al. "Glioma-derived mutations in IDH1 dominantly inhibit IDH1 catalytic activity and induce HIF-1alpha", Science (2009) vol. 324, No. 5924, pp. 261-265.
Zheng et al. "Synthesis and antitumor evaluation of a novel series of triaminotriazine derivatives" Bioorganic & Medicinal Chemistry (2007) vol. 15, pp. 1815-1827.
Aghili et al. "Hydroxyglutaric aciduria and malignant brain tumor: a case report and literature review", Journal of Neuroncology (2008) 91 pp. 233-236.
Ansell et al. "The interactions of artificial coenzymes with alcohol dehydrogenase and other NAD(P)(H) dependent enzymes" Journal of Molecular Catalysis B: Enzymatic (1999) vol. 6, No. 1-2, pp. 111-123.
Balss, "Analysis of the IDH1 codon 132 mutation in brain tumors", Acta Neuropathol (2008) vol. 116, pp. 597-602.
Benner et al, "Evolution, language and analogy in functional genomics", Trends in Genetics (2001) vol. 17, pp. 114-418.
Bhushan et al. "Reversed-phase liquid chromatographic resolution of diastereomers of protein and non-protein amino acids prepared with newly synthesized chiral derivatizing reagents based on cyanuric chloride" Amino Acids (2011) vol. 40, pp. 403-409.
Bleeker et al., "IDH1 mutations at residue p.R132 (IDH1 (R132)) occur frequently in high-grade 18-22 gliomas but not in other solid tumors." Hum Muta1., (2009) vol. 30, No. 1, pp. 7-11.
Braun et al. "Triazine-based polymers: 4. MALDI-MS of triazine-based polyamines" Polymer (1996) vol. 37, No. 5, pp. 777-783.
Cairns et al. "Oncogenic Isocitrate Dehydrogenase Mutations: Mechanisms, Models, and Clinical Opportunities" Cancer Discovery (2013) vol. 3, Iss 7, pp. 730-741.
Cecil Text Book of Medicine, edited by Bennet and Plum, (1997) 20th edition, vol. 1, pp. 1004-1010.
Chan et al. "Multi-domain hydrogen-bond forming metal chelates: X-ray crystal structures of dicyclopalladated 2,3-bis[6-(2-amino-4-phenylamino-1,3,5-triazinyl)]pyrazine (H2L) [Pd2Br2L] and 2,6-bis[6-(2-amino-4-phenylamino-1,3,5-triazinylium)]- pyridine dichloride" Chemical Communications (1996) No. 1, pp. 81-83.
Chapman et al. "Substituted aminopyrimidine protein kinase B (PknB) inhibitors show activity against *Mycobacterium tuberculosis*" Bioorganic & Medicinal Chemistry Letters (2012) vol. 22, pp. 3349-3353.
Chen et al. "Cytotoxicity, Hemolysis, and Acute in Vivo Toxicity of Dendrimers Based on Melamine, Candidate Vehicles for Delivery" J. Am. Chem. Soc. (2004) vol. 126, No. 32, pp. 10044-10048.
Cocco et al. "Synthesis of Triflouromethylated Pyridinecarbonitriles" Journal of Heterocyclic Chemistry (1995) vol. 32, pp. 543-545.
Dang et al., "Cancer-associated IDH1 mutations produce 2-hydroxyglutarate." Nature (2009) vol. 462, No. 7274, pp. 739-744.
Dang et al. "IDH Mutations in Glioma and Acute Myeloid Leukemia" Trends in Molecular Medicine (2010) vol. 16, No. 3, pp. 387-397.
Davis et al. "Biochemical, Cellular, and Biophysical Characterization of a Potent Inhibitor of Mutant Isocitrate Dehydrogenase IDH1" The Journal of Biological Chemistry (2014) vol. 289, No. 20, pp. 13717-13725.

(56) References Cited

OTHER PUBLICATIONS

Dermer "Another Anniversary for the War on Cancer" Bio/Technology (1994) vol. 12, p. 320.
Docoslis et al., "Characterization of the Distribution, Polymorphism, and Stability of Nimodipine in Its Solid Dispersions in Polyethylene Glycol by Micro-Raman Spectroscopy and Powder X-Ray Diffraction". The AAPS Journal 2007; 9 (3) Article 43, E361-E370.
Dohner et al. "Impact of Genetic Features on Treatment Decisions in AML" American Society of Hematology (2011) pp. 36-42.
Duanmu et al. "Dendron-Functionalized Superparamagnetic Nanoparticles with Switchable Solubility in Organic and Aqueous Media: Matriced for Homogeneous Catalysis and Potential MRI Contrast Agents" Chem. Mater. (2006) vol. 18, No. 25, pp. 5973-5981.
EP Search Report & Written Opinion for EP 10825706 Dated Mar. 20, 2013.
European Search Report for Application No. 10751525.6 dated Dec. 14, 2012.
European Search Report for European Application No. 12799802.9 dated Sep. 24, 2014.
European Search Report for European Application No. EP 12800001.5 dated Oct. 10, 2014.
Eurpoean Search Report for EP Application No. 11763425.3 dated Sep. 23, 2013.
Extended European Search Report for European application No. 16152308.9 dated Jul. 18, 2016.
Freshney et al. "Culture of Animal Cells, A Manual of Basic Techniques" Alan R. Liss, Inc. (1983) pp. 1-6.
Genetics Home Reference, "L2HGDH". <http:...ghr.nlm.nih.gove/gene/L2HGDH> accessed on Sep. 4, 2015.
Gewald et al. "Discovery of triazines as potent, selective and orally active PDE4 inhibitors" Bioorganic & medicinal Chemistry Letters (2013) vol. 23, pp. 4308-4314.
Golub et al. "Molecular Classification of Cancer: Class Discovery and Class Prediction by Gene Expression Monitoring" Science (1999) vol. 286, pp. 531-537.
Hartmann et al. "Type and Frequency of IDH1 and IDH2 mutations are related to astrocytic and oligodendroglial differentiation and age: a study of 1010 diffuse gliomas" Acta Neuropathologica (2009) vol. 118, pp. 469-474.
Holmes et al. "750 MHz 1H NMR spectroscopy characterisation of the complex metabolic pattern of urine from patients with inborn errors of metabolism: 2-hydroxyglutaric aciduria and maple syrup urine disease" Journal of Pharmaceutical and Biomedical Analysis (1997) vol. 15, pp. 1647-1659.
International Preliminary Report for related application No. PCT/US2010/059778 dated Jun. 12, 2012.
International Preliminary Report for related application No. PCT/US2011/067752 dated Apr. 11, 2013.
International Preliminary Report on Patentability for International Application No. PCT/CN2012/000841 dated Dec. 17, 2013.
International Preliminary Report on Patentability for International Application No. PCT/CN2012/077096 dated Sep. 17, 2013.
International Preliminary Report on Patentability for PCT/CN2012/000841 dated Dec. 17, 2013.
International Preliminary Report on Patentability for PCT/CN2012/077096 dated Dec. 17, 2013.
International Preliminary Report on Patentability for PCT/US2010/027253 dated Sep. 13, 2011.
International Preliminary Report on Patentability for PCT/US2010/040486 dated Jan. 12, 2012.
International Preliminary Report on Patentability for PCT/US2010/053623 dated Apr. 24, 2012.
International Preliminary Report on Patentability for PCT/US2010/053624 dated Apr. 7, 2011.
International Preliminary Report on Patentability for PCT/US2011/030692 dated Oct. 2, 2012.
International Preliminary Report on Patentability for PCT/US2011/067752 dated Apr. 11, 2013.
International Search Report & Written Opinion for PCT/CN2013/070755 dated Apr. 25, 2013.
International Search Report and Written Opinion for Internatinal Application No. PCT/US2013/064601 dated Feb. 24, 2014.
International Search Report and Written Opinion for International Application No. PCT/CN2013/080105 dated Jul. 11, 2014.
International Search Report and Written Opinion for International Application No. PCT/CN2013/081170 dated Apr. 30, 2014.
International Search Report and Written Opinion for International Application No. PCT/CN2014/081957 dated Sep. 30, 2014.
International Search Report and Written Opinion for International Application No. PCT/CN2014/081958 dated Sep. 29, 2014.
International Search Report for PCT/CN2013/000068 dated Apr. 25, 2013.
International Search Report for PCT/US2010053624 dated Apr. 7, 2011.
McRobbie et al. "MRI from Picture to Proton," Cambridge University Press, 2007, pp. 307-308.
STN Tokyo, Registry No. 1001833-18-6, Entered STN on Feb. 6, 2008, Chemical Abstracts Index Name "1,4-Benzodioxin-6-sulfonamide, 2,3-dihydro-N-[4-[(4-methyl-l-piperazinyl)carbonyl]phenyl]-".
STN Tokyo, Registry No. 1030142-35-8, Entered STN on Jun. 24, 2008, Chemical Abstracts Index Name "1,4-Benzodioxin-6-sulfonamide, 2,3-dihydro-N-[4-[[4-[(5 methyl-3-isoxazolyl)methyl]-l-piperazinyl]carbonyl]phenyl]-".
STN Tokyo, Registry No. 1031531-78-8, Entered STN on Jun. 29, 2008 Chemical Abstracts Index Name "1,4-Benzodioxin-6-sulfonamide, N-4[4-[(4-acetyl-1-piperazinyl)carbonyl]phenyl]-2,3-dihydro-".
STN Tokyo, Registry No. 1057928-35-4, Entered STN on Oct. 7, 2008, Chemical Abstracts Index Name "1,4-Benzodioxin-6-sulfonamide, 2,3-dihydro-N-[4-[[4-(2 pyridinyl)-l-piperazinyl]carbonyl]phenyl]-".
STN Tokyo, Registry No. 1240875-00-6, entered STN on Sep. 14, 2010, Chemical Abstracts Index Name "1,4-Benzodioxin-6-sulfonamide, 2,3-dihydro-N-[4-[[4-(2 thiazolyl)-1-piperazinyl]carbonyl]phenyl]-".
STN Tokyo, Registry No. 748791-86-8, Entered STN on Sep. 21, 2004, Chemical Abstracts Index Name "1,4-Benzodioxin-6-sulfonamide, N-[4-[[4-(2-furanylcarbonyl)-1-piperazinyl]carbonyl]phenyl]-2,3-dihydro-".
STN Tokyo, Registry No. 878469-24-0, Entered STN on Mar. 29, 2006, Chemical Abstracts Index Name "1,4-Benzodioxin-6-sulfonamide, 2,3-dihydro-N-[4-[[4-(2-pyrimidinyl)-1-piperazinyl]carbonyl]phenyl]-".
STN Tokyo, Registry No. 878474-39-6, Entered STN on Mar. 29, 2006, Chemical Abstracts Index Name "1,4-Benzodioxin-6-sulfonamide, 2,3-dihydro-N-[4[(4-phenyl-1-piperazinyl)carbonyl]phenyl]-".
STN Tokyo, Registry No. 878590-33-1, Entered STN on Mar. 30, 2006, Chemical Abstracts Index Name "1,4-Benzodioxin-6-sulfonamide, 2,3-dihydro-N-[4-{{4-(tetrahydro-2-furanyl)methyl]-1-piperazinyl]carbonyl]phenyl]-".
STN Tokyo, Registry No. 878943-66-9 Entered STN on Apr. 2, 2006, Chemical Abstracts Index Name "1,4-Benzodioxin-6-sulfonamide, 3,4-dihydro-N-[[4-(2-pyrimidinyl)-1-piperazinyl)carbonyl]phenyl]-".
STN Tokyo, Registry No. 878956-06-0, Entered STN on Apr. 2, 2006, Chemical Abstracts Index Name "1,4-Benzodioxin-6-sulfonamide, N-[4-[[4-(cyclopropylcarbonyl)-1-piperazinyl]carbonyl]phenyl]-2,3-dihydro-".
STN Tokyo, Registry No. 920679-46-5, Entered STN on Feb. 13, 2007, Chemical Abstracts Index Name "1,4-Benzodioxin-6-sulfonamide, 2,3-dihydro-N-[4-[[4-(4-pyridinyl)-1-piperazinyl]carbonyl]phenyl]-".
STN Tokyo, Registry No. 920822-52-2, Entered STN on Feb. 14, 2007, Chemical Abstracts Index Name "1,4-Benzodioxin-6-sulfonamide, N-[4-[[4-(4-fluoropheyl)-1-piperazinyl]carbonyl]phenyl]-2,3dihydro-".

(56) References Cited

OTHER PUBLICATIONS

STN Tokyo, Registry No. 920824-56-2, Entered STN on Feb. 14, 2007, Chemical Abstracts Index Name "1,4-Benzodioxin-6-sulfonamide, 2,3-dihydro-N-[4-[[4-(3-thienylmethyl)-1-piperazinyl]carbonyl]phenyl]-".
STN Tokyo, Registry No. 920847-34-3, Entered STN on Feb. 14, 2007, Chemical Abstracts Index Name "1,4-Benzodioxin-6-sulfonamide, 2,3-dihydro-N-[4-[[4-(2-methylphenyl)-1-piperazinyl]carbonyl]phenyl]-".
STN Tokyo, Registry No. 920875-39-4, Entered STN on Feb. 14, 2007, Chemical Abstracts Index Name "1,4-Benzodioxin-6-sulfonamide, 2,3-dihydro-N-[4-[[4-(2-hydroxyphenyl)-1-piperazinyl]carbonyl]phenyl]-".
STN Tokyo, Registry No. 920902-88-1, Entered STN on Feb. 14, 2007, Chemical Abstracts Index Name "1,4-Benzodioxin-6-sulfonamide, 2,3-dihydro-N-[4-[[4-(2-thienylmethyl)-1-piperazinyl]carbonyl]phenyl]-".
STN Tokyo, Registry No. 920921-09-1 Entered STN on Feb. 14, 2007, Chemical Abstracts Index Name "2H-1, 5-Benzodioxepin-7-sulfonamide, 3,4-dihydro-N-[4-[[4-(2pyridinyl)-1-piperazinyl]carbonyl]phenyl]-".
STN Tokyo, Registry No. 920924-42-1, Entered STN on Feb. 14, 2007, Chemical Abstracts Index Name "1,4-Benzodioxin-6-sulfonamide, 2,3-dihydro-N-[4-[[4-(2-pyridinylmethyl)-1-piperazinyl]carbonyl]phenyl]-".
STN Tokyo, Registry No. 941220-77-5, Entered STN on Jul. 4, 2007, Chemical Abstracts Index Name "2H-1, 5-Benzodioxepin-7-sulfonamide, 3,4-dihydro-N-[4-[(4-methyl-l-piperazinyl)carbonyl]phenyl]-".

\* cited by examiner

LC-MS/MS analysis of the spiked control reaction. The LC-MS/MS instrument as configured can readily detect the presumptive final concentration of isocitrate. When the terminated R132H - containing reaction was spiked to a final concentration of 1 mM isocitrate, it was readily observed (red); essentially complete consumption of a-KG was confirmed (blue).

LC-MS/MS analysis of alpha-hydroxyglutarate. The instrument was optimized for the detection of 2-hydroxyglutarate and identified the 147.1/128.7 MRM transition as a peak retained at 7.14 minutes. The peak at 0.52 minutes is an instrument artifact caused by switching of an inline diversion valve.

```
  1 mskkisggsv vemqgdemtr iiwelikekl ifpyveldlh sydlgienrd atndqvtkda
 61 aeaikkhnvg vkcatitpde krveefklkq mwkspngtir nilggtvfre aiickniprl
121 vsgwvkpiii grhaygdqyr atdfvvpgpg kveitytpsd gtqkvtylvh nfeegggvam
181 gmynqdksie dfahssfqma lskgwplyls tkntilkkyd grfkdifqei ydkqyksqfe
241 aqkiwyehrl iddmvaqamk seggfiwack nydgdvqsds vaqgygslgm mtsvlvcpdg
301 ktveaeaahg tvtrhyrmyq kgqetstnpi asifawtrgl ahrakldnnk elaffanale
361 evsietieag fmtkdlaaci kglpnvqrsd ylntfefmdk lgenlkikla qakl
```

Fig. 21

```
   1 atgtccaaaa aaatcagtgg cggttctgtg gtagagatgc aaggagatga aatgacacga
  61 atcatttggg aattgattaa agagaaactc attttcccct acgtggaatt ggatctacat
 121 agctatgatt taggcataga gaatcgtgat gccaccaacg accaagtcac caaggatgct
 181 gcagaagcta taaagaagca taatgttggc gtcaaatgtg ccactatcac tcctgatgag
 241 aagagggttg aggagttcaa gttgaaacaa atgtggaaat caccaaatgg caccatacga
 301 aatattctgg gtggcacggt cttcagagaa gccattatct gcaaaaatat cccccggctt
 361 gtgagtggat gggtaaaacc tatcatcata ggtcgtcatg cttatgggga tcaatacaga
 421 gcaactgatt ttgttgttcc tgggcctgga aaagtagaga taacctacac accaagtgac
 481 ggaacccaaa aggtgacata cctggtacat aactttgaag aaggtggtgg tgttgccatg
 541 gggatgtata atcaagataa gtcaattgaa gattttgcac acagttcctt ccaaatggct
 601 ctgtctaagg gttggccttt gtatctgagc accaaaaaca ctattctgaa gaaatatgat
 661 gggcgtttta aagacatctt tcaggagata tatgacaagc agtacaagtc ccagtttgaa
 721 gctcaaaaga tctggtatga gcataggctc atcgacgaca tggtggccca agctatgaaa
 781 tcagagggag gcttcatctg ggcctgtaaa aactatgatg gtgacgtgca gtcggactct
 841 gtggcccaag ggtatggctc tctcggcatg atgaccagcg tgctggtttg tccagatggc
 901 aagacagtag aagcagaggc tgcccacggg actgtaaccc gtcactaccg catgtaccag
 961 aaaggacagg agacgtccac caatcccatt gcttccattt ttgcctggac cagagggtta
1021 gcccacagag caaagcttga taacaataaa gagcttgcct tctttgcaaa tgctttggaa
1081 gaagtctcta ttgagacaat tgaggctggc ttcatgacca aggacttggc tgcttgcatt
1141 aaaggtttac ccaatgtgca acgttctgac tacttgaata catttgagtt catggataaa
1201 cttggagaaa acttgaagat caaactagct caggccaaac tttaa
```

Fig. 21A

```
   1 cctgtggtcc cgggtttctg cagagtctac ttcagaagcg gaggcactgg gagtccggtt
  61 tgggattgcc aggctgtggt tgtgagtctg agcttgtgag cggctgtggc gccccaactc
 121 ttcgccagca tatcatcccg gcaggcgata aactacattc agttgagtct gcaagactgg
 181 gaggaactgg ggtgataaga aatctattca ctgtcaaggt ttattgaagt caaaatgtcc
 241 aaaaaaatca gtggcggttc tgtggtagag atgcaaggag atgaaatgac acgaatcatt
 301 tgggaattga ttaaagagaa actcattttt ccctacgtgg aattggatct acatagctat
 361 gatttaggca tagagaatcg tgatgccacc aacgaccaag tcaccaagga tgctgcagaa
 421 gctataaaga agcataatgt tggcgtcaaa tgtgccacta tcactcctga tgaagagg
 481 gttgaggagt tcaagttgaa acaaatgtgg aaatcaccaa atggcaccat acgaaatatt
 541 ctgggtggca cggtcttcag agaagccatt atctgcaaaa atatccccg gcttgtgagt
 601 ggatgggtaa aacctatcat cataggtcgt catgcttatg gggatcaata cagagcaact
 661 gattttgttg ttcctgggcc tggaaaagta gagataacct acacaccaag tgacggaacc
 721 caaaaggtga catacctggt acataacttt gaagaaggtg gtggtgttgc catggggatg
 781 tataatcaag ataagtcaat tgaagatttt gcacacagtt ccttccaaat ggctctgtct
 841 aagggttggc ctttgtatct gagcaccaaa aacactattc tgaagaaata tgatgggcgt
 901 tttaaagaca tctttcagga gatatatgac aagcagtaca gtcccagtt tgaagctcaa
 961 aagatctggt atgagcatag gctcatcgac gacatggtgg cccaagctat gaaatcagag
1021 ggaggcttca tctgggcctg taaaaactat gatggtgacg tgcagtcgga ctctgtggcc
1081 caagggtatg gctctctcgg catgatgacc agcgtgctgg tttgtccaga tggcaagaca
1141 gtagaagcag aggctgccca cgggactgta acccgtcact accgcatgta ccagaaagga
1201 caggagacgt ccaccaatcc cattgcttcc attttgcct ggaccagagg gttagcccac
1261 agagcaaagc ttgataacaa taaagagctt gccttctttg caaatgcttt ggaagaagtc
1321 tctattgaga caattgaggc tggcttcatg accaaggact ggctgcttg cattaaaggt
1381 ttacccaatg tgcaacgttc tgactacttg aatacatttg agttcatgga taaacttgga
1441 gaaacttga agatcaaact agctcaggcc aaactttaag ttcatacctg agctaagaag
1501 gataattgtc ttttggtaac taggtctaca ggtttacatt tttctgtgtt acactcaagg
1561 ataaaggcaa aatcaattt gtaatttgtt tagaagccag agttatctt ttctataagt
1621 ttacagcctt tttcttatat atacagttat tgccaccttt gtgaacatgg caagggactt
1681 ttttacaatt tttatttat tttctagtac cagcctagga attcggttag tactcatttg
1741 tattcactgt cactttttct catgttctaa ttataaatga ccaaaatcaa gattgctcaa
1801 aagggtaaat gatagccaca gtattgctcc ctaaaatatg cataaagtag aaattcactg
1861 ccttccccctc ctgtccatga ccttgggcac agggaagttc tggtgtcata gatatcccgt
1921 tttgtgaggt agagctgtgc attaaacttg cacatgactg gaacgaagta tgagtgcaac
1981 tcaaatgtgt tgaagatact gcagtcattt ttgtaaagac cttgctgaat gtttccaata
2041 gactaaatac tgtttaggcc gcaggagagt ttggaatccg gaataaatac tacctggagg
2101 tttgtcctct ccatttttct ctttctcctc ctggcctggc ctgaatatta tactactcta
2161 aatagcatat ttcatccaag tgcaataatg taagctgaat cttttttgga cttctgctgg
2221 cctgttttat ttcttttata taatgtgat ttctcagaaa ttgatattaa acactatctt
2281 atcttctcct gaactgttga ttttaattaa aattaagtgc taattaccaa aaaaaaaaa
```

Fig. 21B

MAGYLRVVRSLCRASGSRPAWAPAALTAPTSQEQPRRHYADKRIKVAKPV
VEMDGDEMTRIIWQFIKEKLILPHVDIQLKYFDLGLPNRDQTDDQVTIDS
ALATQKYSVAVKCATITPDEARVEEFKLKKMWKSPNGTIRNILGGTVFRE
PIICKNIPRLVPGWTKPITIGRHAHGDQYKATDFVADRAGTFKMVFTPKD
GSGVKEWEVYNFPAGGVGMGMYNTDESISGFAHSCFQYAIQKKWPLYMST
KNTILKAYDGRFKDIFQEIFDKHYKTDFDKNKIWYEHRLIDDMVAQVLKS
SGGFVWACKNYDGDVQSDILAQGFGSLGLMTSVLVCPDGKTIEAEAAHGT
VTRHYREHQKGRPTSTNPIASIFAWTRGLEHRGKLDGNQDLIRFAQMLEK
VCVETVESGAMTKDLAGCIHGLSNVKLNEHFLNTTDFLDTIKSNLDRALG
RQ

Fig. 22

```
   1 atggccggct acctgcgggt cgtgcgctcg ctctgcagag cctcaggctc gcggccggcc
  61 tgggcgccgg cggccctgac agcccccacc tcgcaagagc agccgcggcg ccactatgcc
 121 gacaaaagga tcaaggtggc gaagcccgtg gtggagatgg atggtgatga gatgacccgt
 181 attatctggc agttcatcaa ggagaagctc atcctgcccc acgtggacat ccagctaaag
 241 tattttgacc tcgggctccc aaaccgtgac cagactgatg accaggtcac cattgactct
 301 gcactggcca cccagaagta cagtgtggct gtcaagtgtg ccaccatcac ccctgatgag
 361 gcccgtgtgg aagagttcaa gctgaagaag atgtggaaaa gtcccaatgg aactatccgg
 421 aacatcctgg ggggactgt cttccgggag cccatcatct gcaaaaacat cccacgccta
 481 gtccctggct ggaccaagcc catcaccatt ggcaggcacg cccatggcga ccagtacaag
 541 gccacagact tgtggcaga ccgggccggc actttcaaaa tggtcttcac cccaaaagat
 601 ggcagtggtg tcaaggagtg ggaagtgtac aacttccccg caggcggcgt gggcatgggc
 661 atgtacaaca ccgacgagtc catctcaggt tttgcgcaca gctgcttcca gtatgccatc
 721 cagaagaaat ggccgctgta catgagcacc aagaacacca tactgaaagc ctacgatggg
 781 cgtttcaagg acatcttcca ggagatcttt gacaagcact ataagaccga cttcgacaag
 841 aataagatct ggtatgagca ccggctcatt gatgacatgg tggctcaggt cctcaagtct
 901 tcgggtggct ttgtgtgggc ctgcaagaac tatgacggag atgtgcagtc agacatcctg
 961 gcccagggct ttggctccct tggcctgatg acgtccgtcc tggtctgccc tgatgggaag
1021 acgattgagg ctgaggccgc tcatgggacc gtcacccgcc actatcggga gcaccagaag
1081 ggccggccca ccagcaccaa ccccatcgcc agcatctttg cctggacacg tggcctggag
1141 caccggggga agctggatgg gaaccaagac ctcatcaggt tgcccagat gctggagaag
1201 gtgtgcgtgg agacgtggga gagtggagcc atgaccaagg acctggcggg ctgcattcac
1261 ggcctcagca atgtgaagct gaacgagcac ttcctgaaca ccacggactt cctcgacacc
1321 atcaagagca acctggacag agccctgggc aggcagtag
```

Fig. 22A

```
   1 ccagcgttag cccgcggcca ggcagccggg aggagcggcg cgcgctcgga cctctcccgc
  61 cctgctcgtt cgctctccag cttgggatgg ccggctacct gcgggtcgtg cgctcgctct
 121 gcagagcctc aggctcgcgg ccggcctggg cgccggcggc cctgacagcc cccacctcgc
 181 aagagcagcc gcggcgccac tatgccgaca aaaggatcaa ggtggcgaag cccgtggtgg
 241 agatggatgg tgatgagatg acccgtatta tctggcagtt catcaaggag aagctcatcc
 301 tgccccacgt ggacatccag ctaaagtatt ttgacctcgg gctcccaaac cgtgaccaga
 361 ctgatgacca ggtcaccatt gactctgcac tggccaccca gaagtacagt gtggctgtca
 421 agtgtgccac catcacccct gatgaggccc gtgtggaaga gttcaagctg aagaagatgt
 481 ggaaaagtcc caatggaact atccggaaca tcctgggggg gactgtcttc gggagccca
 541 tcatctgcaa aaacatccca cgcctagtcc ctggctggac caagcccatc accattggca
 601 ggcacgccca tggcgaccag tacaaggcca cagactttgt ggcagaccgg gccggcactt
 661 tcaaaatggt cttccccca aaagatggca gtggtgtcaa ggagtgggaa gtgtacaact
 721 tccccgcagg cggcgtgggc atgggcatgt acaacaccga cgagtccatc tcaggttttg
 781 cgcacagctg cttccagtat gccatccaga cgccctggcc gctgtacatg agcaccaaga
 841 acaccatact gaaagcctac gatgggcgtt tcaaggacat cttccaggag atctttgaca
 901 agcactataa gaccgacttc gacaagaata agatctggta tgagcaccgg ctcattgatg
 961 acatggtggc tcaggtcctc aagtcttcgg gtggctttgt gtgggcctgc aagaactatg
1021 acggagatgt gcagtcagac atcctggccc agggctttgg ctcccttggc ctgatgacgt
1081 ccgtcctggt ctgccctgat gggaagacga ttgagctga ggccgctcat ggaccgtca
1141 cccgccacta tcgggagcac agaagggcc ggcccaccag caccaacccc atcgccagca
1201 tctttgcctg gacacgtggc ctggagcacc ggggaagct ggatgggaac caagacctca
1261 tcaggtttgc ccagatgctg gagaaggtgt gcgtggagac ggtggagagt ggagccatga
1321 ccaaggacct ggcgggctgc attcacggcc tcagcaatgt gaagctgaac gagcacttcc
1381 tgaacaccac ggacttcctc gacaccatca agagcaacct ggacagagcc ctgggcaggc
1441 agtaggggga ggcgccaccc atggctgcag tggaggggcc agggctgagc cggcgggtcc
1501 tcctgagcgc ggcagagggt gagcctcaca gcccctctct ggaggccttt ctaggggatg
1561 ttttttata agccagatgt ttttaaaagc atatgtgtgt ttccctcat ggtgacgtga
1621 ggcaggagca gtgcgtttta cctcagccag tcagtatgtt ttgcatactg taatttatat
1681 tgcccttgga acacatggtg ccatatttag ctactaaaaa gctcttcaca aaaaaaaaa
```

Fig. 22B gcataatgagctctatatgccatcactgcagttgtaggttataactatccatttgtctgaaaaactttgcttc
taattttctctttcaagCTATGATTTAGGCATAGAGAATCGTGATGCCACCAACGACCAAGTCACCAAGGAT
GCTGCAGAAGCTATAAAGAAGCATAATGTTGGCGTCAAATGTGCCACTATCACTCCTGATGAGAAGAGGGTTG
AGGAGTTCAAGTTGAAACAAATGTGGAAATCACCAAATGGCACCATACGAAATATTCTGGGTGGCJGTCTTCA
GAGAAGCCATTATCTGCAAAAATATCCCCCGGCTTGTGAGTGGATGGGTAAAACCTATCATCATAGGTCGTCA
TGCTTATGGGGATCAAgtaagtcatgttggcaataatgtgattttgcatgbtggcccagaaatttccaacttg
tatgtgttttattcttatcttttggtatctacacccattaagcaaggta

Fig. 27

| Oxidative (→ NADPH) | WT | R132H | Reductive (→ NADP+) | WT | R132H |
|---|---|---|---|---|---|
| $K_{M,NADP^+}$ (μM) | 49 | 84 | $K_{M,NADPH}$ (μM) | n/a* | 0.44 |
| $K_{M,isocitrate}$ (μM) | 65 | 370 | $K_{M,\alpha KG}$ (μM) | n/a | 965 |
| $K_{M,MgCl_2}$ (μM) | 29 | 10085 | $k_{cat}$ (s$^{-1}$) | n/a | $1.0 \times 10^3$ |
| $K_{i,\alpha KG}$ (μM) | 1871 | 24 | | | |
| $k_{cat}$ (s$^{-1}$) | $4.4 \times 10^5$ | 37.5 | *n/a = No measurable enzymatic activity | | |

Fig. 30C

Comparison of NADPH reduction between IDH2-R172K, IDH2-wt, IDH1-R132H, and IDH1-wt enzymes. Final reactant concentrations for each reaction was as follow: 20mM Tris 7.5, 150 mM NaCl, 2 mM $MnCl_2$, 10% Glycerol, 0.03% BSA, varied enzyme (1-120 ug/mL), 1 mM NADPH, 5 mM aKG.

IDH1/2 mutant AML cells do not display altered levels of central carbon metabolites.

SEQUENCE LISTING

```
<160> NUMBER OF SEQ ID NOS: 804

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
taatcatatg tccaaaaaaa tcagt                                            25

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
taatctcgag tgaaagtttg gcctgagcta gtt                                   33

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      8xHis tag

<400> SEQUENCE: 3

His His His His His His His His
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 4

Ser Leu Glu His His His His His His His
1               5                   10

<210> SEQ ID NO 5
<211> LENGTH: 1245
<212> TYPE: DNA
<213> ORGANISM: Homo sapiens

<400> SEQUENCE: 5

```
atgtccaaaa aaatcagtgg cggttctgtg gtagagatgc aaggagatga atgacacga     60 atcatttggg aattgattaa agagaaactc attttcccct acgtggaatt ggatctacat    120
agctatgatt taggcataga gaatcgtgat gccaccaacg accaagtcac caaggatgct    180
gcagaagcta taaagaagca taatgttggc gtcaaatgtg ccactatcac tcctgatgag    240
aagagggttg aggagttcaa gttgaaacaa atgtggaaat caccaaatgg caccatacga    300
aatattctgg gtggcacggt cttcagagaa gccattatct gcaaaaatat ccccggctt    360 gtgagtggat gggtaaaacc tatcatcata ggtcgtcatg cttatgggga tcaatacaga    420
gcaactgatt ttgttgttcc tgggcctgga aaagtagaga taacctacac accaagtgac    480
ggaacccaaa aggtgacata cctggtacat aactttgaag aaggtggtgg tgttgccatg    540
gggatgtata atcaagataa gtcaattgaa gattttgcac acagttcctt ccaaatggct    600
ctgtctaagg gttggccttt gtatctgagc accaaaaaca ctattctgaa gaaatatgat    660
gggcgtttta agacatctt tcaggagata tatgacaagc agtacaagtc ccagtttgaa    720
gctcaaaaga tctggtatga gcataggctc atcgacgaca tggtggccca agctatgaaa    780
tcagagggag gcttcatctg ggcctgtaaa aactatgatg gtgacgtgca gtcggactct    840
gtggcccaag gtatggctc tctcggcatg atgaccagcg tgctggtttg tccagatggc    900
aagacagtag aagcagaggc tgcccacggg actgtaaccc gtcactaccg catgtaccag    960
aaaggacagg agacgtccac caatcccatt gcttccattt ttgcctggac cagagggtta   1020
gcccacagag caaagcttga taacaataaa gagcttgcct tctttgcaaa tgctttggaa   1080
gaagtctcta ttgagacaat tgaggctggc ttcatgacca aggacttggc tgcttgcatt   1140
aaaggtttac ccaatgtgca acgttctgac tacttgaata catttgagtt catggataaa   1200
cttggagaaa acttgaagat caaactagct caggccaaac tttaa                    1245
```

<210> SEQ ID NO 6
<211> LENGTH: 1297
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
atgtccaaaa aaatcagtgg cggttctgtg gtagagatgc aaggagatga atgacacga     60 atcatttggg aattgattaa agagaaactc attttcccct acgtggaatt ggatctacat    120
agctatgatt taggcataga gaatcgtgat gccaccaacg accaagtcac caaggatgct    180
gcagaagcta taaagaagca taatgttggc gtcaaatgtg ccactatcac tcctgatgag    240
aagagggttg aggagttcaa gttgaaacaa atgtggaaat caccaaatgg caccatacga    300
aatattctgg gtggcacggt cttcagagaa gccattatct gcaaaaatat ccccggctt    360
```

```
gtgagtggat gggtaaaacc tatcatcata ggtcgtcatg cttatgggga tcaatacaga      420
gcaactgatt ttgttgttcc tgggcctgga aaagtagaga taacctacac accaagtgac      480
ggaacccaaa aggtgacata cctggtacat aactttgaag aaggtggtgg tgttgccatg      540
gggatgtata atcaagataa gtcaattgaa gattttgcac acagttcctt ccaaatggct      600
ctgtctaagg gttggccttt gtatctgagc accaaaaaca ctattctgaa gaaatatgat      660
gggcgtttta aagacatctt tcaggagata tatgacaagc agtacaagtc ccagtttgaa      720
gctcaaaaga tctggtatga gcataggctc atcgacgaca tggtggccca agctatgaaa      780
tcagagggag gcttcatctg ggcctgtaaa aactatgatg gtgacgtgca gtcggactct      840
gtggcccaag ggtatggctc tctcggcatg atgaccagcg tgctggtttg tccagatggc      900
aagacagtag aagcagaggc tgcccacggg actgtaaccc gtcactaccg catgtaccag      960
aaaggacagg agacgtccac caatcccatt gcttccattt ttgcctggac cagagggtta     1020
gcccacagag caaagcttga taacaataaa gagcttgcct tctttgcaaa tgctttggaa     1080
gaagtctcta ttgagacaat tgaggctggc ttcatgacca aggacttggc tgcttgcatt     1140
aaaggtttac ccaatgtgca acgttctgac tacttgaata catttgagtt catggataaa     1200
cttggagaaa acttgaagat caaactagct caggccaaac tttcactcga gcaccaccac     1260
caccaccacc accactaatt gattaatacc taggctg                              1297
```

```
<210> SEQ ID NO 7
<211> LENGTH: 1245
<212> TYPE: DNA
<213> ORGANISM: Artificial Sequence
<220> FEATURE:
<223> OTHER INFORMATION: Description of Artificial Sequence: Synthetic
      consensus sequence

<400> SEQUENCE: 7
atgtccaaaa aaatcagtgg cggttctgtg gtagagatgc aaggagatga aatgacacga       60
atcatttggg aattgattaa agagaaactc atttttccct acgtggaatt ggatctacat      120
agctatgatt taggcataga gaatcgtgat gccaccaacg accaagtcac caaggatgct      180
gcagaagcta taaagaagca taatgttggc gtcaaatgtg ccactatcac tcctgatgag      240
aagagggttg aggagttcaa gttgaaacaa atgtggaaat caccaaatgg caccatacga      300
aatattctgg gtggcacggt cttcagagaa gccattatct gcaaaaatat cccccggctt      360
gtgagtggat gggtaaaacc tatcatcata ggtcgtcatg cttatgggga tcaatacaga      420
gcaactgatt ttgttgttcc tgggcctgga aaagtagaga taacctacac accaagtgac      480
ggaacccaaa aggtgacata cctggtacat aactttgaag aaggtggtgg tgttgccatg      540
gggatgtata atcaagataa gtcaattgaa gattttgcac acagttcctt ccaaatggct      600
ctgtctaagg gttggccttt gtatctgagc accaaaaaca ctattctgaa gaaatatgat      660
gggcgtttta aagacatctt tcaggagata tatgacaagc agtacaagtc ccagtttgaa      720
gctcaaaaga tctggtatga gcataggctc atcgacgaca tggtggccca agctatgaaa      780
tcagagggag gcttcatctg ggcctgtaaa aactatgatg gtgacgtgca gtcggactct      840
gtggcccaag ggtatggctc tctcggcatg atgaccagcg tgctggtttg tccagatggc      900
aagacagtag aagcagaggc tgcccacggg actgtaaccc gtcactaccg catgtaccag      960
aaaggacagg agacgtccac caatcccatt gcttccattt ttgcctggac cagagggtta     1020
gcccacagag caaagcttga taacaataaa gagcttgcct tctttgcaaa tgctttggaa     1080
```

```
gaagtctcta ttgagacaat tgaggctggc ttcatgacca aggacttggc tgcttgcatt    1140
aaaggtttac ccaatgtgca acgttctgac tacttgaata catttgagtt catggataaa    1200
cttggagaaa acttgaagat caaactagct caggccaaac tttma                    1245
```

<210> SEQ ID NO 8
<211> LENGTH: 414
<212> TYPE: PRT
<213> ORGANISM: Homo sapiens

<400> SEQUENCE: 8

```
Met Ser Lys Lys Ile Ser Gly Gly Ser Val Val Glu Met Gln Gly Asp
1               5                   10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
        35                  40                  45

Arg Asp Ala Thr Asn Asp Gln Val Thr Lys Asp Ala Ala Glu Ala Ile
    50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
                85                  90                  95

Gly Thr Ile Arg Asn Ile Leu Gly Gly Thr Val Phe Arg Glu Ala Ile
            100                 105                 110

Ile Cys Lys Asn Ile Pro Arg Leu Val Ser Gly Trp Val Lys Pro Ile
        115                 120                 125

Ile Ile Gly Arg His Ala Tyr Gly Asp Gln Tyr Arg Ala Thr Asp Phe
    130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
                165                 170                 175

Gly Val Ala Met Gly Met Tyr Asn Gln Asp Lys Ser Ile Glu Asp Phe
            180                 185                 190

Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

Asp Ile Phe Gln Glu Ile Tyr Asp Lys Gln Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
    290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
```

```
                340                 345                 350
Ala Phe Phe Ala Asn Ala Leu Glu Glu Val Ser Ile Glu Thr Ile Glu
        355                 360                 365

Ala Gly Phe Met Thr Lys Asp Leu Ala Ala Cys Ile Lys Gly Leu Pro
370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410

<210> SEQ ID NO 9
<211> LENGTH: 2339
<212> TYPE: DNA
<213> ORGANISM: Homo sapiens

<400> SEQUENCE: 9
cctgtggtcc cgggtttctg cagagtctac ttcagaagcg gaggcactgg gagtccggtt      60
tgggattgcc aggctgtggt tgtgagtctg agcttgtgag cggctgtggc gccccaactc     120
ttcgccagca tatcatcccg gcaggcgata aactacattc agttgagtct gcaagactgg     180
gaggaactgg ggtgataaga aatctattca ctgtcaaggt ttattgaagt caaaatgtcc     240
aaaaaaatca gtggcggttc tgtggtagag atgcaaggag atgaaatgac acgaatcatt     300
tgggaattga ttaaagagaa actcattttt ccctacgtgg aattggatct acatagctat     360
gatttaggca tagagaatcg tgatgccacc aacgaccaag tcaccaagga tgctgcagaa     420
gctataaaga agcataatgt tggcgtcaaa tgtgccacta tcactcctga tgaagagag      480 gttgaggagt tcaagttgaa acaaatgtgg aaatcaccaa atggcaccat acgaaatatt     540
ctgggtggca cggtcttcag agaagccatt atctgcaaaa atatccccccg gcttgtgagt     600 ggatgggtaa aacctatcat cataggtcgt catgcttatg gggatcaata cagagcaact     660
gattttgttg ttcctgggcc tggaaaagta gagataaacct acacaccaag tgacggaacc     720
caaaaggtga catacctggt acataacttt gaagaaggtg gtggtgttgc catggggatg     780
tataatcaag ataagtcaat tgaagatttt gcacacagtt ccttccaaat ggctctgtct     840
aagggttggc ctttgtatct gagcaccaaa acactattc tgaagaaata tgatgggcgt     900
tttaaagaca tctttcagga gatatatgac aagcagtaca agtcccagtt tgaagctcaa     960
aagatctggt atgagcatag gctcatcgac gacatggtgg cccaagctat gaaatcagag    1020
ggaggcttca tctgggcctg taaaaactat gatggtgacg tgcagtcgga ctctgtggcc    1080
caagggtatg gctctctcgg catgatgacc agcgtgctgg tttgtccaga tggcaagaca    1140
gtagaagcag aggctgccca cgggactgta acccgtcact accgcatgta ccagaaagga    1200
caggagacgt ccaccaatcc cattgcttcc atttttgcct ggaccagagg gttagcccac    1260
agagcaaagc ttgataacaa taagagcttt gccttctttg caaatgcttt ggaagaagtc    1320
tctattgaga caattgaggc tggcttcatg accaaggact ggctgcttg cattaaaggt     1380 ttacccaatg tgcaacgttc tgactacttg aatacatttg agttcatgga taaacttgga    1440
gaaaacttga gatcaaaact agctcaggcc aaactttaag ttcatacctg agctaagaag    1500
gataattgtc ttttggtaac taggtctaca ggtttacatt tttctgtgtt acactcaagg    1560
ataaaggcaa aatcaatttt gtaatttgtt tagaagccag agtttatctt ttctataagt    1620
ttacagcctt tttcttatat atacagttat tgccacctt gtgaacatgg caagggactt    1680
ttttacaatt tttattttat tttctagtac cagcctagga attcggttag tactcatttg    1740
```

-continued

```
tattcactgt cacttttct catgttctaa ttataaatga ccaaaatcaa gattgctcaa    1800
aagggtaaat gatagccaca gtattgctcc ctaaaatatg cataaagtag aaattcactg    1860
ccttcccctc ctgtccatga ccttgggcac agggaagttc tggtgtcata gatatcccgt    1920
tttgtgaggt agagctgtgc attaaacttg cacatgactg gaacgaagta tgagtgcaac    1980
tcaaatgtgt tgaagatact gcagtcattt ttgtaaagac cttgctgaat gtttccaata    2040
gactaaatac tgtttaggcc gcaggagagt ttggaatccg gaataaatac tacctggagg    2100
tttgtcctct ccattttct ctttctcctc ctggcctggc ctgaatatta tactactcta    2160
aatagcatat ttcatccaag tgcaataatg taagctgaat cttttttgga cttctgctgg    2220
cctgttttat ttcttttata taatgtgat ttctcagaaa ttgatattaa acactatctt    2280
atcttctcct gaactgttga ttttaattaa aattaagtgc taattaccaa aaaaaaaaa    2339
```

<210> SEQ ID NO 10
<211> LENGTH: 452
<212> TYPE: PRT
<213> ORGANISM: Homo sapiens

<400> SEQUENCE: 10

```
Met Ala Gly Tyr Leu Arg Val Val Arg Ser Leu Cys Arg Ala Ser Gly
 1               5                  10                  15

Ser Arg Pro Ala Trp Ala Pro Ala Ala Leu Thr Ala Pro Thr Ser Gln
            20                  25                  30

Glu Gln Pro Arg Arg His Tyr Ala Asp Lys Arg Ile Lys Val Ala Lys
        35                  40                  45

Pro Val Val Glu Met Asp Gly Asp Glu Met Thr Arg Ile Ile Trp Gln
    50                  55                  60

Phe Ile Lys Glu Lys Leu Ile Leu Pro His Val Asp Ile Gln Leu Lys
65                  70                  75                  80

Tyr Phe Asp Leu Gly Leu Pro Asn Arg Asp Gln Thr Asp Asp Gln Val
                85                  90                  95

Thr Ile Asp Ser Ala Leu Ala Thr Gln Lys Tyr Ser Val Ala Val Lys
           100                 105                 110

Cys Ala Thr Ile Thr Pro Asp Glu Ala Arg Val Glu Glu Phe Lys Leu
       115                 120                 125

Lys Lys Met Trp Lys Ser Pro Asn Gly Thr Ile Arg Asn Ile Leu Gly
   130                 135                 140

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
                165                 170                 175

Asp Gln Tyr Lys Ala Thr Asp Phe Val Ala Asp Arg Ala Gly Thr Phe
            180                 185                 190

Lys Met Val Phe Thr Pro Lys Asp Gly Ser Gly Val Lys Glu Trp Glu
        195                 200                 205

Val Tyr Asn Phe Pro Ala Gly Gly Val Gly Met Gly Met Tyr Asn Thr
    210                 215                 220

Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
                245                 250                 255

Ala Tyr Asp Gly Arg Phe Lys Asp Ile Phe Gln Glu Ile Phe Asp Lys
            260                 265                 270
```

His Tyr Lys Thr Asp Phe Asp Lys Asn Lys Ile Trp Tyr Glu His Arg
    275                 280                 285

Leu Ile Asp Asp Met Val Ala Gln Val Leu Lys Ser Ser Gly Gly Phe
    290                 295                 300

Val Trp Ala Cys Lys Asn Tyr Asp Gly Asp Val Gln Ser Asp Ile Leu
305                 310                 315                 320

Ala Gln Gly Phe Gly Ser Leu Gly Leu Met Thr Ser Val Leu Val Cys
                325                 330                 335

Pro Asp Gly Lys Thr Ile Glu Ala Glu Ala Ala His Gly Thr Val Thr
                340                 345                 350

Arg His Tyr Arg Glu His Gln Lys Gly Arg Pro Thr Ser Thr Asn Pro
            355                 360                 365

Ile Ala Ser Ile Phe Ala Trp Thr Arg Gly Leu Glu His Arg Gly Lys
    370                 375                 380

Leu Asp Gly Asn Gln Asp Leu Ile Arg Phe Ala Gln Met Leu Glu Lys
385                 390                 395                 400

Val Cys Val Glu Thr Val Glu Ser Gly Ala Met Thr Lys Asp Leu Ala
                405                 410                 415

Gly Cys Ile His Gly Leu Ser Asn Val Lys Leu Asn Glu His Phe Leu
                420                 425                 430

Asn Thr Thr Asp Phe Leu Asp Thr Ile Lys Ser Asn Leu Asp Arg Ala
            435                 440                 445

Leu Gly Arg Gln
    450

<210> SEQ ID NO 11
<211> LENGTH: 1359
<212> TYPE: DNA
<213> ORGANISM: Homo sapiens

<400> SEQUENCE: 11
atggccggct acctgcgggt cgtgcgctcg ctctgcagag cctcaggctc gcggccggcc      60
tgggcgccgg cggccctgac agcccccacc tcgcaagagc agccgcggcg ccactatgcc     120
gacaaaagga tcaaggtggc gaagcccgtg gtggagatgg atggtgatga atgacccgt      180 attatctggc agttcatcaa ggagaagctc atcctgcccc acgtggacat ccagctaaag     240
tattttgacc tcgggctccc aaaccgtgac cagactgatg accaggtcac cattgactct     300
gcactggcca cccagaagta cagtgtggct gtcaagtgtg ccaccatcac ccctgatgag     360
gcccgtgtgg aagagttcaa gctgaagaag atgtggaaaa gtcccaatgg aactatccgg     420
aacatcctgg ggggactgt cttccgggag cccatcatct gcaaaaacat cccacgccta     480
gtccctggct ggaccaagcc catcaccatt ggcaggcacg cccatggcga ccagtacaag     540
gccacagact tgtggcaga ccgggccggc actttcaaaa tggtcttcac cccaaaagat     600
ggcagtggtg tcaaggagtg gaagtgtac aacttccccg caggcggcgt gggcatgggc     660
atgtacaaca ccgacgagtc catctcaggt tttgcgcaca gctgcttcca gtatgccatc     720
cagaagaaat ggccgctgta catgagcacc aagaacacca tactgaaagc ctacgatggg     780
cgtttcaagg acatcttcca ggagatcttt gacaagcact ataagaccga cttcgacaag     840
aataagatct ggtatgagca ccggctcatt gatgacatgg tggctcaggt cctcaagtct     900
tcgggtggct tgtgtgggc ctgcaagaac tatgacggag atgtgcagtc agacatcctg     960
gcccagggct tggctccct ggcctgatg acgtccgtcc tggtctgccc tgatgggaag    1020

| | |
|---|---|
| acgattgagg ctgaggccgc tcatgggacc gtcacccgcc actatcggga gcaccagaag | 1080 |
| ggccggccca ccagcaccaa ccccatcgcc agcatctttg cctggacacg tggcctggag | 1140 |
| caccggggga agctggatgg gaaccaagac ctcatcaggt ttgcccagat gctggagaag | 1200 |
| gtgtgcgtgg agacggtgga gagtggagcc atgaccaagg acctggcggg ctgcattcac | 1260 |
| ggcctcagca atgtgaagct gaacgagcac ttcctgaaca ccacggactt cctcgacacc | 1320 |
| atcaagagca acctggacag agccctgggc aggcagtag | 1359 |

<210> SEQ ID NO 12
<211> LENGTH: 1740
<212> TYPE: DNA
<213> ORGANISM: Homo sapiens

<400> SEQUENCE: 12

| | |
|---|---|
| ccagcgttag cccgcggcca ggcagccggg aggagcggcg cgcgctcgga cctctcccgc | 60 |
| cctgctcgtt cgctctccag cttgggatgg ccggctacct gcgggtcgtg cgctcgctct | 120 |
| gcagagcctc aggctcgcgg ccggcctggg cgccggcggc cctgacagcc ccacctcgc | 180 |
| aagagcagcc gcggcgccac tatgccgaca aaaggatcaa ggtggcgaag cccgtggtgg | 240 |
| agatggatgg tgatgagatg acccgtatta tctggcagtt catcaaggag aagctcatcc | 300 |
| tgccccacgt ggacatccag ctaaagtatt ttgacctcgg gctcccaaac cgtgaccaga | 360 |
| ctgatgacca ggtcaccatt gactctgcac tggccacccca gaagtacagt gtggctgtca | 420 |
| agtgtgccac catcacccct gatgaggccc gtgtggaaga gttcaagctg aagaagatgt | 480 |
| ggaaaagtcc caatggaact atccggaaca tcctggggggg gactgtcttc cgggagccca | 540 |
| tcatctgcaa aaacatccca cgcctagtcc ctggctggac caagcccatc accattggca | 600 |
| ggcacgccca tggcgaccag tacaaggcca cagactttgt ggcagaccgg gccggcactt | 660 |
| tcaaaatggt cttcccccca aaagatggca gtggtgtcaa ggagtgggaa gtgtacaact | 720 |
| tccccgcagg cggcgtgggc atgggcatgt acaacaccga cgagtccatc tcaggttttg | 780 |
| cgcacagctg cttccagtat gccatccaga gaaatggcc gctgtacatg agcaccaaga | 840 |
| acaccatact gaaagcctac gatgggcgtt caaggacat cttccaggag atctttgaca | 900 |
| agcactataa gaccgacttc gacaagaata agatctggta tgagcaccgg ctcattgatg | 960 |
| acatggtggc tcaggtcctc aagtcttcgg gtggctttgt gtgggcctgc aagaactatg | 1020 |
| acggagatgt gcagtcagac atcctggccc agggctttgg ctcccttggc ctgatgacgt | 1080 |
| ccgtcctggt ctgccctgat gggaagacga ttgaggctga ggccgctcat ggaccgtca | 1140 |
| cccgccacta tcgggagcac cagaagggcc ggccaccag caccaacccc atcgccagca | 1200 |
| tctttgcctg gacacgtggc ctggagcacc gggggaagct ggatgggaac caagacctca | 1260 |
| tcaggtttgc ccagatgctg gagaaggtgt gcgtggagac ggtggagagt ggagccatga | 1320 |
| ccaaggacct ggcgggctgc attcacggcc tcagcaatgt gaagctgaac gagcacttcc | 1380 |
| tgaacaccac ggacttcctc gacaccatca agagcaacct ggacagagcc ctgggcaggc | 1440 |
| agtaggggga ggcgccaccc atggctgcag tggagggggcc agggctgagc cggcgggtcc | 1500 |
| tcctgagcgc ggcagagggt gagcctcaca gcccctctct ggaggccttt ctaggggatg | 1560 |
| tttttttata agccagatgt ttttaaaagc atatgtgtgt ttcccctcat ggtgacgtga | 1620 |
| ggcaggagca gtgcgtttta cctcagccag tcagtatgtt ttgcatactg taatttatat | 1680 |
| tgcccttgga acacatggtg ccatatttag ctactaaaaa gctcttcaca aaaaaaaaaa | 1740 |

```
<210> SEQ ID NO 13
<211> LENGTH: 1245
<212> TYPE: DNA
<213> ORGANISM: Homo sapiens

<400> SEQUENCE: 13
atgtccaaaa aaatcagtgg cggttctgtg gtagagatgc aaggagatga atgacacga       60 atcatttggg aattgattaa agagaaactc attttttccct acgtggaatt ggatctacat    120
agctatgatt taggcataga gaatcgtgat gccaccaacg accaagtcac caaggatgct    180
gcagaagcta taaagaagca taatgttggc gtcaaatgtg ccactatcac tcctgatgag    240
aagagggttg aggagttcaa gttgaaacaa atgtggaaat caccaaatgg caccatacga    300
aatattctgg gtggcacggt cttcagagaa gccattatct gcaaaaatat cccccggctt    360
gtgagtggat gggtaaaacc tatcatcata ggtcgtcatg cttatgggga tcaatacaga    420
gcaactgatt ttgttgttcc tgggcctgga aaagtagaga taacctacac accaagtgac    480
ggaacccaaa aggtgacata cctggtacat aactttgaag aaggtggtgg tgttgccatg    540
gggatgtata atcaagataa gtcaattgaa gattttgcac acagttcctt ccaaatggct    600
ctgtctaagg gttggccttt gtatctgagc accaaaaaca ctattctgaa gaaatatgat    660
gggcgtttta aagacatctt tcaggagata tatgacaagc agtacaagtc ccagtttgaa    720
gctcaaaaga tctggtatga gcataggctc atcgacgaca tggtggccca agctatgaaa    780
tcagagggag gcttcatctg ggcctgtaaa aactatgatg gtgacgtgca gtcggactct    840
gtggcccaag ggtatggctc tctcggcatg atgaccagcg tgctggtttg tccagatggc    900
aagacagtag aagcagaggc tgcccacggg actgtaaccc gtcactaccg catgtaccag    960
aaaggacagg agacgtccac caatcccatt gcttccattt ttgcctggac cagagggtta   1020
gcccacagag caaagcttga taacaataaa gagcttgcct tctttgcaaa tgctttggaa   1080
gaagtctcta ttgagacaat tgaggctggc ttcatgacca aggacttggc tgcttgcatt   1140
aaaggtttac ccaatgtgca acgttctgac tacttgaata catttgagtt catggataaa   1200
cttggagaaa acttgaagat caaactagct caggccaaac tttaa                    1245

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gguuucugca gagucuacu                                                    19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
aguagacucu gcagaaacc                                                    19

<210> SEQ ID NO 16
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 16
cucuucgcca gcauaucau                                                      19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
augauaugcu ggcgaagag                                                      19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ggcaggcgau aaacuacau                                                      19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
auguaguuua ucgccugcc                                                      19

<210> SEQ ID NO 20
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
gcgauaaacu acauucagu                                                      19

<210> SEQ ID NO 21
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
acugaaugua guuuaucgc                                                      19

<210> SEQ ID NO 22
<211> LENGTH: 19
<212> TYPE: RNA
<213> ORGANISM: Artificial Sequence
```

<220> FEATURE:
<223> OTHER INFORMATION: Description of Artificial Sequence: Synthetic
     oligonucleotide

<400> SEQUENCE: 22
gaaaucuauu cacugucaa                                                19

<210> SEQ ID NO 23
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 23
uugacaguga auagauuuc                                                19

<210> SEQ ID NO 24
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 24
guucuguggu agagaugca                                                19

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 25
ugcaucucua ccacagaac                                                19

<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 26
gcaaggagau gaaaugaca                                                19

<210> SEQ ID NO 27
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide

<400> SEQUENCE: 27
ugucauuuca ucuccuugc                                                19

<210> SEQ ID NO 28
<211> LENGTH: 19
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 28
ggagaugaaa ugacacgaa                                                       19

<210> SEQ ID NO 29
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
uucgugucau uucaucucc                                                       19

<210> SEQ ID NO 30
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
gagaugaaau gacacgaau                                                       19

<210> SEQ ID NO 31
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
auucguguca uuucaucuc                                                       19

<210> SEQ ID NO 32
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
gaugaaauga cacgaauca                                                       19

<210> SEQ ID NO 33
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ugauucgugu cauuucauc                                                       19

<210> SEQ ID NO 34
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 34
cgaaucauuu gggaauuga                                              19

<210> SEQ ID NO 35
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ucaauuccca aaugauucg                                              19

<210> SEQ ID NO 36
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
gggaauugau uaaagagaa                                              19

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
uucucuuuaa ucaauuccc                                              19

<210> SEQ ID NO 38
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ccuacgugga auuggaucu                                              19

<210> SEQ ID NO 39
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
agauccaauu ccacguagg                                              19

<210> SEQ ID NO 40
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cuacguggaa uuggaucua                                                     19

<210> SEQ ID NO 41
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
uagauccaau uccacguag                                                     19

<210> SEQ ID NO 42
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ggaucuacau agcuaugau                                                     19

<210> SEQ ID NO 43
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
aucauagcua uguagaucc                                                     19

<210> SEQ ID NO 44
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
gcuaugauuu aggcauaga                                                     19

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
ucuaugccua aaucauagc                                                     19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 46
ggaugcugca gaagcuaua                                                      19

<210> SEQ ID NO 47
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
uauagcuucu gcagcaucc                                                      19

<210> SEQ ID NO 48
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
cagaagcuau aaagaagca                                                      19

<210> SEQ ID NO 49
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
ugcuucuuua uagcuucug                                                      19

<210> SEQ ID NO 50
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
gaagcuauaa agaagcaua                                                      19

<210> SEQ ID NO 51
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
uaugcuucuu uauagcuuc                                                      19

<210> SEQ ID NO 52
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
```
gcauaauguu ggcgucaaa                                                    19

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uuugacgcca acauuaugc                                                    19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
cugaugagaa gagguuga                                                     19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ucaacccucu ucucaucag                                                    19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
guugaggagu ucaaguuga                                                    19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
ucaacuugaa cuccucaac                                                    19

<210> SEQ ID NO 58
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58

```
gaguucaagu ugaaacaaa                                              19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uuuguuucaa cuugaacuc                                              19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
guugaaacaa auuggaaa                                               19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uuuccacauu uguuucaac                                              19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
caaaugugga aaucaccaa                                              19

<210> SEQ ID NO 63
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
uuggugauuu ccacauuug                                              19

<210> SEQ ID NO 64
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
ccaaauggca ccauacgaa                                              19
```

```
<210> SEQ ID NO 65
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
uucguauggu gccauuugg                                                  19

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
cauacgaaau auucggggu                                                  19

<210> SEQ ID NO 67
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
acccagaaua uuucguaug                                                  19

<210> SEQ ID NO 68
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
gagaagccau uaucugcaa                                                  19

<210> SEQ ID NO 69
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uugcagauaa uggcuucuc                                                  19

<210> SEQ ID NO 70
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
cuaucaucau aggucguca                                                  19
```

```
<210> SEQ ID NO 71
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
ugacgaccua ugaugauag                                                      19

<210> SEQ ID NO 72
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
caucauaggu cgucaugcu                                                      19

<210> SEQ ID NO 73
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
agcaugacga ccuaugaug                                                      19

<210> SEQ ID NO 74
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
cauaggucgu caugcuuau                                                      19

<210> SEQ ID NO 75
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
auaagcauga cgaccuaug                                                      19

<210> SEQ ID NO 76
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
gagauaaccu acacaccaa                                                      19
```

```
<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
uuggugugua gguaucuc                                              19

<210> SEQ ID NO 78
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
ccugguacau aacuuugaa                                             19

<210> SEQ ID NO 79
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
uucaaaguua uguaccagg                                             19

<210> SEQ ID NO 80
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
cuuugaagaa gguggggu                                              19

<210> SEQ ID NO 81
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
accaccaccu ucuucaaag                                             19

<210> SEQ ID NO 82
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
gggauguaua aucaagaua                                             19

<210> SEQ ID NO 83
```

<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
uaucuugauu auacauccc                                                19

<210> SEQ ID NO 84
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
gcacacaguu ccuuccaaa                                                19

<210> SEQ ID NO 85
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
uuuggaagga acugugugc                                                19

<210> SEQ ID NO 86
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86 guccuucca aauggcucu                                                 19

<210> SEQ ID NO 87
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
agagccauuu ggaaggaac                                                19

<210> SEQ ID NO 88
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
gguuggccuu uguaucuga                                                19

<210> SEQ ID NO 89
<211> LENGTH: 19

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ucagauacaa aggccaacc                                              19

<210> SEQ ID NO 90
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
cuuuguaucu gagcaccaa                                              19

<210> SEQ ID NO 91
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uuggugcuca gauacaaag                                              19

<210> SEQ ID NO 92
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
gaagaaauau gaugggcgu                                              19

<210> SEQ ID NO 93
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
acgcccauca uauuucuuc                                              19

<210> SEQ ID NO 94
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
gucccaguuu gaagcucaa                                              19

<210> SEQ ID NO 95
<211> LENGTH: 19
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 95
uugagcuuca aacugggac                                                    19

<210> SEQ ID NO 96
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
gguaugagca uaggcucau                                                    19

<210> SEQ ID NO 97
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
augagccuau gcucauacc                                                    19

<210> SEQ ID NO 98
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ggcccaagcu augaaauca                                                    19

<210> SEQ ID NO 99
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
ugauuucaua gcuugggcc                                                    19

<210> SEQ ID NO 100
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
cccaagcuau gaaaucaga                                                    19

<210> SEQ ID NO 101
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 101
ucugauuuca uagcuuggg                                                    19

<210> SEQ ID NO 102
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
cagauggcaa gacaguaga                                                    19

<210> SEQ ID NO 103
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
ucuacugucu ugccaucug                                                    19

<210> SEQ ID NO 104
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
gcaagacagu agaagcaga                                                    19

<210> SEQ ID NO 105
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
ucugcuucua cugucuugc                                                    19

<210> SEQ ID NO 106
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gcauguacca gaaaggaca                                                    19

<210> SEQ ID NO 107
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 107
uguccuuucu gguacaugc                                                  19

<210> SEQ ID NO 108
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
ccaaucccau ugcuuccau                                                  19

<210> SEQ ID NO 109
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
auggaagcaa ugggauugg                                                  19

<210> SEQ ID NO 110
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
ccacagagca aagcuugau                                                  19

<210> SEQ ID NO 111
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
aucaagcuuu gcucugugg                                                  19

<210> SEQ ID NO 112
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
cacagagcaa agcuugaua                                                  19

<210> SEQ ID NO 113
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
                              oligonucleotide

<400> SEQUENCE: 113
uaucaagcuu ugcucugug                                                    19

<210> SEQ ID NO 114
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gagcaaagcu ugauaacaa                                                    19

<210> SEQ ID NO 115
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
uuguuaucaa gcuuugcuc                                                    19

<210> SEQ ID NO 116
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
gagcuugccu ucuuugcaa                                                    19

<210> SEQ ID NO 117
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
uugcaaagaa ggcaagcuc                                                    19

<210> SEQ ID NO 118
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
cuuugcaaau gcuuuggaa                                                    19

<210> SEQ ID NO 119
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 119
uuccaaagca uuugcaaag                                                    19

<210> SEQ ID NO 120
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
caaaugcuuu ggaagaagu                                                    19

<210> SEQ ID NO 121
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
acuucuucca aagcauuug                                                    19

<210> SEQ ID NO 122
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
cuuuggaaga agucucuau                                                    19

<210> SEQ ID NO 123
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
auagagacuu cuuccaaag                                                    19

<210> SEQ ID NO 124
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gaagaagucu cuauugaga                                                    19

<210> SEQ ID NO 125
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 125
ucucaauaga gacuucuuc                                                   19

<210> SEQ ID NO 126
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gaagucucua uugagacaa                                                   19

<210> SEQ ID NO 127
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
uugucucaau agagacuuc                                                   19

<210> SEQ ID NO 128
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ggacuuggcu gcuugcauu                                                   19

<210> SEQ ID NO 129
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
aaugcaagca gccaagucc                                                   19

<210> SEQ ID NO 130
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
cuuggcugcu ugcauuaaa                                                   19

<210> SEQ ID NO 131
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
```
uuuaaugcaa gcagccaag						19

<210> SEQ ID NO 132
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
cauuaaaggu uuacccaau						19

<210> SEQ ID NO 133
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
auuggguaaa ccuuuaaug						19

<210> SEQ ID NO 134
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ccaaugugca acguucuga						19

<210> SEQ ID NO 135
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
ucagaacguu gcacauugg						19

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
gugcaacguu cugacuacu						19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137

```
aguagucaga acguugcac                                                    19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
cguucugacu acuugaaua                                                    19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
uauucaagua gucagaacg                                                    19

<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
cauuugaguu cauggauaa                                                    19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
uuauccauga acucaaaug                                                    19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
guucauggau aaacuugga                                                    19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
uccaaguuua uccaugaac                                                    19
```

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
cauggauaaa cuuggagaa                                               19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uucuccaagu uuauccaug                                               19

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
caaacuagcu caggccaaa                                               19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
uuuggccuga gcuaguuug                                               19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
ccugagcuaa gaaggauaa                                               19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
uuauccuucu uagcucagg                                               19

-continued

```
<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 150
cuaagaagga uaauugucu                                                    19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
agacaauuau ccuucuuag                                                    19

<210> SEQ ID NO 152
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
cuguguuaca cucaaggau                                                    19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
auccuugagu guaacacag                                                    19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
guguuacacu caaggauaa                                                    19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
uuauccuuga guguaacac                                                    19
```

```
<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
cacucaagga uaaaggcaa                                                      19

<210> SEQ ID NO 157
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
uugccuuuau ccuugagug                                                      19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
guaauuuguu uagaagcca                                                      19

<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
uggcuucuaa acaaauuac                                                      19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
guuauugcca ccuuuguga                                                      19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ucacaaaggu ggcaauaac                                                      19

<210> SEQ ID NO 162
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 162
cagccuagga auucgguua                                                19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
uaaccgaauu ccuaggcug                                                19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
gccuaggaau ucgguuagu                                                19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
acuaaccgaa uuccuaggc                                                19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ccuaggaauu cgguuagua                                                19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
uacuaaccga auuccuagg                                                19

<210> SEQ ID NO 168
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
ggaauucggu uaguacuca                                               19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
ugaguacuaa ccgaauucc                                               19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
gaauucgguu aguacucau                                               19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
augaguacua accgaauuc                                               19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
gguuaguacu cauuuguau                                               19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
auacaaauga guacuaacc                                               19

<210> SEQ ID NO 174
<211> LENGTH: 19
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 174
guacucauuu guauucacu                                                19

<210> SEQ ID NO 175
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 175
agugaauaca aaugaguac                                                19

<210> SEQ ID NO 176
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 176
gguaaaugau agccacagu                                                19

<210> SEQ ID NO 177
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 177
acuguggcua ucauuuacc                                                19

<210> SEQ ID NO 178
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 178
guaaaugaua gccacagua                                                19

<210> SEQ ID NO 179
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 179
uacuguggcu aucauuuac                                                19

<210> SEQ ID NO 180
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 180
ccacaguauu gcucccuaa                                                    19

<210> SEQ ID NO 181
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
uuagggagca auacugugg                                                    19

<210> SEQ ID NO 182
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
gggaaguucu ggugucaua                                                    19

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
uaugacacca gaacuuccc                                                    19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
guucuggugu cauagauau                                                    19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
auaucuauga caccagaac                                                    19

<210> SEQ ID NO 186
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 186
gcugugcauu aaacuugca                                                       19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
ugcaaguuua augcacagc                                                       19

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
gugcauuaaa cuugcacau                                                       19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
augugcaagu uuaaugcac                                                       19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
gcauuaaacu ugcacauga                                                       19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
ucaugugcaa guuuaaugc                                                       19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic

```
                        oligonucleotide

<400> SEQUENCE: 192
caugacugga acgaaguau                                                  19

<210> SEQ ID NO 193
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
auacuucguu ccagucaug                                                  19

<210> SEQ ID NO 194
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
ggaacgaagu augagugca                                                  19

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
ugcacucaua cuucguucc                                                  19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
gaacgaagua ugagugcaa                                                  19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
uugcacucau acuucguuc                                                  19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 198
gagugcaacu caaaugugu                                                19

<210> SEQ ID NO 199
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
acacauuuga guugcacuc                                                19

<210> SEQ ID NO 200
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
gcaacucaaa uguuugaa                                                 19

<210> SEQ ID NO 201
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
uucaacacau uugaguugc                                                19

<210> SEQ ID NO 202
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
caaauguguu gaagauacu                                                19

<210> SEQ ID NO 203
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
aguaucuuca acacauuug                                                19

<210> SEQ ID NO 204
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 204
guguugaaga uacugcagu                                                19

<210> SEQ ID NO 205
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
acugcaguau cuucaacac                                                19

<210> SEQ ID NO 206
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
guugaagaua cugcaguca                                                19

<210> SEQ ID NO 207
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
ugacugcagu aucuucaac                                                19

<210> SEQ ID NO 208
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
ccuugcugaa uguuuccaa                                                19

<210> SEQ ID NO 209
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
uuggaaacau ucagcaagg                                                19

<210> SEQ ID NO 210
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 210
```
cuugcugaau guuuccaau                                          19

<210> SEQ ID NO 211
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
auuggaaaca uucagcaag                                          19

<210> SEQ ID NO 212
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
gcugaauguu uccaauaga                                          19

<210> SEQ ID NO 213
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
ucuauuggaa acauucagc                                          19

<210> SEQ ID NO 214
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
ccaauagacu aaauacugu                                          19

<210> SEQ ID NO 215
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
acaguauuua gucuauugg                                          19

<210> SEQ ID NO 216
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216

```
gaguuuggaa uccggaaua                                                    19

<210> SEQ ID NO 217
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
uauuccggau uccaaacuc                                                    19

<210> SEQ ID NO 218
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
ggaauccgga auaaauacu                                                    19

<210> SEQ ID NO 219
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
aguauuuauu ccggauucc                                                    19

<210> SEQ ID NO 220
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
gaauccggaa uaaauacua                                                    19

<210> SEQ ID NO 221
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
uaguauuuau uccggauuc                                                    19

<210> SEQ ID NO 222
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
ggaauaaaua cuaccugga                                                    19
```

```
<210> SEQ ID NO 223
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
uccagguagu auuuauucc                                                 19

<210> SEQ ID NO 224
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
ggccuggccu gaauauuau                                                 19

<210> SEQ ID NO 225
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
auaauauuca ggccaggcc                                                 19

<210> SEQ ID NO 226
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
gccugaauau uauacuacu                                                 19

<210> SEQ ID NO 227
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
aguaguauaa uauucaggc                                                 19

<210> SEQ ID NO 228
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
cuggccugaa uauuauacu                                                 19
```

<210> SEQ ID NO 229
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
aguauaauau ucaggccag                                                19

<210> SEQ ID NO 230
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
cauauuucau ccaagugca                                                19

<210> SEQ ID NO 231
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
ugcacuugga ugaaauaug                                                19

<210> SEQ ID NO 232
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
gugcaauaau guaagcuga                                                19

<210> SEQ ID NO 233
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
ucagcuuaca uuauugcac                                                19

<210> SEQ ID NO 234
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
gcaauaaugu aagcugaau                                                19

```
<210> SEQ ID NO 235
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
auucagcuua cauuauugc                                                      19

<210> SEQ ID NO 236
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
cacuaucuua ucuucuccu                                                      19

<210> SEQ ID NO 237
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
aggagaagau aagauagug                                                      19

<210> SEQ ID NO 238
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
cuucuccuga acuguugau                                                      19

<210> SEQ ID NO 239
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
aucaacaguu caggagaag                                                      19

<210> SEQ ID NO 240
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
aaccuaucau cauaggucg                                                      19

<210> SEQ ID NO 241
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
cgaccuauga ugauagguu                                                    19

<210> SEQ ID NO 242
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
accuaucauc auaggucgu                                                    19

<210> SEQ ID NO 243
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
acgaccuaug augauaggu                                                    19

<210> SEQ ID NO 244
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
ccuaucauca uaggucguc                                                    19

<210> SEQ ID NO 245
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
gacgaccuau gaugauagg                                                    19

<210> SEQ ID NO 246
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
cuaucaucau aggucguca                                                    19

<210> SEQ ID NO 247
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
ugacgaccua ugaugauag                                                    19

<210> SEQ ID NO 248
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
uaucaucaua ggucgucau                                                    19

<210> SEQ ID NO 249
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
augacgaccu augaugaua                                                    19

<210> SEQ ID NO 250
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
aucaucauag gucgucaug                                                    19

<210> SEQ ID NO 251
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
caugacgacc uaugaugau                                                    19

<210> SEQ ID NO 252
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
ucaucauagg ucgucaugc                                                    19

<210> SEQ ID NO 253
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 253
gcaugacgac cuaugauga                                                  19

<210> SEQ ID NO 254
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
caucauaggu cgucaugcu                                                  19

<210> SEQ ID NO 255
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
agcaugacga ccuaugaug                                                  19

<210> SEQ ID NO 256
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256 aucuagguc gucaugcuu                                                   19

<210> SEQ ID NO 257
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
aagcaugacg accuaugau                                                  19

<210> SEQ ID NO 258
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
ucauaggucg ucaugcuua                                                  19

<210> SEQ ID NO 259
<211> LENGTH: 19
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 259
uaagcaugac gaccuauga                                                  19

<210> SEQ ID NO 260
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
cauaggucgu caugcuuau                                                  19

<210> SEQ ID NO 261
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
auaagcauga cgaccuaug                                                  19

<210> SEQ ID NO 262
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
auaggucguc augcuuaug                                                  19

<210> SEQ ID NO 263
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 263
cauaagcaug acgaccuau                                                  19

<210> SEQ ID NO 264
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
uaggucguca ugcuuaugg                                                  19

<210> SEQ ID NO 265
<211> LENGTH: 19
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 265
ccauaagcau gacgaccua                                                  19

<210> SEQ ID NO 266
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
aggucgucau gcuuauggg                                                  19

<210> SEQ ID NO 267
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
cccauaagca ugacgaccu                                                  19

<210> SEQ ID NO 268
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 268
ggucgucaug cuuaugggg                                                  19

<210> SEQ ID NO 269
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
ccccauaagc augacgacc                                                  19

<210> SEQ ID NO 270
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
gucgucaugc uuauggga                                                   19

<210> SEQ ID NO 271
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 271
ucccauaagc augacgacc                                                    19

<210> SEQ ID NO 272
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 272
ucgucaugcu uaugggau                                                     19

<210> SEQ ID NO 273
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
aucccauaag caugacgac                                                    19

<210> SEQ ID NO 274
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 274
aaccuaucau cauagguca                                                    19

<210> SEQ ID NO 275
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275 ugaccauga ugauagguu                                                     19

<210> SEQ ID NO 276
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
accuaucauc auaggucau                                                    19

<210> SEQ ID NO 277
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 277
augaccuaug augauaggu                                                19

<210> SEQ ID NO 278
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
ccuaucauca uaggucauc                                                19

<210> SEQ ID NO 279
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
gaugaccuau gaugauagg                                                19

<210> SEQ ID NO 280
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
cuaucaucau aggucauca                                                19

<210> SEQ ID NO 281
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ugaugaccua ugaugauag                                                19

<210> SEQ ID NO 282
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
uaucaucaua ggucaucau                                                19

<210> SEQ ID NO 283
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
augaugaccu augaugaua                                              19

<210> SEQ ID NO 284
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
aucaucauag gucaucaug                                              19

<210> SEQ ID NO 285
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
caugaugacc uaugaugau                                              19

<210> SEQ ID NO 286
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
ucaucauagg ucaucaugc                                              19

<210> SEQ ID NO 287
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
gcaugaugac cuaugauga                                              19

<210> SEQ ID NO 288
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
caucauaggu caucaugcu                                              19

<210> SEQ ID NO 289
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
agcaugauga ccuaugaug                                              19

<210> SEQ ID NO 290
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
aucauagguc aucaugcuu                                              19

<210> SEQ ID NO 291
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
aagcaugaug accuaugau                                              19

<210> SEQ ID NO 292
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292 ucaugguca ucaugcuua                                               19

<210> SEQ ID NO 293
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
uaagcaugau gaccuauga                                              19

<210> SEQ ID NO 294
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
cauaggucau caugcuuau                                              19

<210> SEQ ID NO 295
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295

-continued auaagcauga ugaccuaug                                          19

<210> SEQ ID NO 296
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296 auaggcauc augcuuaug                                           19

<210> SEQ ID NO 297
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
cauaagcaug augaccuau                                          19

<210> SEQ ID NO 298
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
uaggucauca ugcuuaugg                                          19

<210> SEQ ID NO 299
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
ccauaagcau gaugaccua                                          19

<210> SEQ ID NO 300
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
aggucaucau gcuuauggg                                          19

<210> SEQ ID NO 301
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
cccauaagca ugaugaccu                                          19

<210> SEQ ID NO 302
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
ggucaucaug cuuaugggg                                                    19

<210> SEQ ID NO 303
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ccccauaagc augaugacc                                                    19

<210> SEQ ID NO 304
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
gucaucaugc uuauggga                                                     19

<210> SEQ ID NO 305
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
uccccauaag caugaugac                                                    19

<210> SEQ ID NO 306
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
ucaucaugcu uauggggau                                                    19

<210> SEQ ID NO 307
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
auccccauaa gcaugauga                                                    19

```
<210> SEQ ID NO 308
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
aaccuaucau cauaggusg                                                  19

<210> SEQ ID NO 309
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
cuaccuauga ugauagguu                                                  19

<210> SEQ ID NO 310
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
accuaucauc auagguagu                                                  19

<210> SEQ ID NO 311
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
acuaccuaug augauaggu                                                  19

<210> SEQ ID NO 312
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
ccuaucauca uagguaguc                                                  19

<210> SEQ ID NO 313
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
gacuaccuau gaugauagg                                                  19
```

```
<210> SEQ ID NO 314
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
cuaucaucau agguaguca                                                 19

<210> SEQ ID NO 315
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
ugacuaccua ugaugauag                                                 19

<210> SEQ ID NO 316
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
uaucaucaua gguagucau                                                 19

<210> SEQ ID NO 317
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
augacuaccu augaugaua                                                 19

<210> SEQ ID NO 318
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
aucaucauag guagucaug                                                 19

<210> SEQ ID NO 319
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
caugacuacc uaugaugau                                                 19

<210> SEQ ID NO 320
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
ucaucauagg uagucaugc                                                19

<210> SEQ ID NO 321
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
gcaugacuac cuaugauga                                                19

<210> SEQ ID NO 322
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
caucauaggu agucaugcu                                                19

<210> SEQ ID NO 323
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 323
agcaugacua ccuaugaug                                                19

<210> SEQ ID NO 324
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
aucauaggua gucaugcuu                                                19

<210> SEQ ID NO 325
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
aagcaugacu accuaugau                                                19

<210> SEQ ID NO 326
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
ucauagguag ucaugcuua                                                    19

<210> SEQ ID NO 327
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
uaagcaugac uaccauga                                                     19

<210> SEQ ID NO 328
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
cauagguagu caugcuuau                                                    19

<210> SEQ ID NO 329
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 329
auaagcauga cuaccuaug                                                    19

<210> SEQ ID NO 330
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
auagguaguc augcuuaug                                                    19

<210> SEQ ID NO 331
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
cauaagcaug acuaccuau                                                    19

<210> SEQ ID NO 332
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 332
uagguaguca ugcuuaugg                                                  19

<210> SEQ ID NO 333
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
ccauaagcau gacuaccua                                                  19

<210> SEQ ID NO 334
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
agguagucau gcuuauggg                                                  19

<210> SEQ ID NO 335
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 335
cccauaagca ugacuaccu                                                  19

<210> SEQ ID NO 336
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
gguagucaug cuuaugggg                                                  19

<210> SEQ ID NO 337
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
ccccauaagc augacuacc                                                  19

<210> SEQ ID NO 338
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 338
guagucaugc uuaugggga                                                      19

<210> SEQ ID NO 339
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
uccccauaag caugacuac                                                      19

<210> SEQ ID NO 340
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
uagucaugcu uaugggau                                                       19

<210> SEQ ID NO 341
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
auccccauaa gcaugacua                                                      19

<210> SEQ ID NO 342
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
aaccuaucau cauagguug                                                      19

<210> SEQ ID NO 343
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
caaccuauga ugauagguu                                                      19

<210> SEQ ID NO 344
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 344
accuaucauc auagguugu                                                    19

<210> SEQ ID NO 345
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
acaaccuaug augauaggu                                                    19

<210> SEQ ID NO 346
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
ccuaucauca uagguuguc                                                    19

<210> SEQ ID NO 347
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
gacaaccuau gaugauagg                                                    19

<210> SEQ ID NO 348
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
cuaucaucau agguuguca                                                    19

<210> SEQ ID NO 349
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
ugacaaccua ugaugauag                                                    19

<210> SEQ ID NO 350
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 350
uaucaucaua gguugucau                                                    19

<210> SEQ ID NO 351
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
augacaaccu augaugaua                                                    19

<210> SEQ ID NO 352
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
aucaucauag guugucaug                                                    19

<210> SEQ ID NO 353
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
caugacaacc uaugaugau                                                    19

<210> SEQ ID NO 354
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
ucaucauagg uugucaugc                                                    19

<210> SEQ ID NO 355
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
gcaugacaac cuaugauga                                                    19

<210> SEQ ID NO 356
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 356
caucauaggu ugucaugcu                                                    19

<210> SEQ ID NO 357
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
agcaugacaa ccuaugaug                                                    19

<210> SEQ ID NO 358
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
aucauagguu gucaugcuu                                                    19

<210> SEQ ID NO 359
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
aagcaugaca accuaugau                                                    19

<210> SEQ ID NO 360
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
ucauagguug ucaugcuua                                                    19

<210> SEQ ID NO 361
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
uaagcaugac aaccuauga                                                    19

<210> SEQ ID NO 362
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 362
cauagguugu caugcuuau                                                    19

<210> SEQ ID NO 363
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
auaagcauga caaccuaug                                                    19

<210> SEQ ID NO 364
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
auagguuguc augcuuaug                                                    19

<210> SEQ ID NO 365
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
cauaagcaug acaaccuau                                                    19

<210> SEQ ID NO 366
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
uagguuguca ugcuuaugg                                                    19

<210> SEQ ID NO 367
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
ccauaagcau gacaaccua                                                    19

<210> SEQ ID NO 368
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
```
agguugucau gcuuauggg					19

<210> SEQ ID NO 369
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
cccauaagca ugacaaccu					19

<210> SEQ ID NO 370
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
gguugucaug cuuaugggg					19

<210> SEQ ID NO 371
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
ccccauaagc augacaacc					19

<210> SEQ ID NO 372
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
guugucaugc uuaugggga					19

<210> SEQ ID NO 373
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
uccccauaag caugacaac					19

<210> SEQ ID NO 374
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
uugucaugcu uaugggau　　　　　　　　　　　　　　　　　　　　　　　19

<210> SEQ ID NO 375
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
auccccauaa gcaugacaa　　　　　　　　　　　　　　　　　　　　　　　19

<210> SEQ ID NO 376
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
aaccuaucau cauaggugg　　　　　　　　　　　　　　　　　　　　　　　19

<210> SEQ ID NO 377
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
ccaccuauga ugauagguu　　　　　　　　　　　　　　　　　　　　　　　19

<210> SEQ ID NO 378
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378 accaucauc auagguggu　　　　　　　　　　　　　　　　　　　　　　　19

<210> SEQ ID NO 379
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
accaccuaug augauaggu　　　　　　　　　　　　　　　　　　　　　　　19

<210> SEQ ID NO 380
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
ccuaucauca uaggugguc　　　　　　　　　　　　　　　　　　　　　　　19

<210> SEQ ID NO 381
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
gaccaccuau gaugauagg                                                19

<210> SEQ ID NO 382
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
cuaucaucau aggugguca                                                19

<210> SEQ ID NO 383
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
ugaccaccua ugaugauag                                                19

<210> SEQ ID NO 384
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
uaucaucaua gguggucau                                                19

<210> SEQ ID NO 385
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
augaccaccu augaugaua                                                19

<210> SEQ ID NO 386
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
aucaucauag guggucaug                                                19

<210> SEQ ID NO 387
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
caugaccacc uaugaugau                                                  19

<210> SEQ ID NO 388
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
ucaucauagg uggucaugc                                                  19

<210> SEQ ID NO 389
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
gcaugaccac cuaugauga                                                  19

<210> SEQ ID NO 390
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
caucauaggu ggucaugcu                                                  19

<210> SEQ ID NO 391
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
agcaugacca ccuaugaug                                                  19

<210> SEQ ID NO 392
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
aucauaggug gucaugcuu                                                  19

```
<210> SEQ ID NO 393
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
aagcaugacc accaugau                                                   19

<210> SEQ ID NO 394
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
ucauaggugg ucaugcuua                                                  19

<210> SEQ ID NO 395
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
uaagcaugac caccauga                                                   19

<210> SEQ ID NO 396
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
cauagguggu caugcuuau                                                  19

<210> SEQ ID NO 397
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
auaagcauga ccaccaug                                                   19

<210> SEQ ID NO 398
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
auaggugguc augcuuaug                                                  19

<210> SEQ ID NO 399
```

-continued

<210> SEQ ID NO 399
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
cauaagcaug accaccuau                                                  19

<210> SEQ ID NO 400
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
uaggugguca ugcuuaugg                                                  19

<210> SEQ ID NO 401
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 401
ccauaagcau gaccaccua                                                  19

<210> SEQ ID NO 402
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 402
agguugucau gcuuauggg                                                  19

<210> SEQ ID NO 403
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
cccauaagca ugaccaccu                                                  19

<210> SEQ ID NO 404
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 404
gguugucaug cuuauggg                                                   19

<210> SEQ ID NO 405
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 405
ccccauaagc augaccacc                                                  19

<210> SEQ ID NO 406
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
guugucaugc uuaugggga                                                  19

<210> SEQ ID NO 407
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
uccccauaag caugaccac                                                  19

<210> SEQ ID NO 408
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
uugucaugcu uauggggau                                                  19

<210> SEQ ID NO 409
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
auccccauaa gcaugacca                                                  19

<210> SEQ ID NO 410
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
aaccuaucau cauaggucg                                                  19

<210> SEQ ID NO 411
<211> LENGTH: 19
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 411 cgaccauga ugauagguu                                              19

<210> SEQ ID NO 412
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
accuaucauc auaggucgu                                             19

<210> SEQ ID NO 413
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 413
acgaccuaug augauaggu                                             19

<210> SEQ ID NO 414
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
ccuaucauca uaggucguc                                             19

<210> SEQ ID NO 415
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 415
gacgaccuau gaugauagg                                             19

<210> SEQ ID NO 416
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
cuaucaucau aggucguca                                             19

<210> SEQ ID NO 417
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 417
ugacgaccua ugaugauag                                                    19

<210> SEQ ID NO 418
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
uaucaucaua ggucgucau                                                    19

<210> SEQ ID NO 419
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
augacgaccu augaugaua                                                    19

<210> SEQ ID NO 420
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
aucaucauag gucgucaug                                                    19

<210> SEQ ID NO 421
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 421
caugacgacc uaugaugau                                                    19

<210> SEQ ID NO 422
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
ucaucauagg ucgucaugc                                                    19

<210> SEQ ID NO 423
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 423
gcaugacgac cuaugauga                                                19

<210> SEQ ID NO 424
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
caucauaggu cgucaugcu                                                19

<210> SEQ ID NO 425
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
agcaugacga ccuaugaug                                                19

<210> SEQ ID NO 426
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
aucauagguc gucaugcuu                                                19

<210> SEQ ID NO 427
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 427
aagcaugacg accuaugau                                                19

<210> SEQ ID NO 428
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
ucauaggucg ucaugcuua                                                19

<210> SEQ ID NO 429
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 429
uaagcaugac gaccuauga                                              19

<210> SEQ ID NO 430
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
cauaggucgu caugcuuau                                              19

<210> SEQ ID NO 431
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
auaagcauga cgaccuaug                                              19

<210> SEQ ID NO 432
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
auaggucguc augcuuaug                                              19

<210> SEQ ID NO 433
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
cauaagcaug acgaccuau                                              19

<210> SEQ ID NO 434
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
uaggucguca ugcuuaugg                                              19

<210> SEQ ID NO 435
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 435
ccauaagcau gacgaccua                                              19

<210> SEQ ID NO 436
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
aggucgucau gcuuauggg                                              19

<210> SEQ ID NO 437
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
cccauaagca ugacgaccu                                              19

<210> SEQ ID NO 438
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 438
ggucgucaug cuuaugggg                                              19

<210> SEQ ID NO 439
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 439
ccccauaagc augacgacc                                              19

<210> SEQ ID NO 440
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 440
gucgucaugc uuaugggga                                              19

<210> SEQ ID NO 441
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 441
uccccauaag caugacgac                                                19

<210> SEQ ID NO 442
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
ucgucaugcu uauggggau                                                19

<210> SEQ ID NO 443
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
auccccauaa gcaugacga                                                19

<210> SEQ ID NO 444
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
aaccuaucau cauaggucu                                                19

<210> SEQ ID NO 445
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
agaccuauga ugauagguu                                                19

<210> SEQ ID NO 446
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
accuaucauc auaggucuu                                                19

<210> SEQ ID NO 447
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 447
```
aagaccuaug augauaggu                                                        19

<210> SEQ ID NO 448
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
ccuaucauca uaggucuuc                                                        19

<210> SEQ ID NO 449
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
gaagaccuau gaugauagg                                                        19

<210> SEQ ID NO 450
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 450
cuaucaucau aggucuuca                                                        19

<210> SEQ ID NO 451
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
ugaagaccua ugaugauag                                                        19

<210> SEQ ID NO 452
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
uaucaucaua ggucuucau                                                        19

<210> SEQ ID NO 453
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 453
augaagaccu augaugaua                                              19

<210> SEQ ID NO 454
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 454
aucaucauag gucuucaug                                               19

<210> SEQ ID NO 455
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
caugaagacc uaugaugau                                               19

<210> SEQ ID NO 456
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
ucaucauagg ucuucaugc                                               19

<210> SEQ ID NO 457
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
gcaugaagac cuaugauga                                               19

<210> SEQ ID NO 458
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
caucauaggu cuucaugcu                                               19

<210> SEQ ID NO 459
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
agcaugaaga ccuaugaug                                               19

<210> SEQ ID NO 460
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
aucauagguc uucaugcuu                                                  19

<210> SEQ ID NO 461
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461
aagcaugaag accuaugau                                                  19

<210> SEQ ID NO 462
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
ucauaggucu ucaugcuua                                                  19

<210> SEQ ID NO 463
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
uaagcaugaa gaccuauga                                                  19

<210> SEQ ID NO 464
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
cauaggucuu caugcuuau                                                  19

<210> SEQ ID NO 465
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
auaagcauga agaccuaug                                                  19

<210> SEQ ID NO 466
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 466
auaggucuuc augcuuaug                                           19

<210> SEQ ID NO 467
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 467
cauaagcaug aagaccuau                                           19

<210> SEQ ID NO 468
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 468
uaggucuuca ugcuuaugg                                           19

<210> SEQ ID NO 469
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 469
ccauaagcau gaagaccua                                           19

<210> SEQ ID NO 470
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 470
aggucuucau gcuuauggg                                           19

<210> SEQ ID NO 471
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 471
cccauaagca ugaagaccu                                           19

-continued

<210> SEQ ID NO 472
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
ggucuucaug cuuaugggg                                                19

<210> SEQ ID NO 473
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
ccccauaagc augaagacc                                                19

<210> SEQ ID NO 474
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
gucuucaugc uuauggga                                                 19

<210> SEQ ID NO 475
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
uccccauaag caugaagac                                                19

<210> SEQ ID NO 476
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 476
ucuucaugcu uaugggau                                                 19

<210> SEQ ID NO 477
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
auccccauaa gcaugaaga                                                19

<210> SEQ ID NO 478

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 478
gugaugagau gacccguau                                                    19

<210> SEQ ID NO 479
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 479
auacggguca ucucaucac                                                    19

<210> SEQ ID NO 480
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 480
gaugagauga cccguauua                                                    19

<210> SEQ ID NO 481
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
uaauacgggu caucucauc                                                    19

<210> SEQ ID NO 482
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
cguauuaucu ggcaguuca                                                    19

<210> SEQ ID NO 483
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 483
ugaacugcca gauaauacg                                                    19

<210> SEQ ID NO 484
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 484
ggcaguucau caaggagaa                                                  19

<210> SEQ ID NO 485
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 485
uucuccuuga ugaacugcc                                                  19

<210> SEQ ID NO 486
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 486 gugggaaga guucaagcu                                                   19

<210> SEQ ID NO 487
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
agcuugaacu cuuccacac                                                  19

<210> SEQ ID NO 488
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 488
guggaagagu ucaagcuga                                                  19

<210> SEQ ID NO 489
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 489
ucagcuugaa cucuuccac                                                  19

<210> SEQ ID NO 490
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 490
gaagaguuca agcugaaga                                                       19

<210> SEQ ID NO 491
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 491
ucuucagcuu gaacucuuc                                                       19

<210> SEQ ID NO 492
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492
caguaugcca uccagaaga                                                       19

<210> SEQ ID NO 493
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 493
ucuucuggau ggcauacug                                                       19

<210> SEQ ID NO 494
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
cuguacauga gcaccaaga                                                       19

<210> SEQ ID NO 495
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
ucuuggugcu cauguacag                                                       19

<210> SEQ ID NO 496
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 496
gcaccaagaa caccauacu                                                    19

<210> SEQ ID NO 497
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
aguauggugu ucuuggugc                                                    19

<210> SEQ ID NO 498
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 498
ccauacugaa agccuacga                                                    19

<210> SEQ ID NO 499
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
ucguaggcuu ucaguaugg                                                    19

<210> SEQ ID NO 500
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 500
cauacugaaa gccuacgau                                                    19

<210> SEQ ID NO 501
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 501
aucguaggcu uucaguaug                                                    19

<210> SEQ ID NO 502
<211> LENGTH: 19
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 502
guuucaagga caucuucca                                                19

<210> SEQ ID NO 503
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 503
uggaagaugu ccuugaaac                                                19

<210> SEQ ID NO 504
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 504
ccgacuucga caagaauaa                                                19

<210> SEQ ID NO 505
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
uuauucuugu cgaagucgg                                                19

<210> SEQ ID NO 506
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 506
gacuucgaca agaauaaga                                                19

<210> SEQ ID NO 507
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 507
ucuuauucuu gucgaaguc                                                19

<210> SEQ ID NO 508
<211> LENGTH: 19
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 508
gacaagaaua agaucuggu                                             19

<210> SEQ ID NO 509
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
accagaucuu auucuuguc                                             19

<210> SEQ ID NO 510
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
ggcucauuga ugacauggu                                             19

<210> SEQ ID NO 511
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
accaugucau caaugagcc                                             19

<210> SEQ ID NO 512
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
gcaagaacua ugacggaga                                             19

<210> SEQ ID NO 513
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
ucuccgucau aguucuugc                                             19

<210> SEQ ID NO 514
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
caagaacuau gacggagau					19

<210> SEQ ID NO 515
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
aucuccguca uaguucuug					19

<210> SEQ ID NO 516
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
gagaugugca gucagacau					19

<210> SEQ ID NO 517
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
augucugacu gcacaucuc					19

<210> SEQ ID NO 518
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
cugaugggaa gacgauuga					19

<210> SEQ ID NO 519
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
ucaaucgucu ucccaucag					19

<210> SEQ ID NO 520
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 520
gcaaugugaa gcugaacga                                                19

<210> SEQ ID NO 521
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
ucguucagcu ucacauugc                                                19

<210> SEQ ID NO 522
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
cuguaauuua uauugcccu                                                19

<210> SEQ ID NO 523
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
agggcaauau aaauuacag                                                19

<210> SEQ ID NO 524
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 524
cauggugcca uauuuagcu                                                19

<210> SEQ ID NO 525
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
agcuaaauau ggcaccaug                                                19

<210> SEQ ID NO 526
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
```

```
ggugccauau uuagcuacu                                               19

<210> SEQ ID NO 527
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 527
aguagcuaaa uauggcacc                                               19

<210> SEQ ID NO 528
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
gugccauauu uagcuacua                                               19

<210> SEQ ID NO 529
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
uaguagcuaa auauggcac                                               19

<210> SEQ ID NO 530
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
gccauauuua gcuacuaaa                                               19

<210> SEQ ID NO 531
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
uuuaguagcu aaauauggc                                               19

<210> SEQ ID NO 532
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
```
gcccaucacc auuggcagg                                           19

<210> SEQ ID NO 533
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
ccugccaaug gugaugggc                                           19

<210> SEQ ID NO 534
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
cccaucacca uuggcaggc                                           19

<210> SEQ ID NO 535
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
gccugccaau ggugauggg                                           19

<210> SEQ ID NO 536
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 536
ccaucaccau uggcaggca                                           19

<210> SEQ ID NO 537
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
ugccugccaa uggugaugg                                           19

<210> SEQ ID NO 538
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
caucaccauu ggcaggcac                                           19

<210> SEQ ID NO 539
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
gugccugcca auggugaug                                                  19

<210> SEQ ID NO 540
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
aucaccauug gcaggcacg                                                  19

<210> SEQ ID NO 541
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 541
cgugccugcc aauggugau                                                  19

<210> SEQ ID NO 542
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
ucaccauugg caggcacgc                                                  19

<210> SEQ ID NO 543
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
gcgugccugc caaugguga                                                  19

<210> SEQ ID NO 544
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
caccauuggc aggcacgcc                                                  19

```
<210> SEQ ID NO 545
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
ggcgugccug ccaauggug                                              19

<210> SEQ ID NO 546
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
accauuggca ggcacgccc                                              19

<210> SEQ ID NO 547
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 547
gggcgugccu gccaauggu                                              19

<210> SEQ ID NO 548
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
ccauuggcag gcacgccca                                              19

<210> SEQ ID NO 549
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
ugggcgugcc ugccaaugg                                              19

<210> SEQ ID NO 550
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
cauuggcagg cacgcccau                                              19
```

```
<210> SEQ ID NO 551
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
augggcgugc cugccaaug                                                  19

<210> SEQ ID NO 552
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
auuggcaggc acgcccaug                                                  19

<210> SEQ ID NO 553
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
caugggcgug ccugccaau                                                  19

<210> SEQ ID NO 554
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
uuggcaggca cgcccaugg                                                  19

<210> SEQ ID NO 555
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
ccaugggcgu gccugccaa                                                  19

<210> SEQ ID NO 556
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
uggcaggcac gcccauggc                                                  19

<210> SEQ ID NO 557
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
gccaugggcg ugccugcca                                               19

<210> SEQ ID NO 558
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
ggcaggcacg cccauggcg                                               19

<210> SEQ ID NO 559
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 559
cgccaugggc gugccugcc                                               19

<210> SEQ ID NO 560
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
gcaggcacgc ccauggcga                                               19

<210> SEQ ID NO 561
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
ucgccauggg cgugccugc                                               19

<210> SEQ ID NO 562
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
caggcacgcc cauggcgac                                               19

<210> SEQ ID NO 563
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 563
gucgccaugg gcgugccug                                                      19

<210> SEQ ID NO 564
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
aggcacgccc auggcgacc                                                      19

<210> SEQ ID NO 565
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
ggucgccaug ggcgugccu                                                      19

<210> SEQ ID NO 566
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566
gcccaucacc auuggcggg                                                      19

<210> SEQ ID NO 567
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567
cccgccaaug gugaugggc                                                      19

<210> SEQ ID NO 568
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568
cccaucacca uuggcgggc                                                      19

<210> SEQ ID NO 569
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 569
gcccgccaau ggugaugggg                                              19

<210> SEQ ID NO 570
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570
ccaucaccau uggcgggca                                               19

<210> SEQ ID NO 571
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
ugcccgccaa uggugaugg                                               19

<210> SEQ ID NO 572
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
caucaccauu ggcgggcac                                               19

<210> SEQ ID NO 573
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
gugcccgcca auggugaug                                               19

<210> SEQ ID NO 574
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
aucaccauug gcgggcacg                                               19

<210> SEQ ID NO 575
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 575
cgugcccgcc aauggugau                                                19

<210> SEQ ID NO 576
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
ucaccauugg cgggcacgc                                                19

<210> SEQ ID NO 577
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
gcgugcccgc caaugguga                                                19

<210> SEQ ID NO 578
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
caccauuggc gggcacgcc                                                19

<210> SEQ ID NO 579
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
ggcgugcccg ccaauggug                                                19

<210> SEQ ID NO 580
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
accauuggcg ggcacgccc                                                19

<210> SEQ ID NO 581
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 581
gggcgugccc gccaauggu                                                   19

<210> SEQ ID NO 582
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
ccauuggcgg gcacgccca                                                   19

<210> SEQ ID NO 583
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
ugggcgugcc cgccaaugg                                                   19

<210> SEQ ID NO 584
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
cauuggcggg cacgcccau                                                   19

<210> SEQ ID NO 585
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
augggcgugc ccgccaaug                                                   19

<210> SEQ ID NO 586
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
auuggcgggc acgcccaug                                                   19

<210> SEQ ID NO 587
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 587
caugggcgug cccgccaau                                                    19

<210> SEQ ID NO 588
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
uuggcgggca cgcccaugg                                                    19

<210> SEQ ID NO 589
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
ccaugggcgu gcccgccaa                                                    19

<210> SEQ ID NO 590
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
uggcgggcac gcccauggc                                                    19

<210> SEQ ID NO 591
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
gccaugggcg ugcccgcca                                                    19

<210> SEQ ID NO 592
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
ggcgggcacg cccauggcg                                                    19

<210> SEQ ID NO 593
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 593
cgccaugggc gugcccgcc                                                19

<210> SEQ ID NO 594
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
gcgggcacgc ccauggcga                                                19

<210> SEQ ID NO 595
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
ucgccauggg cgugcccgc                                                19

<210> SEQ ID NO 596
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
cgggcacgcc cauggcgac                                                19

<210> SEQ ID NO 597
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597
gucgccaugg gcgugcccg                                                19

<210> SEQ ID NO 598
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
gggcacgccc auggcgacc                                                19

<210> SEQ ID NO 599
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 599
ggucgccaug ggcgugccc                                                19

<210> SEQ ID NO 600
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
gcccaucacc auuggcugg                                                19

<210> SEQ ID NO 601
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
ccagccaaug gugaugggc                                                19

<210> SEQ ID NO 602
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
cccaucacca uuggcuggc                                                19

<210> SEQ ID NO 603
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
gccagccaau ggugauggg                                                19

<210> SEQ ID NO 604
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
ccaucaccau uggcuggca                                                19

<210> SEQ ID NO 605
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
```
ugccagccaa uggugaugg                                                19

<210> SEQ ID NO 606
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
caucaccauu ggcuggcac                                                19

<210> SEQ ID NO 607
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
gugccagcca auggugaug                                                19

<210> SEQ ID NO 608
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
aucaccauug gcuggcacg                                                19

<210> SEQ ID NO 609
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
cgugccagcc aauggugau                                                19

<210> SEQ ID NO 610
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
ucaccauugg cuggcacgc                                                19

<210> SEQ ID NO 611
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 611

```
gcgugccagc caaugguga                                              19

<210> SEQ ID NO 612
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
caccauuggc uggcacgcc                                              19

<210> SEQ ID NO 613
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
ggcgugccag ccaauggug                                              19

<210> SEQ ID NO 614
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
accauuggcu ggcacgccc                                              19

<210> SEQ ID NO 615
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
gggcgugcca gccaauggu                                              19

<210> SEQ ID NO 616
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 616
ccauuggcug gcacgccca                                              19

<210> SEQ ID NO 617
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
ugggcgugcc agccaaugg                                              19
```

<210> SEQ ID NO 618
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
cauuggcugg cacgcccau                                                19

<210> SEQ ID NO 619
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
augggcgugc cagccaaug                                                19

<210> SEQ ID NO 620
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
auuggcuggc acgcccaug                                                19

<210> SEQ ID NO 621
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621 cauggcgug ccagccaau                                                 19

<210> SEQ ID NO 622
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
uuggcuggca cgcccaugg                                                19

<210> SEQ ID NO 623
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 623
ccaugggcgu gccagccaa                                                19

<210> SEQ ID NO 624
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 624
uggcuggcac gcccauggc                                                19

<210> SEQ ID NO 625
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 625
gccaugggcg ugccagcca                                                19

<210> SEQ ID NO 626
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 626
ggcuggcacg cccauggcg                                                19

<210> SEQ ID NO 627
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 627
cgccaugggc gugccagcc                                                19

<210> SEQ ID NO 628
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 628
gcuggcacgc ccauggcga                                                19

<210> SEQ ID NO 629
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 629
ucgccauggg cgugccagc                                                19

-continued

```
<210> SEQ ID NO 630
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 630
cuggcacgcc cauggcgac                                                       19

<210> SEQ ID NO 631
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 631
gucgccaugg gcgugccag                                                       19

<210> SEQ ID NO 632
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 632
uggcacgccc auggcgacc                                                       19

<210> SEQ ID NO 633
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 633
ggucgccaug ggcgugcca                                                       19

<210> SEQ ID NO 634
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
gcccaucacc auuggcaag                                                       19

<210> SEQ ID NO 635
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 635
cuugccaaug gugaugggc                                                       19

<210> SEQ ID NO 636
```

```
<210> SEQ ID NO 636
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 636
cccaucacca uuggcaagc                                                19

<210> SEQ ID NO 637
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
gcuugccaau ggugauggg                                                19

<210> SEQ ID NO 638
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 638
ccaucaccau uggcaagca                                                19

<210> SEQ ID NO 639
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
ugcuugccaa uggugaugg                                                19

<210> SEQ ID NO 640
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 640
caucaccauu ggcaagcac                                                19

<210> SEQ ID NO 641
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
gugcuugcca auggugaug                                                19

<210> SEQ ID NO 642
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
aucaccauug gcaagcacg                                                19

<210> SEQ ID NO 643
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 643
cgugcuugcc aauggugau                                                19

<210> SEQ ID NO 644
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
ucaccauugg caagcacgc                                                19

<210> SEQ ID NO 645
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
gcgugcuugc caaugguga                                                19

<210> SEQ ID NO 646
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
caccauuggc aagcacgcc                                                19

<210> SEQ ID NO 647
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647
ggcgugcuug ccaauggug                                                19

<210> SEQ ID NO 648
<211> LENGTH: 19
<212> TYPE: RNA
```

-continued

<213> ORGANISM: Artificial Sequence
<220> FEATURE:
<223> OTHER INFORMATION: Description of Artificial Sequence: Synthetic
      oligonucleotide

<400> SEQUENCE: 648
accauuggca agcacgccc                                                    19

<210> SEQ ID NO 649
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 649
gggcgugcuu gccaauggu                                                    19

<210> SEQ ID NO 650
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
ccauuggcaa gcacgccca                                                    19

<210> SEQ ID NO 651
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 651
ugggcgugcu ugccaaugg                                                    19

<210> SEQ ID NO 652
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
cauuggcaag cacgcccau                                                    19

<210> SEQ ID NO 653
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
augggcgugc uugccaaug                                                    19

<210> SEQ ID NO 654
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 654
auuggcaagc acgcccaug                                               19

<210> SEQ ID NO 655
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 655
caugggcgug cuugccaau                                               19

<210> SEQ ID NO 656
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
uuggcaagca cgcccaugg                                               19

<210> SEQ ID NO 657
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
ccaugggcgu gcuugccaa                                               19

<210> SEQ ID NO 658
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
uggcaagcac gcccauggc                                               19

<210> SEQ ID NO 659
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 659
gccaugggcg ugcuugcca                                               19

<210> SEQ ID NO 660
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 660
ggcaagcacg cccauggcg                                                    19

<210> SEQ ID NO 661
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 661
cgccaugggc gugcuugcc                                                    19

<210> SEQ ID NO 662
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
gcaagcacgc ccauggcga                                                    19

<210> SEQ ID NO 663
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
ucgccauggg cgugcuugc                                                    19

<210> SEQ ID NO 664
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 664
caagcacgcc cauggcgac                                                    19

<210> SEQ ID NO 665
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 665
gucgccaugg gcgugcuug                                                    19

<210> SEQ ID NO 666
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 666
aagcacgccc auggcgacc                                               19

<210> SEQ ID NO 667
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 667
ggucgccaug ggcgugcuu                                               19

<210> SEQ ID NO 668
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 668
gcccaucacc auuggcacg                                               19

<210> SEQ ID NO 669
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 669
cgugccaaug gugaugggc                                               19

<210> SEQ ID NO 670
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
cccaucacca uuggcacgc                                               19

<210> SEQ ID NO 671
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 671
gcgugccaau ggugauggg                                               19

<210> SEQ ID NO 672
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 672
ccaucaccau uggcacgca                                                    19

<210> SEQ ID NO 673
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 673
ugcgugccaa uggugaugg                                                    19

<210> SEQ ID NO 674
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
caucaccauu ggcacgcac                                                    19

<210> SEQ ID NO 675
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
gugcgugcca auggugaug                                                    19

<210> SEQ ID NO 676
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 676
aucaccauug gcacgcacg                                                    19

<210> SEQ ID NO 677
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 677
cgugcgugcc aauggugau                                                    19

<210> SEQ ID NO 678
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 678
ucaccauugg cacgcacgc                                                19

<210> SEQ ID NO 679
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 679
gcgugcgugc caaugguga                                                19

<210> SEQ ID NO 680
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 680
caccauuggc acgcacgcc                                                19

<210> SEQ ID NO 681
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
ggcgugcgug ccaauggug                                                19

<210> SEQ ID NO 682
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 682
accauuggca cgcacgccc                                                19

<210> SEQ ID NO 683
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 683
gggcgugcgu gccaauggu                                                19

<210> SEQ ID NO 684
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 684
```
ccauuggcac gcacgccca                                                        19

<210> SEQ ID NO 685
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
ugggcgugcg ugccaaugg                                                        19

<210> SEQ ID NO 686
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
cauuggcacg cacgcccau                                                        19

<210> SEQ ID NO 687
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
augggcgugc gugccaaug                                                        19

<210> SEQ ID NO 688
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 688
auuggcacgc acgcccaug                                                        19

<210> SEQ ID NO 689
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 689
caugggcgug cgugccaau                                                        19

<210> SEQ ID NO 690
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
uuggcacgca cgcccaugg          19

<210> SEQ ID NO 691
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
ccaugggcgu gcgugccaa          19

<210> SEQ ID NO 692
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 692
uggcacgcac gcccauggc          19

<210> SEQ ID NO 693
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 693
gccaugggcg ugcgugcca          19

<210> SEQ ID NO 694
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 694
ggcacgcacg cccauggcg          19

<210> SEQ ID NO 695
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 695
cgccaugggc gugcgugcc          19

<210> SEQ ID NO 696
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 696
gcacgcacgc ccauggcga          19

```
<210> SEQ ID NO 697
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 697
ucgccauggg cgugcgugc                                                   19

<210> SEQ ID NO 698
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 698
cacgcacgcc cauggcgac                                                   19

<210> SEQ ID NO 699
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
gucgccaugg gcgugcgug                                                   19

<210> SEQ ID NO 700
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 700
acgcacgccc auggcgacc                                                   19

<210> SEQ ID NO 701
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
ggucgccaug ggcgugcgu                                                   19

<210> SEQ ID NO 702
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
gcccaucacc auuggcaug                                                   19
```

<210> SEQ ID NO 703
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
caugccaaug gugaugggc                                                19

<210> SEQ ID NO 704
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 704
cccaucacca uuggcaugc                                                19

<210> SEQ ID NO 705
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 705
gcaugccaau ggugauggg                                                19

<210> SEQ ID NO 706
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 706
ccaucaccau uggcaugca                                                19

<210> SEQ ID NO 707
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 707
ugcaugccaa uggugaugg                                                19

<210> SEQ ID NO 708
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 708
caucaccauu ggcaugcac                                                19

```
<210> SEQ ID NO 709
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 709
gugcaugcca auggugaug                                                   19

<210> SEQ ID NO 710
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
aucaccauug gcaugcacg                                                   19

<210> SEQ ID NO 711
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
cgugcaugcc aauggugau                                                   19

<210> SEQ ID NO 712
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
ucaccauugg caugcacgc                                                   19

<210> SEQ ID NO 713
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
gcgugcaugc caaugguga                                                   19

<210> SEQ ID NO 714
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 714
caccauuggc augcacgcc                                                   19

<210> SEQ ID NO 715
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
ggcgugcaug ccaauggug                                                19

<210> SEQ ID NO 716
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 716
accauuggca ugcacgccc                                                19

<210> SEQ ID NO 717
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 717
gggcgugcau gccaauggu                                                19

<210> SEQ ID NO 718
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 718
ccauuggcau gcacgccca                                                19

<210> SEQ ID NO 719
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 719
ugggcgugca ugccaaugg                                                19

<210> SEQ ID NO 720
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 720
cauuggcaug cacgcccau                                                19

<210> SEQ ID NO 721
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 721
augggcgugc augccaaug                                               19

<210> SEQ ID NO 722
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 722
auuggcaugc acgcccaug                                               19

<210> SEQ ID NO 723
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 723
caugggcgug caugccaau                                               19

<210> SEQ ID NO 724
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
uuggcaugca cgcccaugg                                               19

<210> SEQ ID NO 725
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 725
ccaugggcgu gcaugccaa                                               19

<210> SEQ ID NO 726
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
uggcaugcac gcccauggc                                               19

<210> SEQ ID NO 727
<211> LENGTH: 19
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 727
gccaugggcg ugcaugcca                                              19

<210> SEQ ID NO 728
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 728
ggcaugcacg cccauggcg                                              19

<210> SEQ ID NO 729
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 729
cgccaugggc gugcaugcc                                              19

<210> SEQ ID NO 730
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 730
gcaugcacgc ccauggcga                                              19

<210> SEQ ID NO 731
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 731
ucgccauggg cgugcaugc                                              19

<210> SEQ ID NO 732
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 732
caugcacgcc cauggcgac                                              19

<210> SEQ ID NO 733
<211> LENGTH: 19
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 733
gucgccaugg gcgugcaug                                                  19

<210> SEQ ID NO 734
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 734
augcacgccc auggcgacc                                                  19

<210> SEQ ID NO 735
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 735
ggucgccaug ggcgugcau                                                  19

<210> SEQ ID NO 736
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 736
gcccaucacc auuggcagc                                                  19

<210> SEQ ID NO 737
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 737
gcugccaaug gugaugggc                                                  19

<210> SEQ ID NO 738
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 738
cccaucacca uuggcagcc                                                  19

<210> SEQ ID NO 739
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 739
ggcugccaau ggugauggg                                                      19

<210> SEQ ID NO 740
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 740
ccaucaccau uggcagcca                                                      19

<210> SEQ ID NO 741
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 741
uggcugccaa uggugaugg                                                      19

<210> SEQ ID NO 742
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 742
caucaccauu ggcagccac                                                      19

<210> SEQ ID NO 743
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 743
guggcugcca auggugaug                                                      19

<210> SEQ ID NO 744
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 744
aucaccauug gcagccacg                                                      19

<210> SEQ ID NO 745
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 745
cguggcugcc aauggugau                                                19

<210> SEQ ID NO 746
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 746
ucaccauugg cagccacgc                                                19

<210> SEQ ID NO 747
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
gcguggcugc caaugguga                                                19

<210> SEQ ID NO 748
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 748
caccauuggc agccacgcc                                                19

<210> SEQ ID NO 749
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 749
ggcguggcug ccaauggug                                                19

<210> SEQ ID NO 750
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 750
accauuggca gccacgccc                                                19

<210> SEQ ID NO 751
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 751
gggcguggcu gccaauggu				19

<210> SEQ ID NO 752
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 752
ccauuggcag ccacgccca				19

<210> SEQ ID NO 753
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 753
ugggcguggc ugccaaugg				19

<210> SEQ ID NO 754
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 754
cauuggcagc cacgcccau				19

<210> SEQ ID NO 755
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 755
augggcgugg cugccaaug				19

<210> SEQ ID NO 756
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 756
auuggcagcc acgcccaug				19

<210> SEQ ID NO 757
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 757
caugggcgug gcugccaau                                                19

<210> SEQ ID NO 758
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 758
uuggcagcca cgcccaugg                                                19

<210> SEQ ID NO 759
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 759
ccaugggcgu ggcugccaa                                                19

<210> SEQ ID NO 760
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 760
uggcagccac gcccauggc                                                19

<210> SEQ ID NO 761
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 761
gccaugggcg uggcugcca                                                19

<210> SEQ ID NO 762
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 762
ggcagccacg cccauggcg                                                19

<210> SEQ ID NO 763
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 763
```

```
cgccaugggc guggcugcc                                                    19
```

<210> SEQ ID NO 764
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 764

```
gcagccacgc ccauggcga                                                    19
```

<210> SEQ ID NO 765
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 765

```
ucgccauggg cguggcugc                                                    19
```

<210> SEQ ID NO 766
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 766

```
cagccacgcc cauggcgac                                                    19
```

<210> SEQ ID NO 767
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 767

```
gucgccaugg gcguggcug                                                    19
```

<210> SEQ ID NO 768
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 768

```
agccacgccc auggcgacc                                                    19
```

<210> SEQ ID NO 769
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 769

```
ggucgccaug ggcguggcu                                            19
```

<210> SEQ ID NO 770
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 770

```
gcccaucacc auuggcagu                                            19
```

<210> SEQ ID NO 771
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 771

```
acugccaaug gugaugggc                                            19
```

<210> SEQ ID NO 772
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 772

```
cccaucacca uuggcaguc                                            19
```

<210> SEQ ID NO 773
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 773

```
gacugccaau ggugauggg                                            19
```

<210> SEQ ID NO 774
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 774

```
ccaucaccau uggcaguca                                            19
```

<210> SEQ ID NO 775
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 775

```
ugacugccaa uggugaugg                                            19
```

<210> SEQ ID NO 776
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 776
caucaccauu ggcagucac                                              19

<210> SEQ ID NO 777
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 777
gugacugcca auggugaug                                              19

<210> SEQ ID NO 778
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 778
aucaccauug gcagucacg                                              19

<210> SEQ ID NO 779
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 779
cgugacugcc aauggugau                                              19

<210> SEQ ID NO 780
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 780
ucaccauugg cagucacgc                                              19

<210> SEQ ID NO 781
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 781
gcgugacugc caaugguga                                              19

```
<210> SEQ ID NO 782
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782
caccauuggc agucacgcc                                                    19

<210> SEQ ID NO 783
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 783
ggcgugacug ccaauggug                                                    19

<210> SEQ ID NO 784
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 784
accauuggca gucacgccc                                                    19

<210> SEQ ID NO 785
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 785
gggcgugacu gccaauggu                                                    19

<210> SEQ ID NO 786
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 786
ccauuggcag ucacgccca                                                    19

<210> SEQ ID NO 787
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 787
ugggcgugac ugccaaugg                                                    19
```

```
<210> SEQ ID NO 788
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 788
cauuggcagu cacgcccau                                                19

<210> SEQ ID NO 789
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 789
augggcguga cugccaaug                                                19

<210> SEQ ID NO 790
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 790
auuggcaguc acgcccaug                                                19

<210> SEQ ID NO 791
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 791
caugggcgug acugccaau                                                19

<210> SEQ ID NO 792
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 792
uuggcaguca cgcccaugg                                                19

<210> SEQ ID NO 793
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 793
ccaugggcgu gacugccaa                                                19

<210> SEQ ID NO 794
```

```
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 794
uggcagucac gcccauggc                                                 19

<210> SEQ ID NO 795
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 795
gccaugggcg ugacugcca                                                 19

<210> SEQ ID NO 796
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 796
ggcagucacg cccauggcg                                                 19

<210> SEQ ID NO 797
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 797
cgccaugggc gugacugcc                                                 19

<210> SEQ ID NO 798
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 798
gcagucacgc ccauggcga                                                 19

<210> SEQ ID NO 799
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 799
ucgccauggg cgugacugc                                                 19

<210> SEQ ID NO 800
<211> LENGTH: 19
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 800
cagucacgcc cauggcgac                                                    19

<210> SEQ ID NO 801
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 801
gucgccaugg gcgugacug                                                    19

<210> SEQ ID NO 802
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 802
agucacgccc auggcgacc                                                    19

<210> SEQ ID NO 803
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 803
ggucgccaug ggcgugacu                                                    19

<210> SEQ ID NO 804
<211> LENGTH: 489
<212> TYPE: DNA
<213> ORGANISM: Homo sapiens

<400> SEQUENCE: 804
gcataatgag ctctatatgc catcactgca gttgtaggtt ataactatcc atttgtctga       60
aaaactttgc ttctaatttt tctctttcaa gctatgattt aggcatagag aatcgtgatg      120
ccaccaacga ccaagtcacc aaggatgctg cagaagctat aaagaagcat aatgttggcg      180
tcaaatgtgc cactatcact cctgatgaga agagggttga ggagttcaag ttgaaacaaa      240
tgtggaaatc accaaatggc accatacgaa atattctggg tggcacggtc ttcagagaag      300
ccattatctg caaaaatatc ccccggcttg tgagtggatg ggtaaaacct atcatcatag      360
gtcgtcatgc ttatggggat caagtaagtc atgttggcaa taatgtgatt ttgcatgbtg      420
gcccagaaat ttccaacttg tatgtgtttt attcttatct tttggtatct acacccatta      480
agcaaggta                                                              489
```

METHOD FOR TREATING CELL PROLIFERATION RELATED DISORDERS

CLAIM OF PRIORITY

This application is a continuation of U.S. application Ser. No. 14/504,983, filed Oct. 2, 2014, now abandoned which is a continuation of U.S. application Ser. No. 13/617,332, filed Sep. 14, 2012, now abandoned which is a continuation of U.S. application Ser. No. 13/452,136, filed Apr. 20, 2012, now U.S. Pat. No. 9,434,979 which is a continuation of International Application No. PCT/US2010/053623, filed Oct. 21, 2010, which claims priority to U.S. Ser. No. 61/253,821, filed on Oct. 21, 2009 and U.S. Ser. No. 61/266,930, filed on Dec. 4, 2009, the contents of each of which are incorporated herein by reference.

FIELD OF INVENTION

The invention relates to methods and compositions for evaluating and treating cell proliferation-related disorders, e.g., proliferative disorders such as cancer.

BACKGROUND

Isocitrate dehydrogenase, also known as IDH, is an enzyme which participates in the citric acid cycle. It catalyzes the third step of the cycle: the oxidative decarboxylation of isocitrate, producing alpha-ketoglutarate (α-ketoglutarate or α-KG) and $CO_2$ while converting NAD+ to NADH. This is a two-step process, which involves oxidation of isocitrate (a secondary alcohol) to oxalosuccinate (a ketone), followed by the decarboxylation of the carboxyl group beta to the ketone, forming alpha-ketoglutarate. Another isoform of the enzyme catalyzes the same reaction; however this reaction is unrelated to the citric acid cycle, is carried out in the cytosol as well as the mitochondrion and peroxisome, and uses NADP+ as a cofactor instead of NAD+.

SUMMARY OF THE INVENTION

Methods and compositions disclosed herein relate to the role played in disease by neoactive products produced by neoactive mutant IDH enzymes (e.g., IDH1 or IDH2). The inventors have discovered, inter alia, a neoactivity associated with IDH mutants and that the product of the neoactivity can be significantly elevated in cancer cells. Disclosed herein are methods and compositions for treating, and methods of evaluating, subjects having or at risk for a disorder, e.g., a cell proliferation-related disorder characterized by IDH neoactivity. Such disorders include e.g., proliferative disorders such as cancer. The inventors have discovered and disclosed herein novel therapeutic agents for the treatment of disorders, e.g., cancers, characterized by, e.g., by an IDH neoactivity, neoactive protein, neoactive mRNA, or neoactive mutations. In embodiments a therapeutic agent reduces levels of neoactivity or neoactive product or ameliorates an effect of a neoactive product. Methods described herein also allow the identification of a subject, or identification of a treatment for the subject, on the basis of neaoctivity genotype or phenotype. This evaluation can allow for optimal matching of subject with treatment, e.g., where the selection of subject, treatment, or both, is based on an analysis of neoactivity genotype or phenotype. E.g., methods describe herein can allow selection of a treatment regimen comprising administration of a novel compound, e.g., a novel compound disclosed herein, or a known compound, e.g., a known compound not previously recommended for a selected disorder. In embodiments the known compound reduces levels of neoactivity or neoactive product or ameliorates an effect of a neoactive product. Methods described herein can guide and provide a basis for selection and administration of a novel compound or a known compound, or combination of compounds, not previously recommended for subjects having a disorder characterized by a somatic neoactive mutation in an IDH. In embodiments the neoactive genotype or phenotype can act as a biomarker the presence of which indicates that a compound, either novel, or previously known, should be administered, to treat a disorder characterized by a somatic neoactive mutation in a metabolic pathway enzyme. Neoactive mutants of IDH1 or IDH2 having a neoactivity that results in the production of an alpha hydroxy product such as 2-hydroxyglutarate, e.g., R-2-hydroxyglutarate and associated disorders are discussed in detail herein.

While not wishing to be bound by theory it is believed that the balance between the production and elimination of neoactive product, e.g., 2HG, e.g., R-2HG, is important in disease. Neoactive mutants can increase the level of neoactive product, while other processes, e.g., in the case of 2HG, e.g., R-2HG, enzymatic degradation of 2HG, e.g., by 2HG dehydrogenase, reduce the level of neoative product. An incorrect balance is associated with disease. In embodiments, the net result of a neoactive mutation at IDH1 or IDH2 result in increased levels, in affected cells, of neoactive product, 2HG, e.g., R-2HG, Accordingly, in one aspect, the invention features, a method of treating a subject having a cell proliferation-related disorder, e.g., a precancerous disorder, or cancer. In an embodiment the subject does not have, or has not been diagnosed as having, 2-hydroxyglutaric aciduria. The cell proliferation-related disorder is characterized by a somatic allele, e.g., a preselected allele, or mutant allele, of an IDH, e.g., IDH1 or IDH2, which encodes a mutant IDH, e.g., IDH1 or IDH2, enzyme having a neoactivity.

As used herein, neoactivity refers to alpha hydroxy neoactivity. Neoactivity and alpha hydroxyl neoactivity are used interchangeably herein. Alpha hydroxy neoactivity is the ability to convert an alpha ketone to an alpha hydroxy. In embodiments alpha hydroxy neoactivity proceeds with a reductive cofactor, e.g., NADPH or NADH. In embodiments the alpha hydroxy neoactivity is 2HG neoactivity. 2HG neoactivity, as used herein, refers to the ability to convert alpha ketoglutarate to 2-hydroxyglutarate (sometimes referred to herein as 2HG), e.g., R-2-hydroxyglutarate (sometimes referred to herein as R-2HG). In embodiments 2HG neoactivity proceeds with a reductive cofactor, e.g., NADPH or NADH. In an embodiment a neoactive enzyme can act on more than one substrate, e.g., more than one alpha keto substrate.

The method comprises administering to the subject an effective amount of a therapeutic agent of type described herein to thereby treat the subject.

In an embodiment the rapeutic agent:
results in lowering the level of a neoactivity product, e.g., 2HG, e.g., R-2HG;
comprises an agent which is a cellular structural analog of a neoactive product, or prodrug thereof, or which decreases the competition between a product of the neoactivity and a cellular structural analog of the product of the neoactivity;
comprises an agent that ameliorates the effects of an unwanted, i.e., increased, neoactivity product;
comprises an anti-glycolytic agent;

comprises an antioxidant; or
comprises a hypomethylating agent.

In an embodiment the method comprises administering a therapeutic agent that lowers neoactivity, e.g., 2HG neoactivity. In an embodiment the method comprises administering an inhibitor of a mutant IDH protein, e.g., a mutant IDH1 or mutant IDH2 protein, having a neoactivity, e.g., 2HG neoactivity.

In an embodiment the rapeutic agent comprises a compound from Table 24a or Table 24b, a compound having the structure of Formula (X) or (Formula (XI) described herein, or a compound as described in U.S. provisional application 61/365,072, the content of which is incorporated herein by reference.

In an embodiment the rapeutic agent comprises nucleic acid-based therapeutic agent, e.g., a dsRNA, e.g., a dsRNA described herein.

In an embodiment the rapeutic agent is a cellular structural analog of a neoactivity product, a substrate of a neoactive IDH mutant, or a prodrug thereof, e.g., as described in the section entitled "Cellular structural analogs of neoactivity products, and prodrugs thereof" elsewhere herein.

In an embodiment the rapeutic agent is an antiglycolytic agent, e.g., an anti-glycolytic agent described in the section entitled "Anti-glycolytic compounds" herein.

In an embodiment the rapeutic agent is an antioxidant, e.g., an antioxidant agent described in the section entitled "Anti oxidants" herein.

In an embodiment the rapeutic agent is a hypomethylating agent, e.g., a hypomethylating agent described in the section entitled "Hypomethylating Agents" herein.

In an embodiment therapeutic agent that makes the 2HG, e.g., R-2HG, more toxic to cells, e.g., by modulating an enzyme that results in converting 2HG, e.g., R-2HG, into a more toxic substance, e.g., where the 2 HG, e.g., R-2HG, acts as a prodrug or an inhibitor that targets 2HG dehydrogenase, or a modulator that leads to the conversion of 2HG to another metabolite that is toxic to the cancer cell.

In an embodiment the rapeutic agent is an inhibitor, e.g., a polypeptide, peptide, or small molecule (e.g., a molecule of less than 1,000 daltons), or aptomer, that binds to an IDH1 or IDH2 mutant or wildtype subunit and inhibits neoactivity, e.g., by inhibiting formation of a dimer, e.g., a homodimer of mutant IDH1 or IDH2 subunits or a heterodimer of a mutant and a wildtype subunit. In an embodiment the inhibitor is a polypeptide. In an embodiment the polypeptide acts as a dominant negative with respect to the neoactivity of the mutant enzyme. The polypeptide can correspond to full length IDH1 or IDH2 or a fragment thereof. The polypeptide need not be identical with the corresponding residues of wildtype IDH1 or IDH2, but in embodiments has at least 60, 70, 80, 90 or 95% homology with wildtype IDH1 or IDH2.

In an embodiment the rapeutic agent decreases the affinity of an IDH, e.g., IDH1 or IDH2 neoactive mutant protein for NADH, NADPH or a divalent metal ion, e.g., $Mg^{2+}$ or $Mn^{2+}$, or decreases the levels or availability of NADH, NADPH or divalent metal ion, e.g., $Mg^{2+}$ or $Mn^{2+}$, e.g., by competing for binding to the mutant enzyme. In an embodiment the enzyme is inhibited by replacing $Mg^{2+}$ or $Mn^{2+}$ with $Ca^{2+}$.

In an embodiment the rapeutic agent is an inhibitor that reduces the level a neoactivity of an IDH, e.g., IDH1 or IDH2, e.g., 2HG neoactivity.

In an embodiment the rapeutic agent is an inhibitor that reduces the level of the product of a mutant having a neoactivity of an IDH, e.g., IDH1 or IDH2 mutant, e.g., it reduces the level of 2HG, e.g., R-2HG.

In an embodiment the rapeutic agent is an inhibitor that:
inhibits, e.g., specifically, a neoactivity of an IDH, e.g., IDH1 or IDH2, e.g., 2HG neoactivity; or
inhibits both the wildtype activity and a neoactivity of an IDH, e.g., IDH1 or IDH2, e.g., 2HG neoactivity.

In an embodiment the rapeutic agent is an inhibitor that is selected on the basis that it:
inhibits, e.g., specifically, a neoactivity of an IDH, e.g., IDH1 or IDH2, e.g., 2HG neoactivity; or
inhibits both the wildtype activity and a neoactivity of an IDH1, e.g., IDH1 or IDH2, e.g., 2HG neoactivity.

In an embodiment the rapeutic agent is an inhibitor that reduces the amount of a mutant IDH, e.g., IDH1 or IDH2, protein or mRNA.

In an embodiment the rapeutic agent is an inhibitor that interacts directly with, e.g., it binds to, the mutant IDH, e.g., IDH1 or IDH2 mRNA.

In an embodiment the rapeutic agent is an inhibitor that interacts directly with, e.g., it binds to, the mutant IDH, e.g., IDH1 or IDH2, protein.

In an embodiment the rapeutic agent is an inhibitor that reduces the amount of neoactive IDH enzyme activity, e.g., by interacting with, e.g., binding to, mutant IDH, e.g., IDH1 or IDH2, protein. In an embodiment the inhibitor is other than an antibody.

In an embodiment, the inhibitor binds mutant IDH1 and reduces the interaction between reside N96 or S94 with alpha ketoglutarate.

In an embodiment, the inhibitor binds IDH1 and causes an alteration in the positions of N96 or S94 of the mutant IDH1.

In an embodiment, the inhibitor binds IDH1 and causes an alteration in the position of residue Y139.

In an embodiment the rapeutic agent is an inhibitor that is a small molecule and interacts with, e.g., binds, the mutant RNA, e.g., mutant IDH1 mRNA or mutant IDH2 mRNA.

In an embodiment the rapeutic agent is an inhibitor that interacts directly with, e.g., binds, either the mutant IDH, e.g., IDH1 or IDH2, protein or interacts directly with, e.g., binds, the mutant IDH mRNA, e.g., IDH1 or IDH2 mRNA.

In an embodiment the IDH is IDH1 and the neoactivity is 2HG neoactivity. Mutations in IDH1 associated with 2HG neoactivity include mutations at residue 132, e.g., R132H, R132C, R132S, R132G, R132L, or R132V (e.g., R132H or R132C).

Other IDH1 mutations associated with alpha hydroxy neoactivity, e.g., 2HG neoactivity include mutations at residue 71, e.g., a mutation having other than a Val at residue 71, e.g., V71I.

Other IDH1 mutations associated with alpha hydroxy neoactivity, e.g., 2HG neoactivity include mutations at residue 100, e.g., a mutation having other than an Arg at residue 100, and mutations at residue 109, e.g., a mutation having other than an Arg atu residue 109.

Still other mutations associated with alpha hydroxy neoactivity, e.g., 2HG neoactivity include mutations at residue 70, e.g., a mutation having other than a Gly at residue 70, (e.g., G70D); a mutation having other than an Ile at residue 130 (e.g., I130M); a mutation having other than a His at residue 133 (e.g., H133Q); a mutation having other than an Ala at residue 134 (e.g., A134D); or a mutation having a residue other than a Val at residue 178 (e.g., V178I).

In an embodiment the IDH is IDH2 and the neoactivity of the IDH2 mutant is 2HG neoactivity. Mutations in IDH2 associated with 2HG neoactivity include mutations at residue 172 such as R172X (e.g., R172K, R172M, R172S, R172G, or R172W). Additional mutations in IDH2 associated with 2HG neoactivity include mutations at residue 140, for example, R140X (e.g., IDH2R140Q, IDH2R140W, or IDH2R140L) and mutations at residue 294, for example V294X (e.g., IDH2V294M).

Treatment methods described herein can comprise evaluating a neoactivity genotype or phenotype. Methods of obtaining and analyzing samples, and the in vivo analysis in subjects, described elsewhere herein, e.g., in the section entitled, "Methods of evaluating samples and/or subjects," can be combined with this method.

In an embodiment, prior to or after treatment, the method includes evaluating the growth, size, weight, invasiveness, stage or other phenotype of the cell proliferation-related disorder.

In an embodiment, prior to or after treatment, the method includes evaluating the IDH, e.g., IDH1 or IDH2, neoactivity genotype, e.g., 2HG genotype, or neoactivity phenotype, e.g., 2HG, e.g., R-2HG, phenotype. Evaluating the 2HG genotype can comprise determining if an IDH1 or IDH2 mutation having neoactivity, e.g., 2HG neoactivity, is present, e.g., a mutation disclosed herein having neoactivity, e.g., 2HG neoactivity. Neoactivity phenotype, e.g., 2HG, e.g., R-2HG, phenotype, as used herein, refers to the level of neoactivity product (i.e., alpha hydroxyl neoactivity product), e.g., 2HG, e.g., R-2HG, level of neoactivity, e.g., 2HG neoactivity, or level of mutant IDH enzyme having neoactivity, e.g., 2HG neoactivity (or corresponding mRNA). The evaluation can be by a method described herein.

In an embodiment the subject can be evaluated, before or after treatment, to determine if the cell proliferation-related disorder is characterized by a neoactivity product, e.g., 2HG, e.g., R-2HG.

In an embodiment a cancer, e.g., a glioma or brain tumor in a subject, can be analyzed, e.g., by imaging and/or spectroscopic analysis, e.g., magnetic resonance-based analysis, e.g., MRI and/or MRS, e.g., before or after treatment, to determine if it is characterized by presence of an alpha hydroxy neoactivity product, e.g., 2HG, e.g., R-2HG.

In an embodiment the method comprises evaluating, e.g., by direct examination or evaluation of the subject, or a sample from the subject, or receiving such information about the subject, the IDH, e.g., IDH1 or IDH2, genotype, or an alpha hydroxy neoactivity product, e.g., 2HG, e.g., R-2HG phenotype of, the subject, e.g., of a cell, e.g., a cancer cell, characterized by the cell proliferation-related disorder. (As described in more detail elsewhere herein the evaluation can be, e.g., by DNA sequencing, immuno analysis, evaluation of the presence, distribution or level of an alpha hydroxy neoactivity product, e.g., 2HG, e.g., R-2HG, e.g., from spectroscopic analysis, e.g., magnetic resonance-based analysis, e.g., MRI and/or MRS measurement, sample analysis such as serum or spinal cord fluid analysis, or by analysis of surgical material, e.g., by mass-spectroscopy). In embodiments this information is used to determine or confirm that a proliferation-related disorder, e.g., a cancer, is characterized by an alpha hydroxy neoactivity product, e.g., 2HG, e.g., R-2HG. In embodiments this information is used to determine or confirm that a cell proliferation-related disorder, e.g., a cancer, is characterized by an IDH, e.g., IDH1 or IDH2, allele described herein, e.g., an IDH1 allele having a mutation, e.g., a His, Ser, Cys, Gly, Val, or Leu at residue 132, or an IDH2 allele having a mutation, e.g., a mutation at residue 172 (e.g., a K, M, S, G, or W) or at residue 140 (e.g., a Q, W, or L).

In an embodiment, before and/or after treatment has begun, the subject is evaluated or monitored by a method described herein, e.g., the analysis of the presence, distribution, or level of an alpha hydroxy neoactivity product, e.g., 2HG, e.g., R-2HG, e.g., to select, diagnose or prognose the subject, to select an inhibitor, or to evaluate response to the treatment or progression of disease.

In an embodiment the cell proliferation-related disorder is a tumor of the CNS, e.g., a glioma, a leukemia, e.g., AML or ALL, e.g., B-ALL or T-ALL, prostate cancer, fibrosarcoma, paraganglioma, follicular thyroid cancer, myeloma, thyroid cancer, sarcoma, osteosarcoma, myeloproliferative neoplasms (e.g., CML), or myelodysplasia or myelodysplastic syndrome and the evaluation is: evaluation of the presence, distribution, or level of an alpha hydroxy neoactivity product, e.g., 2HG, e.g., R-2HG; or evaluation of the presence, distribution, or level of a neoactivity, e.g., 2HG neoactivity, of an IDH1 or IDH2, mutant protein.

In an embodiment, before or after treatment has begun, the genotype of an IDH mutation associated with alpha hydroxy neoactivity, e.g., 2HG neoactivity, other than a mutation at reside 132 of IDH1 or other than a mutation at residue 140 or 172 of IDH2, is determined.

In an embodiment the presence of an IDH1 mutation at residue 71 of IDH1 associated with alpha hydroxy neoactivity, e.g., 2HG neoactivity, e.g., a mutation having other than a Val at residue 71, e.g., V71I, is determined, e.g., by sequencing genomic DNA or cDNA, from an affected cell.

In an embodiment the presence of an IDH1 mutation at residue 100 or 109 of IDH1 associated with alpha hydroxy neoactivity, e.g., 2HG neoactivity, e.g., a mutation having other than an Arg at residue 100 or 109 is determined, e.g., by sequencing genomic DNA or cDNA, from an affected cell.

In an embodiment, the presence of an IDH1 mutation at residue 70 (e.g., a mutation having other than a Gly at residue 70, (e.g., G70V)), 99 (e.g., a mutation having other than an Ile at residue 99 (e.g., I99M)), 130 (e.g., a mutation having other than an Ile at residue 130 (e.g., I130M)), 133 (e.g., a mutation having other than a His at residue 133 (e.g., H133Q)), 134 (e.g., a mutation having other than a Ala at residue 134 (e.g., A134D)), or 178 (e.g., a mutation having a residue other than a Val at residue 178 (e.g., V178I)) associated with alpha hydroxy neoactivity, e.g., 2HG neoactivity, is determined, e.g., by sequencing genomic DNA or cDNA, from an affected cell.

In an embodiment, the presence of an IDH2 mutation at residue 140 (e.g., a mutation having other than an Arg at residue 140 (e.g., R140Q, R140W, or R140L), 172 (e.g., a mutation having other than an Arg at residue 172 (e.g., R172K, R172M, R172G, R172S, R172W), or 294 (e.g., a mutation having other than a Val at residue 294 (e.g., V294M) associated with alpha hydroxy neoactivity, e.g., 2HG neoactivity, is determined, e.g., by sequencing genomic DNA or cDNA, from an affected cell.

In an embodiment the disorder is other than a solid tumor. In an embodiment the disorder is a tumor that, at the time of diagnosis or treatment, does not have a necrotic portion. In an embodiment the disorder is a tumor in which at least 30, 40, 50, 60, 70, 80 or 90% of the tumor cells carry an IHD, e.g., IDH1 or IDH2, mutation having 2HG neoactivity, at the time of diagnosis or treatment.

In an embodiment the cell proliferation-related disorder is a cancer, e.g., a cancer described herein, characterized by an IDH1 somatic mutant having alpha hydroxy neoactivity, e.g., 2HG neoactivity, e.g., a mutant described herein. In an embodiment the tumor is characterized by increased levels of an alpha hydroxy neoactivity product, 2HG, e.g., R-2HG, as compared to non-diseased cells of the same type.

In an embodiment the method comprises selecting a subject having a glioma, on the basis of the cancer being characterized by unwanted, i.e., increased, levels of an alpha hydroxy neoactivity, product, e.g., 2HG, e.g., R-2HG.

In an embodiment the cell proliferation-related disorder is a tumor of the CNS, e.g., a glioma, e.g., wherein the tumor is characterized by an IDH1 somatic mutant having alpha hydroxy neoactivity, e.g., 2HG neoactivity, e.g., a mutant described herein. Gliomas include astrocytic tumors, oligodendroglial tumors, oligoastrocytic tumors, anaplastic astrocytomas, and glioblastomas. In an embodiment the tumor is characterized by increased levels of an alpha hydroxy neoactivity product, e.g., 2HG, e.g., R-2HG, as compared to non-diseased cells of the same type. E.g., in an embodiment, the IDH1 allele encodes an IDH1 having other than an Arg at residue 132. E.g., the allele encodes His, Ser, Cys, Gly, Val, Pro or Leu (e.g., His, Ser, Cys, Gly, Val, or Leu), or any residue described in Yan et al., at residue 132, according to the sequence of SEQ ID NO:8 (see also FIG. 21). In an embodiment the allele encodes an IDH1 having His at residue 132. In an embodiment the allele encodes an IDH1 having Ser at residue 132.

In an embodiment the IDH1 allele has an A (or any other nucleotide other than C) at nucleotide position 394, or an A (or any other nucleotide other than G) at nucleotide position 395. In an embodiment the allele is a C394A or a G395A mutation according to the sequence of SEQ ID NO:5.

In an embodiment the method comprises selecting a subject having a glioma, wherein the cancer is characterized by having an IDH1 allele described herein, e.g., an IDH1 allele having His, Ser, Cys, Gly, Val, Pro or Leu at residue 132 (SEQ ID NO:8), more specifically His, Ser, Cys, Gly, Val, or Leu; or His or Cys.

In an embodiment the method comprises selecting a subject having a glioma, on the basis of the cancer being characterized by an IDH1 allele described herein, e.g., an IDH1 allele having His, Ser, Cys, Gly, Val, Pro or Leu at residue 132 (SEQ ID NO:8), more specifically His, Ser, Cys, Gly, Val, or Leu; or His or Cys.

In an embodiment, the IDH1 allele encodes an IDH1 having other than a Val at residue 71, e.g., V71I.

In an embodiment the method comprises selecting a subject having a glioma, wherein the cancer is characterized by having an IDH1 allele described herein, e.g., an IDH1 allele having Ile at residue 71 (SEQ ID NO:8).

In an embodiment the method comprises selecting a subject having a glioma, on the basis of the cancer being characterized by an IDH1 allele described herein, e.g., an IDH1 allele having Ile at residue 71 (SEQ ID NO:8).

In an embodiment, the IDH1 allele encodes an IDH1 having other than an Arg at residue 109.

In an embodiment the method comprises selecting a subject having a glioma, wherein the cancer is characterized by having an IDH1 allele described herein, e.g., an IDH1 allele other than an Arg at residue 100 or other than an Arg at residue 109.

In an embodiment the method comprises selecting a subject having a glioma, on the basis of the cancer being characterized by an IDH1 allele described herein, e.g., an IDH1 allele having other than an Arg at residue 100 or other than an Arg at residue 109.

In an embodiment the method comprises selecting a subject having a glioma, on the basis of the cancer being characterized by unwanted, i.e., increased, levels of an alpha hydroxy neoactivity, product, e.g., 2HG, e.g., R-2HG.

In an embodiment, the cell proliferation disorder is fibrosarcoma or paraganglioma wherein the cancer is characterized by an IDH1 allele described herein, e.g., an IDH1 allele having Cys at residue 132 (SEQ ID NO:8).

In an embodiment, the cell proliferation disorder is fibrosarcoma or paraganglioma wherein the cancer is characterized by increased levels of an alpha hydroxy neoactivity, product, e.g., 2HG, e.g., R-2HG.

In an embodiment the cell proliferation-related disorder is localized or metastatic prostate cancer, e.g., prostate adenocarcinoma, e.g., wherein the cancer is characterized by an IDH1 somatic mutant having alpha hydroxy neoactivity, e.g., 2HG neoactivity, e.g., a mutant described herein. In an embodiment the cancer is characterized by increased levels of an alpha hydroxy neoactivity product, e.g., 2HG, e.g., R-2HG, as compared to non-diseased cells of the same type.

E.g., in an embodiment, the IDH1 allele encodes an IDH1 having other than an Arg at residue 132. E.g., the allele encodes His, Ser, Cys, Gly, Val, Pro or Leu, or any residue described in Kang et al, 2009, Int. J. Cancer, 125: 353-355 at residue 132 (e.g., His, Ser, Cys, Gly, Val, or Leu), according to the sequence of SEQ ID NO:8 (see also FIG. 21). In an embodiment the allele encodes an IDH1 having His or Cys at residue 132, specifically, Cys.

In an embodiment the IDH1 allele has a T (or any other nucleotide other than C) at nucleotide position 394, or an A (or any other nucleotide other than G) at nucleotide position 395. In an embodiment the allele is a C394T or a G395A mutation according to the sequence of SEQ ID NO:5.

In an embodiment the method comprises selecting a subject having prostate cancer, e.g., prostate adenocarcinoma, wherein the cancer is characterized by an IDH1 allele described herein, e.g., an IDH1 allele having His or Cys at residue 132 (SEQ ID NO:8).

In an embodiment the method comprises selecting a subject having prostate cancer, e.g., prostate adenocarcinoma, on the basis of the cancer being characterized by an IDH1 allele described herein, e.g., an IDH1 allele having His or Cys at residue 132 (SEQ ID NO:8).

In an embodiment, the IDH1 allele encodes an IDH1 having other than a Val at residue 71, e.g., V71I.

In an embodiment the method comprises selecting a subject having prostate cancer, wherein the cancer is characterized by having an IDH1 allele described herein, e.g., an IDH1 allele having Ile at residue 71 (SEQ ID NO:8).

In an embodiment the method comprises selecting a subject having prostate cancer, on the basis of the cancer being characterized by an IDH1 allele described herein, e.g., an IDH1 allele having Ile at residue 71 (SEQ ID NO:8).

In an embodiment, the IDH1 allele encodes an IDH1 having other than an Arg at residue 100 or other than an Arg at residue 109.

In an embodiment the method comprises selecting a subject having prostate cancer, wherein the cancer is characterized by having an IDH1 allele described herein, e.g., an IDH1 allele other than an Arg at residue 100 or other than an Arg at residue 109.

In an embodiment the method comprises selecting a subject having prostate cancer, on the basis of the cancer being characterized by an IDH1 allele described herein, e.g., an IDH1 allele having other than an Arg at residue 100 or other than an Arg at residue 109.

In an embodiment the method comprises selecting a subject having prostate cancer, on the basis of the cancer being characterized by unwanted, i.e., increased, levels of an alpha hydroxy neoactivity product, e.g., 2HG, e.g., R-2HG.

In an embodiment the cell proliferation-related disorder is a hematological cancer, e.g., a leukemia, e.g., AML, or ALL, wherein the hematological cancer is characterized by an IDH1 somatic mutant having alpha hydroxy neoactivity, e.g., 2HG neoactivity, e.g., a mutant described herein. In an embodiment the cancer is characterized by increased levels of an alpha hydroxy neoactivity product, e.g., 2HG, e.g., R-2HG, as compared to non-diseased cells of the same type.

In an embodiment the cell proliferation-related disorder is acute lymphoblastic leukemia (e.g., an adult or pediatric form), e.g., wherein the acute lymphoblastic leukemia (sometimes referred to herein as ALL) is characterized by an IDH1 somatic mutant having alpha hydroxy neoactivity, e.g., 2HG neoactivity, e.g., a mutant described herein. The ALL can be, e.g., B-ALL or T-ALL. In an embodiment the cancer is characterized by increased levels of an alpha hydroxy neoactivity product, e.g., 2HG, e.g., R-2HG, as compared to non-diseased cells of the same type. E.g., in an embodiment, the IDH1 allele is an IDH1 having other than an Arg at residue 132 (SEQ ID NO:8). E.g., the allele encodes His, Ser, Cys, Gly, Val, Pro or Leu, or any residue described in Kang et al., at residue 132 (e.g., His, Ser, Cys, Gly, Val, or Leu), according to the sequence of SEQ ID NO:8 (see also FIG. 21). In an embodiment the allele encodes an IDH1 having Cys at residue 132.

In an embodiment the IDH1 allele has a T (or any other nucleotide other than C) at nucleotide position 394. In an embodiment the allele is a C394T mutation according to the sequence of SEQ ID NO:5.

In an embodiment the method comprises selecting a subject having ALL, e.g., B-ALL or T-ALL, characterized by an IDH1 allele described herein, e.g., an IDH1 allele having Cys, His or Gly at residue 132 according to the sequence of SEQ ID NO:8.

In an embodiment the method comprises selecting a subject ALL, e.g., B-ALL or T-ALL, on the basis of cancer being characterized by having an IDH1 allele described herein, e.g., an IDH1 allele having Cys at residue 132 (SEQ ID NO:8).

In an embodiment, the IDH1 allele encodes an IDH1 having other than a Val at residue 71, e.g., V71I.

In an embodiment the method comprises selecting a subject having ALL, e.g., B-ALL or T-ALL, wherein the cancer is characterized by having an IDH1 allele described herein, e.g., an IDH1 allele having Ile at residue 71 (SEQ ID NO:8).

In an embodiment the method comprises selecting a subject having ALL, e.g., B-ALL or T-ALL, on the basis of the cancer being characterized by an IDH1 allele described herein, e.g., an IDH1 allele having Ile at residue 71 (SEQ ID NO:8).

In an embodiment, the IDH1 allele encodes an IDH1 having other than an Arg at residue 100 or other than an Arg at residue 109.

In an embodiment the method comprises selecting a subject having ALL, e.g., B-ALL or T-ALL, wherein the cancer is characterized by having an IDH1 allele described herein, e.g., an IDH1 allele other than an Arg at residue 100 or other than an Arg at residue 109.

In an embodiment the method comprises selecting a subject having ALL, e.g., B-ALL or T-ALL, on the basis of the cancer being characterized by an IDH1 allele described herein, e.g., an IDH1 allele having other than an Arg at residue 100 or other than an Arg at residue 109.

In an embodiment the method comprises selecting a subject having ALL, e.g., B-ALL or T-ALL, on the basis of the cancer being characterized by unwanted, i.e., increased, levels of an alpha hydroxy neoactivity product, e.g., 2HG, e.g., R-2HG.

In an embodiment the cell proliferation-related disorder is acute myelogenous leukemia (e.g., an adult or pediatric form), e.g., wherein the acute myelogenous leukemia (sometimes referred to herein as AML) is characterized by an IDH1 somatic mutant having alpha hydroxy neoactivity, e.g., 2HG neoactivity, e.g., a mutant described herein. In an embodiment the cancer is characterized by increased levels of an alpha hydroxy neoactivity product, e.g., 2HG, e.g., R-2HG, as compared to non-diseased cells of the same type. E.g., in an embodiment, the IDH1 allele is an IDH1 having other than an Arg at residue 132 (SEQ ID NO:8). E.g., the allele encodes His, Ser, Cys, Gly, Val, Pro or Leu, or any residue described in Kang et al., at residue 132 (e.g., His, Ser, Cys, Gly, Val, or Leu), according to the sequence of SEQ ID NO:8 (see also FIG. 21). In an embodiment the allele encodes an IDH1 having Cys, His or Gly at residue 132 according to the sequence of SEQ ID NO:8, specifically, Cys.

In an embodiment the IDH1 allele has a T (or any other nucleotide other than C) at nucleotide position 394. In an embodiment the allele is a C394T mutation according to the sequence of SEQ ID NO:5.

In an embodiment the method comprises selecting a subject having acute myelogenous lymphoplastic leukemia (AML) characterized by an IDH1 allele described herein, e.g., an IDH1 allele having Cys, His, Leu or Gly at residue 132 according to the sequence of SEQ ID NO:8, for example, Cys. In an embodiment, the IDH1 allele is an IDH1 having other than an Ile at residue 99 (SEQ ID NO:8), e.g., the allele encodes Met at residue 99.

In an embodiment the method comprises selecting a subject having acute myelogenous lymphoplastic leukemia (AML) on the basis of cancer being characterized by having an IDH1 allele described herein, e.g., an IDH1 allele having Cys, His Leu, or Gly at residue 132 according to the sequence of SEQ ID NO:8, for example, Cys; or an IDH1 allele having Met at residue 99.

In an embodiment the method comprises selecting a subject having acute myelogenous lymphoplastic leukemia (AML), on the basis of the cancer being characterized by unwanted, i.e., increased, levels of an alpha hydroxy neoactivity product, e.g., 2HG, e.g., R-2HG.

In an embodiment, the IDH1 allele encodes an IDH1 having other than a Val at residue 71, e.g., V71I.

In an embodiment the method comprises selecting a subject having AML wherein the cancer is characterized by having an IDH1 allele described herein, e.g., an IDH1 allele having Ile at residue 71 (SEQ ID NO:8).

In an embodiment the method comprises selecting a subject having AML, on the basis of the cancer being characterized by an IDH1 allele described herein, e.g., an IDH1 allele having Ile at residue 71 (SEQ ID NO:8).

In an embodiment, the IDH1 allele encodes an IDH1 having other than an Arg at residue 100 or other than an Arg at residue 109.

In an embodiment the method comprises selecting a subject having AML, wherein the cancer is characterized by having an IDH1 allele described herein, e.g., an IDH1 allele other than an Arg at residue 100 or other than an Arg at residue 109.

In an embodiment the method comprises selecting a subject having AML, on the basis of the cancer being characterized by an IDH1 allele described herein, e.g., an IDH1 allele having other than an Arg at residue 100 or other than an Arg at residue 109.

In an embodiment the method further comprises evaluating the subject for the presence of a mutation in the NRAS or NPMc gene.

In an embodiment the cell proliferation-related disorder is myelodysplasia or myelodysplastic syndrome, e.g., wherein the myelodysplasia or myelodysplastic syndrome is characterized by having an IDH1 somatic mutant having alpha hydroxy neoactivity, e.g., 2HG neoactivity, e.g., a mutant described herein. In an embodiment the disorder is characterized by increased levels of an alpha hydroxy neoactivity product, e.g., 2HG, e.g., R-2HG, as compared to non-diseased cells of the same type. E.g., in an embodiment, the IDH1 allele is an IDH1 having other than an Arg at residue 132 (SEQ ID NO:8). E.g., the allele encodes His, Ser, Cys, Gly, Val, Pro or Leu, or any residue described in Kang et al (e.g., His, Ser, Cys, Gly, Val, or Leu; e.g., Ser, Cys, Gly, or Leu), according to the sequence of SEQ ID NO:8 (see also FIG. 21). In an embodiment the allele encodes an IDH1 having Cys at residue 132.

In an embodiment the IDH1 allele has a T (or any other nucleotide other than C) at nucleotide position 394. In an embodiment the allele is a C394T mutation according to the sequence of SEQ ID NO:5.

In an embodiment the method comprises selecting a subject having myelodysplasia or myelodysplastic syndrome characterized by an IDH1 allele described herein, e.g., an IDH1 allele having Cys at residue 132 according to the sequence of SEQ ID NO:8.

In an embodiment the method comprises selecting a subject having myelodysplasia or myelodysplastic syndrome on the basis of cancer being characterized by having an IDH1 allele described herein, e.g., an IDH1 allele having Cys at residue 132 (SEQ ID NO:8).

In an embodiment, the IDH1 allele encodes an IDH1 having other than a Val at residue 71, e.g., V71I.

In an embodiment the method comprises selecting a subject having myelodysplasia or myelodysplastic syndrome wherein the disorder is characterized by having an IDH1 allele described herein, e.g., an IDH1 allele having Ile at residue 71 (SEQ ID NO:8).

In an embodiment the method comprises selecting a subject having myelodysplasia or myelodysplastic syndrome, on the basis of the disorder being characterized by an IDH1 allele described herein, e.g., an IDH1 allele having Ile at residue 71 (SEQ ID NO:8).

In an embodiment, the IDH1 allele encodes an IDH1 having other than an Arg at residue 100 or other than an Arg at residue 109.

In an embodiment the method comprises selecting a subject having myelodysplasia or myelodysplastic syndrome wherein the disorder is characterized by having an IDH1 allele described herein, e.g., an IDH1 allele other than an Arg at residue 100 or other than an Arg at residue 109.

In an embodiment the method comprises selecting a subject having myelodysplasia or myelodysplastic syndrome on the basis that the disorder is characterized by an IDH1 allele described herein, e.g., an IDH1 allele having other than an Arg at residue 100 or other than an Arg at residue 109.

In an embodiment the method comprises selecting a subject having myelodysplasia or myelodysplastic syndrome, on the basis of the cancer being characterized by unwanted, i.e., increased, levels of an alpha hydroxy neoactivity product, e.g., 2HG, e.g., R-2HG.

In an embodiment, the disorder is thyroid cancer. In an embodiment the method comprises selecting a subject having thyroid cancer wherein the thyroid cancer is characterized by having an IDH1 allele described herein, e.g., an IDH1 allele having mutation at residue 70, 130, 133, 134, or 178 (SEQ ID NO:8) (e.g., G70D, I130M, H133Q, A134D or V178I).

In an embodiment the method comprises selecting a subject having thyroid cancer, on the basis of the thyroid cancer being characterized by an IDH1 allele described herein, e.g., an IDH1 allele having mutation at residue 70, 130, 133, 134, or 178 (SEQ ID NO:8) (e.g., G70D, I130M, H133Q, A134D or V178I).

In an embodiment the method comprises selecting a subject having thyroid cancer, on the basis of the cancer being characterized by unwanted, i.e., increased, levels of an alpha hydroxy neoactivity product, e.g., 2HG, e.g., R-2HG. In an embodiment, the disorder is follicular thyroid cancer or myeloma. In an embodiment the method comprises selecting a subject having follicular thyroid cancer or myeloma, on the basis of the follicular thyroid cancer or myeloma being characterized by unwanted, i.e., increased, levels of an alpha hydroxy neoactivity product, e.g., 2HG, e.g., R-2HG. In an embodiment, the disorder is myeloproliferative neoplasms (e.g., CML).

In an embodiment the method comprises selecting a subject having myeloproliferative neoplasms wherein the myeloproliferative neoplasms is characterized by having an IDH1 allele described herein, e.g., an IDH1 allele having mutation at residue 132 (SEQ ID NO:8) (e.g., R132C or R132G).

In an embodiment the method comprises selecting a subject having myeloproliferative neoplasms, on the basis of the myeloproliferative neoplasms being characterized by an IDH1 allele described herein, e.g., an IDH1 allele having mutation at residue 132 (SEQ ID NO:8) (e.g., R132C or R132G).

In an embodiment the method comprises selecting a subject having myeloproliferative neoplasms, on the basis of the cancer being characterized by unwanted, i.e., increased, levels of an alpha hydroxy neoactivity product, e.g., 2HG, e.g., R-2HG.

In an embodiment the cell proliferation-related disorder is a glioma, characterized by a mutation, or preselected allele, of IDH2 associated with an alpha hydroxy neoactivity, e.g., 2HG neoactivity. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, for example, Lys, Gly, Met, Trp, or Ser according to the sequence of SEQ ID NO:10 (see also FIG. 22). In an embodiment the allele encodes an IDH2 having Lys at residue 172. In an embodiment the allele encodes an IDH2 having Met at residue 172. In an embodiment, the IDH2 allele encodes an IDH2 having other than an Arg at residue 140.

In an embodiment the method comprises selecting a subject having a glioma, wherein the cancer is characterized by having an IDH2 allele described herein, e.g., an IDH2 allele having Lys, Gly, Met, Trp, Thr, or Ser at residue 172 (SEQ ID NO:10), for example Lys, Gly, Met, Trp, or Ser; or Lys or Met (e.g., Lys or Met); or an IDH2 allele having Gln or Trp at residue 140 (SEQ ID NO:10).

In an embodiment the method comprises selecting a subject having a glioma, on the basis of the cancer being characterized by an IDH2 allele described herein, e.g., an IDH2 allele having Lys, Gly, Met, Trp, Thr, or Ser at residue 172 (SEQ ID NO:10), for example, Lys, Gly, Met, Trp, or Ser; or Lys or Met (e.g., Lys or Met); or an IDH2 allele having Gln or Trp at residue 140 (SEQ ID NO:10).

In an embodiment the method comprises selecting a subject having a glioma, on the basis of the cancer being characterized by unwanted, i.e., increased, levels of an alpha hydroxy neoactivity product, e.g., 2HG, e.g., R-2HG. In an embodiment the cell proliferation-related disorder is a prostate cancer, e.g., prostate adenocarcinoma, characterized by a mutation, or preselected allele, of IDH2 associated with an alpha hydroxy neoactivity, e.g., 2HG neoactivity. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, for example, Lys, Gly, Met, Trp, or Ser, according to the sequence of SEQ ID NO:10 (see also FIG. 22). In an embodiment the allele encodes an IDH2 having Lys at residue 172. In an embodiment the allele encodes an IDH2 having Met at residue 172.

In an embodiment the method comprises selecting a subject having a prostate cancer, e.g., prostate adenocarcinoma, wherein the cancer is characterized by having an IDH2 allele described herein, e.g., an IDH2 allele having Lys or Met at residue 172 (SEQ ID NO:10).

In an embodiment the method comprises selecting a subject having a prostate cancer, e.g., prostate adenocarcinoma, on the basis of the cancer being characterized by an IDH2 allele described herein, e.g., an IDH2 allele having Lys or Met at residue 172 (SEQ ID NO:10).

In an embodiment the method comprises selecting a subject having a prostate cancer, e.g., prostate adenocarcinoma, on the basis of the cancer being characterized by unwanted, i.e., increased, levels of an alpha hydroxy neoactivity product, e.g., 2HG, e.g., R-2HG.

In an embodiment the cell proliferation-related disorder is ALL, e.g., B-ALL or T-ALL, characterized by a mutation, or preselected allele, of IDH2 associated with an alpha hydroxy neoactivity, e.g., 2HG neoactivity. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22). In an embodiment the allele encodes an IDH2 having Lys at residue 172. In an embodiment the allele encodes an IDH2 having Met at residue 172.

In an embodiment the method comprises selecting a subject having ALL, e.g., B-ALL or T-ALL, wherein the cancer is characterized by having an IDH2 allele described herein, e.g., an IDH2 allele having Lys or Met at residue 172 (SEQ ID NO:10).

In an embodiment the method comprises selecting a subject having ALL, e.g., B-ALL or T-ALL, on the basis of the cancer being characterized by an IDH2 allele described herein, e.g., an IDH2 allele having Lys or Met at residue 172 (SEQ ID NO:10).

In an embodiment the method comprises selecting a subject having ALL, e.g., B-ALL or T-ALL, on the basis of the cancer being characterized by unwanted, i.e., increased, levels of an alpha hydroxy neoactivity product, e.g., 2HG, e.g., R-2HG.

In an embodiment the cell proliferation-related disorder is AML, characterized by a mutation, or preselected allele, of IDH2 associated with an alpha hydroxy neoactivity, e.g., 2HG neoactivity. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22), for example, Lys, Gly, Met, or Ser. In an embodiment the allele encodes an IDH2 having Lys at residue 172. In an embodiment the allele encodes an IDH2 having Met at residue 172. In an embodiment, the IDH2 allele encodes an IDH2 having other than an Arg at residue 140 (e.g., the allele encodes a Gln or Leu at residue 140).

In an embodiment the method comprises selecting a subject having AML, wherein the cancer is characterized by having an IDH2 allele described herein, e.g., an IDH2 allele having Lys, Gly or Met at residue 172 (SEQ ID NO:10), for example Lys. In an embodiment, the IDH2 allele encodes an IDH2 having other than an Arg at residue 140 (e.g., the allele encodes a Gln or Leu at residue 140).

In an embodiment the method comprises selecting a subject having AML, on the basis of the cancer being characterized by an IDH2 allele described herein, e.g., an IDH2 allele having Lys, Gly or Met at residue 172 (SEQ ID NO:10), for example Lys. In an embodiment, the IDH2 allele encodes an IDH2 having other than an Arg at residue 140 (e.g., the allele encodes a Gln or Leu at residue 140).

In an embodiment the method comprises selecting a subject having AML, on the basis of the cancer being characterized by unwanted, i.e., increased, levels of an alpha hydroxy neoactivity product, e.g., 2HG, e.g., R-2HG.

In an embodiment the cell proliferation-related disorder is myelodysplasia or myelodysplastic syndrome, characterized by a mutation, or preselected allele, of IDH2. E.g., in an embodiment, the IDH2 allele encodes an IDH2 having other than an Arg at residue 172 or other than an Arg at residue 140. E.g., the allele encodes Lys, Gly, Met, Trp, Thr, Ser, or any residue described in described in Yan et al., at residue 172, for example, Lys, Gly, Met, or Ser, according to the sequence of SEQ ID NO:10 (see also FIG. 22). In an embodiment the allele encodes an IDH2 having Lys at residue 172. In an embodiment the allele encodes an IDH2 having Met at residue 172. E.g., the allele encodes Leu (L) or Gln (Q) at residue 140.

In an embodiment the method comprises selecting a subject having myelodysplasia or myelodysplastic syndrome, wherein the cancer is characterized by having an IDH2 allele described herein, e.g., an IDH2 allele having Lys or Met at residue 172 (SEQ ID NO:10), for example, an IDH2 allele having Lys at residue 172 (SEQ ID NO:10); or an IDH2 allele having Leu or Gln at residue 140.

In an embodiment the method comprises selecting a subject having myelodysplasia or myelodysplastic syndrome, on the basis of the cancer being characterized by an IDH2 allele described herein, e.g., an IDH2 allele having Lys or Met at residue 172 (SEQ ID NO:10), for example, an IDH2 allele having Lys at residue 172 (SEQ ID NO:10); or an IDH2 allele having Leu or Gln at residue 140.

In an embodiment the method comprises selecting a subject having myelodysplasia or myelodysplastic syndrome, on the basis of the cancer being characterized by unwanted, i.e., increased, levels of an alpha hydroxy neoactivity product, e.g., 2HG, e.g., R-2HG.

In an embodiment, the disorder is melanoma. In an embodiment the cell proliferation-related disorder is melanoma, characterized by a mutation, or preselected allele, of IDH2. E.g., in an embodiment, the IDH2 allele encodes an IDH2 having other than a Val at residue 294. E.g., the allele encodes Met at residue 294 according to the sequence of SEQ ID NO:10 (see also FIG. 22).

In an embodiment the method comprises selecting a subject having melanoma, wherein the cancer is characterized by having an IDH2 allele described herein, e.g., an IDH2 allele having Met at residue 294 (SEQ ID NO:10).

In an embodiment the method comprises selecting a subject having melanoma, on the basis of the cancer being characterized by an IDH2 allele described herein, e.g., an IDH2 allele having Met at residue 294 (SEQ ID NO:10).

In an embodiment the method comprises selecting a subject having melanoma, on the basis of the cancer being characterized by unwanted, i.e., increased, levels of an alpha hydroxy neoactivity product, e.g., 2HG, e.g., R-2HG.

In an embodiment, the disorder is myeloproliferative neoplasms (e.g., CML). In an embodiment the cell proliferation-related disorder is myeloproliferative neoplasms (e.g., CML), characterized by a mutation, or preselected allele, of IDH2. E.g., in an embodiment, the IDH2 allele encodes an IDH2 having other than an Arg at residue 140 or 172. E.g., the allele encodes Trp (W) at residue 140 or allele encodes Gly (G) at residue 172 according to the sequence of SEQ ID NO:10 (see also FIG. 22).

In an embodiment the method comprises selecting a subject having myeloproliferative neoplasms (e.g., CML), wherein the cancer is characterized by having an IDH2 allele described herein, e.g., an IDH2 allele having Trp at residue 140 or Gly at residue 172 (SEQ ID NO:10).

In an embodiment the method comprises selecting a subject having myeloproliferative neoplasms (e.g., CML), on the basis of the cancer being characterized by an IDH2 allele described herein, e.g., an IDH2 allele having Trp at residue 140 or Gly at residue 172 (SEQ ID NO:10).

In an embodiment a product of the neoactivity is 2HG (e.g., R-2HG) which acts as a metabolite. In another embodiment a product of the neoactivity is 2HG (e.g., R-2HG) which acts as a toxin, e.g., a carcinogen.

In some embodiments, the methods described herein can result in reduced side effects relative to other known methods of treating cancer.

Therapeutic agents and methods of subject evaluation described herein can be combined with other therapeutic modalities, e.g., with art-known treatments.

In an embodiment the method comprises providing a second treatment, to the subject, e.g., surgical removal, irradiation or administration of a chemotherapeutic agent, e.g., an administration of an alkylating agent. Administration (or the establishment of therapeutic levels) of the second treatment can: begin prior to the beginning or treatment with (or prior to the establishment of therapeutic levels of) the inhibitor; begin after the beginning or treatment with (or after the establishment of therapeutic levels of) the inhibitor, or can be administered concurrently with the inhibitor, e.g., to achieve therapeutic levels of both concurrently.

In an embodiment the cell proliferation-related disorder is a CNS tumor, e.g., a glioma, and the second therapy comprises administration of one or more of: radiation; an alkylating agent, e.g., temozolomide, e.g., Temoader®, or BCNU; or an inhibitor of HER1/EGFR tyrosine kinase, e.g., erlotinib, e.g., Tarceva®.

The second therapy, e.g., in the case of glioma, can comprise implantation of BCNU or carmustine in the brain, e.g., implantation of a Gliadel® wafer.

The second therapy, e.g., in the case of glioma, can comprise administration of imatinib, e.g., Gleevec®.

In an embodiment the cell proliferation-related disorder is prostate cancer and the second therapy comprises one or more of: androgen ablation; administration of a microtubule stabilizer, e.g., docetaxol, e.g., Taxotere®; or administration of a topoisomerase II inhibitor, e.g., mitoxantrone.

In an embodiment the cell proliferation-related disorder is ALL, e.g., B-ALL or T-ALL, and the second therapy comprises one or more of:

induction phase treatment comprising the administration of one or more of: a steroid; an inhibitor of microtubule assembly, e.g., vincristine; an agent that reduces the availability of asparagine, e.g., asparaginase; an anthracycline; or an antimetabolite, e.g., methotrexate, e.g., intrathecal methotrexate, or 6-mercaptopurine;

consolidation phase treatment comprising the administration of one or more of: a drug listed above for the induction phase; an antimetabolite, e.g., a guanine analog, e.g., 6-thioguanine; an alkylating agent, e.g., cyclophosphamide; an anti-metabolite, e.g., AraC or cytarabine; or an inhibitor of topoisomerase I, e.g., etoposide; or maintenance phase treatment comprising the administration of one or more of the drugs listed above for induction or consolidation phase treatment.

In an embodiment the cell proliferation-related disorder is AML and the second therapy comprises administration of one or more of: an inhibitor of topoisomerase II, e.g., daunorubicin, idarubicin, topotecan or mitoxantrone; an inhibitor of topoisomerase I, e.g., etoposide; an anti-metabolite, e.g., AraC or cytarabine; or a hypomethylating agent. In an embodiment, the cell proliferation-related disorder is MDS and the second therapy comprises one or more of: an inhibitor of topoisomerase II, e.g., daunorubicin, idarubicin, topotecan or mitoxantrone; an inhibitor of topoisomerase I, e.g., etoposide; an anti-metabolite, e.g., AraC or cytarabine; or a hypomethylating agent. As discussed above, the inventors have discovered that IDH, e.g., IDH1 or IDH2, somatic mutants having alpha hydroxy neoactivity, e.g., 2HG neoactivity, can result in significant increases in the level of cellular alpha hydroxy neoactivity product, e.g., 2HG, e.g., R-2HG. In embodiments the method includes providing a treatment to the subject wherein the treatment comprises:

i) providing a treatment that decreases the ability of an alpha hydroxy neoactivity product, e.g., 2HG, e.g., R-2HG, to compete with a cellular structural analog of the alpha hydroxy neoactivity product, e.g., 2HG, e.g., R-2HG, for interaction with, e.g., binding, to cellular component;

ii) administering to the subject, a cellular structural analog of the alpha hydroxy neoactivity product, e.g., 2HG, e.g., R-2HG, or prodrug thereof; or iii) administering a compound that reduces the cellular levels of the alpha hydroxy neoactivity product, e.g., 2HG, e.g., R-2HG, e.g., by degrading or metabolizing the alpha hydroxy neoactivity product, e.g., 2HG, e.g., R-2HG, thereby treating said subject.

In an embodiment decreasing the ability of an an alpha hydroxy neoactivity product to compete with a cellular structural analog of the alpha hydroxy neoactivity product means increasing the cellular concentration of the structural analog of the alpha hydroxy neoactivity product relative to the concentration of the alpha hydroxy neoactivity product.

In an embodiment a structural analog of the alpha hydroxy neoactivity product, e.g., 2HG, e.g., R-2HG, is a substance can compete, under physiological conditions, with the alpha hydroxy neoactivity product, e.g., 2HG, e.g., R-2HG, for binding to a cellular component, e.g., an enzyme, e.g., prolyl hydroxylase, a dioxygenase, a histone demethylase such as a member of the JHDM family. (JHDM proteins use alpha ketoglutarate and iron (Fe) as cofactors to hydroxylate the methylated substrate.) The affinity of the alpha hydroxy neoactivity product, e.g., 2HG, e.g., R-2HG, for the substrate is at least as great as the affinity of the structural analog of the alpha hydroxy neoactivity product, e.g., 2HG, e.g., R-2HG, for one or more of the named enzymes.

In an embodiment, the cellular structural analog of the alpha hydroxy neoactivity product is a compound of the following formula:

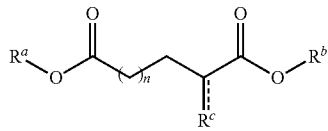

wherein;

each $R^a$ and $R^b$ are independently H, a metal ion, or a negative charge;

$R^c$ is a hydrogen bond donor or acceptor, and can be bound to the carbon chain by way of a single or double bond, as indicated by the dashed line; and n is 0, 1, or 2.

Exemplary hydrogen bond donors include hydroxy and amino groups. An exemplary hydrogen bond acceptor is a carbonyl.

In an embodiment the cellular structural analog of the alpha hydroxy neoactivity product, e.g., 2HG, e.g., R-2HG, is a metabolite, e.g., glutamate or alpha ketoglutarate.

In an embodiment the competition comprises competition between the alpha hydroxy neoactivity product, e.g., 2HG, e.g., R-2HG, and a cellular structural analog of the alpha hydroxy neoactivity product, e.g., alpha ketoglutarate, for interaction with a cellular component, e.g., a cellular protein, e.g., an enzyme. In an embodiment the interaction can comprise binding to the cellular component. In an embodiment the interaction can comprise modification, e.g., covalent modification, of one or more of: the alpha hydroxy neoactivity product, e.g., 2HG, e.g., R-2HG; a cellular structural analog of the alpha hydroxy neoactivity product, e.g., alpha ketoglutarate; or the cellular component, e.g., a cellular protein, e.g., an enzyme. In an embodiment the modification is catalyzed or mediated by the cellular component. E.g., 2HG, e.g., R-2HG, can compete with alpha ketoglutarate, for modification of the alpha ketoglutarate, by the cellular component, e.g., an enzyme.

In embodiments, the increased level of the alpha hydroxy neoactivity product, e.g., 2HG, e.g., R-2HG, alters cellular function, e.g., cellular metabolism or mitochondrial function, by competing with cellular components that are structurally similar to the alpha hydroxy neoactivity product, e.g., 2HG, e.g., R-2HG, e.g., for access to substrates.

In an embodiment the treatment comprises administering a compound, e.g., a compound described herein, which is a naturally occurring cellular structural analog of 2HG, e.g., R-2HG, or prodrug of the naturally occurring cellular structural analog.

Suitable compounds comprise, e.g., a metabolite, e.g., glutamate or alpha ketoglutarate, or a prodrug thereof. In an embodiment the compound competes with 2HG, e.g., R-2HG, for binding to an enzyme. Exemplary enzymes comprise cellular prolyl hydroxylase, a dioxygenase, and a histone demethylase such as a member of the JHDM family In an embodiment the cellular structural analog of alpha hydroxy neoactive product, or prodrug thereof, is a compound of the formula below:

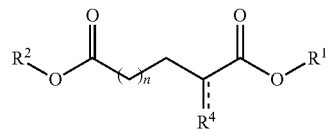

wherein R1, R2, R4 and n are as described herein. Exemplary structural of an alpha hydroxy neoactive product, or prodrug thereof, is a compound of Formula I, II, III, IV or V:

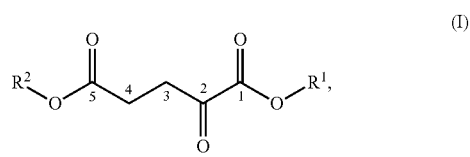

(I)

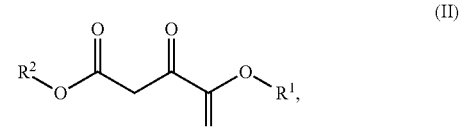

(II)

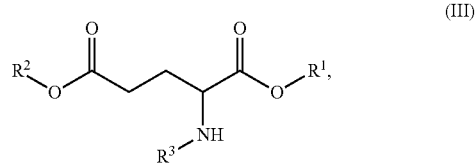

(III)

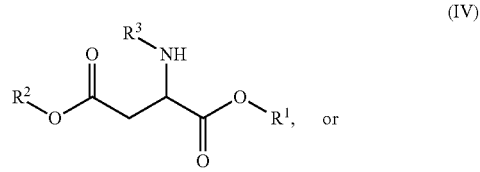

(IV)

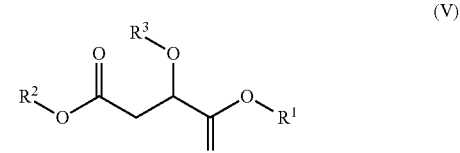

(V)

wherein R1, R2, and R3 are as defined herein.

In an embodiment the treatment comprises administering a compound that reduces the cellular levels of the alpha hydroxy neoactivity product, e.g., 2HG, e.g., R-2HG, e.g., by degrading or metabolizing the alpha hydroxy neoactivity product, e.g., 2HG, e.g., R-2HG. E.g., the treatment can comprise administering a cofactor for an enzyme that metabolizes the alpha hydroxy neoactivity product, e.g., 2HG, e.g., R-2HG, e.g., administering FAD (flavin adenine dinucleotide), or a precursor thereof, e.g., riboflavin, or an analog of FAD, the cofactor for 2HG dehydrogenase.

In an embodiment, the rapeutic agent sequesters an alpha hydroxy neoactivity product, e.g., 2HG, e.g., R-2HG, inactivates an alpha hydroxy neoactivity product, e.g., 2HG, e.g., R-2HG, or increases the metabolic conversion of an alpha hydroxy neoactivity product, e.g., 2HG, e.g., R-2HG, to another product. E.g., such treatment can include the administration of an antibody, aptamer or small molecule that binds to and inactivates an alpha hydroxy neoactivity product, e.g., 2HG, e.g., R-2HG, or the administration of an enzyme, or a nucleic acid encoding an enzyme, that converts an alpha hydroxy neoactivity product, e.g., 2HG, e.g., R-2HG to another compound. E.g, a dehydrogenase, e.g., 2-HG dehydrogenase, or a gene encoding it, or a treatment that increases its activity, can be administered to the subject.

In one aspect, the invention features a method of treating a AML or MDS subject characterized by i) the presence of a mutant IDH having 2HG neoactivity or ii) elevated levels of 2HG, the method comprising administering to the subject in need thereof a therapeutically effective amount of a hypomethylating agent, to thereby treat the subject. In some embodiments, the subject is a subject not having or not diagnosed as having 2-hydroxyglutaric aciduria. In some embodiments, the hypomethylating agent is decitabine (5-aza-deoxycytidine), zebularine, isothiocyanates, azacitidine (5-azacytidine), 5-flouro-2'-deoxycytidine, or 5,6-dihydro-5-azacytidine.

In another aspect, the invention features, a method of evaluating, e.g., diagnosing, a subject, e.g., a subject not having, or not diagnosed as having, 2-hydroxyglutaric aciduria. The method comprises analyzing a parameter related to the neoactivity genotype or phenotype of the subject, e.g., analyzing one or more of:

a) the presence, distribution, or level of a product of an alpha hydroxy neoactivity, e.g., 2HG, e.g., R-2HG, e.g., an increased level of product, 2HG, e.g., R-2HG (as used herein, an increased level of a product of an alpha hydroxy neoactivity, e.g., 2HG, e.g., R-2HG, or similar term, e.g., an increased level of neoactive product or neoactivity product, means increased as compared with a reference, e.g., the level seen in an otherwise similar cell lacking the IDH mutation, e.g., IDH1 or IDH2 mutation, or in a tissue or product from a subject both having);

b) the presence, distribution, or level of an alpha hydroxy neoactivity, e.g., 2HG neoactivity, of an IDH1 or IDH2, mutant protein;

c) the presence, distribution, or level of a neoactive IDH mutant protein, e.g., an IDH1 or IDH2, mutant protein which has alpha hydroxy neoactivity, e.g., 2HG neoactivity, or a corresponding RNA; or d) the presence of a selected somatic allele or mutation conferring IDH neoactivity, e.g., IDH1 or IDH2, which encodes an IDH protein with an alpha hydroxy neoactivity, e.g., 2HG neoactivity, e.g., an allele disclosed herein, in cells characterized by a cell proliferation-related disorder from the subject, thereby evaluating the subject.

In an embodiment analyzing comprises performing a procedure, e.g., a test, to provide data or information on one or more of a-d, e.g., performing a method which results in a physical change in a sample, in the subject, or in a device or reagent used in the analysis, or which results in the formation of an image representative of the data. Methods of obtaining and analyzing samples, and the in vivo analysis in subjects, described elsewhere herein, e.g., in the section entitled, "Methods of evaluating samples and/or subjects," can be combined with this method. In another embodiment analyzing comprises receiving data or information from such test from another party. In an embodiment the analyzing comprises receiving data or information from such test from another party and, the method comprises, responsive to that data or information, administering a treatment to the subject.

As described herein, the evaluation can be used in a number of applications, e.g., for diagnosis, prognosis, staging, determination of treatment efficacy, patent selection, or drug selection.

Thus, in an embodiment method further comprises, e.g., responsive to the analysis of one or more of a-d:

diagnosing the subject, e.g., diagnosing the subject as having a cell proliferation-related disorder, e.g., a disorder characterized by unwanted cell proliferation, e.g., cancer, or a precancerous disorder;

staging the subject, e.g., determining the stage of a cell proliferation-related disorder, e.g., a disorder characterized by unwanted cell proliferation, e.g., cancer, or a precancerous disorder;

providing a prognosis for the subject, e.g., providing a prognosis for a cell proliferation-related disorder, e.g., a disorder characterized by unwanted cell proliferation, e.g., cancer, or a precancerous disorder;

determining the efficacy of a treatment, e.g., the efficacy of a chemotherapeutic agent, irradiation or surgery;

determining the efficacy of a treatment with a therapeutic agent, e.g., an inhibitor, described herein;

selecting the subject for a treatment for a cell proliferation-related disorder, e.g., a disorder characterized by unwanted cell proliferation, e.g., cancer, or a precancerous disorder. The selection can be based on the need for a reduction in alpha hydroxy neoactivity or on the need for amelioration of a condition associated with or resulting from alpha hydroxy neoactivity. For example, if it is determined that the subject has a cell proliferation-related disorder, e.g., cancer, or a precancerous disorder characterized by unwanted, i.e., increased, levels of an alpha hydroxy neoactivity product, e.g., 2HG, e.g., R-2HG, or by a mutant IDH1 or IDH2, having alpha hydroxy neoactivity, e.g., 2HG, neaoctivity, selecting the subject for treatment with a therapeutic agent described herein, e.g., an inhibitor (e.g., a small molecule or a nucleic acid-based inhibitor) of the neoactivity of that mutant (e.g., conversion of alpha-ketoglutarate to 2HG, e.g., R-2HG);

correlating the analysis with an outcome or a prognosis;

providing a value for an analysis on which the evaluation is based, e.g., the value for a parameter correlated to the presence, distribution, or level of an alpha hydroxy neoactivity product, e.g., 2HG, e.g., R-2HG;

providing a recommendation for treatment of the subject; or memorializing a result of, or output from, the method, e.g., a measurement made in the course of performing the method, and optionally transmitting the memorialization to a party, e.g., the subject, a healthcare provider, or an entity that pays for the subject's treatment, e.g., a government, insurance company, or other third party payer.

As described herein, the evaluation can provide information on which a number of decisions or treatments can be based.

Thus, in an embodiment the result of the evaluation, e.g., an unwanted, i.e., increased, level of an alpha hydroxy neoactivity product, e.g., 2HG, e.g., R-2HG, the presence of an IDH, e.g., IDH1 or IDH2, neoactivity, e.g., alpha hydroxy neoactivity, e.g., 2HG neoactivity, the presence of an IDH, e.g., IDH1 or IDH2, mutant protein (or corresponding RNA) which has alpha hydroxy neoactivity, e.g., 2HG neoactivity, the presence of a mutant allele of IDH, e.g., IDH1 or IDH2, having alpha hydroxy neoactivity, 2HG neoactivity, e.g., an allele disclosed herein, is indicative of:

a cell proliferation-related disorder, e.g., cancer, e.g., it is indicative of a primary or metastatic lesion;

the stage of a cell proliferation-related disorder;

a prognosis or outcome for a cell proliferation-related disorder, e.g., it is indicative of a less aggressive form of the disorder, e.g., cancer. E.g., in the case of glioma, presence of an alpha hydroxy neoactivity product, e.g., 2HG, e.g., R-2HG, can indicate a less aggressive form of the cancer;

the efficacy of a treatment, e.g., the efficacy of a chemotherapeutic agent, irradiation or surgery;

the need of a therapy disclosed herein, e.g., inhibition a neoactivity of an IDH, e.g., IDH1 or IDH2, neoactive mutant described herein. In an embodiment relatively higher levels (or the presence of the mutant) is correlated with need of inhibition a neoactivity of an IDH, e.g., IDH1 or IDH2, mutant described herein; or responsiveness to a treatment. The result can be used as a noninvasive biomarker for clinical response. E.g., elevated levels can be predictive on better outcome in glioma patients (e.g., longer life expectancy).

As described herein, the evaluation can provide for the selection of a subject.

Thus, in an embodiment the method comprises, e.g., responsive to the analysis of one or more of a-d, selecting a subject, e.g., for a treatment. The subject can be selected on a basis described herein, e.g., on the basis of:

said subject being at risk for, or having, higher than normal, i.e., increased, levels of an alpha hydroxy neoactivity product, e.g., 2-hydroxyglurarate (e.g., R-2HG) in cell having a cell proliferation-related disorder, e.g., a leukemia such as AML or ALL, e.g., B-ALL or T-ALL, or a tumor lesion, e.g., a glioma or a prostate tumor;

said subject having a proliferation-related disorder characterized by a selected IDH, e.g., IDH1 or IDH2 allele, e.g., an IDH1 or IDH2 mutation, having alpha hydroxy neoactivity, e.g., 2HG neoactivity;

said subject having a selected IDH allele, e.g., a selected IDH1 or IDH2 allele; having alpha hydroxy neoactivity, e.g., 2HG neoactivity;

said subject having a proliferation-related disorder;

said subject being in need of, or being able to benefit from, a therapeutic agent of a type described herein;

said subject being in need of, or being able to benefit from, a compound that inhibits alpha hydroxy neoactivity, e.g., 2HG neoactivity;

said subject being in need of, or being able to benefit from, a compound that lowers the level of an alpha hydroxy neoactivity product, e.g., 2HG, e.g., R-2HG;

said subject being in need of, or being able to benefit from, an antiglycolytic agent or an anti-oxidant, e.g., to ameliorate the effects of an unwanted, i.e., increased, alpha hydroxy neoactivity product, e.g., 2HG. e.g., R-2HG; or said subject being in need of, or being able to benefit from, an treatment that ameliorates an effect of the competition of an alpha hydroxy neoactivity product, e.g., 2HG, e.g., R-2HG, with a cellular component, e.g., alpha ketoglutarate, for interaction with a cellular component.

In an embodiment evaluation comprises selecting the subject, e.g., for treatment with an anti-neoplastic agent, on the establishment of, or determination that, the subject has unwanted, i.e., increased, alpha hydroxy neoactivity product, e.g., 2HG, e.g., R-2HG, or unwanted, i.e., increased, alpha hydroxy neoactivity, e.g., 2HG neoactivity, or that the subject is in need of inhibition of a neoactivity of an IDH, e.g., IDH1 or IDH2, mutant described herein.

As described herein, the evaluations provided for by methods described herein allow the selection of optimal treatment regimens.

Thus, in an embodiment the method comprises, e.g., responsive to the analysis of one or more of a-d, selecting a treatment for the subject, e.g., selecting a treatment on a basis disclosed herein. The treatment can be the administration of a therapeutic agent disclosed herein. The treatment can be selected on the basis that:

it us useful in treating a disorder characterized by one or more of alpha hydroxy neoactivity, e.g., 2HG neoactivity, an IDH1 or IDH2, mutant protein having alpha hydroxy neoactivity, e.g., 2HG neoactivity (or a corresponding RNA);

it is useful in treating a disorder characterized by a selected somatic allele or mutation of an IDH, e.g., IDH1 or IDH2, which encodes a protein with alpha hydroxy neoactivity, e.g., 2HG neoactivity, e.g., an allele disclosed herein, in cells characterized by a cell proliferation-related disorder from the subject;

it reduces the level of an alpha hydroxy neoactivity product, e.g., 2HG, e.g., R-2HG;

it reduces the level of alpha hydroxy neoactivity, e.g., 2HG neoactivity;

it is useful in treating a cancer having mitochondrial damage associated with increased levels of an unwanted, i.e., increased, alpha hydroxy neoactivity product, e.g., 2HG, e.g., R-2HG, and is e.g., an antiglycolytic agent or an anti-oxidant; or it is useful in treating a cancer having levels of an alpha hydroxy neoactivity product, e.g., 2HG, e.g., R-2HG, that compete with a cellular component, e.g., alpha ketoglutarate, for interaction with a cellular component.

In an embodiment evaluation comprises selecting the subject, e.g., for treatment.

In embodiments the treatment is the administration of a therapeutic agent described herein.

The methods can also include treating a subject, e.g., with a treatment selected in response to, or on the basis of, an evaluation made in the method.

Thus, in an embodiment the method comprises, e.g., responsive to the analysis of one or more of a-d, administerin a treatment to the subject, e.g., the administration of a therapeutic agent of a type described herein.

In an embodiment the rapeutic agent comprises a compound from Table 24a or Table 24b or a compound having the structure of Formula (X) or (XI) described below, or a compound as described in U.S. provisional application 61/365,072, the content of which is incorporated herein by reference.

In an embodiment the rapeutic agent comprises nucleic acid, e.g., dsRNA, e.g., a dsRNA described herein.

In an embodiment the rapeutic agent is a cellular structural analog of an alpha hydroxy neoactivity product, or a prodrug thereof, e.g., as described in the section entitled "Cellular structural analogs of neoactivity products, and prodrugs thereof" elsewhere herein.

In an embodiment the rapeutic agent is an antiglycolytic agent, e.g., an anti-glycolytic agent described in the section entitled "Anti-glycolytic compounds" herein.

In an embodiment the rapeutic agent is an antioxidant, e.g., an antioxidant agent described in the section entitled "Anti oxidants" herein.

In an embodiment the rapeutic agent is a hypomethylating agent, e.g., a hypomethylating agent described in the section entitled "Hypomethylating Agents" herein.

In an embodiment the rapeutic agent is an inhibitor, e.g., a polypeptide, peptide, or small molecule (e.g., a molecule of less than 1,000 daltons), or aptomer, that binds to an IDH1 or IDH2 mutant or wildtype subunit and inhibits neoactivity, e.g., by inhibiting formation of a dimer, e.g., a homodimer of mutant IDH1 or IDH2 subunits or a heterodimer of a mutant and a wildtype subunit. In an embodiment the inhibitor is a polypeptide. In an embodiment the polypeptide acts as a dominant negative with respect to the neoactivity of the IDH mutant enzyme. The polypeptide can correspond to full length IDH1 or IDH2 or a fragment thereof. The polypeptide need not be identical with the corresponding residues of wildtype IDH1 or IDH2, but in embodiments has at least 60, 70, 80, 90 or 95% homology with wildtype IDH1 or IDH2.

In an embodiment the rapeutic agent decreases the affinity of an IDH, e.g., IDH1 or IDH2 neoactive mutant protein for NADH, NADPH or a divalent metal ion, e.g., $Mg^{2+}$ or $Mn^{2+}$, or decreases the levels or availability of NADH, NADPH or divalent metal ion, e.g., $Mg^{2+}$ or $Mn^{2+}$, e.g., by competing for binding to the mutant enzyme. In an embodiment the enzyme is inhibited by replacing $Mg^{2+}$ or $Mn^{2+}$ with $Ca^{2+}$.

In an embodiment the rapeutic agent is an inhibitor that reduces the level a neoactivity of an IDH, e.g., IDH1 or IDH2, e.g., 2HG neoactivity.

In an embodiment the rapeutic agent is an inhibitor that reduces the level of the product of a mutant having a neoactivity of an IDH, e.g., IDH1 or IDH2 mutant, e.g., it reduces the level of 2HG, e.g., R-2HG.

In an embodiment the rapeutic agent is an inhibitor that:
inhibits, e.g., specifically, a neoactivity of an IDH, e.g., IDH1 or IDH2, e.g., a neoactivity described herein, e.g., 2HG neoactivity; or
inhibits both the wildtype activity and a neoactivity of an IDH, e.g., IDH1 or IDH2, e.g., a neoactivity described herein, e.g., 2HG neoactivity.

In an embodiment the rapeutic agent is an inhibitor that is selected on the basis that it:
inhibits, e.g., specifically, a neoactivity of an IDH, e.g., IDH1 or IDH2, e.g., a neoactivity described herein e.g., 2HG neoactivity; or
inhibits both the wildtype activity and a neoactivity of an IDH1, e.g., IDH1 or IDH2, e.g., a neoactivity described herein, e.g., 2HG neoactivity.

In an embodiment the rapeutic agent is an inhibitor that reduces the amount of a mutant IDH, e.g., IDH1 or IDH2, protein or mRNA.

In an embodiment the rapeutic agent is an inhibitor that interacts directly with, e.g., it binds to, the mutant IDH, e.g., IDH1 or IDH2 mRNA.

In an embodiment the rapeutic agent is an inhibitor that interacts directly with, e.g., it binds to, the mutant IDH, e.g., IDH1 or IDH2, protein.

In an embodiment the rapeutic agent is an inhibitor that reduces the amount of neoactive IDH enzyme activity, e.g., by interacting with, e.g., binding to, mutant IDH, e.g., IDH1 or IDH2, protein. In an embodiment the inhibitor is other than an antibody.

In an embodiment, the inhibitor binds mutant IDH1 and reduces the interaction between reside N96 or S94 with alpha ketoglutarate.

In an embodiment, the inhibitor binds IDH1 and causes an alteration in the positions of N96 or S94 of the mutant IDH1.

In an embodiment, the inhibitor binds IDH1 and causes an alteration in the position of residue Y139.

In an embodiment the rapeutic agent is an inhibitor that is a small molecule and interacts with, e.g., binds, the mutant RNA, e.g., mutant IDH1 or IDH2 mRNA.

In an embodiment the rapeutic agent is an inhibitor that interacts directly with, e.g., binds, either the mutant IDH, e.g., IDH1 or IDH2, protein or interacts directly with, e.g., binds, the mutant IDH mRNA, e.g., IDH1 or IDH2 mRNA.

In an embodiment the rapeutic agent is administered.

In an embodiment the treatment: inhibits, e.g., specifically, a neoactivity of IDH1 or IDH2; or inhibits both the wildtype and activity and a neoactivity of IDH1 or IDH2. In an embodiment, the subject is subsequently evaluated or monitored by a method described herein, e.g., the analysis of the presence, distribution, or level of an alpha hydroxy neoactivity product, e.g., 2HG, e.g., R-2HG, e.g., to evaluate response to the treatment or progression of disease.

In an embodiment the treatment is selected on the basis that it: inhibits, e.g., specifically, a neoactivity of IDH1 or IDH2, e.g., alpha hydroxy neoactivity, e.g., 2HG neoactivity; or inhibits both the wildtype and activity and a neoactivity of IDH1 or IDH2, e.g., a neoactivity described herein.

In an embodiment, the method comprises determining the possibility of a mutation other than a mutation in IDH1 or in IDH2. In embodiments, a relatively high level of 2HG, e.g., R-2HG is indicative of another mutation.

In an embodiment, which embodiment includes selecting or administering a treatment for the subject, the subject:
has not yet been treated for the subject the cell proliferation-related disorder and the selected or administered treatment is the initial or first line treatment;
has already been treated for the cell proliferation-related and the selected or administered treatment results in an alteration of the existing treatment;
has already been treated for the cell proliferation-related, and the selected treatment results in continuation of the existing treatment; or
has already been treated for the cell proliferation-related disorder and the selected or administered treatment is different, e.g., as compared to what was administered prior to the evaluation or to what would be administered in the absence of elevated levels of an alpha hydroxy neoactivity product, e.g., 2HG, e.g., R-2HG.

In an embodiment, which embodiment includes selecting or administering a treatment for the subject, the selected or administered treatment can comprise:
a treatment which includes administration of a therapeutic agent at different, e.g., a greater (or lesser) dosage (e.g., different as compared to what was administered prior to the evaluation or to what would be administered in the absence of elevated levels of an alpha hydroxy neoactivity product, e.g., 2HG, e.g., R-2HG);
a treatment which includes administration of a therapeutic agent at a different frequency, e.g., more or less frequently, or not at all (e.g., different as compared to what was administered prior to the evaluation or to what would be administered in the absence of elevated levels of an alpha hydroxy neoactivity product, e.g., 2HG, e.g., R-2HG); or
a treatment which includes administration of a therapeutic agent in a different therapeutic setting (e.g., adding or deleting a second treatment from the treatment regimen) (e.g., different as compared to what was administered prior to the evaluation or to what would be administered in the absence of elevated levels of an alpha hydroxy neoactivity product, e.g., 2HG, e.g., R-2HG).

Methods of evaluating a subject described herein can comprise evaluating a neoactivity genotype or phenotype. Methods of obtaining and analyzing samples, and the in vivo analysis in subjects, described elsewhere herein, e.g., in the section entitled, "Methods of evaluating samples and/or subjects," can be combined with this method.

In an embodiment the method comprises:
subjecting the subject (e.g., a subject not having 2-hydroxyglutaric aciduria) to imaging and/or spectroscopic analysis, e.g., magnetic resonance-based analysis, e.g., MRI and/or MRS e.g., imaging analysis, to provide a determination of the presence, distribution, or level of an alpha hydroxy neoactivity product, e.g., 2HG, e.g., R-2HG, e.g., as associated with a tumor, e.g., a glioma, in the subject;

optionally storing a parameter related to the determination, e.g., the image or a value related to the image from the imaging analysis, in a tangible medium; and responsive to the determination, performing one or more of: correlating the determination with outcome or with a prognosis; providing an indication of outcome or prognosis; providing a value for an analysis on which the evaluation is based, e.g., the presence, distribution, or level of an alpha hydroxy neoactivity product, e.g., 2HG, e.g., R-2HG; providing a recommendation for treatment of the subject; selecting a course of treatment for the subject, e.g., a course of treatment described herein, e.g., selecting a course of treatment that includes inhibiting a neoactivity of a mutant IDH, e.g., IDH1 or IDH2, allele, e.g., a neoactivity described herein; administering a course of treatment to the subject, e.g., a course of treatment described herein, e.g., a course of treatment that includes inhibiting a neoactivity of a mutant IDH, e.g., IDH1 or IDH2, allele, e.g., a neoactivity described herein; and memorializing a result of the method or a measurement made in the course of the method, e.g., one or more of the above and/or transmitting memorialization of one or more of the above to a party, e.g., the subject, a healthcare provider, or an entity that pays for the subject's treatment, e.g., a government, insurance company, or other third party payer.

In an embodiment the method comprises confirming or determining, e.g., by direct examination or evaluation of the subject, or sample e.g., tissue, product (e.g., feces, sweat, semen, exhalation, hair or nails), or bodily fluid (e.g., blood (e.g., blood plasma), urine, lymph, or cerebrospinal fluid or other sample sourced disclosed herein) therefrom, (e.g., by DNA sequencing or immuno analysis or evaluation of the presence, distribution or level of an alpha hydroxy neoactivity product, e.g., 2HG, e.g., R-2HG), or receiving such information about the subject, that the subject has a cancer characterized by an IDH, e.g., IDH1 or IDH2, allele described herein, e.g., an IDH1 allele having His or Cys at residue 132 (SEQ ID NO:8) or an IDH2 allele having a mutation at residue 172 or 140 such as a mutation described herein.

In an embodiment, prior to or after treatment, the method includes evaluating the growth, size, weight, invasiveness, stage or other phenotype of the cell proliferation-related disorder.

In an embodiment the cell proliferation-related disorder is a tumor of the CNS, e.g., a glioma, a leukemia, e.g., AML or ALL, e.g., B-ALL or T-ALL, prostate cancer, or myelodysplasia or myelodysplastic syndrome, thyroid cancer such as follicular thyroid cancer, fibrosarcoma, paraganglioma, myeloma, melanoma, myeloproliferative neoplasms such as CML and the evaluation is a or b. In an embodiment the method comprises evaluating a sample, e.g., a sample described herein, e.g., a tissue, e.g., a cancer sample, or a bodily fluid, e.g., serum or blood, for increased alpha neoactivity product, e.g., 2HG, e.g., R-2HG.

In an embodiment the tumor is other than a tumor of the CNS, e.g., other than a glioma, and the analysis includes determining the sequence of a mutation at position 132 of IDH1, or a mutation at position 172 of IDH2. E.g., the sequence of IDH1 at any of position 70, 71, 100, 109, 130, 132, 133, 134, or 178 can be determined, e.g., to detect the presence of a mutation having 2HG neoactivity. In an embodiment the tumor is a glioma and the presence of an IDH1 2HG neoactive mutation other than a mutation at 132 of IDH1 is determined. In an embodiment the tumor is a glioma and the presence of an IDH1 2HG neoactive mutation other than a mutation at 172 at IDH2 is determined, e.g., a mutation at either 140 or 294.

In an embodiment, a subject is subjected to MRS and the evaluation comprises evaluating the presence or elevated amount of a peak correlated to or corresponding to 2HG, e.g., R-2HG, as determined by magnetic resonance. For example, a subject can be analyzed for the presence and/or strength of a signal at about 2.5 ppm to determine the presence and/or amount of 2HG, e.g., R-2HG in the subject.

In an embodiment the method comprises obtaining a sample from the subject and analyzing the sample, or analyzing the subject, e.g., by imaging the subject and optionally forming a representation of the image on a computer.

In an embodiment the results of the analysis is compared to a reference.

In an embodiment a value for a parameter correlated to the presence, distribution, or level, e.g., of 2HG, e.g., R-2HG, is determined. It can be compared with a reference value, e.g., the value for a reference subject not having abnormal presence, level, or distribution, e.g., a reference subject cell not having a mutation in IDH, e.g., IDH1 or IDH2, having a neoactivity described herein.

In an embodiment the method comprises determining if an IDH, e.g., IDH1 or IDH2, mutant allele that is associated with 2HG neoactivity is present. E.g., in the case of IDH1, the presence of a mutation at residue 132 associated with 2HG neoactivity can be determined.

In an embodiment the presence of a mutation at residue 71 having alpha hydroxy neoactivity, e.g., 2HG neoactivity, e.g., a mutation having other than a Val at residue 71, e.g., V71I, can be determined.

In an embodiment the presence of a mutation at residue 100 or 109 having alpha hydroxy neoactivity, e.g., 2HG neoactivity, e.g., a mutation having other than an Arg at residue 100 or 109, can be determined.

In an embodiment, the presence of an IDH1 mutation at residue 70 (e.g., a mutation having other than a Gly at residue 70, (e.g., G70D)), 99 (e.g., a mutation having other than an Ile at residue 99 (e.g., I99M)), 130 (e.g., a mutation having other than an Ile at residue 130 (e.g., I130M)), 133 (e.g., a mutation having other than a His at residue 133 (e.g., H133Q)), 134 (e.g., a mutation having other than an Ala at residue 134 (e.g., A134D)), or 178 (e.g., a mutation having a residue other than a Val at residue 178 (e.g., V178I)) associated with alpha hydroxy neoactivity, e.g., 2HG neoactivity, can be determined. In the case of IDH2, the presence of a mutation at residue 140, 172, or 294 (e.g., 172) associated with 2HG neoactivity can be determined. The determination can comprise sequencing a nucleic acid, e.g., genomic DNA or cDNA, from an affected cell, which encodes the relevant amino acid(s). The mutation can be a deletion, insertion, rearrangement, or substitution. The mutation can involve a single nucleotide, e.g., a single substitution, or more than one nucleotide, e.g., a deletion of more than one nucleotides.

In an embodiment the method comprises determining the sequence at position 394 or 395 of the IDH1 gene, or determining the identity of amino acid residue 132 (SEQ ID NO:8) in the IDH1 gene in a cell characterized by the cell proliferation related disorder.

In an embodiment the method comprises, e.g., step d comprises, determining the genotype of an IDH mutation associated with alpha hydroxy neoactivity, e.g., 2HG neoactivity, other than a mutation at reside 132 of IDH1 or other than a mutation at residue 172 of IDH2.

In an embodiment the presence of an IDH1 mutation at residue 100 or 109 of IDH1 associated with alpha hydroxy neoactivity, e.g., 2HG neoactivity, e.g., a mutation having other than an Arg at residue 100 or residue 109, is determined, e.g., by sequencing genomic DNA or cDNA, from an affected cell.

In an embodiment, the presence of an IDH1 mutation at residue 70 (e.g., a mutation having other than a Gly at residue 70, (e.g., G70D)), 99 (e.g., a mutation having other than an Ile at residue 99 (e.g., I99M)), 130 (e.g., a mutation having other than an Ile at residue 130 (e.g., I130M)), 133 (e.g., a mutation having other than a His at residue 133 (e.g., H133Q)), 134 (e.g., a mutation having other than an Ala at residue 134 (e.g., A134D)), or 178 (e.g., a mutation having a residue other than a Val at residue 178 (e.g., V178I)) associated with alpha hydroxy neoactivity, e.g., 2HG neoactivity, is determined, e.g., by sequencing genomic DNA or cDNA, from an affected cell.

In an embodiment the method comprises determining the amino acid sequence, e.g., by DNA sequencing, at position 140, 172, or 294 (e.g., 140 or 172) of the IDH2 gene in a cell characterized by the cell proliferation related disorder.

In an embodiment a product of the neoactivity is 2-HG, e.g., R-2HG, which acts as a metabolite. In another embodiment a product of the neoactivity is 2HG, e.g., R-2HG, which acts as a toxin, e.g., a carcinogen.

In an embodiment the disorder is other than a solid tumor. In an embodiment the disorder is a tumor that, at the time of diagnosis or treatment, does not have a necrotic portion. In an embodiment the disorder is a tumor in which at least 30, 40, 50, 60, 70, 80 or 90% of the tumor cells carry an IDH, e.g., IDH1 or IDH2, mutation having 2HG neoactivity, at the time of diagnosis or treatment.

In an embodiment the cell proliferation-related disorder is a cancer, e.g., a cancer described herein, characterized by an IDH1 somatic mutant having alpha hydroxy neoactivity, e.g., 2HG neoactivity, e.g., a mutant described herein. In an embodiment the tumor is characterized by increased levels of an alpha hydroxy neoactivity product, 2HG, e.g., R-2HG, as compared to non-diseased cells of the same type.

In an embodiment the method comprises selecting a subject having a glioma, on the basis of the cancer being characterized by unwanted, i.e., increased, levels of an alpha hydroxy neoactivity, product, e.g., 2HG, e.g., R-2HG.

In an embodiment the cell proliferation-related disorder is a tumor of the CNS, e.g., a glioma, e.g., wherein the tumor is characterized by an IDH1 somatic mutant having alpha hydroxy neoactivity, e.g., 2HG neoactivity, e.g., a mutant described herein. Gliomas include astrocytic tumors, oligodendroglial tumors, oligoastrocytic tumors, anaplastic astrocytomas, and glioblastomas. In an embodiment the tumor is characterized by increased levels of an alpha hydroxy neoactivity product, e.g., 2HG, e.g., R-2HG, as compared to non-diseased cells of the same type. E.g., in an embodiment, the IDH1 allele encodes an IDH1 having other than an Arg at residue 132. E.g., the allele encodes His, Ser, Cys, Gly, Val, Pro or Leu, or any residue described in Yan et al., at residue 132, according to the sequence of SEQ ID NO:8 (see also FIG. 21). In an embodiment the allele encodes an IDH1 having His at residue 132. In an embodiment the allele encodes an IDH1 having Ser at residue 132.

In an embodiment the IDH1 allele has an A (or any other nucleotide other than C) at nucleotide position 394, or an A (or any other nucleotide other than G) at nucleotide position 395. In an embodiment the allele is a C394A, a C394G, a C394T, a G395C, a G395T or a G395A mutation, specifically C394A or a G395A mutation according to the sequence of SEQ ID NO:5.

In an embodiment the method comprises selecting a subject having a glioma, wherein the cancer is characterized by having an IDH1 allele described herein, e.g., an IDH1 allele having His, Ser, Cys, Gly, Val, Pro, or Leu at residue 132 (SEQ ID NO:8) (e.g., His, Ser, Cys, Gly, Val, or Leu; or His or Cys).

In an embodiment the method comprises selecting a subject having a glioma, on the basis of the cancer being characterized by an IDH1 allele described herein, e.g., an IDH1 allele having His, Ser, Cys, Gly, Val, Pro or Leu at residue 132 (SEQ ID NO:8) (e.g., His, Ser, Cys, Gly, Val, or Leu; or His or Cys).

In an embodiment, the IDH1 allele encodes an IDH1 having other than a Val at residue 71, e.g., V71I.

In an embodiment the method comprises selecting a subject having a glioma, wherein the cancer is characterized by having an IDH1 allele described herein, e.g., an IDH1 allele having Ile at residue 71 (SEQ ID NO:8).

In an embodiment the method comprises selecting a subject having a glioma, on the basis of the cancer being characterized by an IDH1 allele described herein, e.g., an IDH1 allele having Ile at residue 71 (SEQ ID NO:8).

In an embodiment, the IDH1 allele encodes an IDH1 having other than an Arg at residue 100 or other than an Arg at residue 109.

In an embodiment the method comprises selecting a subject having a glioma, wherein the cancer is characterized by having an IDH1 allele described herein, e.g., an IDH1 allele other than an Arg at residue 100 or other than an Arg at residue 109.

In an embodiment the method comprises selecting a subject having a glioma, on the basis of the cancer being characterized by an IDH1 allele described herein, e.g., an IDH1 allele having other than an Arg at residue 100 or other than an Arg at residue 109.

In an embodiment the method comprises selecting a subject having a glioma, on the basis of the cancer being characterized by unwanted, i.e., increased, levels of an alpha hydroxy neoactivity, product, e.g., 2HG, e.g., R-2HG.

In an embodiment, the cell proliferation disorder is fibrosarcoma wherein the cancer is characterized by having an IDH1 allele described herein, e.g., an IDH1 allele having Cys at residue 132 (SEQ ID NO:8).

In an embodiment, the cell proliferation disorder is fibrosarcoma wherein the cancer is characterized by an IDH1 allele described herein, e.g., an IDH1 allele having Cys at residue 132 (SEQ ID NO:8).

In an embodiment, the cell proliferation disorder is fibrosarcoma wherein the cancer is characterized by increased levels of an alpha hydroxy neoactivity, product, e.g., 2HG, e.g., R-2HG.

In an embodiment, the cell proliferation disorder is paraganglioma wherein the cancer is characterized by having an IDH1 allele described herein, e.g., an IDH1 allele having Cys or His at residue 132 (SEQ ID NO:8).

In an embodiment, the cell proliferation disorder is paraganglioma wherein the cancer is characterized by an IDH1 allele described herein, e.g., an IDH1 allele having Cys or His at residue 132 (SEQ ID NO:8).

In an embodiment, the cell proliferation disorder is paraganglioma wherein the cancer is characterized by increased levels of an alpha hydroxy neoactivity, product, e.g., 2HG, e.g., R-2HG.

In an embodiment the cell proliferation-related disorder is localized or metastatic prostate cancer, e.g., prostate adenocarcinoma, e.g., wherein the cancer is characterized by an IDH1 somatic mutant having alpha hydroxy neoactivity, e.g., 2HG neoactivity, e.g., a mutant described herein. In an embodiment the cancer is characterized by increased levels of an alpha hydroxy neoactivity product, e.g., 2HG, e.g., R-2HG, as compared to non-diseased cells of the same type.

E.g., in an embodiment, the IDH1 allele encodes an IDH1 having other than an Arg at residue 132. E.g., the allele encodes His, Ser, Cys, Gly, Val, Pro or Leu, or any residue described in Kang et al, 2009, Int. J. Cancer, 125: 353-355 at residue 132, according to the sequence of SEQ ID NO:8 (see also FIG. 21) (e.g., His, Ser, Cys, Gly, Val, or Leu). In an embodiment the allele encodes an IDH1 having His or Cys at residue 132.

In an embodiment the IDH1 allele has a T (or any other nucleotide other than C) at nucleotide position 394, or an A (or any other nucleotide other than G) at nucleotide position 395. In an embodiment the allele is a C394T or a G395A mutation according to the sequence of SEQ ID NO:5.

In an embodiment the method comprises selecting a subject having prostate cancer, e.g., prostate adenocarcinoma, wherein the cancer is characterized by an IDH1 allele described herein, e.g., an IDH1 allele having His or Cys at residue 132 (SEQ ID NO:8).

In an embodiment the method comprises selecting a subject having prostate cancer, e.g., prostate adenocarcinoma, on the basis of the cancer being characterized by an IDH1 allele described herein, e.g., an IDH1 allele having His or Cys at residue 132 (SEQ ID NO:8).

In an embodiment, the IDH1 allele encodes an IDH1 having other than a Val at residue 71, e.g., V71I.

In an embodiment the method comprises selecting a subject having prostate cancer, wherein the cancer is characterized by having an IDH1 allele described herein, e.g., an IDH1 allele having Ile at residue 71 (SEQ ID NO:8).

In an embodiment the method comprises selecting a subject having prostate cancer, on the basis of the cancer being characterized by an IDH1 allele described herein, e.g., an IDH1 allele having Ile at residue 71 (SEQ ID NO:8).

In an embodiment, the IDH1 allele encodes an IDH1 having other than an Arg at residue 100 or other than an Arg at residue 109.

In an embodiment the method comprises selecting a subject having prostate cancer, wherein the cancer is characterized by having an IDH1 allele described herein, e.g., an IDH1 allele other than an Arg at residue 100 or other than an Arg at residue 109.

In an embodiment the method comprises selecting a subject having prostate cancer, on the basis of the cancer being characterized by an IDH1 allele described herein, e.g., an IDH1 allele having other than an Arg at residue 100 or other than an Arg at residue 109.

In an embodiment the method comprises selecting a subject having prostate cancer, on the basis of the cancer being characterized by unwanted, i.e., increased, levels of an alpha hydroxy neoactivity product, e.g., 2HG, e.g., R-2HG.

In an embodiment the cell proliferation-related disorder is a hematological cancer, e.g., a leukemia, e.g., AML, or ALL, wherein the hematological cancer is characterized by an IDH1 somatic mutant having alpha hydroxy neoactivity, e.g., 2HG neoactivity, e.g., a mutant described herein. In an embodiment the cancer is characterized by increased levels of an alpha hydroxy neoactivity product, e.g., 2HG, e.g., R-2HG, as compared to non-diseased cells of the same type.

In an embodiment the method comprises evaluating a serum or blood sample for increased alpha neoactivity product, e.g., 2HG, e.g., R-2HG.

In an embodiment the cell proliferation-related disorder is acute lymphoblastic leukemia (e.g., an adult or pediatric form), e.g., wherein the acute lymphoblastic leukemia (sometimes referred to herein as ALL) is characterized by an IDH1 somatic mutant having alpha hydroxy neoactivity, e.g., 2HG neoactivity, e.g., a mutant described herein. The ALL can be, e.g., B-ALL or T-ALL. In an embodiment the cancer is characterized by increased levels of an alpha hydroxy neoactivity product, e.g., 2HG, e.g., R-2HG, as compared to non-diseased cells of the same type. E.g., in an embodiment, the IDH1 allele is an IDH1 having other than an Arg at residue 132 (SEQ ID NO:8). E.g., the allele encodes His, Ser, Cys, Gly, Val, Pro or Leu, or any residue described in Kang et al., at residue 132, according to the sequence of SEQ ID NO:8 (see also FIG. 21) (e.g., His, Ser, Cys, Gly, Val, or Leu). In an embodiment the allele encodes an IDH1 having Cys at residue 132.

In an embodiment the IDH1 allele has a T (or any other nucleotide other than C) at nucleotide position 394. In an embodiment the allele is a C394T mutation according to the sequence of SEQ ID NO:5.

In an embodiment the method comprises selecting a subject having ALL, e.g., B-ALL or T-ALL, characterized by an IDH1 allele described herein, e.g., an IDH1 allele having Cys at residue 132 according to the sequence of SEQ ID NO:8.

In an embodiment the method comprises selecting a subject ALL, e.g., B-ALL or T-ALL, on the basis of cancer being characterized by having an IDH1 allele described herein, e.g., an IDH1 allele having Cys at residue 132 (SEQ ID NO:8).

In an embodiment, the IDH1 allele encodes an IDH1 having other than a Val at residue 71, e.g., V71I.

In an embodiment the method comprises selecting a subject having ALL, e.g., B-ALL or T-ALL, wherein the cancer is characterized by having an IDH1 allele described herein, e.g., an IDH1 allele having Ile at residue 71 (SEQ ID NO:8).

In an embodiment the method comprises selecting a subject having ALL, e.g., B-ALL or T-ALL, on the basis of the cancer being characterized by an IDH1 allele described herein, e.g., an IDH1 allele having Ile at residue 71 (SEQ ID NO:8).

In an embodiment, the IDH1 allele encodes an IDH1 having other than an Arg at residue 100 or other than an Arg at residue 109.

In an embodiment the method comprises selecting a subject having ALL, e.g., B-ALL or T-ALL, wherein the cancer is characterized by having an IDH1 allele described herein, e.g., an IDH1 allele other than an Arg at residue 100 or other than an Arg at residue 109.

In an embodiment the method comprises selecting a subject having ALL, e.g., B-ALL or T-ALL, on the basis of the cancer being characterized by an IDH1 allele described herein, e.g., an IDH1 allele having other than an Arg at residue 100 or other than an Arg at residue 109.

In an embodiment the method comprises selecting a subject having ALL, e.g., B-ALL or T-ALL, on the basis of the cancer being characterized by unwanted, i.e., increased, levels of an alpha hydroxy neoactivity product, e.g., 2HG, e.g., R-2HG. In an embodiment the method comprises evaluating a sample, e.g., a serum or blood sample, for increased alpha neoactivity product, e.g., 2HG, e.g., R-2HG.

In an embodiment the cell proliferation-related disorder is acute myelogenous leukemia (e.g., an adult or pediatric form), e.g., wherein the acute myelogenous leukemia (sometimes referred to herein as AML) is characterized by an IDH1 somatic mutant having alpha hydroxy neoactivity, e.g., 2HG neoactivity, e.g., a mutant described herein. In an embodiment the cancer is characterized by increased levels of an alpha hydroxy neoactivity product, e.g., 2HG, e.g., R-2HG, as compared to non-diseased cells of the same type. E.g., in an embodiment, the IDH1 allele is an IDH1 having other than an Arg at residue 132 (SEQ ID NO:8). E.g., the allele encodes His, Ser, Cys, Gly, Val, Pro or Leu, or any residue described in Kang et al., at residue 132, according to the sequence of SEQ ID NO:8 (see also FIG. 21) (e.g., His, Ser, Cys, Gly, Val or Leu). In an embodiment the allele encodes an IDH1 having Ser, Cys, Leu, or His at residue 132. E.g., in an embodiment, the IDH1 allele is an IDH1 having other than an Ile at residue 99 (SEQ ID NO:8) (e.g., I99M). In an embodiment the IDH1 allele has a T (or any other nucleotide other than C) at nucleotide position 394. In an embodiment the allele is a C394T mutation according to the sequence of SEQ ID NO:5.

In an embodiment the method comprises selecting a subject having acute myelogenous lymphoplastic leukemia (AML) characterized by an IDH1 allele described herein, e.g., an IDH1 allele having Cys, His or Gly at residue 132 according to the sequence of SEQ ID NO:8, for example, Cys.

In an embodiment the method comprises selecting a subject having acute myelogenous lymphoplastic leukemia (AML) on the basis of cancer being characterized by having an IDH1 allele described herein, e.g., an IDH1 allele having Cys, His or Gly at residue 132 according to the sequence of SEQ ID NO:8, specifically, Cys.

In an embodiment the method comprises selecting a subject having acute myelogenous lymphoplastic leukemia (AML), on the basis of the cancer being characterized by unwanted, i.e., increased, levels of an alpha hydroxy neoactivity product, e.g., 2HG, e.g., R-2HG. In an embodiment the method comprises evaluating a sample, e.g., a serum or blood sample, for increased alpha neoactivity product, e.g., 2HG, e.g., R-2HG.

In an embodiment, the IDH1 allele encodes an IDH1 having other than a Val at residue 71, e.g., V71I.

In an embodiment the method comprises selecting a subject having AML wherein the cancer is characterized by having an IDH1 allele described herein, e.g., an IDH1 allele having Ile at residue 71 (SEQ ID NO:8).

In an embodiment the method comprises selecting a subject having AML, on the basis of the cancer being characterized by an IDH1 allele described herein, e.g., an IDH1 allele having Ile at residue 71 (SEQ ID NO:8).

In an embodiment, the IDH1 allele encodes an IDH1 having other than an Arg at residue 100 or other than an Arg at residue 109.

In an embodiment the method comprises selecting a subject having AML, wherein the cancer is characterized by having an IDH1 allele described herein, e.g., an IDH1 allele other than an Arg at residue 100 or other than an Arg at residue 109.

In an embodiment the method comprises selecting a subject having AML, on the basis of the cancer being characterized by an IDH1 allele described herein, e.g., an IDH1 allele having other than an Arg at residue 100 or other than an Arg at residue 109.

In an embodiment the method further comprises evaluating the subject for the presence of a mutation in the NRAS or NPMc gene.

In an embodiment the cell proliferation-related disorder is myelodysplasia or myelodysplastic syndrome, e.g., wherein the myelodysplasia or myelodysplastic syndrome is characterized by having an IDH1 somatic mutant having alpha hydroxy neoactivity, e.g., 2HG neoactivity, e.g., a mutant described herein. In an embodiment the disorder is characterized by increased levels of an alpha hydroxy neoactivity product, e.g., 2HG, e.g., R-2HG, as compared to non-diseased cells of the same type. E.g., in an embodiment, the IDH1 allele is an IDH1 having other than an Arg at residue 132 (SEQ ID NO:8). E.g., the allele encodes His, Ser, Cys, Gly, Val, Pro or Leu, or any residue described in Kang et al., according to the sequence of SEQ ID NO:8 (see also FIG. 21) for example, Ser, Cys, Gly, or Leu. In an embodiment the allele encodes an IDH1 having Cys at residue 132.

In an embodiment the IDH1 allele has a T (or any other nucleotide other than C) at nucleotide position 394. In an embodiment the allele is a C394T mutation according to the sequence of SEQ ID NO:5.

In an embodiment the method comprises selecting a subject having myelodysplasia or myelodysplastic syndrome characterized by an IDH1 allele described herein, e.g., an IDH1 allele having Cys at residue 132 according to the sequence of SEQ ID NO:8.

In an embodiment the method comprises selecting a subject having myelodysplasia or myelodysplastic syndrome on the basis of cancer being characterized by having an IDH1 allele described herein, e.g., an IDH1 allele having Cys at residue 132 (SEQ ID NO:8).

In an embodiment, the IDH1 allele encodes an IDH1 having other than a Val at residue 71, e.g., V71I.

In an embodiment the method comprises selecting a subject having myelodysplasia or myelodysplastic syndrome wherein the disorder is characterized by having an IDH1 allele described herein, e.g., an IDH1 allele having Ile at residue 71 (SEQ ID NO:8).

In an embodiment the method comprises selecting a subject having myelodysplasia or myelodysplastic syndrome, on the basis of the disorder being characterized by an IDH1 allele described herein, e.g., an IDH1 allele having Ile at residue 71 (SEQ ID NO:8).

In an embodiment, the IDH1 allele encodes an IDH1 having other than an Arg at residue 100 or other than an Arg at residue 109.

In an embodiment the method comprises selecting a subject having myelodysplasia or myelodysplastic syndrome wherein the disorder is characterized by having an IDH1 allele described herein, e.g., an IDH1 allele other than an Arg at residue 100 or other than an Arg at residue 109.

In an embodiment the method comprises selecting a subject having myelodysplasia or myelodysplastic syndrome on the basis that the disorder is characterized by an IDH1 allele described herein, e.g., an IDH1 allele having other than an Arg at residue 100 or other than an Arg at residue 109.

In an embodiment the method comprises selecting a subject having myelodysplasia or myelodysplastic syndrome, on the basis of the cancer being characterized by unwanted, i.e., increased, levels of an alpha hydroxy neoactivity product, e.g., 2HG, e.g., R-2HG.

In an embodiment, the disorder is thyroid cancer. In an embodiment the method comprises selecting a subject having thyroid cancer wherein the thyroid cancer is characterized by having an IDH1 allele described herein, e.g., an IDH1 allele having mutation at residue 70, 130, 133, 134, or 178 (SEQ ID NO:8) (e.g., G70D, I130M, H133Q, A134D or V178I).

In an embodiment the method comprises selecting a subject having thyroid cancer, on the basis of the thyroid cancer being characterized by an IDH1 allele described herein, e.g., an IDH1 allele having mutation at residue 70, 130, 133, 134, or 178 (SEQ ID NO:8) (e.g., G70D, I130M, H133Q, A134D or V178I).

In an embodiment the method comprises selecting a subject having thyroid cancer, on the basis of the cancer being characterized by unwanted, i.e., increased, levels of an alpha hydroxy neoactivity product, e.g., 2HG, e.g., R-2HG.

In an embodiment the cell proliferation-related disorder is a glioma, characterized by a mutation, or preselected allele, of IDH2 associated with an alpha hydroxy neoactivity, e.g., 2HG neoactivity. E.g., in an embodiment, the IDH2 allele encodes an IDH2 having other than an Arg at residue 172 or other than an Arg at residue 140. E.g., the allele encodes Lys, Gly, Met, Trp, Thr, Ser, or any residue described in described in Yan et al., at residue 172, according to the sequence of SEQ ID NO:10 (see also FIG. 22) for example, Lys, Gly, Met, Trp or Ser. In an embodiment the allele encodes an IDH2 having Lys at residue 172. In an embodiment the allele encodes an IDH2 having Met at residue 172. In an embodiment the allele encodes an IDH2 having Gln (Q) or Trp (W) at residue 140.

In an embodiment the method comprises selecting a subject having a glioma, wherein the cancer is characterized by having an IDH2 allele described herein, e.g., an IDH2 allele having Lys or Met at residue 172 (SEQ ID NO:10).

In an embodiment the method comprises selecting a subject having a glioma, on the basis of the cancer being characterized by an IDH2 allele described herein, e.g., an IDH2 allele having Lys or Met at residue 172 (SEQ ID NO:10).

In an embodiment the method comprises selecting a subject having a glioma, on the basis of the cancer being characterized by unwanted, i.e., increased, levels of an alpha hydroxy neoactivity product, e.g., 2HG, e.g., R-2HG.

In an embodiment the cell proliferation-related disorder is a prostate cancer, e.g., prostate adenocarcinoma, characterized by a mutation, or preselected allele, of IDH2 associated with an alpha hydroxy neoactivity, e.g., 2HG neoactivity. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22). In an embodiment the allele encodes an IDH2 having Lys at residue 172. In an embodiment the allele encodes an IDH2 having Met at residue 172.

In an embodiment the method comprises selecting a subject having a prostate cancer, e.g., prostate adenocarcinoma, wherein the cancer is characterized by having an IDH2 allele described herein, e.g., an IDH2 allele having Lys or Met at residue 172 (SEQ ID NO:10).

In an embodiment the method comprises selecting a subject having a prostate cancer, e.g., prostate adenocarcinoma, on the basis of the cancer being characterized by an IDH2 allele described herein, e.g., an IDH2 allele having Lys or Met at residue 172 (SEQ ID NO:10).

In an embodiment the method comprises selecting a subject having a prostate cancer, e.g., prostate adenocarcinoma, on the basis of the cancer being characterized by unwanted, i.e., increased, levels of an alpha hydroxy neoactivity product, e.g., 2HG, e.g., R-2HG.

In an embodiment the cell proliferation-related disorder is ALL, e.g., B-ALL or T-ALL, characterized by a mutation, or preselected allele, of IDH2 associated with an alpha hydroxy neoactivity, e.g., 2HG neoactivity. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22). In an embodiment the allele encodes an IDH2 having Lys at residue 172. In an embodiment the allele encodes an IDH2 having Met at residue 172.

In an embodiment the method comprises selecting a subject having ALL, e.g., B-ALL or T-ALL, wherein the cancer is characterized by having an IDH2 allele described herein, e.g., an IDH2 allele having Lys or Met at residue 172 (SEQ ID NO:10).

In an embodiment the method comprises selecting a subject having ALL, e.g., B-ALL or T-ALL, on the basis of the cancer being characterized by an IDH2 allele described herein, e.g., an IDH2 allele having Lys or Met at residue 172 (SEQ ID NO:10).

In an embodiment the method comprises selecting a subject having ALL, e.g., B-ALL or T-ALL, on the basis of the cancer being characterized by unwanted, i.e., increased, levels of an alpha hydroxy neoactivity product, e.g., 2HG, e.g., R-2HG. In an embodiment the method comprises evaluating a sample, e.g., a serum or blood sample, for increased alpha neoactivity product, e.g., 2HG, e.g., R-2HG.

In an embodiment the cell proliferation-related disorder is AML, characterized by a mutation, or preselected allele, of IDH2 associated with an alpha hydroxy neoactivity, e.g., 2HG neoactivity. E.g., in an embodiment, the IDH2 allele encodes an IDH2 having other than an Arg at residue 172 or other than an Arg at residue 140. E.g., the allele encodes Lys, Gly, Met, Trp, Thr, Ser, or any residue described in described in Yan et al., at residue 172, according to the sequence of SEQ ID NO:10 (see also FIG. 22). In an embodiment the allele encodes an IDH2 having Lys at residue 172. In an embodiment the allele encodes an IDH2 having Met at residue 172. In an embodiment the allele encodes an IDH2 having Gln (Q) or Leu (L) at residue 140.

In an embodiment the method comprises selecting a subject having AML, wherein the cancer is characterized by having an IDH2 allele described herein, e.g., an IDH2 allele having Lys or Met at residue 172 (SEQ ID NO:10).

In an embodiment the method comprises selecting a subject having AML, on the basis of the cancer being characterized by an IDH2 allele described herein, e.g., an IDH2 allele having Lys or Met at residue 172 (SEQ ID NO:10).

In an embodiment the method comprises selecting a subject having AML, on the basis of the cancer being characterized by unwanted, i.e., increased, levels of an alpha hydroxy neoactivity product, e.g., 2HG, e.g., R-2HG. In an embodiment the method comprises evaluating a sample, e.g., a serum or blood sample, for increased alpha neoactivity product, e.g., 2HG, e.g., R-2HG.

In an embodiment the cell proliferation-related disorder is myelodysplasia or myelodysplastic syndrome, characterized by a mutation, or preselected allele, of IDH2. E.g., in an embodiment, the IDH2 allele encodes an IDH2 having other than an Arg at residue 172 or other than an Arg at residue 140. E.g., the allele encodes Lys, Gly, Met, Trp, Thr, Ser, or any residue described in described in Yan et al., at residue 172, according to the sequence of SEQ ID NO:10 (see also FIG. 22). In an embodiment the allele encodes an IDH2 having Lys at residue 172. In an embodiment the allele encodes an IDH2 having Met at residue 172. In an embodiment the allele encodes an IDH2 having Gln (Q) or Leu (L) at residue 140.

In an embodiment the method comprises selecting a subject having myelodysplasia or myelodysplastic syndrome, wherein the cancer is characterized by having an IDH2 allele described herein, e.g., an IDH2 allele having Lys or Met at residue 172 (SEQ ID NO:10).

In an embodiment the method comprises selecting a subject having myelodysplasia or myelodysplastic syndrome, on the basis of the cancer being characterized by an IDH2 allele described herein, e.g., an IDH2 allele having Lys or Met at residue 172 (SEQ ID NO:10).

In an embodiment the method comprises selecting a subject having myelodysplasia or myelodysplastic syndrome, on the basis of the cancer being characterized by unwanted, i.e., increased, levels of an alpha hydroxy neoactivity product, e.g., 2HG, e.g., R-2HG.

In an embodiment, the disorder is melanoma. In an embodiment the method comprises selecting a subject having melanoma, characterized by a mutation, or preselected allele, of IDH2. E.g., in an embodiment, the IDH2 allele encodes an IDH2 having other than a Val at residue 294. E.g., the allele encodes Met at residue 294 according to the sequence of SEQ ID NO:10 (see also FIG. 22).

In an embodiment the method comprises selecting a subject having melanoma, wherein the cancer is characterized by having an IDH2 allele described herein, e.g., an IDH2 allele having Met at residue 294 (SEQ ID NO:10).

In an embodiment the method comprises selecting a subject having melanoma, on the basis of the cancer being characterized by an IDH2 allele described herein, e.g., an IDH2 allele having Met at residue 294 (SEQ ID NO:10).

In an embodiment the method comprises selecting a subject having melanoma, on the basis of the cancer being characterized by unwanted, i.e., increased, levels of an alpha hydroxy neoactivity product, e.g., 2HG, e.g., R-2HG.

In another aspect the invention features a pharmaceutical composition of an inhibitor (e.g., a small molecule or a nucleic acid-based inhibitor) described herein.

In one aspect, the method features a method of treating an aciduria subject (e.g., a 2-hydroxyglutaric aciduria subject) comprising:

determining if the subject has an IDH, e.g., IDH1 or IDH2, mutation, e.g., a germline mutation, having 2HG neoactivity, or establishing the absence of a mutation of 2HG dehydrogenase together with elevated levels of 2HG; and responsive to said determination, e.g., responsive to the presence of said mutation, administering one or more of: an inhibitor of IDH, e.g., IDH1 or IDH2, neoactivity; a treatment which decreases the competition between 2HG and a cellular structural analog of 2HG; an anti-glycolytic agent; an antioxidant; or a hypomethylating agent, thereby treating said subject.

In some preferred embodiments, the method includes determining if the subject has an IDH, e.g., IDH1 or IDH2, mutation, e.g., a germline mutation, having 2HG neoactivity.

An aciduria subject can be determined to have an IDH mutation (e.g., an IDH2 mutation) using methods described herein. In a preferred embodiment, the IDH mutation is IDH2R140Q.

In an embodiment a mutant protein specific reagent, e.g., an antibody that specifically binds an IDH mutant protein, e.g., an antibody that specifically binds an IDH1-R132H mutant protein, can be used to detect neoactive mutant enzyme, see, for example, that described by Y. Kato et al., "A monoclonal antibody IMab-1 specifically recognizes IDH1$^{R132H}$, the most common glioma-derived mutation: (Kato, Biochem. Biophys. Res. Commun. (2009), which is hereby incorporated by reference in its entirety.

In another aspect, the invention features a method of evaluating an aciduria subject (e.g., a 2-hydroxyglutaric aciduria subject), the method comprising, determining if the subject has an IDH, e.g., IDH1 or IDH2, mutation, (e.g., a germline mutation such as a mutation described herein), having 2HG neoactivity, or establishing the absence of a mutation of 2HG dehydrogenase together with elevated levels of 2HG. In some embodiments, the method comprises determining if the subject has an IDH2 mutation such as an IDH2 mutation described herein (e.g., IDH2R140Q). The determination can be made using methods described herein.

In some embodiments, the subject does not have or has not been diagnosed with a cancer, for example, a cancer of the CNS.

In some embodiments, responsive to said determination, e.g., responsive to the presence of said mutation, the method comprises administering one or more of: an inhibitor of IDH, e.g., IDH1 or IDH2, neoactivity; a treatment which decreases the competition between 2HG and a cellular structural analog of 2HG; an anti-glycolytic agent; an antioxidant; or a hypomethylating agent, thereby treating said subject.

In another aspect, the invention features, a method of evaluating a candidate compound, e.g., for the ability to inhibit a neoactivity of a mutant IDH enzyme, e.g., for use as an anti-proliferative or anti-cancer agent. In an embodiment the neaoctivity is 2HG neoactivity. The method comprises:

optionally supplying the candidate compound;

contacting the candidate compound with a mutant IDH enzyme having a neoactivity, or with another enzyme, a referred to herein as a proxy enzyme, having an activity, referred to herein as a proxy activity, which is the same as the neoactivity (or with a cell or cell lysate comprising the same); and evaluating the ability of the candidate compound to modulate, e.g., inhibit or promote, the neoactivity or the proxy activity, thereby evaluating the candidate compound.

Exemplary mutations associated with 2HG neoactivity in IDH1 include mutations at residue 132, e.g., R132H or R132C.

Other IDH1 mutations associated with alpha hydroxy neoactivity, e.g., 2HG neoactivity, include mutations at residue 71, e.g., a mutation having other than a Val at residue 71, e.g., V71I.

Other IDH1 mutations associated with alpha hydroxy neoactivity, e.g., 2HG neoactivity, include mutations at residue 100, e.g., a mutation having other than an Arg at residue 100, and mutations at residue 109, e.g., a mutation having other than an Arg at residue 109.

Still other mutations associated with alpha hydroxy neoactivity, e.g., 2HG neoactivity include mutations at residue 70, e.g., a mutation having other than a Gly at residue 70, (e.g., G70D), mutations at residue 99, e.g., a mutation having a residue other than an Ile at residue 99 (e.g., I99M); a mutation having other than an Ile at residue 130 (e.g., I130M); a mutation having other than a His at residue 133 (e.g., H133Q); a mutation having other than an Ala at residue 134 (e.g., A134D); or a mutation having a residue other than a Val at residue 178 (e.g., V178I).

In an embodiment the mutant enzyme is a mutant IDH2, e.g., an IDH2 mutant described herein, and the neoactivity is 2HG neoactivity. Mutations associated with 2HG neoactivity in IDH2 include mutations at residue 172, e.g., R132H or R132C. Other exemplary IDH2 mutations include those at residue 140 (e.g., R140Q, R140L, or R140W) and at residue 294 (e.g., V294M).

In an embodiment the method includes evaluating the ability of the candidate compound to inhibit the neoactivity or the proxy activity.

In an embodiment the method further comprises evaluating the ability of the candidate compound to inhibit the forward reaction of non-mutant or wild type enzyme activity, e.g., IDH1 or IDH2, the conversion of isocitrate to α-ketoglutarate (or an intermediate thereof, including the reduced hydroxy intermediate).

In an embodiment, the contacting step comprises contacting the candidate compound with a cell, or a cell lysate thereof, wherein the cell comprises a mutant enzyme having the neoactivity or an enzyme having the activity.

In an embodiment, the cell comprises a mutation, or preselected allele, of a mutant IDH1 gene. E.g., in an embodiment, the IDH1 allele encodes an IDH1 having other than an Arg at residue 132. E.g., the allele can encode His, Ser, Cys, Gly, Val, Pro or Leu, or any other residue described in Yan et al., at residue 132, according to the sequence of SEQ ID NO:8 (see also FIG. 21), specifically Lys, Gly, Met, Trp, or Ser.

In an embodiment the allele encodes an IDH1 having His at residue 132.

In an embodiment the allele encodes an IDH1 having Ser at residue 132.

In an embodiment the allele is an Arg132His mutation, or an Arg132Ser mutation, according to the sequence of SEQ ID NO:8 (see FIGS. 2 and 21).

In an embodiment the IDH1 allele comprises a mutation at residue 71, e.g., a mutation having other than a Val at residue 71, e.g., V71I.

In an embodiment the IDH1 allele comprises a mutation at residue 100, e.g., a mutation having other than an Arg at residue 100, or a mutation at residue 109, e.g., a mutation having other than an Arg at residue 109.

In an embodiment the IDH1 allele comprises a mutation at residue 70, e.g., a mutation having other than a Gly at residue 70, (e.g., G70D), 99, e.g., a mutation having a residue other than an Ile at residue 99 (e.g., I99M); 130, a mutation having other than an Ile at residue 130 (e.g., I130M); 133, a mutation having other than a His at residue 133 (e.g., H133Q); 134, a mutation having other than an Ala at residue 134 (e.g., A134D); or 178, a mutation having a residue other than a Val at residue 178 (e.g., V178I).

In an embodiment, the cell comprises a mutation, or preselected allele, of a mutant IDH2 gene. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22), specifically, Lys, Gly, Met, Trp, or Ser. In an embodiment the allele encodes an IDH2 having Lys at residue 172. In an embodiment the allele encodes an IDH2 having Met at residue 172. In an embodiment, the IDH2 allele encodes an IDH2 having other than Arg at residue 140 (e.g., R140Q, R140L or R140W) or a residue other than Val at residue 294 (e.g., V294M).

In an embodiment, the cell includes a heterologous copy of a mutant IDH gene, e.g., a mutant IDH1 or IDH2 gene. (Heterologous copy refers to a copy introduced or formed by a genetic engineering manipulation.)

In an embodiment, the cell is transfected (e.g., transiently or stably transfected) or transduced (e.g., transiently or stably transduced) with a nucleic acid sequence encoding an IDH, e.g., IDH1 or IDH2, described herein, e.g., an IDH1 having other than an Arg at residue 132. In an embodiment, the IDH, e.g., IDH1 or IDH2, is epitope-tagged, e.g., myc-tagged.

In an embodiment the IDH1 allele comprises a mutation at residue 71, e.g., a mutation having other than a Val at residue 71, e.g., V71I.

In an embodiment the IDH1 allele comprises a mutation at residue 100, e.g., a mutation having other than an Arg at residue 100, or a mutation at residue 109, e.g., a mutation having other than an Arg at residue 109.

In an embodiment the IDH1 allele comprises a mutation at residue 70, e.g., a mutation having other than a Gly at residue 70, (e.g., G70D), 99, e.g., a mutation having a residue other than an Ile at residue 99 (e.g., I99M); 130, a mutation having other than an Ile at residue 130 (e.g., I130M); 133, a mutation having other than a His at residue 133 (e.g., H133Q); 134, a mutation having other than an Ala at residue 134 (e.g., A134D); or 178, a mutation having a residue other than a Val at residue 178 (e.g., V178I).

In an embodiment, the allele comprises a mutant IDH2 gene. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22), specifically, Lys, Gly, Met, Trp, or Ser. In an embodiment the allele encodes an IDH2 having Lys at residue 172. In an embodiment the allele encodes an IDH2 having Met at residue 172. In an embodiment, the IDH2 allele encodes an IDH2 having other than Arg at residue 140 (e.g., R140Q, R140L, or R140W) or a residue other than Val at residue 294 (e.g., V294M).

In an embodiment, the cell, e.g., a cancer cell, is non-mutant or wild type for the IDH, e.g., IDH1 or IDH2, allele. The cell can include a heterologous IDH1 or IDH2 mutant.

In an embodiment, the cell is a cultured cell, e.g., a primary cell, a secondary cell, or a cell line. In an embodiment, the cell is a cancer cell, e.g., a glioma cell (e.g., a glioblastoma cell), a prostate cancer cell, a leukemia cell (e.g., an ALL, e.g., B-ALL or T-ALL, cell or AML cell), a cell characterized by myelodysplasia or myelodysplastic syndrome, a fibrosarcoma or paraganglioma cell, a thyroid cancer cell, a melanoma cell, or a cell characterized by myeloproliferative neoplasms (e.g., CML). In embodiment, the cell is a 293T cell, a U87MG cell, or an LN-18 cell (e.g., ATCC HTB-14 or CRL-2610).

In an embodiment, the cell is from a subject, e.g., a subject having cancer, e.g., a cancer characterized by an IDH, e.g., IDH1 or IDH2, allele described herein, e.g., an IDH1 allele having His or Cys at residue 132 (SEQ ID NO:8).

In an embodiment the IDH1 allele comprises a mutation at residue 71, e.g., a mutation having other than a Val at residue 71, e.g., V71I.

In an embodiment the IDH1 allele comprises a mutation at residue 100, e.g., a mutation having other than an Arg at residue 100, or a mutation at residue 109, e.g., a mutation having other than an Arg at residue 109.

In an embodiment the IDH1 allele comprises a mutation at residue 70, e.g., a mutation having other than a Gly at residue 70, (e.g., G70D), 99, e.g., a mutation having a residue other than an Ile at residue 99 (e.g., I99M); 130, a mutation having other than an Ile at residue 130 (e.g., I130M); 133, a mutation having other than a His at residue 133 (e.g., H133Q); 134, a mutation having other than an Ala at residue 134 (e.g., A134D); or 178, a mutation having a residue other than a Val at residue 178 (e.g., V178I).

In an embodiment, the allele comprises a mutant IDH2 gene. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22), specifically, Lys, Gly, Met, Trp, or Ser. In an embodiment the allele encodes an IDH2 having Lys at residue 172. In an embodiment the allele encodes an IDH2 having Met at residue 172. In an embodiment, the IDH2 allele encodes an IDH2 having other than Arg at residue 140 (e.g., R140Q, R140L or R140W) or a residue other than Val at residue 294 (e.g., V294M).

In an embodiment, the evaluating step comprises evaluating the presence and/or amount of an alpha hydroxy neoactivity product, e.g., 2HG, e.g., R-2HG, e.g., in the cell lysate or culture medium, e.g., by LC-MS.

In an embodiment, the evaluating step comprises evaluating the presence and/or amount of an alpha hydroxy neoactivity, e.g., 2HG neoactivity, in the cell lysate or culture medium.

In an embodiment, the method further comprises evaluating the presence/amount one or more of TCA metabolite(s), e.g., citrate, α-KG, succinate, fumarate, and/or malate, e.g., by LC-MS, e.g., as a control.

In an embodiment, the method further comprises evaluating the oxidation state of NADPH, e.g., the absorbance at 340 nm, e.g., by spectrophotometer.

In an embodiment, the method further comprises evaluating the ability of the candidate compound to inhibit a second enzymatic activity, e.g., the forward reaction of non-mutant or wild type enzyme activity, e.g., in the case of IDH1, the conversion of isocitrate to α-ketoglutarate (or an intermediate thereof, including the reduced hydroxy intermediate).

In an embodiment, the candidate compound is a small molecule, a polypeptide, peptide, a carbohydrate based molecule, or an aptamer (e.g., a nucleic acid aptamer, or a peptide aptamer). The method can be used broadly and can, e.g., be used as one or more of a primary screen, to confirm candidates produced by this or other methods or screens, or generally to guide drug discovery or drug candidate optimization.

In an embodiment, the method comprises evaluating, e.g., confirming, the ability of a candidate compound (e.g., a candidate compound which meets a predetermined level of inhibition in the evaluating step) to inhibit the neoactivity or proxy activity in a second assay.

In an embodiment, the second assay comprises repeating one or more of the contacting and/or evaluating step(s) of the basic method.

In another embodiment, the second assay is different from the first. E.g., where the first assay can use a cell or cell lysate or other non-whole animal model the second assay can use an animal model, e.g., a tumor transplant model, e.g., a mouse having an IDH, e.g., IDH1 or IDH2, mutant cell or tumor transplanted in it. E.g., a U87 cell, or glioma, e.g., glioblastoma, cell, harboring a transfected IDH, e.g., IDH1 or IDH2, neoactive mutant can be implanted as a xenograft and used in an assay. Primary human glioma or AML tumor cells can be grafted into mice to allow propogation of the tumor and used in an assay. A genetically engineered mouse model (GEMM) harboring an IDH1 or IDH2 mutation and/or other mutation, e.g., a p53 null mutation, can also be used in an assay.

In an embodiment the method comprises:
optionally supplying the candidate compound;
contacting the candidate compound with a cell comprising a nucleic acid sequence, e.g., a heterologous sequence, encoding an IDH1 having other than an Arg at residue 132 (e.g., IDH1R132H); and
evaluating the presence and/or amount of an alpha hydroxy neoactivity product, e.g., 2HG, e.g., R-2HG, in the cell lysate or culture medium, by LC-MS, thereby evaluating the compound.

In an embodiment the IDH1 allele comprises a mutation at residue 71, e.g., a mutation having other than a Val at residue 71, e.g., V71I.

In an embodiment the IDH1 allele comprises a mutation at residue 100, e.g., a mutation having other than an Arg at residue 100, or a mutation at residue 109, e.g., a mutation having other than an Arg at residue 109.

In an embodiment the IDH1 allele comprises a mutation at residue 70, e.g., a mutation having other than a Gly at residue 70, (e.g., G70D), 99, e.g., a mutation having a residue other than an Ile at residue 99 (e.g., I99M); 130, a mutation having other than an Ile at residue 130 (e.g., I130M); 133, a mutation having other than a His at residue 133 (e.g., H133Q); 134, a mutation having other than an Ala at residue 134 (e.g., A134D); or 178, a mutation having a residue other than a Val at residue 178 (e.g., V178I).

In an embodiment, the allele comprises a mutant IDH2 gene. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22), specifically, Lys, Gly, Met, Trp, or Ser. In an embodiment the allele encodes an IDH2 having Lys at residue 172. In an embodiment the allele encodes an IDH2 having Met at residue 172. In an embodiment, the IDH2 allele encodes an IDH2 having other than Arg at residue 140 (e.g., R140Q, R140L, or R140W) or a residue other than Val at residue 294 (e.g., V294M).

In an embodiment the result of the evaluation is compared with a reference, e.g., the level of an alpha hydroxy neoactivity product, e.g., 2HG. e.g., R-2HG, in a control cell, e.g., a cell having inserted therein a wild type or non-mutant copy of IDH1.

In another aspect, the invention features, a method of evaluating a candidate compound, e.g., for the ability to inhibit an RNA encoding a mutant enzyme having a neoactivity, e.g., for use as an anti-proliferative or anti-cancer agent. In an embodiment the mutant enzyme is an IDH, e.g., an IDH1 or IDH2 mutant, e.g., a mutant described herein. In an embodiment the neoactivity is alpha hydroxy neoactivity, e.g., 2HG neoactivity. The method comprises:
optionally supplying the candidate compound, e.g., a nucleic acid based inhibitor (e.g., a dsRNA (e.g., siRNA or shRNA), an antisense, or a microRNA);
contacting the candidate compound with an RNA, e.g., an mRNA, which encodes IDH, e.g., an IDH1 or IDH2, e.g., an RNA that encode mutant enzyme having a neoactivity (or with a cell or cell lysate comprising the same); and
evaluating the ability of the candidate compound to inhibit the RNA, thereby evaluating the candidate compound. By inhibit the RNA means, e.g., to cleave or otherwise inactivate the RNA.

In an embodiment the RNA encodes a fusion of all or part of the IDH, e.g., IDH1 or IDH2, wildtype or mutant protein to a second protein, e.g., a reporter protein, e.g., a fluorescent protein, e.g., a green or red fluorescent protein.

In an embodiment the mutant enzyme is a mutant IDH1, e.g., an IDH1 mutant described herein, and the neoactivity 2HG neoactivity.

In an embodiment the mutant enzyme is a mutant IDH2, e.g., an IDH2 mutant described herein, and the neoactivity is 2HG neoactivity.

In an embodiment, the contacting step comprises contacting the candidate compound with a cell, or a cell lysate thereof, wherein the cell comprises RNA encoding IDH, e.g., IDH1 or IDH2, e.g., a mutant IDH, e.g., IDH1 or IDH2, enzyme having the neoactivity.

In an embodiment, the cell comprises a mutation, or preselected allele, of a mutant IDH1 gene. E.g., in an embodiment, the IDH1 allele encodes an IDH1 having other than an Arg at residue 132. E.g., the allele can encode His, Ser, Cys, Gly, Val, Pro or Leu, or any other residue described in Yan et al., at residue 132, according to the sequence of SEQ ID NO:8 (see also FIG. 21), specifically His, Ser, Cys, Gly, Val, or Leu.

In an embodiment the allele encodes an IDH1 having His at residue 132.

In an embodiment the allele encodes an IDH1 having Ser at residue 132.

In an embodiment the allele is an Arg132His mutation, or an Arg132Ser mutation, according to the sequence of SEQ ID NO:8 (see FIGS. 2 and 21).

In an embodiment the IDH1 allele comprises a mutation at residue 71, e.g., a mutation having other than a Val at residue 71, e.g., V71I.

In an embodiment the IDH1 allele comprises a mutation at residue 100, e.g., a mutation having other than an Arg at residue 100, or a mutation at residue 109, e.g., a mutation having other than an Arg atu residue 109.

In an embodiment the IDH1 allele comprises a mutation at residue 70, e.g., a mutation having other than a Gly at residue 70, (e.g., G70D), 99, e.g., a mutation having a residue other than a Gly at residue 99 (e.g., I99M); 130, a mutation having other than an Ile at residue 130 (e.g., I130M); 133, a mutation having other than a His at residue 133 (e.g., H133Q); 134, a mutation having other than an Ala at residue 134 (e.g., A134D); or 178, a mutation having a residue other than a Val at residue 178 (e.g., V178I).

In an embodiment, the cell comprises a mutation, or preselected allele, of a mutant IDH2 gene. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22), specifically, Lys, Gly, Met, Trp, or Ser. In an embodiment the allele encodes an IDH2 having Lys at residue 172. In an embodiment the allele encodes an IDH2 having Met at residue 172. In an embodiment, the IDH2 allele encodes an IDH2 having other than Arg at residue 140 (e.g., R140Q, R140L or R140W) or a residue other than Val at residue 294 (e.g., V294M).

In an embodiment, the cell includes a heterologous copy of a wildtype or mutant IDH gene, e.g., a wildtype or mutant IDH1 or IDH2 gene. (Heterologous copy refers to a copy introduced or formed by a genetic engineering manipulation.) In an embodiment the heterologous gene comprises a fusion to a reporter protein, e.g., a fluorescent protein, e.g., a green or red fluorescent protein.

In an embodiment, the cell is transfected (e.g., transiently or stably transfected) or transduced (e.g., transiently or stably transduced) with a nucleic acid sequence encoding an IDH, e.g., IDH1 or IDH2, described herein, e.g., an IDH1 having other than an Arg at residue 132. In an embodiment, the IDH, e.g., IDH1 or IDH2, is epitope-tagged, e.g., myc-tagged.

In an embodiment the cell is transfected with an IDH1 allele comprising a mutation at residue 71, e.g., a mutation having other than a Val at residue 71, e.g., V71I.

In an embodiment the cell is transfected with an IDH1 allele comprising a mutation at residue 100, e.g., a mutation having other than an Arg at residue 100, or a mutation at residue 109, e.g., a mutation having other than an Arg at residue 109.

In an embodiment the IDH1 allele comprises a mutation at residue 70, e.g., a mutation having other than a Gly at residue 70, (e.g., G70D), 99, e.g., a mutation having a residue other than an Ile at residue 99 (e.g., I99M); 130, a mutation having other than an Ile at residue 130 (e.g., I130M); 133, a mutation having other than a His at residue 133 (e.g., H133Q); 134, a mutation having other than an Ala at residue 134 (e.g., A134D); or 178, a mutation having a residue other than a Val at residue 178 (e.g., V178I).

In an embodiment, the allele comprises a mutation of a mutant IDH2 gene. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22), specifically, Lys, Gly, Met, Trp, or Ser. In an embodiment the allele encodes an IDH2 having Lys at residue 172. In an embodiment the allele encodes an IDH2 having Met at residue 172. In an embodiment, the IDH2 allele encodes an IDH2 having other than Arg at residue 140 (e.g., R140Q, R140L, or R140K) or a residue other than Val at residue 294 (e.g., V294M).

In an embodiment, the cell, e.g., a cancer cell, is non-mutant or wild type for the IDH, e.g., IDH1 or IDH2, allele. The cell can include a heterologous IDH1 or IDH2 mutant.

In an embodiment, the cell is a cultured cell, e.g., a primary cell, a secondary cell, or a cell line. In an embodiment, the cell is a cancer cell, e.g., a glioma cell (e.g., a glioblastoma cell), a prostate cancer cell, a leukemia cell (e.g., an ALL, e.g., B-ALL or T-ALL cell or AML cell) a cell characterized by myelodysplasia or myelodysplastic syndrome, a fibrosarcoma or paraganglioma cell, a thyroid cancer cell, a melanoma cell or a cell characterized by myeloproliferative neoplasms (e.g., CML). In embodiment, the cell is a 293T cell, a U87MG cell, or an LN-18 cell (e.g., ATCC HTB-14 or CRL-2610).

In an embodiment, the cell is from a subject, e.g., a subject having cancer, e.g., a cancer characterized by an IDH, e.g., IDH1 or IDH2, allele described herein, e.g., an IDH1 allele having His or Cys at residue 132 (SEQ ID NO:8).

In an embodiment the IDH1 allele comprises a mutation at residue 71, e.g., a mutation having other than a Val at residue 71, e.g., V71I.

In an embodiment the IDH1 allele comprises a mutation at residue 100, e.g., a mutation having other than a Arg at residue 100, or a mutation at residue 109, e.g., a mutation having other than an Arg at residue 109.

In an embodiment the IDH1 allele comprises a mutation at residue 70, e.g., a mutation having other than a Gly at residue 70, (e.g., G70D), 99, e.g., a mutation having a residue other than an Ile at residue 99 (e.g., I99M); 130, a mutation having other than an Ile at residue 130 (e.g., I130M); 133, a mutation having other than a His at residue 133 (e.g., H133Q); 134, a mutation having other than an Ala at residue 134 (e.g., A134D); or 178, a mutation having a residue other than a Val at residue 178 (e.g., V178I).

In an embodiment, the allele comprises a mutation of an IDH2 gene. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22), specifically, Lys, Gly, Met, Trp, or Ser. In an embodiment the allele encodes an IDH2 having Lys at residue 172. In an embodiment the allele encodes an IDH2 having Met at residue 172. In an embodiment, the IDH2 allele encodes an IDH2 having other than Arg at residue 140 (e.g., R140Q, R140L, or R140W) or a residue other than Val at residue 294 (e.g., V294M). In an embodiment, the method comprises a second assay and the second assay comprises repeating one or more of the contacting and/or evaluating step(s) of the basic method.

In another embodiment, the second assay is different from the first. E.g., where the first assay can use a cell or cell lysate or other non-whole animal model the second assay can use an animal model In an embodiment the efficacy of the candidate is evaluated by its effect on reporter protein activity.

In another aspect, the invention features, a method of evaluating a candidate compound, e.g., for the ability to inhibit transcription of an RNA encoding a mutant enzyme having a neoactivity, e.g., for use as an anti-proliferative or anti-cancer agent. In an embodiment the mutant enzyme is an IDH1 or IDH2 mutant. The method comprises:

optionally supplying the candidate compound, e.g., a small molecule, polypeptide, peptide, aptomer, a carbohydrate-based molecule or nucleic acid based molecule;

contacting the candidate compound with a system comprising a cell or cell lysate; and evaluating the ability of the candidate compound to inhibit the translation of IDH, e.g., IDH1 or IDH2, RNA, e.g., thereby evaluating the candidate compound.

In an embodiment the system comprises a fusion gene encoding of all or part of the IDH, e.g., IDH1 or IDH2, wildtype or mutant protein to a second protein, e.g., a reporter protein, e.g., a fluorescent protein, e.g., a green or red fluorescent protein.

In an embodiment the mutant enzyme is a mutant IDH1, e.g., an IDH1 mutant described herein, and the neoactivity is 2HG neoactivity.

In an embodiment the mutant enzyme is a mutant IDH2, e.g., an IDH2 mutant described herein, and the neoactivity is 2HG neoactivity.

In an embodiment, the system includes a heterologous copy of a wildtype or mutant IDH gene, e.g., a wildtype or mutant IDH1 or IDH2 gene. (Heterologous copy refers to a copy introduced or formed by a genetic engineering manipulation.) In an embodiment the heterologous gene comprises a fusion to a reporter protein, e.g., a fluorescent protein, e.g., a green or red fluorescent protein.

In an embodiment the cell, e.g., a cancer cell, is non-mutant or wild type for the IDH, e.g., IDH1 or IDH2, allele. The cell can include a heterologous IDH1 or IDH2 mutant.

In an embodiment, the cell is a cultured cell, e.g., a primary cell, a secondary cell, or a cell line. In an embodiment, the cell is a cancer cell, e.g., a glioma cell (e.g., a glioblastoma cell), a prostate cancer cell, a leukemia cell (e.g., an ALL, e.g., B-ALL or T-ALL, cell or AML cell) or a cell characterized by myelodysplasia or myelodysplastic syndrome. In embodiment, the cell is a 293T cell, a U87MG cell, or an LN-18 cell (e.g., ATCC HTB-14 or CRL-2610).

In an embodiment, the cell is from a subject, e.g., a subject having cancer, e.g., a cancer characterized by an IDH, e.g., IDH1 or IDH2, allele described herein, e.g., an IDH1 allele having His or Cys at residue 132 (SEQ ID NO:8).

In an embodiment the IDH1 allele comprises a mutation at residue 71, e.g., a mutation having other than a Val at residue 71, e.g., V71I.

In an embodiment the IDH1 allele comprises a mutation at residue 100, e.g., a mutation having other than an Arg at residue 100, or a mutation at residue 109, e.g., a mutation having other than an Arg at residue 109.

In an embodiment the IDH1 allele comprises a mutation at residue 70, e.g., a mutation having other than a Gly at residue 70, (e.g., G70D), 99, e.g., a mutation having a residue other than an Ile at residue 99 (e.g., I99M); 130, a mutation having other than an Ile at residue 130 (e.g., I130M); 133, a mutation having other than a His at residue 133 (e.g., H133Q); 134, a mutation having other than an Ala at residue 134 (e.g., A134D); or 178, a mutation having a residue other than a Val at residue 178 (e.g., V178I).

In an embodiment, the allele comprises a mutation of an IDH2 gene. E.g., in an embodiment, the IDH2 allele encodes an IDH2 having other than an Arg at residue 172. E.g., the allele encodes Lys, Gly, Met, Trp, Thr, Ser, or any residue described in described in Yan et al., at residue 172, according to the sequence of SEQ ID NO:10 (see also FIG. 22), specifically, Lys, Gly, Met, Trp, or Ser. In an embodiment the allele encodes an IDH2 having Lys at residue 172. In an embodiment the allele encodes an IDH2 having Met at residue 172. In an embodiment, the IDH2 allele encodes an IDH2 having other than Arg at residue 140 (e.g., R140Q, R140L, or R140W) or a residue other than Val at residue 294 (e.g., V294M). In an embodiment, the method comprises a second assay and the second assay comprises repeating the method.

In another embodiment, the second assay is different from the first. E.g., where the first assay can use a cell or cell lysate or other non-whole animal model the second assay can use an animal model.

In an embodiment the efficacy of the candidate is evaluated by its effect on reporter protein activity.

In another aspect, the invention features, a method of evaluating a candidate compound, e.g., a therapeutic agent, or inhibitor, described herein in an animal model. The candidate compound can be, e.g., a small molecule, polypeptide, peptide, aptomer, a carbohydrate-based molecule or nucleic acid based molecule. The method comprises, contacting the candidate with the animal model and evaluating the animal model.

In an embodiment evaluating comprises;

determining an effect of the compound on the general health of the animal;

determining an effect of the compound on the weight of the animal;

determining an effect of the compound on liver function, e.g., on a liver enzyme;

determining an effect of the compound on the cardiovascular system of the animal;

determining an effect of the compound on neurofunction, e.g., on neuromuscular control or response;

determining an effect of the compound on eating or drinking;

determining the distribution of the compound in the animal;

determining the persistence of the compound in the animal or in a tissue or organ of the animal, e.g., determining plasma half-life; or determining an effect of the compound on a selected cell in the animal;

determining an effect of the compound on the growth, size, weight, invasiveness or other phenotype of a tumor, e.g., an endogenous tumor or a tumor arising from introduction of cells from the same or a different species.

In an embodiment the animal is a non-human primate, e.g., a cynomolgus monkey or chimpanzee.

In an embodiment the animal is a rodent, e.g., a rat or mouse.

In an embodiment the animal is a large animal, e.g., a dog or pig, other than a non-human primate.

In an embodiment the evaluation is memorialized and optionally transmitted to another party.

In one aspect, the invention provides, a method of evaluating or processing a therapeutic agent, e.g., a therapeutic agent referred to herein, e.g., a therapeutic agent that results in a lowering of the level of a product of an IDH, e.g., IDH1 or IDH2, mutant having a neoactivity. In an embodiment the level of an alpha hydroxy neoactivity product, e.g., 2HG, e.g., R-2HG, is lowered.

The method includes:
providing, e.g., by testing a sample, a value (e.g., a test value) for a parameter related to a property of the rapeutic agent, e.g., the ability to inhibit the conversion of alpha ketoglutarate to 2 hydroxyglutarate (i.e., 2HG), e.g., R-2 hydroxyglutarate (i.e., R-2HG), and, optionally, providing a determination of whether the value determined for the parameter meets a preselected criterion, e.g., is present, or is present within a preselected range, thereby evaluating or processing the rapeutic agent.

In an embodiment the rapeutic agent is approved for use in humans by a government agency, e.g., the FDA.

In an embodiment the parameter is correlated to the ability to inhibit 2HG neoactivity, and, e.g., the rapeutic agent is an inhibitor which binds to IDH1 or IDH2 protein and reduces an alpha hydroxy neoactivity, e.g., 2HG neoactivity.

In an embodiment the parameter is correlated to the level of mutant IDH, e.g., IDH1 or IDH2, protein, and, e.g., the rapeutic agent is an inhibitor which reduces the level of IDH1 or IDH2 mutant protein.

In an embodiment the parameter is correlated to the level of an RNA that encodes a mutant IDH, e.g., IDH1 or IDH2, protein, and, e.g., the rapeutic agent reduces the level of RNA, e.g., mRNA, that encodes IDH1 or IDH2 mutant protein.

In an embodiment the method includes contacting the rapeutic agent with a mutant IDH, e.g., IDH1 or IDH2, protein (or corresponding RNA).

In an embodiment, the method includes providing a comparison of the value determined for a parameter with a reference value or values, to thereby evaluate the therapeutic agent. In an embodiment, the comparison includes determining if a test value determined for the rapeutic agent has a preselected relationship with the reference value, e.g., determining if it meets the reference value. The value need not be a numerical value but, e.g., can be merely an indication of whether an activity is present.

In an embodiment the method includes determining if a test value is equal to or greater than a reference value, if it is less than or equal to a reference value, or if it falls within a range (either inclusive or exclusive of one or both endpoints). In an embodiment, the test value, or an indication of whether the preselected criterion is met, can be memorialized, e.g., in a computer readable record.

In an embodiment, a decision or step is taken, e.g., a sample containing the therapeutic agent, or a batch of the rapeutic agent, is classified, selected, accepted or discarded, released or withheld, processed into a drug product, shipped, moved to a different location, formulated, labeled, packaged, contacted with, or put into, a container, e.g., a gas or liquid tight container, released into commerce, or sold or offered for sale, or a record made or altered to reflect the determination, depending on whether the preselected criterion is met. E.g., based on the result of the determination or whether an activity is present, or upon comparison to a reference standard, the batch from which the sample is taken can be processed, e.g., as just described.

The evaluation of the presence or level of activity can show if the rapeutic agent meets a reference standard.

In an embodiment, methods and compositions disclosed herein are useful from a process standpoint, e.g., to monitor or ensure batch-to-batch consistency or quality, or to evaluate a sample with regard to a reference, e.g., a preselected value.

In an embodiment, the method can be used to determine if a test batch of a therapeutic agent can be expected to have one or more of the properties. Such properties can include a property listed on the product insert of a therapeutic agent, a property appearing in a compendium, e.g., the US Pharmacopia, or a property required by a regulatory agency, e.g., the FDA, for commercial use.

In an embodiment the method includes testing the rapeutic agent for its effect on the wildtype activity of an IDH, e.g., IDH1 or IDH2, protein, and providing a determination of whether the value determined meets a preselected criterion, e.g., is present, or is present within a preselected range.

In an embodiment the method includes:
contacting a therapeutic agent that is an inhibitor of IDH1 or IDH2 (e.g., IDH1) an alpha hydroxy neoactivity, e.g., 2HG neoactivity, with an IDH1 or IDH2 mutant (e.g., IDH1) having an alpha hydroxy neoactivity, e.g., 2HG neoactivity, determining a value related to the inhibition of an alpha hydroxy neoactivity, e.g., 2HG neoactivity, and comparing the value determined with a reference value, e.g., a range of values, for the inhibition of an alpha hydroxy neoactivity, e.g., 2HG neoactivity. In an embodiment the reference value is an FDA required value, e.g., a release criteria.

In an embodiment the method includes:
contacting a therapeutic agent that is an inhibitor of mRNA which encodes a mutant IDH1 having an alpha hydroxy neoactivity, e.g., 2HG neoactivity, with an mRNA that encodes an IDH1 mutant having an alpha hydroxy neoactivity, e.g., 2HG neoactivity, determining a value related to the inhibition of the mRNA, and, comparing the value determined with a reference value, e.g., a range of values for inhibition of the mRNA. In an embodiment the reference value is an FDA required value, e.g., a release criteria.

In one aspect, the invention features a method of evaluating a sample of a therapeutic agent, e.g., a therapeutic agent referred to herein, that includes receiving data with regard to an activity of the rapeutic agent; providing a record which includes said data and optionally includes an identifier for a batch of therapeutic agent; submitting said record to a decision-maker, e.g., a government agency, e.g., the FDA; optionally, receiving a communication from said decision maker; optionally, deciding whether to release market the batch of therapeutic agent based on the communication from the decision maker. In one embodiment, the method further includes releasing, or other wise processing, e.g., as described herein, the sample.

In another aspect, the invention features, a method of selecting a payment class for treatment with a therapeutic agent described herein, e.g., an inhibitor of IDH, e.g., IDH1 or IDH2, neoactivity, for a subject having a cell proliferation-related disorder. The method includes:

providing (e.g., receiving) an evaluation of whether the subject is positive for unwanted, i.e., increased, levels of an alpha hydroxy neoactivity product, e.g., 2HG, e.g., R-2HG, or neoactivity, e.g., an alpha hydroxy neoactivity, e.g., 2HG neoactivity, a mutant IDH1 or IDH2 having neoactivity, e.g., an alpha hydroxy neoactivity, e.g., 2HG neoactivity, (or a corresponding RNA), or a mutant IDH, e.g., IDH1 or IDH2, somatic gene, e.g., a mutant described herein, and performing at least one of (1) if the subject is positive selecting a first payment class, and (2) if the subject is a not positive selecting a second payment class.

In an embodiment the selection is memorialized, e.g., in a medical records system.

In an embodiment the method includes evaluation of whether the subject is positive for unwanted, i.e., increased, levels of an alpha hydroxy neoactivity product, e.g., 2HG, e.g., R-2HG, or neoactivity, e.g., an alpha hydroxy neoactivity, e.g., 2HG neoactivity In an embodiment the method includes requesting the evaluation.

In an embodiment the evaluation is performed on the subject by a method described herein.

In an embodiment, the method comprises communicating the selection to another party, e.g., by computer, compact disc, telephone, facsimile, email, or letter.

In an embodiment, the method comprises making or authorizing payment for said treatment.

In an embodiment, payment is by a first party to a second party. In some embodiments, the first party is other than the subject. In some embodiments, the first party is selected from a third party payor, an insurance company, employer, employer sponsored health plan, HMO, or governmental entity. In some embodiments, the second party is selected from the subject, a healthcare provider, a treating physician, an HMO, a hospital, a governmental entity, or an entity which sells or supplies the drug. In some embodiments, the first party is an insurance company and the second party is selected from the subject, a healthcare provider, a treating physician, an HMO, a hospital, a governmental entity, or an entity which sells or supplies the drug. In some embodiments, the first party is a governmental entity and the second party is selected from the subject, a healthcare provider, a treating physician, an HMO, a hospital, an insurance company, or an entity which sells or supplies the drug.

As used herein, a cell proliferation-related disorder is a disorder characterized by unwanted cell proliferation or by a predisposition to lead to unwanted cell proliferation (sometimes referred to as a precancerous disorder). Examples of disorders characterized by unwanted cell proliferation include cancers, e.g., tumors of the CNS, e.g., a glioma. Gliomas include astrocytic tumors, oligodendroglial tumors, oligoastrocytic tumors, anaplastic astrocytomas, glioblastomas and myeloproliferative neoplasms. Other examples include hematological cancers, e.g., a leukemia, e.g., AML (e.g., an adult or pediatric form) or ALL, e.g., B-ALL or T-ALL (e.g., an adult or pediatric form), localized or metastatic prostate cancer, e.g., prostate adenocarcinoma, fibrosarcoma, and paraganglioma; specifically a leukemia, e.g., AML (e.g., an adult or pediatric form) or ALL, e.g., B-ALL or T-ALL (e.g., an adult or pediatric form), localized or metastatic prostate cancer, e.g., prostate adenocarcinoma, thyroid cancer, colon cancer, and melanoma. Examples of disorders characterized by a predisposition to lead to unwanted cell proliferation include myelodysplasia or myelodysplastic syndrome, which are a diverse collection of hematological conditions marked by ineffective production (or dysplasia) of myeloid blood cells and risk of transformation to AML.

As used herein, an increased level of a product of an alpha hydroxy neoactivity, e.g., 2HG, e.g., R-2HG, or similar term, e.g., an increased level of neoactive product or neoactivity product, means increased as compared with a reference level which is characteristic of a source which lacks a neoactive IDH, e.g., IDH1 or IDH2, mutation. By way of example, if the level of neoactivity product in cells is being evaluated, increased means increased in comparison to cells which are similar except that they do not carry the neoactive IDH, e.g., IDH1 or IDH2, mutation. By way of further example, if the level of neoactivity product in a sample, e.g., serum, is being evaluated, increased means increased in comparison to a sample which is otherwise similar but from a source or subject not having the neoactive IDH, e.g., IDH1 or IDH2, mutation, or not having a disorder characterized by a neoactive IDH, e.g., IDH1 or IDH2, mutation. By way of further example, if the level of neoactivity product in a tumor sample, e.g., a solid tumor sample or a sample of hematopoietic cells, is being evaluated, increased means increased in comparison to a tumor sample which is otherwise similar but from a source or subject not having the neoactive IDH, e.g., IDH1 or IDH2, mutation, or not having a disorder characterized by a neoactive IDH, e.g., IDH1 or IDH2, mutation.

As used herein, specifically inhibits a neoactivity (and similar language), means the neoactivity of the mutant enzyme is inhibited to a significantly greater degree than is the wildtype enzyme activity. By way of example, "specifically inhibits the 2HG neoactivity of mutant IDH1 (or IDH2)" means the 2HG neoactivity is inhibited to a significantly greater degree than is the forward reaction (the conversion of isocitrate to alpha ketoglutarate) of wildtype IDH1 (or IDH2) activity. In embodiments the reactivity is inhibited at least 2, 5, 10, or 100 fold more than the wildtype activity. In embodiments an inhibitor that is specific for the 2HG neaoctivity of IDH, e.g., IDH1 or IDH2, will also inhibit another dehydrogenase, e.g., malate dehydrogenase. In other embodiments the specific inhibitor does inhibit other dehydrogenases, e.g., malate dehydrogenase.

As used herein, a cell proliferation-related disorder, e.g., a cancer, characterized by a mutation or allele, means a cell proliferation-related disorder having a substantial number of cells which carry that mutation or allele. In an embodiment at least 10, 25, 50, 75, 90, 95 or 99% of the cell proliferation-related disorder cells, e.g., the cells of a cancer, or a representative, average or typical sample of cancer cells, e.g., from a tumor or from affected blood cells, carry at least one copy of the mutation or allele. A cell proliferation-related disorder, characterized by a mutant IDH, e.g., a mutant IDH1 or mutant IDH2, having 2HG neoactivity is exemplary. In an embodiment the mutation or allele is present as a heterozygote at the indicated frequencies.

As used herein, a "SNP" is a DNA sequence variation occurring when a single nucleotide (A, T, C, or G) in the genome (or other shared sequence) differs between members of a species (or between paired chromosomes in an individual).

As used herein, a subject, can be a human or non-human subject. Non-human subjects include non-human primates, rodents, e.g., mice or rats, or other non-human animals.

The details of one or more embodiments of the invention are set forth in the description below. Other features, objects, and advantages of the invention will be apparent from the description and the drawings, and from the claims.

BRIEF DESCRIPTION OF THE DRAWINGS

FIG. 1 depicts DNA sequence verification of pET41a-IDH1 and alignment against published IDH1 CDS. The sequence of IDH1 (CDS) corresponds to SEQ ID NO:5. The sequence of pET41a-IDH1 corresponds to SEQ ID NO:6, and the "consensus" sequence corresponds to SEQ ID NO:7.

FIG. 2 depicts DNA sequence verification of R132S and R132H mutants according to the SEQ ID NO:8. The amino acid sequence of IDH1 (SEQ ID NO:8) is provided in FIG. 21.

FIG. 21 depicts the amino acid sequence of IDH1 (SEQ ID NO:8) as described in GenBank Accession No. NP_005887.2 (GI No. 28178825) (record dated May 10, 2009).

FIG. 21A is the cDNA sequence of IDH1 as presented at GenBank Accession No. NM_005896.2 (Record dated May 10, 2009; GI No. 28178824) (SEQ ID NO:13).

FIG. 21B depicts the mRNA sequence of IDH1 as described in GenBank Accession No. NM_005896.2 (Record dated May 10, 2009; GI No. 28178824) (SEQ ID NO:9).

FIG. 22 is the amino acid sequence of IDH2 as presented at GenBank Accession No. NM_002168.2 (Record dated Aug. 16, 2009; GI28178831) (SEQ ID NO:10).

FIG. 22A is the cDNA sequence of IDH2 as presented at GenBank Accession No. NM_002168.2 (Record dated Aug. 16, 2009; GI28178831) (SEQ ID NO:11).

FIG. 22B is the mRNA sequence of IDH2 as presented at GenBank Accession No. NM_002168.2 (Record dated Aug. 16, 2009; GI28178831) (SEQ ID NO:12).

FIG. 27 depicts human IDH1 genomic DNA: intron/$2^{nd}$ exon sequence.

FIG. 30C depicts kinetic parameters of oxidative and reductive reactions as measured for WT and R132H IDH1 enzymes are shown. $K_m$ and $k_{cat}$ values for the reductive activity of the WT enzyme were unable to be determined as no measurable enzyme activity was detectable at any substrate concentration.

DETAILED DESCRIPTION

Figure 3:
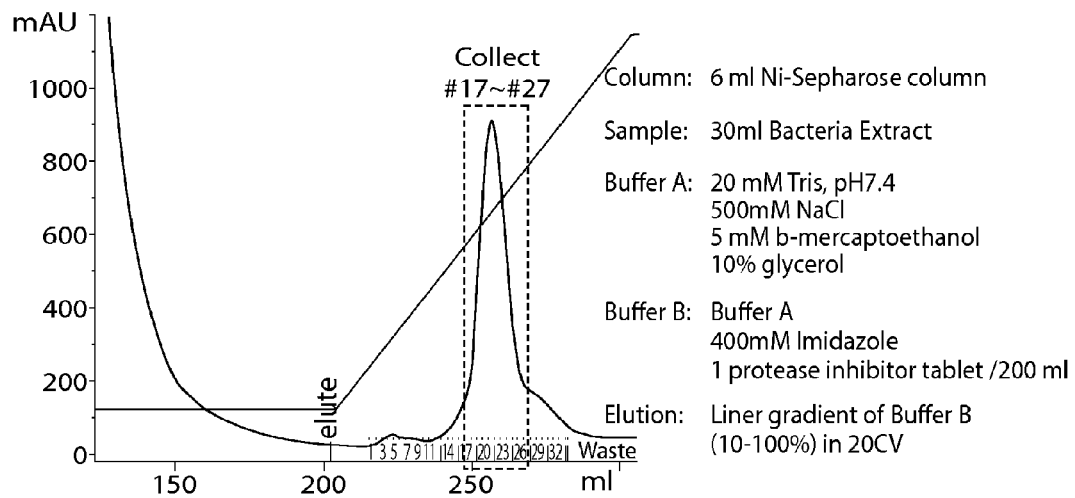
FIG. 3 depicts separation of wild type IDH1 protein on Ni-Sepharose column.
Figure 4:
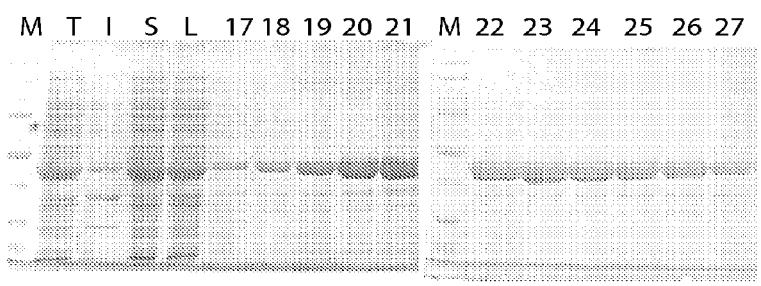
FIG. 4 depicts protein analysis of wild type IDH1 on SDS gel pre and post Ni column fractionation. T: total protein; I: insoluble fractions; S: soluble fraction; L: sample for loading on Ni-column. The numbers in the figure indicates the fraction numbers. Fractions #17~#27 were collected for further purification.
Figure 5A:
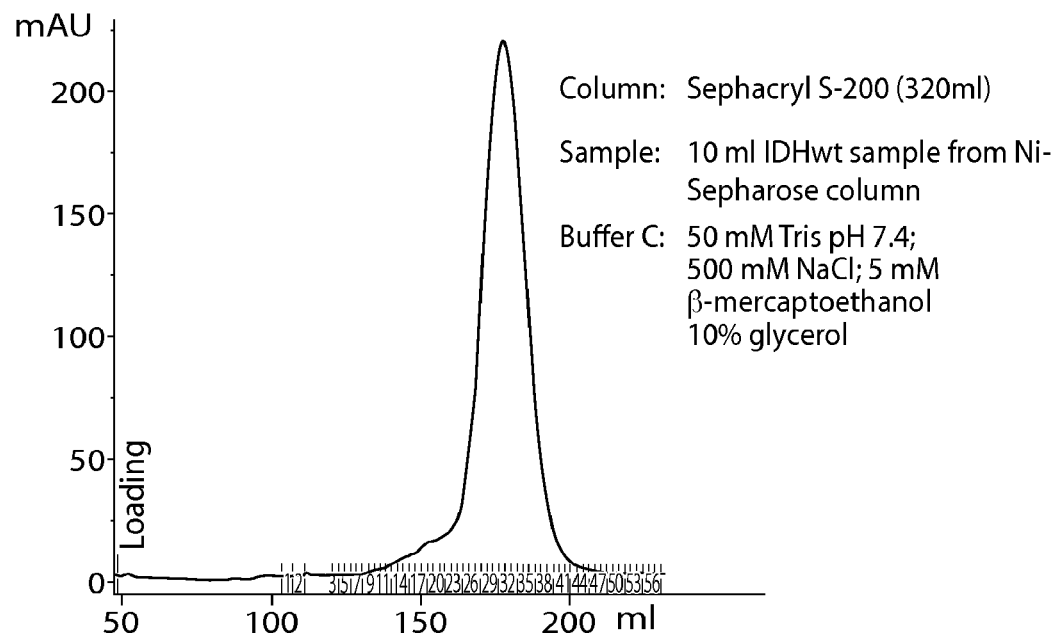
FIG. 5A depicts separation of wild type IDH1 protein through SEC column S-200.
Figure 5B:
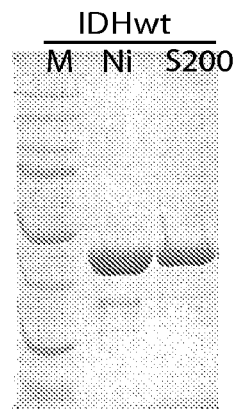
FIG. 5B depicts protein analysis of wild type IDH1 on SDS gel pre and post S-200 column fractionation. M: molecular weight marker; Ni: nickel column fraction prior to S-200; S200: fraction from SEC column.
Figure 6:
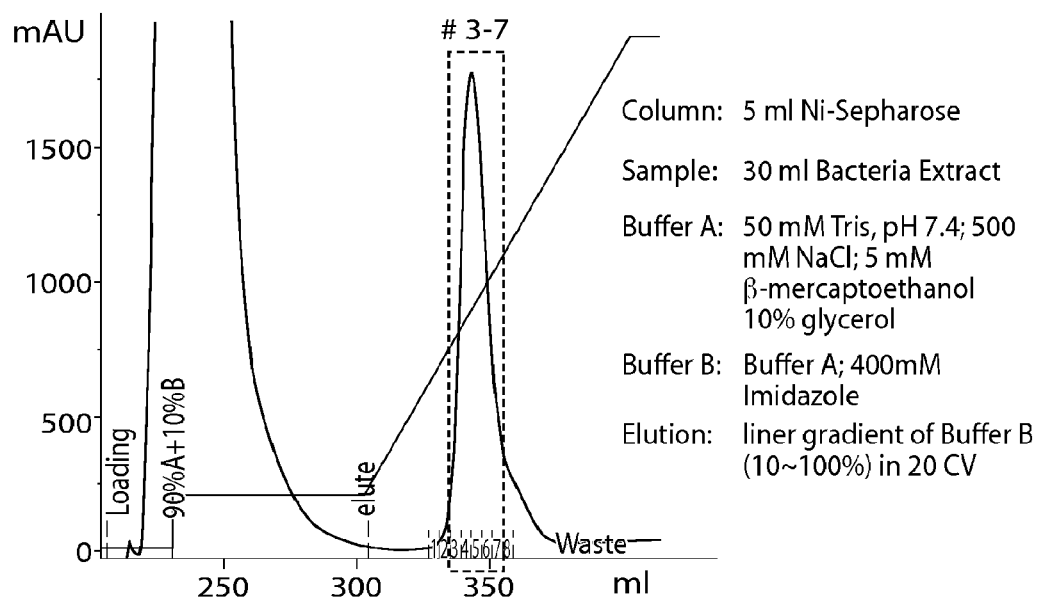
FIG. 6 depicts separation of mutant R132S protein on Ni-Sepharose column.
Figure 7:
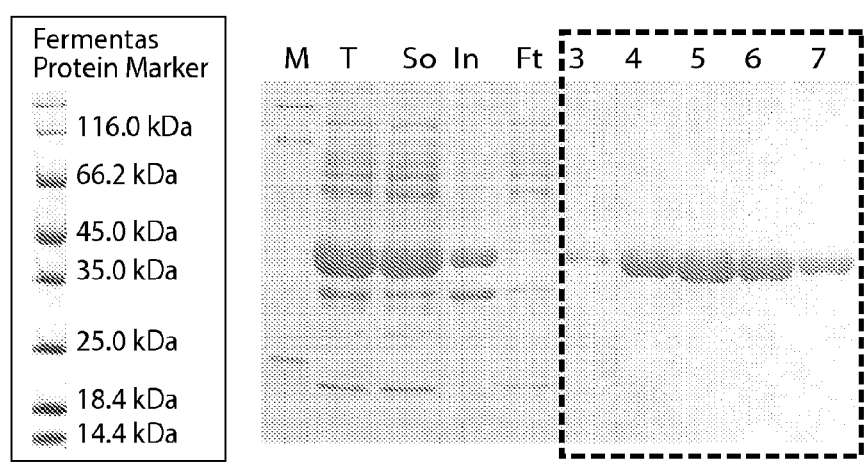
FIG. 7 depicts protein analysis of mutant R132S on SDS gel pre and post Ni column fractionation. M: protein marker (KDa): 116, 66.2, 45, 35, 25, 18.4, 14.4; T: total cell protein; So: soluble fraction; In: insoluble fraction; Ft: flow through. #3-#7 indicate the corresponding eluted fraction numbers.
Figure 8A:
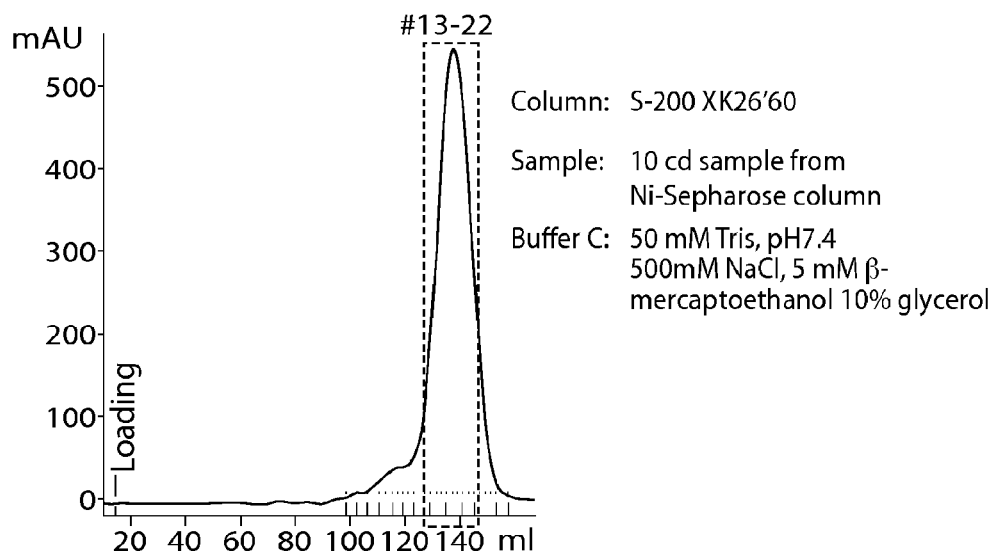
FIG. 8A depicts separation of mutant R132S protein through SEC column S-200.
Figure 8B:
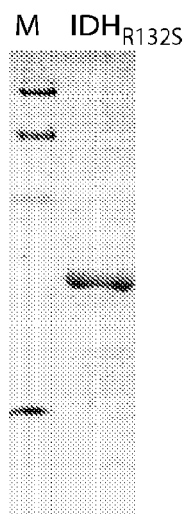
FIG. 8B depicts protein analysis of mutant R132S on SDS gel post S-200 column fractionation. M: molecular weight marker; R132S: fraction from SEC column.
Figure 9:
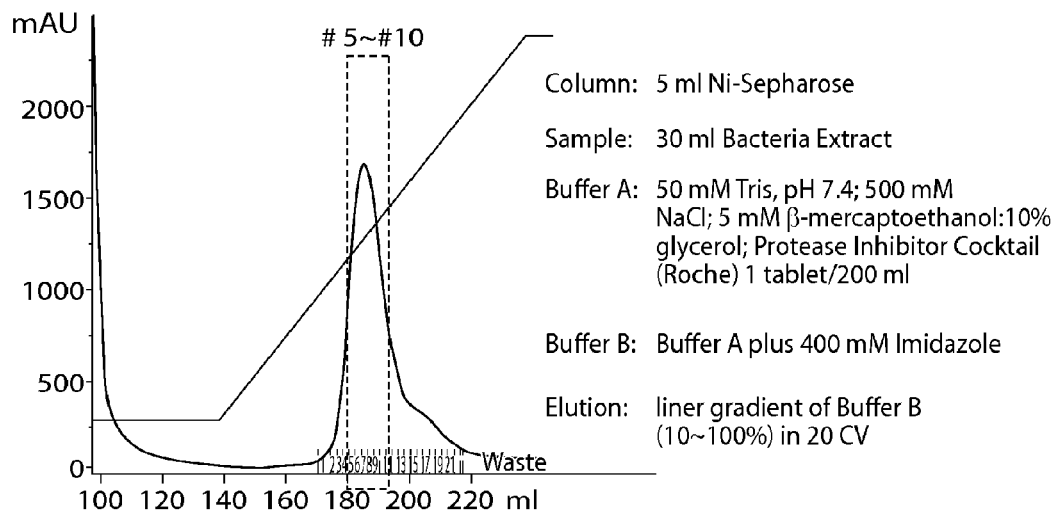
FIG. 9 depicts separation of mutant R132H protein on Ni-Sepharose column.
Figure 10:
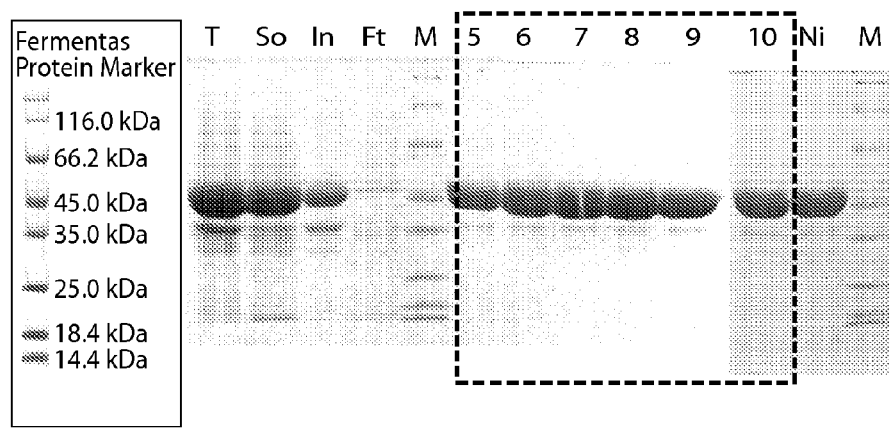
FIG. 10 depicts protein analysis of mutant R132H on SDS gel pre and post Ni column fractionation. M: protein marker (KDa): 116, 66.2, 45, 35, 25, 18.4, 14.4; T: total cell protein; So: soluble fraction; In: insoluble fraction; Ft: flow through; #5-#10 indicate the corresponding eluted fraction numbers; Ni: sample from Ni-Sepharose column, pool #5-#10 together.
Figure 11A:
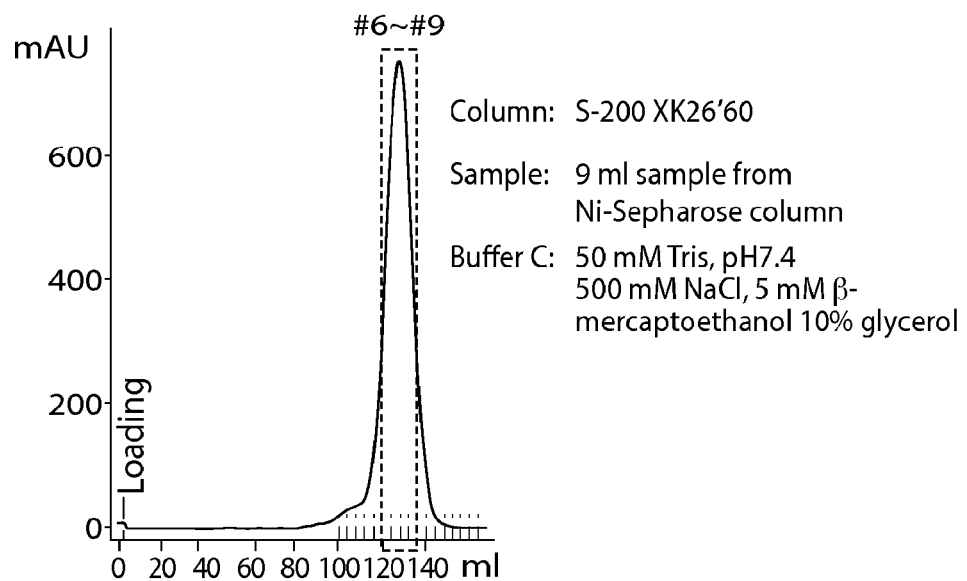
FIG. 11A depicts separation of mutant R132H protein through SEC column S-200.
Figure 11B:
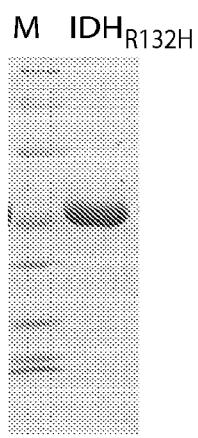
FIG. 11B depicts protein analysis of mutant R132H on SDS gel post S-200 column fractionation. M: molecular weight marker; R132H: fraction from SEC column.

The inventors have discovered that certain mutated forms of an IDH enzyme (e.g., IDH1 or IDH2) have a gain of function, referred to herein as a neoactivity, which can be targeted in the treatment of a cell proliferation-related disorder, e.g., a proliferative disorder such as cancer. Described herein are methods and compositions for the treatment of a cell proliferation-related disorder, e.g., a proliferative disorder such as cancer. The methods include, e.g., treating a subject having a glioma or brain tumor characterized by a preselected IDH1 allele, e.g., an allele having A at position 394 (e.g., a C394A mutant) or an A at position 395 (e.g., a G395A mutant) according to the sequence of SEQ ID NO:5, that encodes a an IDH1 having His at position 132 (e.g., an Arg132His mutation) or Ser at position 132 (e.g., an Arg132Ser mutant) and having a neoactivity disclosed herein, by administering to the subject a therapeutically effective amount of an inhibitor of IDH1, e.g., a small molecule or nucleic acid. The nucleic acid based inhibitor is, for example, a dsRNA, e.g., a dsRNA that comprises the primary sequences of the sense strand and antisense strands of Tables 7-14. The dsRNA is composed of two separate strands, or a single strand folded to form a hairpin structure (e.g., a short hairpin RNA (shRNA)). In some embodiments, the nucleic acid based inhibitor is an antisense nucleic acid, such as an antisense having a sequence that overlaps, or includes, an antisense sequence provided in Tables 7-14.

Neoactivity of an Enzyme

As used herein, neoactivity refers to alpha hydroxy neoactivity. Neoactivity and alpha hydroxyl neoactivity are used interchanagly herein. Alpha hydroxy neoactivity is the ability to convert an alpha ketone to an alpha hydroxy. Neoactivity can arise as a result of a mutation, e.g., a point mutation, e.g., a substitution, e.g., in the active site of an enzyme. In an embodiment the neoactivity is substantially absent from wild type or non-mutant enzyme. This is sometimes referred to herein as a first degree neoactivity. An example of a first degree neoactivity is a "gain of function" wherein the mutant enzyme gains a new catalytic activity. In an embodiment the neoactivity is present in wild type or non-mutant enzyme but at a level which is less than 10, 5, 1, 0.1, 0.01 or 0.001% of what is seen in the mutant enzyme. This is sometimes referred to herein as a second degree neoactivity. An example of a second degree neoactivity is a "gain of function" wherein the mutant enzyme has an increase, for example, a 5 fold increase in the rate of a catalytic activity possessed by the enzyme when lacking the mutation.

In some embodiments, a non-mutant form the enzyme, e.g., a wild type form, converts substance A (e.g., isocitrate) to substance B (e.g., α-ketoglutarate), and the neoactivity converts substance B (e.g., α-ketoglutarate) to substance C, sometimes referred to as the neoactivity product (e.g., 2-hydroxyglutarate, e.g., R-2-hydroxyglutarate).

Isocitrate Dehydrogenases

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2, 4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684 (1998); Geisbrecht et al., J. Biol. Chem. 274:30527-30533 (1999); Wiemann et al., Genome Res. 11:422-435 (2001); The MGC Project Team, Genome Res. 14:2121-2127 (2004); Lubec et al., Submitted (December-2008) to UniProtKB; Kullmann et al., Submitted (June-1996) to the EMBL/GenBank/DDBJ databases; and Sjoeblom et al., Science 314:268-274 (2006).

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November-1992) to the EMBL/GenBank/DDBJ databases; and The MGC Project Team, Genome Res. 14:2121-2127 (2004).

Non-mutant, e.g., wild type, IDH1 catalyzes the oxidative decarboxylation of ioscitrate to α-ketoglutarate thereby reducing $NAD^+$ (NADP) to NADP (NADPH), e.g., in the forward reaction:

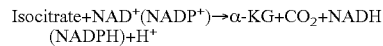
Isocitrate+$NAD^+$($NADP^+$)→α-KG+$CO_2$+NADH (NADPH)+$H^+$

In some embodiments, the neoactivity of a mutant IDH1 can have the ability to convert α-ketoglutarate to 2-hydroxyglutarate, e.g., R-2-hydroxyglutarate:

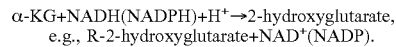
α-KG+NADH(NADPH)+$H^+$→2-hydroxyglutarate, e.g., R-2-hydroxyglutarate+$NAD^+$(NADP).

In some embodiments, the neoactivity can be the reduction of pyruvate or malate to the corresponding α-hydroxy compounds.

In some embodiments, the neoactivity of a mutant IDH1 can arise from a mutant IDH1 having a His, Ser, Cys or Lys, or any other mutations described in Yan et al., at residue 132. In some embodiments, the neoactivity of a mutant IDH2 can arise from a mutant IDH2 having a Gly, Met or Lys, or any other mutations described in Yan H et al., at residue 172. Exemplary mutations include the following: R132H, R132C, R132S, R132G, R132L, and R132V.

In some embodiments, the mutant IDH1 and/or IDH2 (e.g., a mutant IDH1 and/or IDH2 having a neoactivity described herein) could lead to an increased level of 2-hydroxyglutarate, e.g., R-2-hydroxyglutarate in a subject. The accumulation of 2-hydroxyglutarate, e.g., R-2-hydroxyglutarate in a subject, e.g., in the brain of a subject, can be harmful. For example, in some embodiments, elevated levels of 2-hydroxyglutarate, e.g., R-2-hydroxyglutarate can lead to and/or be predictive of cancer in a subject such as a cancer of the central nervous system, e.g., brain tumor, e.g., glioma, e.g., glioblastoma multiforme (GBM). Accordingly, in some embodiments, a method described herein includes administering to a subject an inhibitor of the neoactivity Detection of 2-hydroxyglutarate 2-hydroxyglutarate can be detected, e.g., by LC/MS. To detect secreted 2-hydroxyglutarate in culture media, 500 μL aliquots of conditioned media can be collected, mixed 80:20 with methanol, and centrifuged at 3,000 rpm for 20 minutes at 4 degrees Celsius. The resulting supernatant can be collected and stored at −80 degrees Celsius prior to LC-MS/MS to assess 2-hydroxyglutarate levels. To measure whole-cell associated metabolites, media can be aspirated and cells can be harvested, e.g., at a non-confluent density. A variety of different liquid chromatography (LC) separation methods can be used. Each method can be coupled by negative electrospray ionization (ESI, −3.0 kV) to triple-quadrupole mass spectrometers operating in multiple reaction monitoring (MRM) mode, with MS parameters optimized on infused metabolite standard solutions. Metabolites can be separated by reversed phase chromatography using 10 mM tributylamine as an ion pairing agent in the aqueous mobile phase, according to a variant of a previously reported method (Luo et al. *J Chromatogr A* 1147, 153-64, 2007). One method allows resolution of TCA metabolites: t=0, 50% B; t=5, 95% B; t=7, 95% B; t=8, 0% B, where B refers to an organic mobile phase of 100% methanol. Another method is specific for 2-hydroxyglutarate, running a fast linear gradient from 50%-95% B (buffers as defined above) over 5 minutes. A Synergi Hydro-RP, 100 mm×2 mm, 2.1 µm particle size (Phenomonex) can be used as the column, as described above. Metabolites can be quantified by comparison of peak areas with pure metabolite standards at known concentration. Metabolite flux studies from $^{13}$C-glutamine can be performed as described, e.g., in Munger et al. Nat Biotechnol 26, 1179-86, 2008.

In an embodiment 2HG, e.g., R-2HG, is evaluated and the analyte on which the determination is based is 2HG, e.g., R-2HG. In an embodiment the analyte on which the determination is based is a derivative of 2HG, e.g., R-2HG, formed in process of performing the analytic method. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis. In an embodiment an alpha hydroxy neoactivity product, e.g., 2HG, e.g., R-2HG, can be assayed indirectly. In an indirect assay the analyte is a metabolic derivative of an alpha hydroxy neoactivity product, e.g., 2HG, e.g., R-2HG, or another compound(s), e.g., a cellular compound, that is correlated to the level of an alpha hydroxy neoactivity product, e.g., 2HG, e.g., R-2HG. Examples include species that build up or are elevated, or reduced, as a result of the presence of 2HG, e.g., R-2HG. E.g., in embodiments, cancer cells with the neoactive mutant have elevated levels of glutarate or glutamate that will be correlated to 2HG, e.g., R-2HG.

Exemplary 2HG derivatives include dehydrated derivatives such as the compounds provided below or a salt adduct thereof:

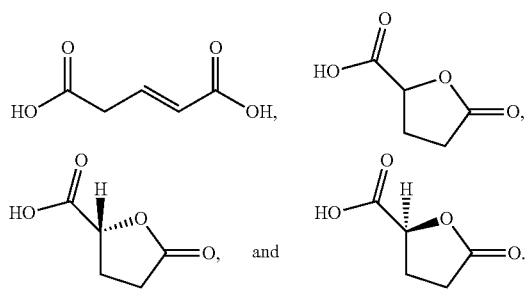

Methods of Evaluating Samples and/or Subjects

This section provides methods of obtaining and analyzing samples and of analyzing subjects.

Embodiments of the method comprise evaluation of one or more parameters related to IDH, e.g., IDH1 or IDH2, an alpha hydroxy neoactivity, e.g., 2HG neoactivity, e.g., to evaluate the IDH1 or IDH2 2HG neoactivity genotype or phenotype. The evaluation can be performed, e.g., to select, diagnose or prognose the subject, to select a therapeutic agent, e.g., an inhibitor, or to evaluate response to the treatment or progression of disease. In an embodiment the evaluation, which can be performed before and/or after treatment has begun, is based, at least in part, on analysis of a tumor sample, cancer cell sample, or precancerous cell sample, from the subject. E.g., a sample from the patient can be analyzed for the presence or level of an alpha hydroxy neoactivity product, e.g., 2HG, e.g., R-2HG, by evaluating a parameter correlated to the presence or level of an alpha hydroxy neoactivity product, e.g., 2HG, e.g., R-2HG. An alpha hydroxy neoactivity product, e.g., 2HG, e.g., R-2HG, in the sample can be determined by a chromatographic method, e.g., by LC-MS analysis. It can also be determined by contact with a specific binding agent, e.g., an antibody, which binds the alpha hydroxy neoactivity product, e.g., 2HG, e.g., R-2HG, and allows detection. In an embodiment the sample is analyzed for the level of neoactivity, e.g., an alpha hydroxy neoactivity, e.g., 2HG neoactivity. In an embodiment the sample is analysed for the presence of a mutant IDH, e.g., IDH1 or IDH2, protein having an alpha hydroxy neoactivity, e.g., 2HG neoactivity (or a corresponding RNA). E.g., a mutant protein specific reagent, e.g., an antibody that specifically binds an IDH mutant protein, e.g., an antibody that specifically binds an IDH1-R132H mutant protein or an IDH2 mutant protein, can be used to detect neoactive mutant enzyme In an embodiment a nucleic acid from the sample is sequenced to determine if a selected allele or mutation of IDH1 or IDH2 disclosed herein is present. In an embodiment the analysis is other than directly determining the presence of a mutant IDH, e.g., IDH1 or IDH2, protein (or corresponding RNA) or sequencing of an IDH, e.g., IDH1 or IDH2 gene. In an embodiment the analysis is other than directly determining, e.g., it is other than sequencing genomic DNA or cDNA, the presence of a mutation at residue 132 of IDH1 and/or a mutation at residue 172 of IDH2. In an embodiment the tumor is other than a tumor of the CNS, e.g., other than a glioma, and the analysis includes determining the sequence of a mutation at position 132 of IDH1, or a mutation at position 172 of IDH2. E.g., the sequence of IDH1 at any position described herein (e.g., of position 71, or 100 or 109) can be determined, e.g., to detect the presence of a mutation having 2HG neoactivity. In an embodiment the tumor is a glioma and the presence of an IDH1 2HG neoactive mutation other than a mutation at 132 of IDH1 is determined. In an embodiment the tumor is a glioma and the presence of an IDH1 2HG neoactive mutation other than a mutation at 172 at IDH2 is determined. E.g., the analysis can be the detection of an alpha hydroxy neoactivity product, e.g., 2HG, e.g., R-2HG, or the measurement of the mutation's an alpha hydroxy neoactivity, e.g., 2HG neoactivity. In an embodiment the sample is removed from the patient and analyzed. In an embodiment the evaluation can include one or more of performing the analysis of the sample, requesting analysis of the sample, requesting results from analysis of the sample, or receiving the results from analysis of the sample. (Generally herein, determination (or determining), analysis or evaluation (or evaluating) can include one or both of performing the underlying method or receiving data from another who has performed the underlying method.)

In an embodiment the evaluation, which can be performed before and/or after treatment has begun, is based, at least in part, on analysis of a tissue (e.g., a tissue other than a tumor sample), or bodily fluid, or bodily product. Exemplary tissues include lymph node, skin, hair follicles and nails.

Exemplary bodily fluids include blood, serum, plasma, urine, lymph, tears, sweat, saliva, semen, and cerebrospinal fluid. Exemplary bodily products include exhaled breath. E.g., the tissue, fluid or product can be analyzed for the presence or level of an alpha hydroxy neoactivity product, e.g., 2HG, e.g., R-2HG, by evaluating a parameter correlated to the presence or level of an alpha hydroxy neoactivity product, e.g., 2HG, e.g., R-2HG. An alpha hydroxy neoactivity product, e.g., 2HG, e.g., R-2HG, in the sample can be determined by a chromatographic method, e.g., by LC-MS analysis. It can also be determined by contact with a specific binding agent, e.g., an antibody, which binds the alpha hydroxy neoactivity product, e.g., 2HG, e.g., R-2HG, and allows detection. In embodiments where sufficient levels are present, the tissue, fluid or product can be analyzed for the level of neoactivity, e.g., an alpha hydroxy neoactivity, e.g., the 2HG neoactivity. In an embodiment the sample is analysed for the presence of a mutant IDH, e.g., IDH1 or IDH2, protein having an alpha hydroxy neoactivity, e.g., 2HG neoactivity (or a corresponding RNA). E.g., a mutant protein specific reagent, e.g., an antibody that specifically binds an IDH mutant protein, e.g., an antibody that specifically binds an IDH1-R132H mutant protein or an IDH2 mutant protein such as one described herein, can be used to detect neoactive mutant enzyme. In an embodiment a nucleic acid from the sample is sequenced to determine if a selected allele or mutation of IDH1 or IDH2 disclosed herein is present. In an embodiment the analysis is other than directly determining the presence of a mutant IDH, e.g., IDH1 or IDH2, protein (or corresponding RNA) or sequencing of an IDH, e.g., IDH1 or IDH2 gene. E.g., the analysis can be the detection of an alpha hydroxy neoactivity product, e.g., 2HG, e.g., R-2HG, or the measurement of 2HG neoactivity. In an embodiment the tissue, fluid or product is removed from the patient and analyzed. In an embodiment the evaluation can include one or more of performing the analysis of the tissue, fluid or product, requesting analysis of the tissue, fluid or product, requesting results from analysis of the tissue, fluid or product, or receiving the results from analysis of the tissue, fluid or product.

In an embodiment the evaluation, which can be performed before and/or after treatment has begun, is based, at least in part, on alpha hydroxy neoactivity product, e.g., 2HG, e.g., R-2HG, imaging of the subject. In embodiments magnetic resonance methods are is used to evaluate the presence, distribution, or level of an alpha hydroxy neoactivity product, e.g., 2HG, e.g., R-2HG, in the subject. In an embodiment the subject is subjected to imaging and/or spectroscopic analysis, e.g., magnetic resonance-based analysis, e.g., MRI and/or MRS e.g., analysis, and optionally an image corresponding to the presence, distribution, or level of an alpha hydroxy neoactivity product, e.g., 2HG, e.g., R-2HG, or of the tumor, is formed. Optionally the image or a value related to the image is stored in a tangible medium and/or transmitted to a second site. In an embodiment the evaluation can include one or more of performing imaging analysis, requesting imaging analysis, requesting results from imaging analysis, or receiving the results from imaging analysis.

Methods of Treating a Proliferative Disorder

Described herein are methods of treating a cell proliferation-related disorder, e.g., a cancer, e.g., a glioma, e.g., by inhibiting a neoactivity of a mutant IDH enzyme, e.g., IDH1 or IDH2. The cancer can be characterized by the presence of a neoactivity. In some embodiments, the gain of function is the conversion of α-ketoglutarate to 2-hydroxyglutarate, e.g., R-2-hydroxyglutarate.

Compounds for the Treatment of Cancer

Compounds disclosed herein for the treatment of a cell proliferation-related disorder, e.g., cancer, include: modulators, e.g., inhibitors, of a neoactive enzyme; compounds, or prodrugs thereof, that are structural analogs of a neoactivity product; anti-glycolytic agents; anti-oxidants; hyopmethylating agents; and nucleic acid-based therapeutic agents. These compounds can be used alone, or in combination with another agent, such as a compound described herein.

Modulators of a Neoactivity

A candidate compound can be evaluated for modulation (e.g., inhibition) of neoactivity, for example, using an assay described herein. A candidate compound can also be evaluated for modulation (e.g., inhibition) of wild type or non-mutant activity. For example, the formation of a product or by-product of any activity (e.g., enzymatic activity) can be assayed, thus evaluating a candidate compound. In some embodiments, the activity (e.g., wild type/non-mutant or neoactivity) can be evaluated by measuring one or more readouts from an enzymatic assay. For example, the change in nature and/or amount of substrate and/or product can be measured, e.g., using methods such as fluorescent or radio-labeled substrates. Exemplary substrates and/or products include α-ketoglutarate, $CO_2$, NADP, NADPH, NAD, NADH, and 2-hydroxyglutarate, e.g., R-2-hydroxyglutarate. In some embodiments, the rate of reaction of the enzyme can also be evaluated as can the nature and/or amount of a product of the enzymatic reaction. In addition to the measurement of potential enzymatic activities, activity (e.g., wild type/non-mutant or neoactivity) can be detected by the quenching of protein fluorescence upon binding of a potential substrate, cofactor, or enzymatic activity modulator to the enzyme.

In one embodiment, assay progress can be monitored by changes in the OD340 or fluorescence of the NAD or NADP cofactor. In another embodiment, the reaction progress can be coupled to a secondary enzyme assay system in continuous mode or endpoint mode for increasing the dynamic range of the assay. For example, an endpoint assay can be performed by adding to the reaction an excess of diaphorase and rezasarin. Diaphorase consumes the remaining NADPH or NADH while producing resorufin from rezasarin. Resorufin is a highly fluorescent product which can be measured by fluorescence at Ex544 Em590. This not only terminates the reaction but also generates an easily detectable signal with greater quantum yield than the fluorescence of the cofactor.

A continuous assay can be implemented through coupling a product of the primary reaction to a secondary enzyme reaction that yields detectable results of greater dynamic range or more convenient detection mode. For example, inclusion in the reaction mix of aldehyde dehydrogenase (ALDH), which is an NADP+ dependent enzyme, and 6-methoxy-2-napthaldehye, a chromogenic substrate for ALDH, will result in the production of the fluorescent product 6-methoxy-2-napthoate (Ex310 Em 360) at a rate dependent on the production of NADP+ by isocitrate dehydrogenase. The inclusion of a coupling enzyme such as aldehyde dehydrogenase has the additional benefit of allowing screening of neoactivity irrespective of whether NADP+ or NAD+ is produced, since this enzyme is capable of utilizing both. Additionally, since the NADPH or NADH cofactor required for the "reverse" assay is regenerated, a coupled enzyme system which cycles the cofactor back to the IDH enzyme has the further advantage of permitting continuous assays to be conducted at cofactor concentrations much below Km for the purpose of enhancing the detection of competitive inhibitors of cofactor binding.

In yet a third embodiment of an activity (e.g., wild type/non-mutant or neoactivity) screen, one or a number of IDH substrates, cofactors, or products can be isotopically labeled with radioactive or "heavy" elements at defined atoms for the purpose of following specific substrates or atoms of substrates through the chemical reaction. For example, the alpha carbon of α-KG, isocitrate, or 2-hydroxyglutarate, e.g., R-2-hydroxyglutarate may be $^{14}$C or $^{13}$C. Amount, rate, identity and structure of products formed can be analyzed by means known to those of skill in the art, for example mass spectroscopy or radiometric HPLC.

Compounds that inhibit a neoactivity, e.g., a neoactivity described herein, can include, e.g., small molecule, nucleic acid, protein and antibody.

Exemplary small molecules include, e.g., small molecules that bind to enzymes and decrease their activity, e.g., a neoactivity described herein. The binding of an inhibitor can stop a substrate from entering the enzyme's active site and/or hinder the enzyme from catalyzing its reaction. Inhibitor binding is either reversible or irreversible. Irreversible inhibitors usually react with the enzyme and change it chemically. These inhibitors can modify key amino acid residues needed for enzymatic activity. In contrast, reversible inhibitors bind non-covalently and different types of inhibition are produced depending on whether these inhibitors bind the enzyme, the enzyme-substrate complex, or both. In some embodiments, the small molecule is oxalomalate, oxalofumarate, or oxalosuccinate. In some embodiments, the small molecule is a compound of formula (X) or (Formula (XI), or a compound as listed in Table 24a or Table 24b, or a compound as described in U.S. provisional application 61/365,072, the content of which is incorporated herein by reference.

The compound of formula (X) is provided below:

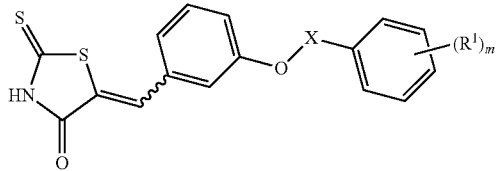

Formula (X)

wherein X is $C_1$-$C_6$ alkylene (e.g., methylene), C(O), or C(O)$C_1$-$C_6$ alkylene; wherein X is optionally substituted; $R^1$ is halo (e.g., fluoro), $C_1$-$C_6$ alkyl, $C_1$-$C_6$ haloalkyl, hydroxyl, $C_1$-$C_6$ alkoxy, cyano, nitro, amino, alkylamino, dialkylamino, amido, —C(O)OH, or C(O)O$C_1$-$C_6$alkyl; and m is 0, 1, 2, or 3.

In some embodiments, the compound is a compound of formula (XI) or a pharmaceutically acceptable salt thereof or a compound listed in Table 24b

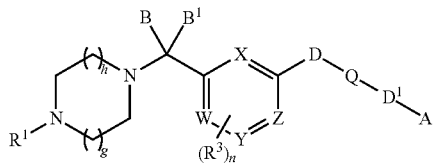

(XI)

wherein:

W, X, Y and Z are each independently selected from CH or N;

B and $B^1$ are independently selected from hydrogen, alkyl or when taken together with the carbon to which they are attached form a carbonyl group;

Q is C=O or $SO_2$;

D and $D^1$ are independently selected from a bond, oxygen or $NR^c$;

A is optionally substituted aryl or optionally substituted heteroaryl;

$R^1$ is independently selected from alkyl, cycloalkyl, aryl, heteroaryl, heterocyclyl, heterocyclylalkyl, cycloalkylalkyl, aralkyl, and heteroaralkyl; each of which may be optionally substituted with 0-3 occurrences of $R^d$;

each $R^3$ is independently selected from halo, haloalkyl, alkyl and —$OR^a$;

each $R^a$ is independently selected from alkyl, and haloalkyl;

each $R^b$ is independently alkyl;

each $R^c$ is independently selected from hydrogen and alkyl;

each $R^d$ is independently selected from halo, haloalkyl, alkyl, nitro, cyano, and —$OR^a$, or two $R^d$ taken together with the carbon atoms to which they are attached form an optionally substituted heterocyclyl;

n is 0, 1, or 2;

h is 0, 1, 2; and g is 0, 1 or 2.

Additional exemplary small molecule inhibitors of the neoactivity are described in U.S. Ser. No. 61/365,072, filed Jul. 16, 2010, the contents of which are incorporated herein by reference.

In some embodiments, the small molecule is a selective inhibitor of the neoactivity (e.g., relative to the wild type activity).

Nucleic acids can be used to inhibit a neoactivity, e.g., a neoactivity described herein, e.g., by decreasing the expression of the enzyme. Exemplary nucleic acids include, e.g., siRNA, shRNA, antisense RNA, aptamer and ribozyme. Art-known methods can be used to select inhibitory molecules, e.g., siRNA molecules, for a particular gene sequence.

Proteins can also be used to inhibit a neoactivity, e.g., a neoactivity described herein, by directly or indirectly binding to the enzyme and/or substrate, or competing binding to the enzyme and/or substrate. Exemplary proteins include, e.g., soluble receptors, peptides and antibodies. Exemplary antibodies include, e.g., whole antibody or a fragment thereof that retains its ability to bind to the enzyme or substrate.

Exemplary candidate compounds, which can be tested for inhibition of a neoactivity described herein (e.g., a neoactivity associated with mutant IDH1 or IDH2), are described in the following references, each of which are incorporated herein by reference: Bioorganic & Medicinal Chemistry (2008), 16(7), 3580-3586; Free Radical Biology & Medicine (2007), 42(1), 44-51; KR 2005036293 A; Applied and Environmental Microbiology (2005), 71(9), 5465-5475; KR 2002095553 A; U.S. Pat. Appl. US 2004067234 A1; PCT Int. Appl. (2002), WO 2002033063 A1; Journal of Organic Chemistry (1996), 61(14), 4527-4531; Biochimica et Biophysica Acta, Enzymology (1976), 452(2), 302-9; Journal of Biological Chemistry (1975), 250(16), 6351-4; Bollettino—Societa Italiana di Biologia Sperimentale (1972), 48(23), 1031-5; Journal of Biological Chemistry (1969), 244(20), 5709-12.

Cellular Structural Analogs of Neoactivity Products, and Prodrugs Thereof

An exemplary cellular structural analog of a neoactivity product is alpha-ketoglutarate. Thus, the invention includes a method of treating a subject, e.g., a subject having a disorder characterized by unwanted cell proliferation, e.g., cancer, by administering a therapeutically effective amount of α-ketoglurarate (e.g., an amount sufficient to produce high levels as compared to the amount present under normal metabolic conditions), an α-ketogluarate prodrug, or a compound that increases the level of α-ketoglurarate to the subject. The cancer can be one described herein.

Exemplary structural analogs include those of the formula below:

In an embodiment the cellular structural analog of a neoactive product or prodrug thereof, is a compound of the formula below:

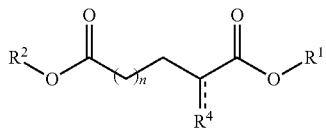

wherein
R1 and R2 are as described below;
===== is a single or double bond; and
$R^4$ is O, when ===== is a double bond, or is selected from —OH, —O-(hydrophoblic moiety), —NH and —N-(hydrophobic moiety) when ===== is a single bond.

A structural representation of alpha-ketoglutarate and exemplary related alpha-ketoglutarate prodrugs is provided in formula (I) below.

In some embodiments certain compounds (referred to herein as "α-ketoglutarate compounds" or "α-ketogluartates" or "α-ketogluartate esters"), can be administered to a subject to treat a cancer described herein. (These compounds may be described as α-ketoglutarates bearing (e.g., conjugated to, coupled to) a hydrophobic moiety. Exemplary compounds are described, for example, in WO2006016143, the contents of which are incorporated by reference in its entirety.

For example, these compounds include α-ketoglutarate esters (i.e., esters of α-ketogluartic acid) having a hydrophobic moiety that is, or is part of, an ester group (i.e., —C(=O)OR) formed from one of the acid groups of α-ketogluartic acid.

For reference, the related parent compounds, glutaric acid and α-ketoglutaric acid are shown below.

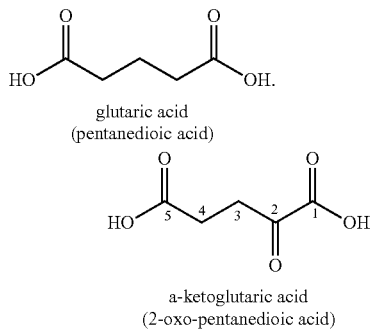

glutaric acid
(pentanedioic acid)

a-ketoglutaric acid
(2-oxo-pentanedioic acid)

Other structural analogues of alpha ketoglutarate can also be used for the treatment of a proliferative disorder described herein such as cancer. Additional exemplary structural analogues and prodrugs thereof are provided in the compounds of formulae (II), (III), (IV), and (V) below.

Thus, in one embodiment, alpha ketoglurarate, a structural analog, or prodrug thereof is a compound of one of the following formula (I), (II), (III), (IV), or (V):

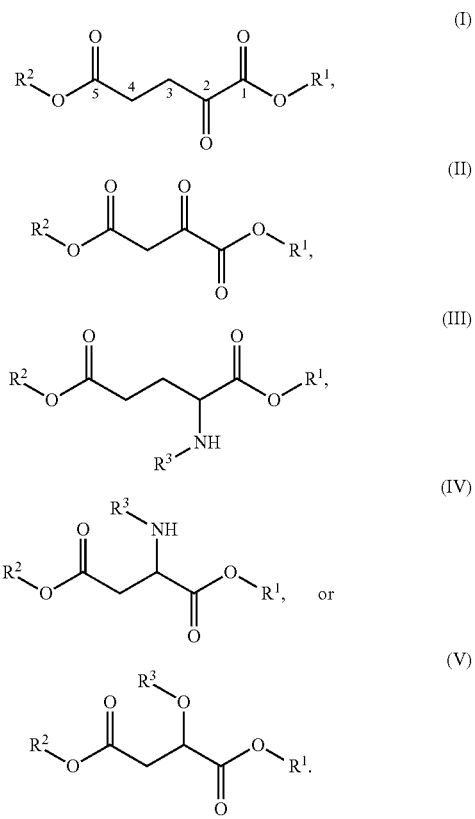

wherein
each of R1 and R2 is independently selected from: (i) H; and (ii) a hydrophobic moiety; and
R3 is H or a hydrophobic moiety,
and pharmaceutically acceptable salts thereof.

In one embodiment, where the compound includes each of R1, R2, and R3, at least one of R1, R2, and R3 is not H.

In one embodiment, R1 and R2 are not both H

In one embodiment, neither R1 nor R2 is H (i.e., diesters).

In one embodiment, neither R1 nor R2 is H; and R1 and R2 are different. In one embodiment, neither R1 nor R2 is H; and R1 and R2 are identical.

In one embodiment, exactly one of R1 and R2 is H (i.e., monoesters).

In one embodiment, the compound is a compound of formula (I) and R1 is H (and R2 is not H):

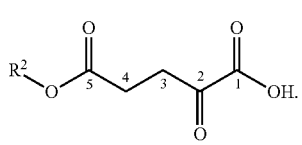

In one embodiment, the compound is a compound of formula (I) and R2 is H (and R1 is not H):

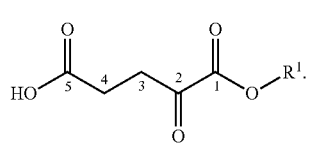

In one embodiment, the compound is a compound of formula (II) and R1 is H (and R2 is not H):

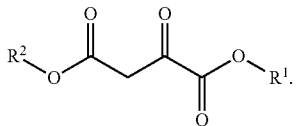

In one embodiment, the compound is a compound of formula (II) and R2 is H (and R1 is not H):

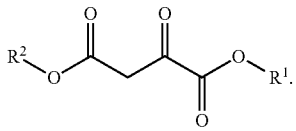

In one embodiment, the compound is a compound of formula (III) and R1 is H (and R2 is not H):

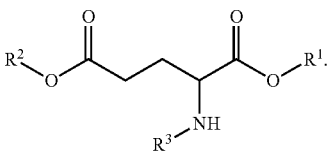

In one embodiment, the compound is a compound of formula (III) and R2 is H (and R1 is not H):

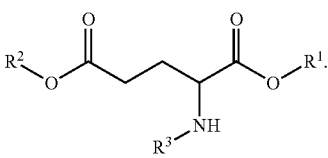

In one embodiment, the compound is a compound of formula (IV) and R1 is H (and R2 is not H):

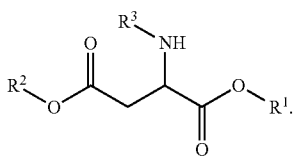

In one embodiment, the compound is a compound of formula (IV) and R2 is H (and R1 is not H):

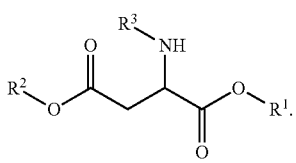

In one embodiment, the compound is a compound of formula (V) and R1 is H (and R2 is not H):

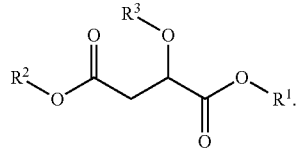

In one embodiment, the compound is a compound of formula (V) and R2 is H (and R1 is not H):

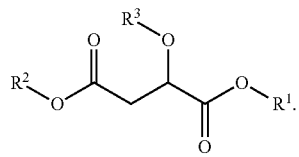

The Hydrophobic Moiety/Moieties

As used herein, the term "hydrophobic moiety" includes, but is not limited to, chemical moieties with non-polar atoms or groups that have a tendency to interact with each other rather than with water or other polar atoms or groups. Hydrophobic moieties are substantially insoluble or only poorly soluble in water. Optionally, the hydrophobic moiety may be selected according to their fusogenic properties or their interactions with components of cellular membranes, such as lectins and lipid head groups. For example, the hydrophobic moiety may comprise a polymer (e.g., a linear or branched polymer); an alkyl, alkenyl, and/or alkynyl group, which may be, for example, linear, branched or cyclic (e.g., C1-C30 alkyl, C2-C30 alkenyl, C2-C30 alkynyl, C3-C30 cycloalkyl, C3-C30 cylcoalkenyl, C3-C30 cycloalkynyl); an aromatic group (e.g., C6-C20 carboaryl, Cs-C20 heteroaryl); or a combination thereof.

Optionally, the hydrophobic moiety may comprise one or more of: a heteroatom, a heterocyclic group, a peptide, a peptoid, a natural product, a synthetic compound, a steroid, and a steroid derivative (e.g., hydrophobic moieties which comprise a steroidal nucleus, e.g., a cholesterol ring system).

It is intended that the hydrophobic moiety be selected so that the α-ketoglutarate compound is capable of performing its intended function, e.g., to cross through lipid membranes into the cytosol/mitochondria.

Examples of hydrophobic moieties include, but are not limited to, those derived from: lipids, fatty acids, phospholipids, sphingolipids, acylglycerols, waxes, sterols, steroids (e.g., cholesterol), terpenes, prostaglandins, thromboxanes, leukotrienes, isoprenoids, retenoids, biotin, and hydrophobic amino acids (e.g., tryptophan, phenylalanine, isoleucine, leucine, valine, methionine, alanine, proline, and tyrosine).

In one embodiment, the hydrophobic moiety, or each hydrophobic moiety, is independently selected from: C1-C30 alkyl; C2-C30 alkenyl; C2-C30 alkynyl; C3-C30 cycloalkyl; C3-C30 cycloalkenyl; C3-C30 cycloalkynyl; C6-C20 carboaryl; C5-C20 heteroaryl; C6-C20 carboaryl-CrC7 alkyl; C5-C20 heteroaryl-d-Cr alkyl; and is unsubstituted or substituted. In one embodiment, the hydrophobic moiety, or each hydrophobic moiety, is independently selected from: C1-C30 alkyl; C2-C30 alkenyl; C2-C30 alkynyl; and is unsubstituted or substituted.

In one embodiment, the bottom of the range (for alkyl, alkenyl, alkynl) is C4. In one embodiment, the bottom of the range is C6. In one embodiment, the bottom of the range is C8. In one embodiment, the bottom of the range is C10. In one embodiment, the bottom of the range is C12.

In one embodiment, the top of the range (for alkyl, alkenyl, alkynl) is C30. In one embodiment, the top of the range is C24. In one embodiment, the top of the range is C22. In one embodiment, the top of the range is C20. In one embodiment, the top of the range is C18. In one embodiment, the top of the range is C16.

In one embodiment, the range (for alkyl, alkenyl, alkynl) is C4-C20. In one embodiment, the range is C6-C18. In one embodiment, the range is C8-C16. In one embodiment, the range is C10-C24. In one embodiment, the range is C12-C22. In one embodiment, the range is C14-C20. In one embodiment, the range is C16-C18.

In one embodiment, the hydrophobic moiety, or each hydrophobic moiety, is independently C1-C30 alkyl and is unsubstituted or substituted.

In one embodiment, the bottom of the range (for alkyl) is C4. In one embodiment, the bottom of the range is C6. In one embodiment, the bottom of the range is C8. In one embodiment, the bottom of the range is C10. In one embodiment, the bottom of the range is C12.

In one embodiment, the top of the range (for alkyl) is C30. In one embodiment, the top of the range is C24. In one embodiment, the top of the range is C22. In one embodiment, the top of the range is C20. In one embodiment, the top of the range is C18. In one embodiment, the top of the range is C16.

In one embodiment, the range (for alkyl) is C4-C20. In one embodiment, the range is C6-C18. In one embodiment, the range is C8-C16. In one embodiment, the range is C10-C24. In one embodiment, the range is C12-C22. In one embodiment, the range is C14-C20. In one embodiment, the range is C16-C18.

In one embodiment, the alkyl group is a linear or branched alkyl group and is unsubstituted or substituted, for example, in one embodiment, the hydrophobic moiety is linear or branched C1-C30 alkyl and is unsubstituted or substituted.

In one embodiment, the hydrophobic moiety, or each hydrophobic moiety, is independently —(CH2)nCH3, wherein n is independently an integer from 0 to 29.

In one embodiment, the bottom of the range for n is 3. In one embodiment, the bottom of the range for n is 5. In one embodiment, the bottom of the range for n is 7. In one embodiment, the bottom of the range for n is 9. In one embodiment, the bottom of the range for n is 11.

In one embodiment, the top of the range for n is 29. In one embodiment, the top of the range for n is 23. In one embodiment, the top of the range for n is 21. In one embodiment, the top of the range for n is 19. In one embodiment, the top of the range for n is 17. In one embodiment, the top of the range for n is 15. In one embodiment, n is independently an integer from 3 to 19. In one embodiment, n is independently an integer from 5 to 17. In one embodiment, n is independently an integer from 7 to 15.

In one embodiment, the hydrophobic moiety, or each hydrophobic moiety, is independently selected from: C6-C20 carboaryl; C5-C20 heteroaryl; C6-C20 carboaryl-C1-C7 alkyl; C5-C20 heteroaryl-C1-C7 alkyl; and is unsubstituted or substituted.

In one embodiment, the hydrophobic moiety, or each hydrophobic moiety, is independently selected from: C6-C12 carboaryl; C5-C12 heteroaryl; C6-C12 carboaryl-C1-C7 alkyl; C5-C12 heteroaryl-C1-C7 alkyl; and is unsubstituted or substituted.

In one embodiment, the hydrophobic moiety, or each hydrophobic moiety, is independently selected from: C6-C10 carboaryl; C5-C10 heteroaryl; C6-C10 carboaryl-C1-C7 alkyl; C5-C10 heteroaryl-C1-C7 alkyl; and is unsubstituted or substituted.

In one embodiment, the hydrophobic moiety, or each hydrophobic moiety, is independently selected from: C6-C20 carboaryl; C6-C20 carboaryl-C1-C7 alkyl; and is unsubstituted or substituted. In one embodiment, the hydrophobic moiety, or each hydrophobic moiety, is independently selected from: C6-C12 carboaryl; C6-C12 carboaryl-C1-C7 alkyl; and is unsubstituted or substituted.

In regard to the phrase "unsubstituted or substituted", any substituents, if present, may be, in one embodiment, as defined below for Rp.

For example, in one embodiment, each carboaryl and heteroaryl group, if present, is unsubstituted or substituted with one or more (e.g., 1, 2, 3, 4, etc.) substituents independently selected from: halo; cyano; nitro; hydroxy; C1-C7 alkyoxy; C1-C7 alkyl; C1-C7 haloalkyl; and C8-C30 alkyl.

In one embodiment, the above C8-C30 alkyl groups are C10-C24 alkyl. In one embodiment, the above C8-C30 alkyl groups are C12-C22 alkyl. In one embodiment, the above C8-C30 alkyl groups are C14-C20 alkyl. In one embodiment, the above C8-C30 alkyl groups are C16-C18 alkyl.

In one embodiment, the hydrophobic moiety, or each hydrophobic moiety, is independently an optionally substituted phenyl group of formula:

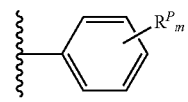

wherein m is independently 0, 1, 2, 3, 4, or 5, and each Rp, if present, is independently a substituent.

In one embodiment, the hydrophobic moiety, or each hydrophobic moiety, is independently an optionally substituted benzyl group of formula:

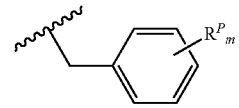

wherein m is independently 0, 1, 2, 3, 4, or 5, and each Rp, if present, is independently a substituent. In one embodiment, m is 0, 1, 2, or 3. In one embodiment, m is 0, 1, or 2. In one embodiment, m is 0 or 1.

In one embodiment, the substituents, Rp, are independently selected from the following:

(1) carboxylic acid; (2) ester; (3) amido or thioamido; (4) acyl; (5) halo; (6) cyano; (7) nitro; (8) hydroxy; (9) ether; (10) thiol; (11) thioether; (12) acyloxy; (13) carbamate; (14) amino; (15) acylamino or thioacylamino; (16) aminoacylamino or aminothioacylamino; (17) sulfonamino; (18) sulfonyl; (19) sulfonate; (20) sulfonamido; (21) C5-20aryl-C1-7alkyl; (22) C6.20carboaryl and C5.2oheteroaryl; (23) C3-2oheterocyclyl; (24) Ci-7alkyl; C8.30alkyl; C2-7alkenyl; C2-7alkynyl; C3-7cycloalkyl; C3.7cycloalkenyl; C3-7cycloalkynyl.

In one embodiment, the substituents, Rp, are independently selected from the following:

(I) —C(O)OH; (2) —C(=O)OR1, wherein R1 is independently as defined in (21), (22), (23) or (24); (3) —C(=O)NR2R3 or —C(=S)NR2R3, wherein each of R2 and R3 is independently —H; or as defined in (21), (22), (23) or (24); or R2 and R3 taken together with the nitrogen atom to which they are attached form a ring having from 3 to 7 ring atoms; (4) —C(=O)R4, wherein R4 is independently —H, or as defined in (21), (22), (23) or (24); (5) —F, —Cl, —Br, —I; (6) —CN; (7) —NO2; (8) —OH; (9) —OR5, wherein R5 is independently as defined in (21), (22), (23) or (24); (1O) —SH; (11) —SR6, wherein R6 is independently as defined in (21), (22), (23) or (24); (12) —OC(=O)R7, wherein R7 is independently as defined in (21), (22), (23) or (24); (13) —OC(O)NR8R9, wherein each of R8 and R9 is independently —H; or as defined in (21), (22), (23) or (24); or R8 and R9 taken together with the nitrogen atom to which they are attached form a ring having from 3 to 7 ring atoms; (14) —NR10R11, wherein each of R10 and R11 is independently —H; or as defined in (21), (22), (23) or (24); or R10 and R11 taken together with the nitrogen atom to which they are attached form a ring having from 3 to 7 ring atoms; (15) —NR12C(=O)R13 or —NR12C(=S)R13, wherein R12 is independently —H; or as defined in (21), (22), (23) or (24); and R13 is independently —H, or as defined in (21), (22), (23) or (24); (16) —NR14C(=O)NR15R16 or —NR14C(=S)NR15R16, wherein R14 is independently —H; or as defined in (21), (22), (23) or (24); and each of R15 and R16 is independently —H; or as defined in (21), (22), (23) or (24); or R15 and R16 taken together with the nitrogen atom to which they are attached form a ring having from 3 to 7 ring atoms; (17) —NR17SO2R18, wherein R17 is independently —H; or as defined in (21), (22), (23) or (24); and R18 is independently —H, or as defined in (21), (22), (23) or (24); (18) —SO2R19, wherein R19 is independently as defined in (21), (22), (23) or (24); (19) —OSO2R20 and wherein R20 is independently as defined in (21), (22), (23) or (24); (20) —SO2NR21R22, wherein each of R21 and R22 is independently —H; or as defined in (21), (22), (23) or (24); or R21 and R22 taken together with the nitrogen atom to which they are attached form a ring having from 3 to 7 ring atoms; (21) C5-2oaryl-Ci-7alkyl, for example, wherein C5.20aryl is as defined in (22); unsubstituted or substituted, e.g., with one or more groups as defined in (1) to (24); (22) C6-20carboaryl; C5-20heteroaryl; unsubstituted or substituted, e.g., with one or more groups as defined in (1) to (24); (23) C3.20heterocyclyl; unsubstituted or substituted, e.g., with one or more groups as defined in (1) to (24); (24) C1-7alkyl; C8-3oalkyl; C2-7alkenyl; C2-7alkynyl; C3-7cycloalkyl; C3-7cycloalkenyl; C3.7cycloalkynyl; unsubstituted or substituted, e.g., with one or more groups as defined in (1) to (23), e.g., halo-C1-7alkyl; e.g., amino-C1-7alkyl (e.g., —(CH2)w-amino, w is 1, 2, 3, or 4); e.g., carboxy-C1-7alkyl (e.g., —(CH2)W—COOH, w is 1, 2, 3, or 4); e.g., acyl-C1-7alkyl (e.g., —(CH2)W—C(=O)R4, w is 1, 2, 3, or 4); e.g., hydroxy-C1-7alkyl (e.g., —(CH2)W—OH, w is 1, 2, 3, or 4); e.g., C1-7alkoxy-C1.7alkyl (e.g., —(CH2)w-O—C1-7alkyl, w is 1, 2, 3, or 4).

In one embodiment, the substituents, Rp, are independently selected from the following:

(1) —C(=O)OH; (2) —C(=O)0Me, —C(=O)OEt, —C(=O)O(iPr), —C(=O)O(tBu); —C(=O)O(cPr); —C(=O)OCH2CH2OH, —C(=O)OCH2CH2OMe, —C(=O)OCH2CH2OEt; —C(=O)OPh, —C(=O)OCH2Ph; (3) —C(=O)NH2, —C(=O)NMe2, —C(=O)NEt2, —C(=O)N(IPr)2, —C(=O)N(CH2CH2OH)2; —C(=O)-morpholino, —C(=O)NHPh, —C(=O)NHCH2Ph; (4) —C(=O)H, —(C=O)Me, —(C=O)Et, —(C=O)(tBu), —(C=O)-cHex, —(C=O)Ph; —(C=O)CH2Ph; (5) —F, —Cl, —Br, —I; (6) —CN; (7) —NO2; (8) —OH; (9) —OMe, -OEt, —O(iPr), —O(tBu), —OPh, —OCH2Ph; —OCF31-OCH2CF3; —OCH2CH2OH, —OCH2CH2OMe, —OCH2CH2OEt; —OCH2CH2NH2, —OCH2CH2NMe2, —OCH2CH2N(JPr)2; —OPh-Me, —OPh-OH, —OPh-OMe, —OPh-F, —OPh-CI, —OPh-Br, —OPh-I; (1O) —SH; (11) —SMe, -SEt, —SPh, —SCH2Ph; (12) —OC(=O)Me, —OC(=O)Et, —OC(=O)(iPr), —OC(=O)(tBu); —OC(=O)(cPr); —OC(O)CH2CH2OH, —OC(=O)CH2CH2OMe, —OC(=O)CH2CH2OEt; —OC(=O)Ph, —OC(=O)CH2Ph; (13) —OC(=O)NH2, -0C(=0)NHMe, -0C(=0)NMe2, —OC(=O)NHEt, —OC(=O)NEt2, —OC(=O) NHPh1-OC(=O)NCH2Ph; (14) —NH2, —NHMe, —NHEt, —NH(iPr), —NMe2, -NEt2, —N(JPr)2, —N(CH2CH2OH)2; —NHPh, —NHCH2Ph; piperidino, piperazino, morpholino; (15) —NH(C=O)Me, —NH(C=O)Et, —NH(C=O)nPr, —NH(C=O)Ph, —NHC(=O)CH2Ph; —NMe(C=O)Me, —NMe(C=O)Et, —NMe(C=O)Ph, —NMeC(=O)CH2Ph; (16) —NH(C=O)NH2, —NH(C=O)NHMe, —NH(C=O)NHEt, —NH(C=O)NPh, —NH(C=O)NHCH2 Ph; —NH(C=S)NH2, —NH(C=S)NHMe, —NH(C=S)NHEt, —NH(C=S)NPh, —NH(C=S)N HCH2Ph; (17) —NHSO2Me, —NHSO2Et, —NHSO2Ph1-NHSO2PhMe, —NHSO2CH2Ph; —NMeSO2Me, —NMeSO2Et1-NMeSO2Ph1-NMeSO2PhMe1-NMeSO2CH2Ph; (18) —SO2Me1-SO2CF3, —SO2Et, —SO2Ph, —SO2PhMe1-SO2CH2Ph; (19) —OSO2Me1 —OSO2CF3, —OSO2Et, —OSO2Ph, —OSO2PhMe, —OSO2CH2Ph; (20) —SO2NH2, —SO2NHMe, —SO2NHEt1-SO2NMe2, —SO2NEt2, —S02-morpholino, —SO2NPh, —SO2NHCH2Ph; (21) —CH2Ph, —CH2Ph-Me, —CH2Ph-OH, —CH2Ph-F, —CH2Ph-CI; (22) -Ph1-Ph-Me, -Ph-OH, -Ph-OMe, -Ph-NH2, -Ph-F, -Ph-Cl, -Ph-Br, -Ph-I; pyridyl, pyrazinyl, pyrimidinyl, pyridazinyl; furanyl, thiophenyl, pyrrolyl, imidazolyl, pyrazolyl, oxazolyl, thiazolyl, thiadiazolyl; (23) pyrrolidinyl, imidazolidinyl, pyrazolidinyl, piperidinyl, piperazinyl, azepinyl, tetrahydrofuranyl, tetrahydropyranyl, morpholinyl, azetidinyl; (24) -Me, -Et, -nPr, -iPr, -nBu, -iBu, -sBu, -tBu, -nPe, -nHex; —(CH2)7CH3, —(CHz)9CH3, —(CHz)11CH3, —(CH2)I3CH3, —(CH2)15CH3, —(CH2)17CH3, —(CH2)19CH3; -cPr, -cHex; —CH=CH2, —CH2-CH=CH2; —CF3, —CHF2, —CH2F, —CCl3, —CBr3, —CH2CH2F, —CH2CHF2, and —CH2CF3; —CH2OH, —CH2OMe, —CH2OEt, —CH2NH2, —CH2NMe2; —CH2CH2OH, —CH2CH2OMe, —CH2CH2OEt, —CH2CH2NH2, —CH2CH2NMe2.

In one embodiment, the substituents, Rp, are independently selected from: halo; cyano; nitro; hydroxy; C1-C7 alkyoxy; C1-C7 alkyl; C1-C7 haloalkyl; and C8-C30 alkyl.

In one embodiment, the substituents, Rp, are independently selected from: halo; cyano; nitro; hydroxy; C1-C4 alkyoxy; C1-C4 alkyl; C1-C4 haloalkyl; and C12-C22 alkyl.

In one embodiment, the substituents, Rp, are independently selected from: halo; C1-C4 alkyl; and C1-C4 haloalkyl.

In one embodiment, the substituents, Rp, are independently selected from: fluoro; C1-C4 alkyl; and C1-C4 fluoroalkyl.

In one embodiment, the substituents, Rp, are independently selected from: F, —CH3, —CF3.

As used herein, the term "halo" includes fluoro, chloro, bromo and iodo.

As used herein, the term "alkyl" pertains to monovalent, monodentate, aliphatic (linear or branched) saturated hydrocarbon moieties, for example, methyl, ethyl, n-propyl, i-propyl, etc.

Examples of (unsubstituted) alkyl groups include methyl (C1), ethyl (C2), propyl (C3), butyl (C4), pentyl (C5), hexyl (C6), heptyl (C7), octyl (C8), nonyl (C9), decyl (C10), undecyl (C11), dodecyl (C12), tridecyl (C13), tetradecyl (C14), pentadecyl (C15), and eicodecyl (C20). Examples of (unsubstituted) linear alkyl groups include methyl (C1), ethyl (C2), n-propyl (C3), n-butyl (C4), n-pentyl (amyl) (C5), n-hexyl (C6), and n-heptyl (C7).

Examples of (unsubstituted) branched alkyl groups include iso-propyl (C3), iso-butyl (C4), sec-butyl (C4), tert-butyl (C4), iso-pentyl (C5), and neo-pentyl (C5).

As used herein, the term "alkenyl" pertains to monovalent, monodentate, aliphatic (linear or branched) hydrocarbon moieties having at least one carbon-carbon double bond.

Examples of (unsubstituted) alkenyl groups include ethenyl (vinyl, —CH=CH2), 1-propenyl (—CH=CH—CH3), 2-propenyl (allyl, —CH—CH=CH2), isopropenyl (1-methylvinyl, —C(CH3)=CH2), butenyl (C4), pentenyl (C5), and hexenyl (C6).

As used herein, the term "alkynyl" pertains to monovalent, monodentate, aliphatic (linear or branched) hydrocarbon moieties having at least one carbon-carbon triple bond.

Examples of (unsubstituted) alkynyl groups include ethynyl (ethinyl, —C≡CH) and 2-propynyl (propargyl, —CH2-C≡CH).

As used herein, the term "cycloalkyl" pertains to monovalent, monodentate, non-aromatic saturated hydrocarbon moieties having at least one carbon-atom ring (preferably having from 3 to 7 ring carbon atoms).

Examples of cycloalkyl groups include those derived from saturated monocyclic hydrocarbon compounds: cyclopropane (C3), cyclobutane (C4), cyclopentane (C5), cyclohexane (C6), cycloheptane (C7), methylcyclopropane (C4), dimethylcyclopropane (C5), methylcyclobutane (C5), dimethylcyciobutane (C6), methylcyclopentane (C6), dimethylcyclopentane (C7), methylcyclohexane (C7), dimethylcyclohexane (C8), menthane (C10); and saturated polycyclic hydrocarbon compounds: thujane (C10), carane (C10), pinane (C10), bornane (C10), norcarane (C7), norpinane (C7), norbornane (C7), adamantane (C10), decalin (decahydronaphthalene) (C10).

As used herein, the term "cycloalkenyl" pertains to monovalent, monodentate, non-aromatic hydrocarbon moieties having at least one carbon-atom ring (preferably having from 3 to 7 ring carbon atoms) and at least one carbon-carbon double bond. Examples of cycloalkenyl groups include those derived from unsaturated monocyclic hydrocarbon compounds: cyclopropene (C3), cyclobutene (C4), cyclopentene (C5), cyclohexene (C6), methylcyclopropene (C4), dimethylcyclopropene (C5), methylcyclobutene (C5), dimethylcyclobutene (C6), methylcyclopentene (C6), dimethylcyclopentene (C7), methylcyclohexene (C7), dimethylcyclohexene (C8); and unsaturated polycyclic hydrocarbon compounds: camphene (C10), limonene (Ci0), pinene As used herein, the term "cycloalkynyl" pertains to monovalent, monodentate, non-aromatic hydrocarbon moieties having at least one carbon-atom ring (preferably having from 3 to 7 ring carbon atoms) and at least one carbon-carbon triple bond.

As used herein, the term "aryl" pertains to monovalent, monodentate, moieties that have an aromatic ring and which has from 3 to 20 ring atoms (unless otherwise specified). Preferably, each ring has from 5 to 7 ring atoms. The ring atoms may be all carbon atoms, as in "carboaryl" groups or the ring atoms may include one or more heteroatoms (e.g., 1, 2, 3, 4, etc.) (e.g., selected from N1 O, and S), as in "heteroaryl" groups. In this context, the prefixes (e.g., C5-C20, C5-C12, C5-C10, etc.) denote the number of ring atoms, or range of number of ring atoms, whether carbon atoms or heteroatoms.

Examples of carboaryl groups include those derived from benzene (i.e., phenyl) (C6), naphthalene (Ci0), azulene (C10), anthracene (C14), phenanthrene (C14), naphthacene (C18), and pyrene (C16).

Examples of carboaryl groups which comprise fused rings, at least one of which is an aromatic ring, include groups derived from indane (e.g., 2,3-dihydro-1H-indene) (C9), indene (C9), isoindene (C9), tetraline (1,2,3,4-tetrahydronaphthalene) (C10), acenaphthene (C12), fluorene (C13), phenalene (C13), acephenanthrene (C15), and aceanthrene (C16).

Additional examples of carboaryl groups include groups derived from: indene (C9), indane (e.g., 2,3-dihydro-1H-indene) (C9), tetraline (1,2,3,4-tetrahydronaphthalene) (C10), acenaphthene (C12), fluorene (C13), phenalene (C13), acephenanthrene (C15), aceanthrene (C16), cholanthrene (C20).

Examples of monocyclic heteroaryl groups include those derived from: N1: pyrrole (azole) (C5), pyridine (azine) (C6); Ov furan (oxole) (C5); S1: thiophene (thiole) (C5); N1O1: oxazole (C5), isoxazole (C5), isoxazine (C6); N2O1: oxadiazole (furazan) (C5); N3O1: oxatriazole (C5); N1S1: thiazole (C5), isothiazole (C5); N2: imidazole (1,3-diazole) (C5), pyrazole (1,2-diazole) (C5), pyridazine (1,2-diazine) (C6), pyrimidine (1,3-diazine) (C6) (e.g., cytosine, thymine, uracil), pyrazine (1,4-diazine) (C6); N3: triazole (C5), triazine (C6); and, N4: tetrazole (C5).

Examples of polycyclic heteroaryl groups include: Cghet-erocyclic groups (with 2 fused rings) derived from benzofuran (O1), isobenzofuran (O1), indole (N1), isoindole (N1), indolizine (N1), indoline (N1), isoindoline (N1), purine (N4) (e.g., adenine, guanine), benzimidazole (N2), indazole (N2), benzoxazole (N1O1), benzisoxazole (N1O1), benzodioxole (O2), benzofurazan (N2O1), benzotriazole (N3), benzothiofuran (S1), benzothiazole (N1S1), benzothiadiazole (N2S); doheterocyclic groups (with 2 fused rings) derived from chromene (O1), isochromene (O1), chroman (O1), isochroman (O1), benzodioxan (O2), quinoline (N1), isoquinoline (N1), quinolizine (N1), benzoxazine (N1O1), benzodiazine (N2), pyridopyridine (N2), quinoxaline (N2), quinazoline (N2), cinnoline (N2), phthalazine (N2), naphthyridine (N2), pteridine (N4); Cnheterocylic groups (with 2 fused rings) derived from benzodiazepine (N2); C13heterocyclic groups (with 3 fused rings) derived from carbazole (N1), dibenzofuran (O1), dibenzothiophene (S1), carboline (N2), perimidine (N2), pyridoindole (N2); and, C14heterocyclic groups (with 3 fused rings) derived from acridine (N1), xanthene (O1), thioxanthene (S1), oxanthrene (O2), phenoxathiin (O1S1), phenazine (N2), phenoxazine (N1O1), phenothiazine (N1S1), thianthrene (S2), phenanthridine (N1), phenanthroline (N2), phenazine (N2).

Heteroaryl groups that have a nitrogen ring atom in the form of an —NH— group may be N-substituted, that is, as —NR—. For example, pyrrole may be N-methyl substituted, to give N-methylpyrrole. Examples of N-substitutents include C1-C7 alkyl; C6-C20 carboaryl; C6-C20 carboaryl-CrC7 alkyl; C1-C7 alkyl-acyl; C6-C20 carboaryl-acyl; C6-C20 carboaryl-CrC7 alkyl-acyl; etc. Heteroaryl groups) which have a nitrogen ring atom in the form of an —N= group may be substituted in the form of an N-oxide, that is, as —N(→O)= (also denoted —N+(→O")=). For example, quinoline may be substituted to give quinoline N-oxide; pyridine to give pyridine N-oxide; benzofurazan to give benzofurazan N-oxide (also known as benzofuroxan).

Molecular Weight

In one embodiment, the compound has a molecular weight of 250 to 1000. In one embodiment, the bottom of range is 275; 300; 325; 350; 375; 400; 425; 450. In one embodiment, the top of range is 900; 800; 700; 600; 500; 400. In one embodiment, the range is 250 to 900. In one embodiment, the range is 250 to 800. In one embodiment, the range is 250 to 700. In one embodiment, the range is 250 to 600. In one embodiment, the range is 250 to 500.

Some Preferred Examples

All plausible and compatible combinations of the embodiments described above are explicitly disclosed herein. Each of these combinations is disclosed herein to the same extent as if each individual combination was specifically and individually recited.

Examples of some preferred compounds include the following:

In embodiments, the compound is a compound of formula (II) wherein R1 is a moiety as shown in compounds, 1, 2, 3, 4, 5, 6, 7, 8, 9, 10, or 11 in the table above:

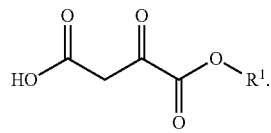

In embodiments, the compound is a compound of formula (III) wherein R1 is a moiety as shown in compounds, 1, 2, 3, 4, 5, 6, 7, 8, 9, 10, or 11 in the table above:

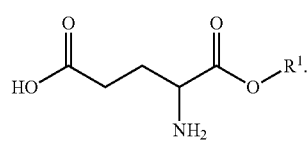

1
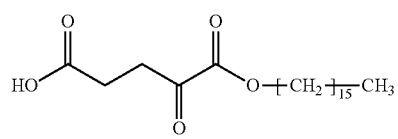

2
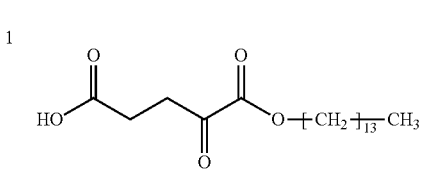

3
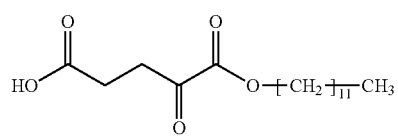

4
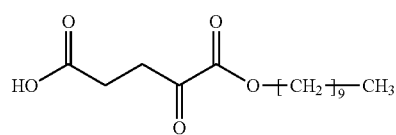

5
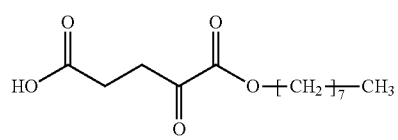

6
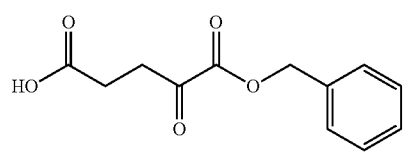

7
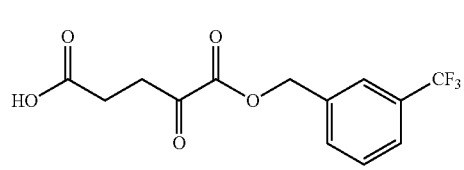

8
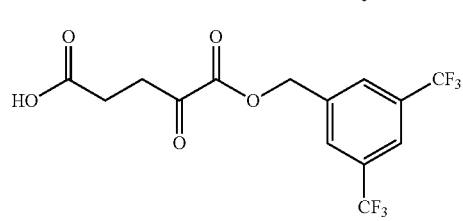

9
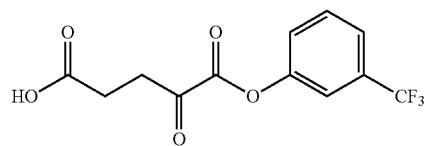

10
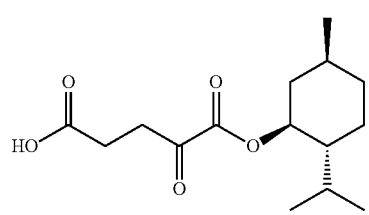

11
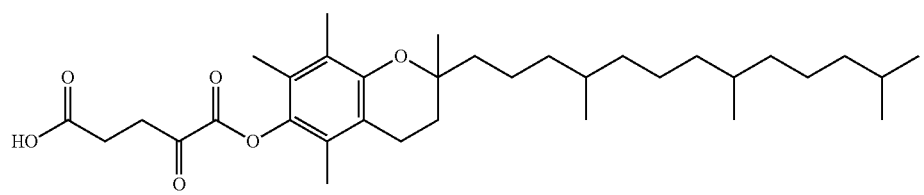

In embodiments, the compound is a compound of formula (IV) wherein R1 is a moiety as shown in compounds, 1, 2, 3, 4, 5, 6, 7, 8, 9, 10, or 11 in the table above:

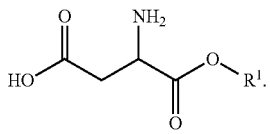

In embodiments, the compound is a compound of formula (V) wherein R1 is a moiety as shown in compounds, 1, 2, 3, 4, 5, 6, 7, 8, 9, 10, or 11 in the table above:

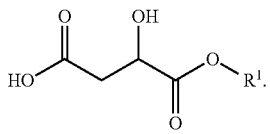

Anti-Glycolytic Compounds

In some embodiments, an anti-glycolytic compound or glycolitic inhibitor can be administered to a subject for the treatment of a proliferative disorder such as cancer such as a cancer described herein. The terms "anti-glycolytic compound" and "glycolitic inhibitor" are used herein interchangeably.

In embodiments a glycolitic inhibitor is a compound, which upon administration, turns a PET positive cancer (e.g., tumor) into a PET negative cancer.

In embodiments a glycolitic inhibitor is a compound, which upon administration of a therapeutically effective amount, inhibits an enzyme in the glycolytic pathway or inhibits glucose uptake (e.g., directly inhibits glucose uptake and/or formation).

In an embodiment a glycolitic inhibitor is a compound, which upon administration, directly competes with glucose, e.g., for a cellular substrate such as an enzyme.

As discussed above, in some embodiments, a glycolitic inhibitor is a compound, which upon administration, turns a PET positive cancer (e.g., tumor) into a PET negative cancer. In some preferred embodiments, the glycolitic inhibitor converts a cancer cell dependent on glycolysis into a cancer cell whose capability for glycolysis is so impaired such that it is essentially incapable of glycolysis. Exemplary glycolitic inhibitors that can render a cancer cell essentially incapable of glycolysis include: Alkylating Agents; Nitrosoureas; Antitumor Antibiotics; Corticosteroid Hormones; Anti-estrogens; Aromatase Inhibitors; Progestins; Anti-androgens; LHRH agonists; Antibody therapies; and other anti-cancer therapies. Examples of Alkylating Agents include busulfan, cisplatin, carboplatin, chlorambucil, cyclophosphamide, ifosfamide, dacarbazine $(DTIC)_5$ mechlorethamine (nitrogen mustard), and melphalan. Examples of Nitrosoureas include carmustine (BCNU) and lomustine (CCNU). Examples of Antitumor Antibiotics include dactinomycin, daunorubicin, doxorubicin (Adriamycin), idarubicin, and mitoxantrone. Examples of Corticosteroid Hormones include prednisone and dexamethasone. Examples of anti-estrogens include tamoxifen and fulvestrant. Examples of aromatase inhibitors include anastrozole and letrozole. An example of a Progestin is megestrol acetate. Examples of anti-androgens include bicalutamide, flutamide. Examples of LHRH agonists include leuprolide and goserelin. Examples of antibody therapies include Herceptin and Avastin. Examples of other anti-cancer compounds include L-asparaginase and tretinoin. In some embodiments, combinations or two or more anticancer compounds may be used.

There are numerous methods of determining whether or not a cancer is dependent upon glycolysis. Samples of tumors can be excised and examined in vitro by any one of several well known assays to determine if the cells are dependent on glycolysis. Such methods can determine whether or not the cells utilize aerobic or anaerobic glycolysis. FDG-PETscan technology uses high levels of glucose uptake as a marker for detection. The cancer cells that take up the detectable glucose derivative $^{18}$fluoro-2-deoxyglucose can be located on a computer image of the patient's anatomy. Those cancers which can be detected by FDG-PETscan technology have a high likelihood of being dependent on glycolysis.

PET methodologies are set forth in Czernin, J. 2002 Acta Medica Austriaca 29:162-170, which is incorporated herein by reference. Many cancers are characterized by a high rate of glycolysis wherein the cancer has cells which exhibit a higher rate of glycolysis than that of the tissue surrounding it. Such cancer cells take up above-average quantities of glucose from the environment. Cancer characterized by a high rate of glycolysis can be identified using PET imaging technology, preferably with $^{18}$fluoro-deoxyglucose. The positive detection of a tumor using such a test indicates that the cancer is characterized by glycolysis.

As discussed elsewhere herein, in some embodiments, a glycolitic inhibitor is a compound, which upon administration, inhibits an enzyme in the glycolytic pathway or inhibits glucose uptake (e.g., directly inhibits glucose uptake and/or formation). In some preferred embodiments, the compound selectively inhibits an isoform of an enzyme in the glycolytic pathway that is present in cancer cells, for example, cancer-specific isoform of a kinase or dehydrogenase such as PKM2 or LDHa. Other exemplary enzymes that can be targeted by a glycolytic inhibitor in the glycolytic pathway include glut1, hexokinase2, phosphofructokinase 3, and pyruvate dehydrogenase kinase 1 (PDK1). Accordingly, included herein are compounds that inhibit an enzyme in the glycolitic pathway such as an enzyme described below.

Glucose Transporter Type 1 (GLUT1)

Glucose transporter type 1 (GLUT1), also known as solute carrier family 2, facilitated glucose transporter member 1, or HepG2 glucose transporter, is an enzyme of the sugar transporter family and glucose transporter subfamily. Glucose transporters (GLUTs) facilitate the energy independent transport of glucose across the hydrophobic cell membrane down its concentration gradient, and each of the GLUTs possesses different affinities for glucose and other sugars. GLUT1 has a broad substrate specificity and can transport a range of aldoses including both pentoses and hexoses. Particularly, it has a high affinity for glucose and may be responsible for constitutive or basal glucose uptake required to sustain respiration in cells.

GLUT1 is primary located on the cell membrane and expressed at variable levels in many human tissues. It has 12 transmembrane α-helical domains, each containing 21 amino acid residues. The precursor of human GLUT1 protein have 492 amino acids and a molecular weight of about 54 kDa, and is encoded by SLC2A1 (also known as GLUT1) gene. Amino acid and nucleotide sequences of human and mouse GLUT1 are described e.g., in Mueckler et al., Science 229:941-945 (1985), and Kaestner et al., Proc. Natl. Acad. Sci. U.S.A. 86:3150-3154 (1989), respectively.

Increased and deregulated expression of GLUT1 is associated with increased glucose transport in a variety of cancer cells (Macheda et al., J Cell Physiol. 202:654-62 (2005)). Oncogenic transformation of cultured mammalian cells can cause an increase of GLUT1 expression via interaction with GLUT1 promoter enhancer elements. GLUT1 is overexpressed in cultured breast cancer cell lines and the levels of GLUT1 correspond to their invasive potentials. GLUT1 levels and glucose uptake can also be increased by hypoxia in ovarian and lung cancer cells. In the clinical setting, elevated GLUT1 expression are observed in a number of cancers including e.g., hepatic, pancreatic, breast, esophageal, brain, renal, lung, cutaneous, colorectal, endometrial, ovarian, and cervical carcinoma. High levels of GLUT1 expression in tumors are also associated with poor survival.

GLUT1 inhibitors are known in the art. Exemplary GLUT1 inhibitors are described e.g., in Macheda et al., J. Cell Physiol. 202:654-62 (2005), Singh et al., Mol Cell Endocrinol. 160:61-66 (2000), and Zhang et al. Bioconjug. Chem. 14:709-714 (2003), each of which is incorporated herein by reference in its entirety.

Hexokinase 2 (HK2)

Hexokinase 2 (HK2), also known as Hexokinase type II or muscle form hexokinase, is an enzyme of hexokinase family. Hexokinases are enzymes that phosphorylate hexose to hexose phosphate. In vertebrates there are four major glucose-phosphorylating isozymes, designated hexokinase 1-4. Hexokinase 2 catalyzes the reaction of ATP+D-hexose=ADP+D-hexose 6-phosphate. It is a low $K_m$ isozyme that has a high affinity for glucose at low concentrations (e.g., below 1 mM) and follows Michaelis-Menton kinetics at physiological concentrations of substrates. Hexokinase 2 is an allosteric enzyme inhibited by its product glucose-6-phospate.

Hexokinase 2 is primary located at the outer mitochondrial membrane and predominantly expressed in insulin-responsive tissues such as skeletal muscle. Human hexokinase 2 has 917 amino acids and a molecular weight of about 102 kDa, and is encoded by HK2 gene. Amino acid and nucleotide sequences of human and mouse hexokinase 2 are described e.g., in Deeb et al., Biochem. Biophys. Res. Commun. 197:68-74 (1993), and Heikkinen et al., Mamm. Genome 11:91-96 (2000), respectively.

Increased expression of hexokinase 2 is associated with a number of cancers e.g., lung, liver, gastrointestinal, and breast cancer. Hexokinase 2 is also overexpressed in brain metastasis in breast cancer patients. In cancer cells, the highly glycolytic phenotype is supported by the overexpression of hexokinase 2. Overexpression of hexokinase 2 leads to the production of glucose-6-phosphate at an elevated rate, thereby promotes an unfavorable environment for normal cells and support cell proliferation. Hexokinase 2 can also increase metastasis by suppression of cancer cell death (Mathupala et al., Oncogene 25:4777-4786 (2006)).

Hexokinase 2 inhibitors are known in the art. Exemplary hexokinase 2 inhibitors are described e.g., in U.S. Pat. No. 5,854,067, Mathupala et al., Oncogene 25:4777-4786 (2006), and Kim et al., Mol. Cancer Ther. 6:2554-2562 (2007), each of which is incorporated herein by reference in its entirety.

Phosphofructokinase 3 (PFKFB3)

Phosphofructokinase 3 (PFKFB3), also known as 6-phosphofructo-2-kinase/fructose-2,6-biphosphatase 3, 6PF-2-K/Fru-2,6-P2ASE brain/placenta-type isozyme, iPFK-2, or renal carcinoma antigen NY-REN-56, is an enzyme of the 6-phosphofructo-2-kinase/fructose-2,6-biphosphatase (PFK2/FBPase) family and the phosphoglycerate mutase family. In humans there are four major PFK2/FBPases, designated PFK2/FBPases 1-4. PFK2/FBPases control the steady-state concentration of fructose-2,6-bisphosphate (Fru-2,6-BP). PFKFB3 can catalyze the following reaction:

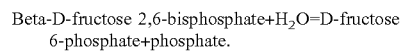

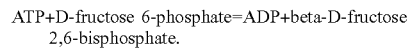

PFKFB3 has both 6-phosphofructo-2-kinase and fructose-2,6-bisphosphatase domains and is ubiquitously expressed in tissues. The precursors of human PFKFB3 isoforms 1 and 2 have 520 amino acids and a molecular weight of about 60 kDa, and 514 amino acids and a molecular weight of about 59 kDa, respectively. Human PFKFB3 is encoded by PFKFB3 gene. Amino acid and nucleotide sequences of human and mouse PFKFB3 are described e.g., in Sakai et al., J. Biochem. 119:506-511 (1996), Manzano et al., Cell Genet. 83:214-217 (1998), and the MGC Project Team, Genome Res. 14:2121-2127 (2004).

The PFKFB3 is overexpressed in a number of cancer cells including e.g., leukemia, colon, prostate, lung, breast, pancrease, thyoid, and ovarian cancer and is required for the growth of certain leukemia and cervical cancer cell lines (Clem et al., Mol Cancer Ther. 7:110-20 (2008)). By regulating the intracellular fructose-2,6-bisphosphate concentration, PFKFB3 controls glycolytic flux to lactate and the nonoxidative pentose shunt, and is required for the high glycolytic rate and anchorage-independent growth of ras-transformed cells (Chesney, Curr. Opin. Clin. Nutr. Metab. Care 9:535-539 (2006)).

PFKFB3 inhibitors are known in the art. Exemplary PFKFB3 inhibitors are described e.g., in US Patent Application Publication No. 2009/0074884 and Clem et al., Mol. Cancer Ther. 7:110-20 (2008), each of which is incorporated herein by reference in its entirety.

Pyruvate Kinase M2 (PKM2)

Pyruvate kinase M2 (PKM2), also known as pyruvate kinase muscle isozyme, pyruvate kinase 2/3, cytosolic thyroid hormone-binding protein, THBP1, p58, M2-PK, or tumor M2-PK, is an enzyme of the pyruvate kinase family. There are four isozymes of pyruvate kinase in mammals: L, R, M1 and M2. L type is major isozyme in the liver, R is found in red cells, M1 is the main form in muscle, heart and brain, and M2 is found in early fetal tissues as well as in most cancer cells. PKM2 is a glycolytic enzyme that catalyzes the transfer of a phosphoryl group from phosphoenolpyruvate (PEP) to ADP, generating ATP. PKM2 exists as a monomer in the absence of FBP, and reversibly associates to form a homotetramer in the presence of FBP. Tetramer formation induces pyruvate kinase activity. The tetrameric form has high affinity for the substrate and is associated within the glycolytic enzyme complex. The ratio between the highly active tetrameric form and nearly inactive dimeric form determines whether glucose carbons are channeled to biosynthetic processes or used for glycolytic ATP production. PKM2 is allosterically activated by D-fructose 1,6-biphosphate (FBP) and inhibited by oxalate and 3,3',5-triiodo-L-thyronine (T3). The activity of the tetrameric form is inhibited by PML.

PKM2 stimulates POU5F1-mediated transcriptional activation and plays a role in caspase independent cell death of tumor cells. It exists in a relatively inactive dimeric form in tumor cells and the dimeric form has less affinity for the substrate. Binding to certain oncoproteins e.g., HPV-16 E7 oncoprotein can trigger dimerization. FBP stimulates the formation of tetramers from dimmers. The transition between the tetrameric and dimeric forms contributes to the control of glycolysis and is important for tumor cell proliferation and survival.

The precursor of human PKM2 has 531 amino acids and a molecular weight of about 58 kDa and is encoded by PKM2 (also known as PK2, PK3, or PKM) gene. Amino acid and nucleotide sequences of human and mouse PKM2 are described e.g., in Tani et al., Gene 73:509-516 (1988), Kato et al., Proc. Natl. Acad. Sci. U.S.A. 86:7861-7865 (1989), Izumi et al., Biochim. Biophys. Acta 1267:135-138 (1995), and de Luis and del Mazo, Biochim. Biophys. Acta 1396:294-305 (1998).

PKM2 inhibitors are known in the art. Exemplary PKM2 inhibitors are described e.g., in US Patent Application Publication No. 2008/0021116, International Patent Application Publication Nos. WO 2008/019139 and WO 2006/125323, Spoden et al., Int. J. Cancer 123:312-321 (2008), and Abstract #4408, AACR 100$^{th}$ annual meeting (Denver, Colo., USA, Apr. 18-22, 2009), each of which is incorporated herein by reference in its entirety.

Lactate Dehydrogenase A (LDHa)

Lactate dehydrogenase A (LDHa), also known as LDH muscle subunit, renal carcinoma antigen NY-REN-59, cell proliferation-inducing gene 19 protein, is an enzyme of the LDH family and LDH/MDH superfamily. LDHa catalyzes the conversion of L-lactate and NAD+ to pyruvate and NADH in the final step of anaerobic glycolysis.

LDHa is primary located in the cytoplasm and can form a homtetramer. Many types of cancers, e.g., testicular cancer, Ewing's sarcoma, non-Hodgkin's lymphoma, and some types of leukemia, as well as other diseases, can cause LDHa levels to be elevated. Reduction in LDHa activity can stimulate mitochondrial respiration and compromise the ability of tumor cells to proliferate under hypoxia (Fantin et al., Cancer Cell. 9:425-434 (2006)). Defects in LDHa are also a cause of exertional myoglobinuria.

The precursor of human LDHa isoform 1 has 332 amino acids and a molecular weight of about 37 kDa, and the precursor of human LDHa isoform 2 has 332 amino acids and a molecular weight of about 36 kDa. Human LDHa is encoded by LDHA gene. Amino acid and nucleotide sequences of human and mouse LDHa are described e.g., in Tsujibo et al., Eur. J. Biochem. 147:9-15 (1985), Ota et al., Nat. Genet. 36:40-45 (2004) Li et al., Eur. J. Biochem. 149:215-225 (1985), and Akai et al., Int. J. Biochem. 17:645-648 (1985).

LDHa inhibitors are known in the art. Exemplary LDHa inhibitors are described e.g. in U.S. Pat. Nos. 5,853,742 and 6,124,498, and International Patent Application Publication No. WO 98/36774, each of which is incorporated herein by reference in its entirety.

Pyruvate Dehydrogenase Kinase Isoform 1 (PDK1)

Pyruvate dehydrogenase kinase isoform 1 (PDK1), is an enzyme of the pyruvate dehydrogenase kinase/branched-chain alpha-ketoacid dehydrogenase kinasePDK/BCKDK protein kinase family. Pyruvate dehydrogenase kinases inactivate pyruvate dehydrogenase by phosphorylating it using ATP. PDK has four isozymes, designated as PDK1-4. PDK1 inhibits the mitochondrial pyruvate dehydrogenase complex by phosphorylation of the E1 alpha subunit, thus contributing to the regulation of glucose metabolism. The catalytic activity of PDK1 can be illustrated as:

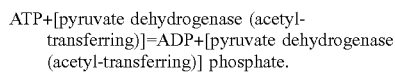

PDK1 is primarily located in the mitochondrion matrix and expressed predominantly in the heart. The inhibition of pyruvate dehydrogenase complex (PDC) activity by PDK1 contributes to the malignant phenotype in a number of cancers, e.g., head and neck squamous cell carcinoma, and is associated with the stabilization of HIF-1α. Inhibition of PDK1 expression can lead to the reduction of lactate levels, HIF-1α expression, and the degree of malignant phenotype in cancer cells (McFate et al., J. Biol. Chem. 283:22700-22708 (2008)).

The precursor of PDK1 has 436 amino acids and a molecular weight of about 49 kDa. Human PDK1 is encoded by PDK1 gene. Amino acid and nucleotide sequences of human PDK1 are described e.g., in Gudi et al., J. Biol. Chem. 270:28989-28994 (1995), the MGC Project Team, Genome Res. 14:2121-2127 (2004), and Carninci et al. Science 309:1559-1563 (2005).

PDK1 inhibitors are known in the art. Exemplary PDK1 inhibitors are described e.g. in U.S. Pat. No. 6,878,712, US Patent Application Publication No. 2009/0209618, International Patent Application Publication Nos: WO 2001/052825, WO 2002/081751 and WO 2005/092040, Cairns et al., Proc. Natl. Acad. Sci. U.S.A. 104:9445-9450 (2007), Mann et al., Biochim. Biophys. Acta. 1480:283-292 (2000), and Aicher et al., J. Med. Chem. 42:2741-2746 (1999), each of which is incorporated herein by reference in its entirety.

Candidate compounds can be evaluated for inhibition of an enzyme described herein, e.g., a glycolytic enzyme, using methods known in the art.

As is discussed above, in some embodiments, a glycolitic inhibitor is a compound, which upon administration, directly competes with glucose. Exemplary compounds include structural derivatives of glucose such as 2 deoxyglucose (i.e., 2 dg).

Antioxidants

In some embodiments, an antioxidant compound can be administered to a subject for the treatment of a cell proliferation-related disorder such as cancer such as a cancer described herein.

The term "antioxidant," as used herein, refers to a compound that slows or prevents the oxidation of a molecule, e.g., the transfer of electrons from a substance to an oxidizing agent. Oxidation reactions can produce free radicals, which can start a chain reaction that damage cells. Antioxidants can terminate these chain reactions by removing free radical intermediates, and inhibit other oxidation reactions by being oxidized themselves. Exemplary antioxidants include reducing agents such as thiols, ascorbic acids, or phenols (e.g., a polyphenol).

In general, antioxidants are classified into two broad divisions, water soluble (i.e., hydrophilic) or lipid soluble (i.e., hydrophobic). In general, water-soluble antioxidants react with oxidants in the cell cytosol and the blood plasma, while lipid-soluble antioxidants protect the cell membrane from lipid peroxidation. Exemplary water soluble antioxidants include ascorbic acid, glutathione, lipoic acid, and uric acid. Exemplary lipid soluble antioxidants include carotenes, alpha-tocopherol, and ubiquinol. Exemplary phenolic antioxidants include resveritrol and flavinoids. In some embodiments, the antioxidant is an enzymatic antioxidant such as superoxide dismutase, catalase, peroxiredoxin, thioredoxin and glutathione systems.

Candidate compounds can be evaluated for antioxidant activity using assays known in the art.

Hypomethylating Agents

It has been discovered that certain genes in patients (e.g., AML, MDS or glioma patients) harboring an IDH mutation (e.g., an IDH1 or IDH2 mutation) have increased methylation (e.g., hypermethylation) in the promoter region. In some embodiments, a hypomethylating agent can be administered to a subject for the treatment of a cell proliferation-related disorder such as cancer such as a cancer described herein.

The term "hypomethylating agent" as used herein, refers to a compound that inhibits DNA methylation. The term "hypomethylating agent" can be used interchangeably with the term "demethylating agent."

Exemplary hypomethylating agents include the following compounds, decitabine (5-aza-deoxycytidine), zebularine, isothiocyanates, azacitidine (5-azacytidine), 5-flouro-2'-deoxycytidine, 5,6-dihydro-5-azacytidine, ethionine, S-adenosyl-L-homocysteine, mitoxantrone, neplanocin A, 3-deazaneplanocin A, cycloleucine, hydralazine, phenylhexyl isothiocyanate, curcumin, parthenolide, and SGI-1027.

Additional Therapeutic Compounds—Compounds that Increase the Level of α-Ketoglutarate In some embodiments, a compound (generally) that increases the level of α-ketoglutarate (e.g., in a cell) can be used in a method described herein. For example, a compound may increase α-ketoglutarate levels by inhibiting other enzymes such as α-ketoglutarate dehydrogenase and/or branched-chain keto acid dehydrogenase. Blocking these enzymes can have a dual effect of increasing α-ketoglutarate levels and decreasing succinate levels.

Moreover, both enzymes are structural homologs that use lipoic acid as a cofactor. Therefore, a lipoic acid analogue may be another potential inhibitor of these enzymes, and so be a compound that increases the level of α-ketoglutarate Alternatively, a compound might increase the level of α-ketoglutarate by enhancing glutamate oxaloacetate transaminase (GOT) activity. Glutamate itself will activate GOT activity leading to increased α-ketoglutarate levels.

Moreover, the compound may be selected from upstream metabolites of the TCA cycle including oxaloacetate, citrate, isocitrate, and derivatives thereof.

Additional Compounds—α-Ketoglutarates Generally.

Described herein are α-ketoglutaric acid, α-ketoglutarate salts, and α-ketoglutaric acid derivatives (e.g., esters of α-ketoglutaric acid, generally), and, especially, their use in medicine, for example, in the treatment of a cancer described herein.

In one embodiment, the compound is an α-ketoglutarate bearing (e.g., conjugated to, coupled to) an amino acid moiety (e.g., an α-amino acid moiety) (e.g., an ornithine or arginine moiety).

In one embodiment, the compound is an α-ketoglutarate ester (i.e., an ester of α-ketoglutaric acid) having an amino acid moiety (e.g., an α-amino acid moiety) (e.g., an ornithine or arginine moiety) that is, or is part of, an ester group (i.e., —C(=O)OR) formed from one of the acid groups of α-ketoglutaric acid.

Such compounds are known in the literature (see, e.g. Le Boucher et al. (1997)) and/or are commercially available and/or may be prepared using conventional synthetic procedures known to the skilled person.

Isomers

Certain compounds may exist in one or more particular geometric, optical, enantiomeric, diasteriomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

In one embodiment, a compound described herein, e.g., an inhibitor of a neoactivity or 2-HG is an enantiomerically enriched isomer of a stereoisomer described herein. For example, the compound has an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter, e.g., the 2-position of 2-hydroxyglutaric acid. 2HG can be purchased from commercial sources or can be prepared using methods known in the art, for example, as described in Org. Syn. Coll vol., 7, P-99, 1990. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter, e.g., the 2-position of 2-hydroxyglutaric acid. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH3, is not to be construed as a reference to its structural isomer, a hydroxymethyl group, —CH2OH. Similarly, a reference to ortho-chlorophenyl is not to be construed as a reference to its structural isomer, meta-chlorophenyl. However, a reference to a class of structures may well include structurally isomeric forms falling within that class (e.g., C1-7alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

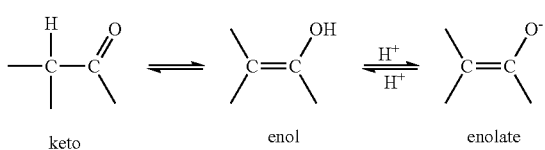

keto ⇌ enol ⇌ enolate

Note that specifically included in the term "isomer" are compounds with one or more isotopic substitutions. For example, H may be in any isotopic form, including 1H, 2H (D), and 3H (T); C may be in any isotopic form, including 12C, 13C, and 14C; O may be in any isotopic form, including 16O and 18O; and the like. Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts." J. Pharm. ScL. Vol. 66, pp. 1-19.

For example, if the compound is anionic, or has a functional group which may be anionic (e.g., —COOH may be —COO"), then a salt may be formed with a suitable cation. Examples of suitable inorganic cations include, but are not limited to, alkali metal ions such as Na+ and K+, alkaline earth cations such as Ca2+ and Mg2+, and other cations such as Al+3. Examples of suitable organic cations include, but are not limited to, ammonium ion (i.e., NH4+) and substituted ammonium ions (e.g., NH3R+, NH2R2+, NHR3+, NR4+). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH3)4+.

If the compound is cationic, or has a functional group that may be cationic (e.g., —NH2 may • be —NH3+), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Chemically Protected Forms

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH3, —OAc).

For example, an aldehyde or ketone group may be protected as an acetal (R—CH(OR)2) or ketal (R2C(OR)2), respectively, in which the carbonyl group (>C=O) is converted to a diether (>C(OR)2), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH3); a benzyloxy amide (—NHCO—OCH2C6H5, —NH-Cbz); as a t-butoxy amide (—NHCO—OC(CH3)3, —NH-Boc); a 2-biphenyl-2-propoxy amide (—NHCO—OC(CH3)2C6H4C6H5, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O<<).

For example, a carboxylic acid group may be protected as an ester for example, as: an C^alkyl ester (e.g., a methyl ester; a t-butyl ester); a Cvrhaloalkyl ester (e.g., a C1-7trihaloalkyl ester); a triC1-7alkylsilyl-Ci.7alkyl ester; or a C5.2oaryl-C1-7alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH2NHC(=O)CH3).

Prodrugs

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

Unless otherwise specified, a reference to a particular compound also includes prodrugs thereof.

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Chemical Synthesis

The synthesis method may employ protective groups, for example, O-protecting groups, such as groups known to be suitable for protecting primary and/or secondary hydroxy groups, for example, the O-protecting groups mentioned in "Protective Groups in Organic Chemistry", edited by J. W. F. McOmie, Plenum Press (1973), and "Protective Groups in Organic Synthesis", 3rd edition, T. W. Greene & P. G. M. Wutz, Wiley-Interscience (1999). Some preferred O-protecting groups include alkylcarbonyl and arylcarbonyl groups (e.g., acyl, e.g., benzoyl), triarylmethyl groups (e.g., triphenylmethyl (trityl) and dimethoxytrityl) and silyl groups (e.g., trialkylsilyl, such as trimethylsilyl).

Nucleic Acid Based Inhibitors

Nucleic acid-based inhibitors for inhibition IDH, e.g., IDH1, can be, e.g., double stranded RNA (dsRNA) that function, e.g., by an RNA interference (RNAi mechanism), an antisense RNA, or a microRNA (miRNA). In an embodiment the nucleic-acid based inhibitor binds to the target mRNA and inhibits the production of protein therefrom, e.g., by cleavage of the target mRNA.

Double Stranded RNA (dsRNA)

A nucleic acid based inhibitor useful for decreasing IDH1 or IDH2 mutant function is, e.g., a dsRNA, such as a dsRNA that acts by an RNAi mechanism. RNAi refers to the process of sequence-specific post-transcriptional gene silencing in animals mediated by short interfering RNAs (siRNAs). dsRNAs as used herein are understood to include siRNAs. Typically, inhibition of IDH, e.g., IDH1, by dsRNAs does not trigger the interferon response that results from dsRNA-mediated activation of protein kinase PKR and 2',5'-oligoadenylate synthetase resulting in non-specific cleavage of mRNA by ribonuclease L.

dsRNAs targeting an IDH, e.g., IDH1, enzyme, e.g., a wildtype or mutant IDH1, can be unmodified or chemically modified. The dsRNA can be chemically synthesized, expressed from a vector or enzymatically synthesized. The invention also features various chemically modified synthetic dsRNA molecules capable of modulating IDH1 gene expression or activity in cells by RNA interference (RNAi). The use of chemically modified dsRNA improves various properties of native dsRNA molecules, such as through increased resistance to nuclease degradation in vivo and/or through improved cellular uptake.

The dsRNAs targeting nucleic acid can be composed of two separate RNAs, or of one RNA strand, which is folded to form a hairpin structure. Hairpin dsRNAs are typically referred to as shRNAs.

An shRNA that targets IDH, e.g., a mutant or wildtype IDH1 gene can be expressed from a vector, e.g., viral vector, such as a lentiviral or adenoviral vector. In certain embodiments, a suitable dsRNA for inhibiting expression of an IDH1 gene will be identified by screening an siRNA library, such as an adenoviral or lentiviral siRNA library.

In an embodiment, a dsRNA that targets IDH, e.g., IDH1, is about 15 to about 30 base pairs in length (e.g., about 16, 17, 18, 19, 20, 21, 22, 23, 24, 25, 26, 27, 28, or 29) basepairs in length. In another embodiment, the dsRNA includes overhanging ends of about 1 to about 3 (e.g., about 1, 2, or 3) nucleotides. By "overhang" is meant that 3'-end of one strand of the dsRNA extends beyond the 5'-end of the other strand, or vice versa. The dsRNA can have an overhang on one or both ends of the dsRNA molecule. In some embodiments, the single-stranded overhang is located at the 3'-terminal end of the antisense strand, or, alternatively, at the 3'-terminal end of the sense strand. In some embodiments, the overhang is a TT or UU dinucleotide overhang, e.g., a TT or UU dinucleotide overhang. For example, in an embodiment, the dsRNA includes a 21-nucleotide antisense strand, a 19 base pair duplex region, and a 3'-terminal dinucleotide. In yet another embodiment, a dsRNA includes a duplex nucleic acid where both ends are blunt, or alternatively, where one of the ends is blunt.

In an embodiment, the dsRNA includes a first and a second strand, each strand is about 18 to about 28 nucleotides in length, e.g., about 19 to about 23 nucleotides in length, the first strand of the dsRNA includes a nucleotide sequence having sufficient complementarity to the IDH, e.g., IDH1, RNA for the dsRNA to direct cleavage of the IDH, e.g., IDH1, mRNA via RNA interference, and the second strand of the dsRNA includes a nucleotide sequence that is complementary to the first strand.

Figure 2:
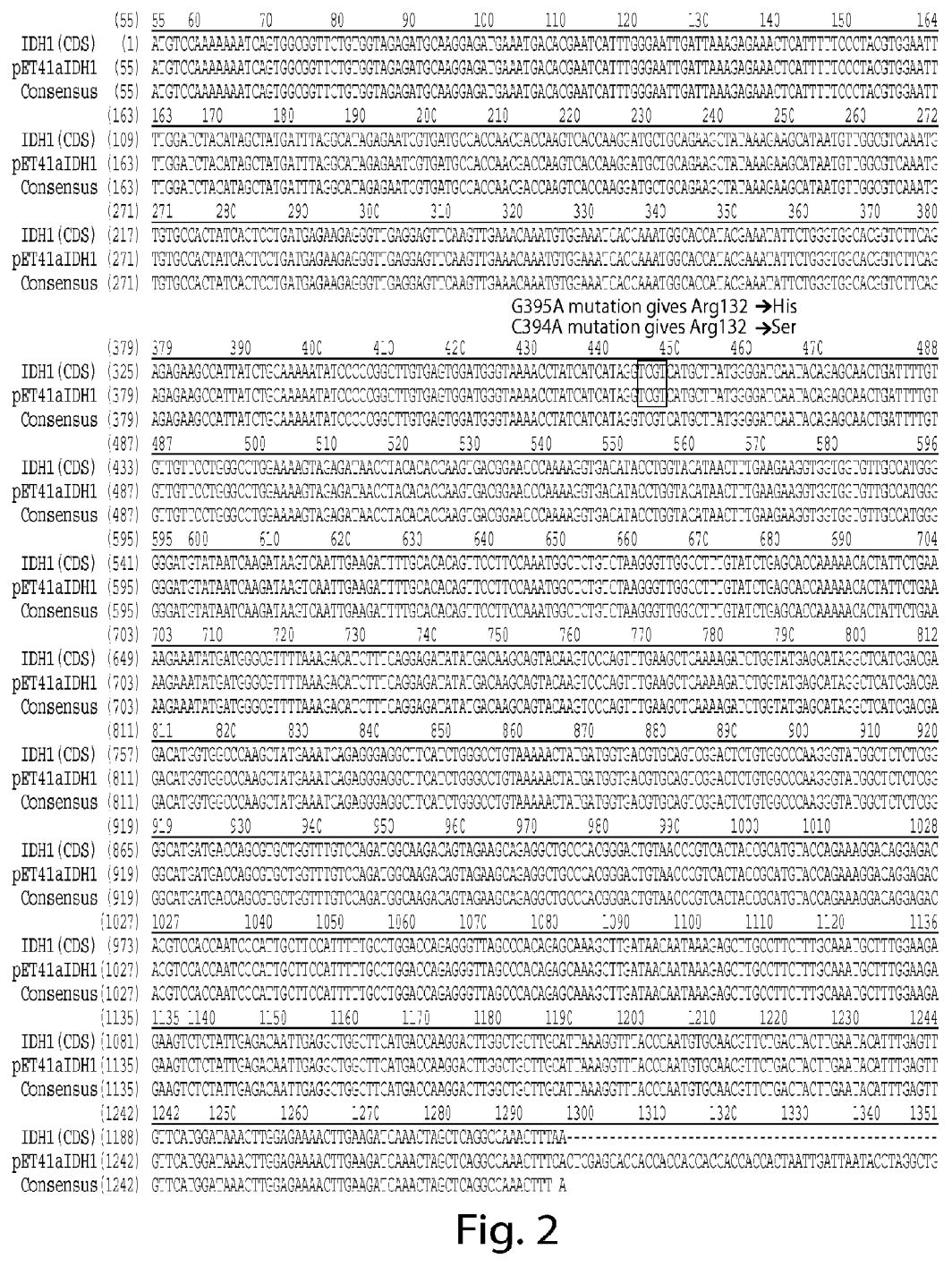

In an embodiment, a dsRNA targeting an IDH, e.g., IDH1, gene can target wildtype and mutant forms of the gene, or can target different allelic isoforms of the same gene. For example, the dsRNA will target a sequence that is identical in two or more of the different isoforms. In an embodiment, the dsRNA targets an IDH1 having G at position 395 or C at position 394 (e.g., a wildtype IDH1 RNA) and an IDH1 having A at position 395 or A at position 394 (e.g., an IDH1 RNA carrying a G395A and/or a C394A mutation) (FIG. 2).

In an embodiment, a dsRNA will preferentially or specifically target a mutant IDH RNA, or a particular IDH polymorphism. For example, in an embodiment, the dsRNA targets an IDH1 RNA carrying an A at position 395, e.g., G395A, and in another embodiment, the dsRNA targets an IDH1 RNA carrying an A at position 394, e.g., C394A mutation.

In an embodiment, a dsRNA targeting an IDH RNA includes one or more chemical modifications. Non-limiting examples of such chemical modifications include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. Such chemical modifications have been shown to preserve RNAi activity in cells while at the same time, dramatically increasing the serum stability of these compounds. Furthermore, one or more phosphorothioate substitutions are well-tolerated and have been shown to confer substantial increases in serum stability for modified dsRNA constructs.

In an embodiment, a dsRNA targeting an IDH, e.g., IDH1, RNA includes modified nucleotides while maintaining the ability to mediate RNAi. The modified nucleotides can be used to improve in vitro or in vivo characteristics such as stability, activity, and/or bioavailability. For example, the dsRNA can include modified nucleotides as a percentage of the total number of nucleotides present in the molecule. As such, the dsRNA can generally include about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides).

In some embodiments, the dsRNA targeting IDH, e.g., IDH1, is about 21 nucleotides long. In another embodiment, the dsRNA does not contain any ribonucleotides, and in another embodiment, the dsRNA includes one or more ribonucleotides. In an embodiment, each strand of the dsRNA molecule independently includes about 15 to about 30 (e.g., about 15, 16, 17, 18, 19, 20, 21, 22, 23, 24, 25, 26, 27, 28, 29, or 30) nucleotides, wherein each strand includes about 15 to about 30 (e.g., about 15, 16, 17, 18, 19, 20, 21, 22, 23, 24, 25, 26, 27, 28, 29, or 30) nucleotides that are complementary to the nucleotides of the other strand. In an embodiment, one of the strands of the dsRNA includes a nucleotide sequence that is complementary to a nucleotide sequence or a portion thereof of the IDH1 or IDH2 gene, and the second strand of the dsRNA includes a nucleotide sequence substantially similar to the nucleotide sequence of the IDH1 or IDH2 gene or a portion thereof.

In an embodiment, the dsRNA targeting IDH1 or IDH2 includes an antisense region having a nucleotide sequence that is complementary to a nucleotide sequence of the IDH1 or IDH2 gene or a portion thereof, and a sense region having a nucleotide sequence substantially similar to the nucleotide sequence of the IDH1 or IDH2 gene or a portion thereof. In an embodiment, the antisense region and the sense region independently include about 15 to about 30 (e.g., about 15, 16, 17, 18, 19, 20, 21, 22, 23, 24, 25, 26, 27, 28, 29, or 30) nucleotides, where the antisense region includes about 15 to about 30 (e.g., about 15, 16, 17, 18, 19, 20, 21, 22, 23, 24, 25, 26, 27, 28, 29, or 30) nucleotides that are complementary to nucleotides of the sense region.

As used herein, the term "dsRNA" is meant to include nucleic acid molecules that are capable of mediating sequence specific RNAi, such as short interfering RNA (siRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term "RNAi" is meant to include sequence specific RNA interference, such as post transcriptional gene silencing, translational inhibition, or epigenetics.

Nucleic Acid-Based IDH Inhibitors

In an embodiment the inhibitor is a nucleic acid-based inhibitor, such as a double stranded RNA (dsRNA) or antisense RNA that targets a mutant IDH, e.g., mutant IDH1 or IDH2.

In one embodiment, the nucleic acid based inhibitor, e.g., a dsRNA or antisense molecule, decreases or inhibits expression of an IDH1 having other than an Arg, e.g., having a His, Ser, Cys, Gly, Val, Pro or Leu, or any residue described in Yan et al., N. Eng. J. Med. 360:765-73, at residue 132, according to the sequence of SEQ ID NO:8 (see also FIG. 21), specifically His, Ser, Cys, Gly, Val, or Leu. In one embodiment, the nucleic acid based inhibitor decreases or inhibits expression of an IDH1 enzyme having His at residue 132. Other IDH1 mutations associated with alpha hydroxy neoactivity, e.g., 2HG neoactivity, include mutations at residue 100, e.g., a mutation having other than an Arg at residue 100, and mutations at residue 109, e.g., a mutation having other than an Arg at residue 109. Still other mutations associated with alpha hydroxy neoactivity, e.g., 2HG neoactivity include mutations at residue 70, e.g., a mutation having other than a Gly at residue 70, (e.g., G70D), mutations at residue 99, e.g., a mutation having a residue other than an Ile at residue 99 (e.g., I99M); a mutation having other than an Ile at residue 130 (e.g., I130M); a mutation having other than a His at residue 133 (e.g., H133Q); a mutation having other than an Ala at residue 134 (e.g., A134D); or a mutation having a residue other than a Val at residue 178 (e.g., V178I). In an embodiment the nucleic acid-based inhibitor is a dsRNA that targets an mRNA that encodes an IDH1 allele described herein, e.g., an IDH1 allele having other than an Arg at residue 132. E.g., the allele encodes His, Ser, Cys, Gly, Val, Pro or Leu, or any residue described in Yan et al., at residue 132, specifically His, Ser, Cys, Gly, Val, or Leu, according to the sequence of SEQ ID NO:8 (see also FIG. 21). Other IDH1 mutations associated with alpha hydroxy neoactivity, e.g., 2HG neoactivity, include mutations at residue 100, e.g., a mutation having other than an Arg at residue 100, and mutations at residue 109, e.g., a mutation having other than an Arg at residue 109. Still other mutations associated with alpha hydroxy neoactivity, e.g., 2HG neoactivity include mutations at residue 70, e.g., a mutation having other than a Gly at residue 70, (e.g., G70V); a mutation having other than an Ile at residue 130 (e.g., I130M); a mutation having other than a His at residue 133 (e.g., H133Q); a mutation having other than an Ala at residue 134 (e.g., A134D); or a mutation having a residue other than a Val at residue 178 (e.g., V178I).

In an embodiment the allele encodes an IDH1 having His at residue 132.

In an embodiment the allele encodes an IDH1 having Ser at residue 132.

In an embodiment, the nucleic acid-based inhibitor is a dsRNA that targets IDH1, e.g., an IDH1 having an A or a T (or a nucleotide other than C) at nucleotide position 394 or an A (or a nucleotide other than G) at nucleotide position 395, e.g., a mutant allele carrying a C394T mutation or a G395A mutation according to the IDH1 sequence of SEQ ID NO:13 (see also FIG. 21A).

In an embodiment, the dsRNA targets an IDH1 having other than C, e.g., a T or an A, at nucleotide position 394 or and other than G, e.g., an A, at 395 (e.g., a mutant) and an IDH1 having a C at nucleotide position 394 or a G at nucleotide position 395 (e.g., a wildtype), e.g., by targeting a region of the IDH1 mRNA that is identical between the wildtype and mutant transcripts. In yet another embodiment, the dsRNA targets a particular mutant or polymorphism (such as a single nucleotide polymorphism (SNP)), but not a wildtype allele. In this case, the nucleic acid based inhibitor, e.g., a dsRNA, targets the region of the IDH1 containing the mutation.

In some embodiments, the nucleic acid based inhibitor, e.g., a dsRNA preferentially or specifically inhibits the product of a mutant IDH1 as compared to the product of a wildtype IDH1. For example, in one embodiment, a dsRNA targets a region of an IDH1 mRNA that carries the mutation (e.g., a C394A of C394T or a G395A mutation according to SEQ ID NO:5).

In one embodiment, the nucleic acid-based inhibitor is a dsRNA including a sense strand and an antisense strand having a primary sequence presented in Tables 7-14. In another embodiment, the nucleic acid based inhibitor is an antisense oligonucleotide that includes all or a part of an antisense primary sequence presented in Tables 7-14 or which targets the same or substantially the same region as does a dsRNA from Tables 7-14.

In one embodiment, the nucleic acid based inhibitor decreases or inhibits expression of an IDH2 having Lys, Gly, Met, Trp, Thr, Ser, or any residue described in Yan et al., at residue 172, according to the amino acid sequence of SEQ ID NO:10 (see also FIG. 22). In one embodiment, the nucleic acid based inhibitor decreases or inhibits expression of an IDH2 enzyme having Lys at residue 172. Other exemplary IDH2 mutations include those at residue 140 (e.g., R140Q, R140L, or R140W) and at residue 294 (e.g., V294M).

In an embodiment the nucleic acid-based inhibitor is a dsRNA that targets an mRNA that encodes an IDH2 allele described herein, e.g., an IDH2 allele having other than an Arg at residue 172. E.g., the allele can have Lys, Gly, Met, Trp, Thr, Ser, or any residue described in Yan et al., at residue 172, according to the sequence of SEQ ID NO:10 (see also FIG. 22). Other exemplary IDH2 mutations include those at residue 140 (e.g., R140Q, R140L, or R140W) and at residue 294 (e.g., V294M).

In an embodiment the allele encodes an IDH2 having Lys at residue 172.

In an embodiment the allele encodes an IDH2 having Met at residue 172.

In an embodiment, the nucleic acid-based inhibitor is a dsRNA that targets IDH2, e.g., an IDH2 having a G or a T (or a nucleotide other than A or C) at nucleotide position 514 or an A or T or C (or a nucleotide other than G) at nucleotide position 515, e.g., a mutant allele carrying a A514G mutation or a G515T or a G515A mutation according to the IDH2 sequence of SEQ ID NO:11 (FIG. 22A). In one embodiment, the nucleic acid-based inhibitor is a dsRNA that targets IDH2, e.g., an IDH2 having a C or a T (or a nucleotide other than G or A) at nucleotide position 516 according to the IDH2 sequence of SEQ ID NO:11.

In an embodiment, the nucleic acid-based inhibitor is a dsRNA that targets IDH2, e.g., an IDH2 having a G at nucleotide position 514 or a T at nucleotide position 515 or an A at position 515, according to the IDH2 sequence of SEQ ID NO:11.

In an embodiment, the dsRNA targets an IDH2 having other than A, e.g., a G or a T, at nucleotide position 514, or other than G, e.g., an A or C or T at position 515 (e.g., a mutant), or other than G, e.g., C or T, and an IDH2 having an A at nucleotide position 514 or a G at nucleotide position 515 or a G at position 516 (e.g., a wildtype), e.g., by targeting a region of the IDH2 mRNA that is identical between the wildtype and mutant transcripts. In yet another embodiment, the dsRNA targets a particular mutant or polymorphism (such as a single nucleotide polymorphism (SNP)), but not a wildtype allele. In this case, the nucleic acid based inhibitor, e.g., a dsRNA, targets the region of the IDH2 containing the mutation.

In some embodiments, the nucleic acid based inhibitor, e.g., a dsRNA, preferentially or specifically inhibits the product of a mutant IDH2 as compared to the product of a wildtype IDH2. For example, in one embodiment, a dsRNA targets a region of an IDH2 mRNA that carries the mutation (e.g., an A514G or G515T or a G515U mutation according to SEQ ID NO:11).

In one embodiment, the nucleic acid-based inhibitor is a dsRNA including a sense strand and an antisense strand having a primary sequence presented in Tables 15-23. In another embodiment, the nucleic acid based inhibitor is an antisense oligonucleotide that includes all or a part of an antisense primary sequence presented in Tables 15-23 or which targets the same or substantially the same region as does a dsRNA from Tables 15-23.

In an embodiment, the nucleic acid based inhibitor is delivered to the brain, e.g., directly to the brain, e.g., by intrathecal or intraventricular delivery. The nucleic acid based inhibitor can also be delivered from an inplantable device. In an embodiment, the nucleic acid-based inhibitor is delivered by infusion using, e.g., a catheter, and optionally, a pump.

Antisense

Suitable nucleic acid based inhibitors include antisense nucleic acids. While not being bound by theory it is believed that antisense inhibition is typically based upon hydrogen bonding-based hybridization of oligonucleotide strands or segments such that at least one strand or segment is cleaved, degraded, or otherwise rendered inoperable.

An antisense agent can bind IDH1 or IDH2 DNA. In embodiments it inhibits replication and transcription. While not being bound by theory it is believed that an antisense agent can also function to inhibit target RNA translocation, e.g., to a site of protein translation, translation of protein from the RNA, splicing of the RNA to yield one or more RNA species, and catalytic activity or complex formation involving the RNA.

An antisense agents can have a chemical modification described above as being suitable for dsRNA.

Antisense agents can include, for example, from about 8 to about 80 nucleobases (i.e., from about 8 to about 80 nucleotides), e.g., about 8 to about 50 nucleobases, or about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA (e.g., an mRNA encoding IDH1) can interfere with one or more of the normal functions of mRNA. While not being bound by theory it is believed that the functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding IDH1. The complementary region can extend for between about 8 to about 80 nucleobases. The compounds can include one or more modified nucleobases. Modified nucleobases may include, e.g., 5-substituted pyrimidines such as 5-iodouracil, 5-iodocytosine, and C5-propynyl pyrimidines such as C5-propynylcytosine and C5-propynyluracil. Other suitable modified nucleobases include $N^4$—$(C_1-C_{12})$ alkylaminocytosines and $N^4,N^4$—$(C_1-C_{12})$ dialkylaminocytosines. Modified nucleobases may also include 7-substituted-5-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. Furthermore, $N^6$—$(C_1-C_{12})$ alkylaminopurines and $N^6,N^6$—$(C_1-C_{12})$ dialkylaminopurines, including $N^6$-methylaminoadenine and $N^6,N^6$-dimethylaminoadenine, are also suitable modified nucleobases. Similarly, other 6-substituted purines including, for example, 6-thioguanine may constitute appropriate modified nucleobases. Other suitable nucleobases include 2-thiouracil, 8-bromoadenine, 8-bromoguanine, 2-fluoroadenine, and 2-fluoroguanine. Derivatives of any of the aforementioned modified nucleobases are also appropriate. Substituents of any of the preceding compounds may include $C_1-C_{30}$ alkyl, $C_2-C_{30}$ alkenyl, $C_2-C_{30}$ alkynyl, aryl, aralkyl, heteroaryl, halo, amino, amido, nitro, thio, sulfonyl, carboxyl, alkoxy, alkylcarbonyl, alkoxycarbonyl, and the like.

MicroRNA

In some embodiments, the nucleic acid-based inhibitor suitable for targeting IDH, e.g., IDH1, is a microRNA (miRNA). A miRNA is a single stranded RNA that regulates the expression of target mRNAs either by mRNA cleavage, translational repression/inhibition or heterochromatic silencing. The miRNA is 18 to 25 nucleotides, typically 21 to 23 nucleotides in length. In some embodiments, the miRNA includes chemical modifications, such as one or more modifications described herein.

In some embodiments, a nucleic acid based inhibitor targeting IDH has partial complementarity (i.e., less than 100% complementarity) with the target IDH, e.g., IDH1, mRNA. For example, partial complementarity can include various mismatches or non-base paired nucleotides (e.g., 1, 2, 3, 4, 5 or more mismatches or non-based paired nucleotides, such as nucleotide bulges), which can result in bulges, loops, or overhangs that result between the antisense strand or antisense region of the nucleic acid-based inhibitor and the corresponding target nucleic acid molecule.

The nucleic acid-based inhibitors described herein, e.g., antisense nucleic acid described herein, can be incorporated into a gene construct to be used as a part of a gene therapy protocol to deliver nucleic acids that can be used to express and produce agents within cells. Expression constructs of such components may be administered in any biologically-effective carrier, e.g., any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g., antibody conjugated) polylysine conjugates, gramacidin S, artificial viral envelopes or other such intracellular earners, as well as direct injection of the gene construct or $CaPO_4$ precipitation carried out in vivo.

In an embodiment, in vivo introduction of nucleic acid into a cell includes use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retroviral vectors and adeno-associated virus vectors can be used as a recombinant gene delivery system for the transfer of exogenous genes in vivo particularly into humans. These vectors provide efficient delivery of genes into cells, and the transferred nucleic acids are stably integrated into the chromosomal DNA of the host. Protocols for producing recombinant retroviruses and for infecting cells in vitro or in vivo with such viruses can be found in Current Protocols in Molecular Biology, Ausubel, F. M. et al. (eds.) Greene Publishing Associates (1989), Sections 9.10-9.14 and other standard laboratory manuals. Examples of suitable retroviruses include pLJ, pZIP, pWE, and pEM which are known to those skilled in the art. Examples of suitable packaging virus lines for preparing both ecotropic and amphotropic retroviral systems include Crip, Cre, 2, and Am. Retroviruses have been used to introduce a variety of genes into many different cell types, including epithelial cells, in vitro and/or in vivo (see, for example, Eglitis et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116 and 4,980,286; PCT Pub. Nos. WO 89/07136, WO 89/02468, WO 89/05345, and WO 92/07573).

Another viral gene delivery system utilizes adenovirus-derived vectors. See, for example, Berkner et al. (1988) BioTechniques 6:616; Rosenfeld et al. (1991) Science 252: 431-434; and Rosenfeld et al. (1992) Cell 68:143-155. Suitable adenoviral vectors derived from the adenovirus strain Ad type 5 d1324 or other strains of adenovirus (e.g., Ad2, Ad3, Ad7 etc.) are known to those skilled in the art.

Yet another viral vector system useful for delivery of the subject gene is the adeno-associated virus (AAV). See, for example, Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973.

Pharmaceutical Compositions

The compositions delineated herein include the compounds delineated herein, as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions containing compounds described herein may be administered directly to the central nervous system, such as into the cerebrospinal fluid or into the brain. Delivery can be, for example, in a bolus or by continuous pump infusion. In certain embodiments, delivery is by intrathecal delivery or by intraventricular injection directly into the brain. A catheter and, optionally, a pump can be used for delivery. The inhibitors can be delivered in and released from an implantable device, e.g., a device that is implanted in association with surgical removal of tumor tissue. E.g., for delivery to the brain, the delivery can be analogous to that with Gliadel, a biopolymer wafer designed to deliver carmustine directly into the surgical cavity created when a brain tumor is resected. The Gliadel wafer slowly dissolves and delivers carmustine.

The therapeutics disclosed herein, e.g., nucleic acid based inhibitors, e.g. siRNAs can be administered directly to the CNS, e.g., the brain, e.g., using a pump and/or catheter system. In one embodiment, the pump is implanted under the skin. In an embodiment and a catheter attached to a pump is inserted into the CNS, e.g., into the brain or spine. In one embodiment, the pump (such as the IsoMed Drug Pump from Medtronic) delivers dosing, e.g., constant dosing, of a nucleic acid based inhibitor. In an embodiment, the pump is programmable to administer variable or constant doses at predetermined time intervals. For example, the IsoMed Drug pump from Medtronic (or a similar device) can be used to administer a constant supply of the inhibitor, or the SynchroMedII Drug Pump (or a similar device) can be used to administer a variable dosing regime.

Methods and devices described in U.S. Pat. Nos. 7,044,932, 6,620,151, 6,283,949, and 6,685,452 can be used in methods described herein.

The pharmaceutical compositions of this invention may be administered orally, parenterally, by inhalation, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.02 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Kits

A compound described herein can be provided in a kit.

In an embodiment the kit includes (a) a compound described herein, e.g., a composition that includes a compound described herein (wherein, e.g., the compound can be an inhibitor described herein), and, optionally (b) informational material. The informational material can be descriptive, instructional, marketing or other material that relates to the methods described herein and/or the use of a compound described herein for the methods described herein.

In an embodiment the kit provides materials for evaluating a subject. The evaluation can be, e.g., for: identifying a subject having unwanted, i.e., increased, levels (e.g., higher than present in normal or wildtype cells) of any of 2HG, 2HG neoactivity, or mutant IDH1 or IDH2 protein having 2HG neoactivity (or corresponding RNA), or having a somatic mutation in IDH1 or IDH2 characterized by 2HG neoactivity; diagnosing, prognosing, or staging, a subject, e.g., on the basis of having unwanted, i.e., increased, levels of 2HG, 2HG neoactivity, or mutant IDH1 or IDH2 protein having 2HG neoactivity (or corresponding RNA), or having a somatic mutation in IDH1 or IDH2 characterized by 2HG neoactivity; selecting a treatment for, or evaluating the efficacy of, a treatment, e.g., on the basis of the subject having unwanted, i.e., increased, levels of 2HG, 2HG neoactivity, or mutant IDH1 or IDH2 protein having 2HG neoactivity (or corresponding RNA), or having a somatic mutation in IDH1 or IDH2 characterized by 2HG neoactivity. The kit can include one or more reagent useful in the evaluation, e.g., reagents mentioned elsewhere herein. A detection reagent, e.g., an antibody or other specific binding reagent can be included. Standards or reference samples, e.g., a positive or negative control standard can be included. E.g., if the evaluation is based on the presence of 2HG the kit can include a reagent, e.g., a positive or negative control standards for an assay, e.g., a LC-MS assay.

If the evaluation is based on the presence of 2HG neoactivity, the kit can include a reagent, e.g., one or more of those mentioned elsewhere herein, for assaying 2HG neoactivity. If the evaluation is based on sequencing, the kit can include primers or other materials useful for sequencing the relevant nucleic acids for identifying an IDH, e.g., IDH1 or IDH2, neoactive mutant. E.g., the kit can contain a reagent that provides for interrogation of the identity, i.e., sequencing of, residue 132, 71, 100 or 109 of IDH1 to determine if a neoactive mutant is present. The kit can include nucleic acids, e.g., an oligomer, e.g., primers, which allow sequencing of the nucleotides that encode residue 70, 99, 100, 109, 130, 132, 133, 134, or 178, for example 132, 100 or 109 of IDH (e.g., an IDH1). In an embodiment, the kit can include nucleic acids, e.g., an oligomer, e.g., primers, which allow sequencing of the nucleotides that encode residue 140, 172, or 294 of an IDH2. In an embodiment the kit includes a nucleic acid whose hybridization, or ability to be amplified, is dependent on the identity of residue 70, 99, 100, 109, 130, 132, 133, 134, or 178, for example 132, 100 or 109 of IDH (e.g., an IDH1). In an embodiment, the kit can include a nucleic acid whose hybridization, or ability to be amplified, is dependent on the identity of residue 140, 172, or 294 of an IDH2. In other embodiments the kit includes a reagent, e.g., an antibody or other specific binding molecule, which can identify the presence of a neoactive mutant, e.g., a protein encoded by a neoactive mutant at 70, 99, 100, 109, 130, 132, 133, 134, or 178, for example, 132, 100 or 109 of IDH (e.g., an IDH1) or 140, 172, or 294 of an IDH2. As described below, a kit can also include buffers, solvents, and information related to the evaluation.

In one embodiment, the informational material can include information about production of the compound, molecular weight of the compound, concentration, date of expiration, batch or production site information, and so forth. In one embodiment, the informational material relates to methods for administering the compound.

In one embodiment, the informational material can include instructions to administer a compound described herein in a suitable manner to perform the methods described herein, e.g., in a suitable dose, dosage form, or mode of administration (e.g., a dose, dosage form, or mode of administration described herein). In another embodiment, the informational material can include instructions to administer a compound described herein to a suitable subject, e.g., a human, e.g., a human having or at risk for a disorder described herein.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein, the composition of the kit can include other ingredients, such as a solvent or buffer, a stabilizer, a preservative, a flavoring agent (e.g., a bitter antagonist or a sweetener), a fragrance or other cosmetic ingredient, and/or a second agent for treating a condition or disorder described herein. Alternatively, the other ingredients can be included in the kit, but in different compositions or containers than a compound described herein. In such embodiments, the kit can include instructions for admixing a compound described herein and the other ingredients, or for using a compound described herein together with the other ingredients.

A compound described herein can be provided in any form, e.g., liquid, dried or lyophilized form. It is preferred that a compound described herein be substantially pure and/or sterile. When a compound described herein is provided in a liquid solution, the liquid solution preferably is an aqueous solution, with a sterile aqueous solution being preferred. When a compound described herein is provided as a dried form, reconstitution generally is by the addition of a suitable solvent. The solvent, e.g., sterile water or buffer, can optionally be provided in the kit.

The kit can include one or more containers for the composition containing a compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In an embodiment, the device is a medical implant device, e.g., packaged for surgical insertion.

Combination Therapies

In some embodiments, a compound or composition described herein is administered together with an additional cancer treatment. Exemplary cancer treatments include, for example: surgery, chemotherapy, targeted therapies such as antibody therapies, immunotherapy, and hormonal therapy. Examples of each of these treatments are provided below.

Chemotherapy

In some embodiments, a compound or composition described herein is administered with a chemotherapy. Chemotherapy is the treatment of cancer with drugs that can destroy cancer cells. "Chemotherapy" usually refers to cytotoxic drugs which affect rapidly dividing cells in general, in contrast with targeted therapy. Chemotherapy drugs interfere with cell division in various possible ways, e.g., with the duplication of DNA or the separation of newly formed chromosomes. Most forms of chemotherapy target all rapidly dividing cells and are not specific for cancer cells, although some degree of specificity may come from the inability of many cancer cells to repair DNA damage, while normal cells generally can.

Examples of chemotherapeutic agents used in cancer therapy include, for example, antimetabolites (e.g., folic acid, purine, and pyrimidine derivatives) and alkylating agents (e.g., nitrogen mustards, nitrosoureas, platinum, alkyl sulfonates, hydrazines, triazenes, aziridines, spindle poison, cytotoxic agents, toposimerase inhibitors and others). Exemplary agents include Aclarubicin, Actinomycin, Alitretinon, Altretamine, Aminopterin, Aminolevulinic acid, Amrubicin, Amsacrine, Anagrelide, Arsenic trioxide, Asparaginase, Atrasentan, Belotecan, Bexarotene, endamustine, Bleomycin, Bortezomib, Busulfan, Camptothecin, Capecitabine, Carboplatin, Carboquone, Carmofur, Carmustine, Celecoxib, Chlorambucil, Chlormethine, Cisplatin, Cladribine, Clofarabine, Crisantaspase, Cyclophosphamide, Cytarabine, Dacarbazine, Dactinomycin, Daunorubicin, Decitabine, Demecolcine, Docetaxel, Doxorubicin, Efaproxiral, Elesclomol, Elsamitrucin, Enocitabine, Epirubicin, Estramustine, Etoglucid, Etoposide, Floxuridine, Fludarabine, Fluorouracil (5FU), Fotemustine, Gemcitabine, Gliadel implants, Hydroxycarbamide, Hydroxyurea, Idarubicin, Ifosfamide, Irinotecan, Irofulven, Ixabepilone, Larotaxel, Leucovorin, Liposomal doxorubicin, Liposomal daunorubicin, Lonidamine, Lomustine, Lucanthone, Mannosulfan, Masoprocol, Melphalan, Mercaptopurine, Mesna, Methotrexate, Methyl aminolevulinate, Mitobronitol, Mitoguazone, Mitotane, Mitomycin, Mitoxantrone, Nedaplatin, Nimustine, Oblimersen, Omacetaxine, Ortataxel, Oxaliplatin, Paclitaxel, Pegaspargase, Pemetrexed, Pentostatin, Pirarubicin, Pixantrone, Plicamycin, Porfimer sodium, Prednimustine, Procarbazine, Raltitrexed, Ranimustine, Rubitecan, Sapacitabine, Semustine, Sitimagene ceradenovec, Strataplatin, Streptozocin, Talaporfin, Tegafur-uracil, Temoporfin, Temozolomide, Teniposide, Tesetaxel, Testolactone, Tetranitrate, Thiotepa, Tiazofurine, Tioguanine, Tipifarnib, Topotecan, Trabectedin, Triaziquone, Triethylenemelamine, Triplatin, Tretinoin, Treosulfan, Trofosfamide, Uramustine, Valrubicin, Verteporfin, Vinblastine, Vincristine, Vindesine, Vinflunine, Vinorelbine, Vorinostat, Zorubicin, and other cytostatic or cytotoxic agents described herein.

Because some drugs work better together than alone, two or more drugs are often given at the same time. Often, two or more chemotherapy agents are used as combination chemotherapy. In some embodiments, the chemotherapy agents (including combination chemotherapy) can be used in combination with a compound described herein, e.g., phenformin.

Targeted Therapy

In some embodiments, a compound or composition described herein is administered with a targeted therapy. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, desatinib, erlotinib, imatinib, gefitinib, lapatinib, Lestaurtinib, Nilotinib, Semaxanib, Sorafenib, Sunitinib, and Vandetanib, and also cyclin-depdendent kinase inhibitors such as Alvocidib and Seliciclib. Monoclonal antibody therapy is another strategy in which the rapeutic agent is an antibody which specifically binds to a protein on the surface of the cancer cells. Examples include the anti-HER2/neu antibody trastuzumab (HERCEPTIN®) typically used in breast cancer, and the anti-CD20 antibody rituximab and Tositumomab typically used in a variety of B-cell malignancies. Other exemplary antibodies include Cetuximab, Panitumumab, Trastuzumab, Alemtuzumab, Bevacizumab, Edrecolomab, and Gemtuzumab. Exemplary fusion proteins include Aflibercept and Denileukin diftitox. In some embodiments, the targeted therapy can be used in combination with a compound described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

Immunotherapy

In some embodiments, a compound or composition described herein is administered with an immunotherapy. Cancer immunotherapy refers to a diverse set of therapeutic strategies designed to induce the patient's own immune system to fight the tumor. Contemporary methods for generating an immune response against tumors include intravesicular BCG immunotherapy for superficial bladder cancer, and use of interferons and other cytokines to induce an immune response in renal cell carcinoma and melanoma patients.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with a compound or composition described herein.

Hormonal Therapy

In some embodiments, a compound or composition described herein is administered with a hormonal therapy. The growth of some cancers can be inhibited by providing or blocking certain hormones. Common examples of hormone-sensitive tumors include certain types of breast and prostate cancers. Removing or blocking estrogen or testosterone is often an important additional treatment. In certain cancers, administration of hormone agonists, such as progestogens may be therapeutically beneficial. In some embodiments, the hormonal therapy agents can be used in combination with a compound or a composition described herein.

In some embodiments, a compound or composition described herein is administered together with an additional cancer treatment (e.g., surgical removal), in treating cancer in nervous system, e.g., cancer in central nervous system, e.g., brain tumor, e.g., glioma, e.g., glioblastoma multiforme (GBM).

Several studies have suggested that more than 25% of glioblastoma patients obtain a significant survival benefit from adjuvant chemotherapy. Meta-analyses have suggested that adjuvant chemotherapy results in a 6-10% increase in 1-year survival rate.

Temozolomide is an orally active alkylating agent that is used for persons newly diagnosed with glioblastoma multiforme. It was approved by the United States Food and Drug Administration (FDA) in March 2005. Studies have shown that the drug was well tolerated and provided a survival benefit. Adjuvant and concomitant temozolomide with radiation was associated with significant improvements in median progression-free survival over radiation alone (6.9 vs 5 mo), overall survival (14.6 vs 12.1 mo), and the likelihood of being alive in 2 years (26% vs 10%).

Nitrosoureas: BCNU (carmustine)-polymer wafers (Gliadel) were approved by the FDA in 2002. Though Gliadel wafers are used by some for initial treatment, they have shown only a modest increase in median survival over placebo (13.8 vs. 11.6 months) in the largest such phase III trial, and are associated with increased rates of CSF leak and increased intracranial pressure secondary to edema and mass effect.

MGMT is a DNA repair enzyme that contributes to temozolomide resistance. Methylation of the MGMT promoter, found in approximately 45% of glioblastoma multiformes, results in an epigenetic silencing of the gene, decreasing the tumor cell's capacity for DNA repair and increasing susceptibility to temozolomide.

When patients with and without MGMT promoter methylation were treated with temozolomide, the groups had median survivals of 21.7 versus 12.7 months, and 2-year survival rates of 46% versus 13.8%, respectively.

Though temozolomide is currently a first-line agent in the treatment of glioblastoma multiforme, unfavorable MGMT methylation status could help select patients appropriate for future therapeutic investigations.

O6-benzylguanine and other inhibitors of MGMT as well as RNA interference-mediated silencing of MGMT offer promising avenues to increase the effectiveness of temozolomide and other alkylating antineoplastics, and such agents are under active study.

Carmustine (BCNU) and cis-platinum (cisplatin) have been the primary chemotherapeutic agents used against malignant gliomas. All agents in use have no greater than a 30-40% response rate, and most fall into the range of 10-20%.

Data from the University of California at San Francisco indicate that, for the treatment of glioblastomas, surgery followed by radiation therapy leads to 1-, 3-, and 5-year survival rates of 44%, 6%, and 0%, respectively. By comparison, surgery followed by radiation and chemotherapy using nitrosourea-based regimens resulted in 1-, 3-, and 5-year survival rates of 46%, 18%, and 18%, respectively.

A major hindrance to the use of chemotherapeutic agents for brain tumors is the fact that the blood-brain barrier (BBB) effectively excludes many agents from the CNS. For this reason, novel methods of intracranial drug delivery are being developed to deliver higher concentrations of chemotherapeutic agents to the tumor cells while avoiding the adverse systemic effects of these medications.

Pressure-driven infusion of chemotherapeutic agents through an intracranial catheter, also known as convection-enhanced delivery (CED), has the advantage of delivering drugs along a pressure gradient rather than by simple diffusion. CED has shown promising results in animal models with agents including BCNU and topotecan.

Initial attempts investigated the delivery of chemotherapeutic agents via an intraarterial route rather than intravenously. Unfortunately, no survival advantage was observed.

Chemotherapy for recurrent glioblastoma multiforme provides modest, if any, benefit, and several classes of agents are used. Carmustine wafers increased 6-month survival from 36% to 56% over placebo in one randomized study of 222 patients, though there was a significant association between the treatment group and serious intracranial infections.

Genotyping of brain tumors may have applications in stratifying patients for clinical trials of various novel therapies.

The anti-angiogenic agent bevacizumab, when used with irinotecan improved 6-month survival in recurrent glioma patients to 46% compared with 21% in patients treated with temozolomide. This bevacizumab and irinotecan combination for recurrent glioblastoma multiforme has been shown to improve survival over bevacizumab alone. Anti-angiogenic agents also decrease peritumoral edema, potentially reducing the necessary corticosteroid dose.

Some glioblastomas responds to gefitinib or erlotinib (tyrosine kinase inhibitors). The simultaneous presence in glioblastoma cells of mutant EGFR (EGFRviii) and PTEN was associated with responsiveness to tyrosine kinase inhibitors, whereas increased p-akt predicts a decreased effect. Other targets include PDGFR, VEGFR, mTOR, farnesyltransferase, and PI3K.

Other possible therapy modalities include imatinib, gene therapy, peptide and dendritic cell vaccines, synthetic chlorotoxins, and radiolabeled drugs and antibodies.

Patient Selection/Monitoring

Described herein are methods of treating a cell proliferation-related disorder, e.g., cancer, in a subject and methods of identifying a subject for a treatment described herein. Also described herein are methods of predicting a subject who is at risk of developing cancer (e.g., a cancer associate with a mutation in an IDH enzyme (e.g., IDH1 and/or IDH2)). The cancer is generally characterized by the presence of a neoactivity, such as a gain of function in one or more mutant IDH enzymes (e.g., IDH1 or IDH2). The subject can be selected on the basis of the subject having a mutant gene having a neoactivity, e.g., a neoactivity described herein. As used herein, "select" means selecting in whole or part on said basis.

In some embodiments, a subject is selected for treatment with a compound described herein based on a determination that the subject has a mutant IDH enzyme described herein. In some embodiments, the mutant enzyme has a neoactivity and the patient is selected on that basis. The neoactivity of the enzyme can be identified, for example, by evaluating the subject or sample (e.g., tissue or bodily fluid) therefrom, for the presence or amount of a substrate, cofactor and/or product of the enzyme. The presence and/or amount of substrate, cofactor and/or product can correspond to the wild-type/non-mutant activity or can correspond to the neoactivity of the enzyme. Exemplary bodily fluid that can be used to identify (e.g., evaluate) the neoactivity of the enzyme include amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

In some embodiments, a subject can be evaluated for neoactivity of an enzyme using magnetic resonance. For example, where the mutant enzyme is IDH1 and the neoactivity is conversion of α-ketoglutarate to 2-hydroxyglutarate, the subject can be evaluated for the presence of and/or an elevated amount of 2-hydroxyglutarate, e.g., R-2-hydroxyglutarate relative to the amount of 2-hydroxyglutarate, e.g., R-2-hydroxyglutarate present in a subject who does not have a mutation in IDH1 having the above neoactivity. In some embodiments, neoactivity of IDH1 can be determined by the presence or elevated amount of a peak corresponding to 2-hydroxyglutarate, e.g., R-2-hydroxyglutarate as determined by magnetic resonance. For example, a subject can be evaluated for the presence and/or strength of a signal at about 2.5 ppm to determine the presence and/or amount of 2-hydroxyglutarate, e.g., R-2-hydroxyglutarate in the subject. This can be correlated to and/or predictive of a neoactivity described herein for the mutant enzyme IDH. Similarly, the presence, strength and/or absence of a signal at about 2.5 ppm could be predictive of a response to treatment and thereby used as a noninvasive biomarker for clinical response.

Neoactivity of a mutant IDH enzyme can also be evaluated using other techniques known to one skilled in the art. For example, the presence or amount of a labeled substrate, cofactor, and/or reaction product can be measured such as a $^{13}C$ or $^{14}C$ labeled substrate, cofactor, and/or reaction product. The neoactivity can be evaluated by evaluating the forward reaction of the wild-type/non mutant enzyme (such as the oxidative decarboxylation of ioscitrate to α-ketoglutarate in a mutant IDH1 enzyme) and/or the reaction corresponding to the neoactivity (e.g., the conversion of α-ketoglutarate to 2-hydroxyglutarate, e.g., R-2-hydroxyglutarate in a mutant IDH enzyme (e.g., an IDH1 enzyme or IDH2 enzyme).

Disorders

The IDH-related methods disclosed herein, e.g., methods of evaluating or treating subjects, are directed to subjects having a cell proliferation-related disorder characterized by an IDH mutant, e.g., an IDH1 or IDH2, mutant having neoactivity, e.g., 2HG neoactivity. Examples of some of the disorders below have been shown to be characterized by an IDH1 or IDH2 mutation. Others can be analyzed, e.g., by sequencing cell samples to determine the presence of a somatic mutation at amino acid 132 of IDH1 or at amino acid 172 of IDH2 or another mutation described herein. Without being bound by theory it is expected that a portion of the tumors of given type of cancer will have an IDH, e.g., IDH1 or IDH2, mutant having 2HG neoactivity.

The disclosed methods are useful in evaluating or treating proliferative disorders, e.g. evaluating or treating solid tumors, soft tissue tumors, and metastases thereof wherein the solid tumor, soft tissue tumor or metastases thereof is a cancer described herein. Exemplary solid tumors include malignancies (e.g., sarcomas, adenocarcinomas, and carcinomas) of the various organ systems, such as those of brain, lung, breast, lymphoid, gastrointestinal (e.g., colon), and genitourinary (e.g., renal, urothelial, or testicular tumors) tracts, pharynx, prostate, and ovary. Exemplary adenocarcinomas include colorectal cancers, renal-cell carcinoma, liver cancer, non-small cell carcinoma of the lung, and cancer of the small intestine. The disclosed methods are also useful in evaluating or treating non-solid cancers.

The methods described herein can be used with any cancer, for example those described herein, including glioma, AML, ALL (e.g., B-ALL or T-ALL), prostate cancer, or myelodysplasia or myelodysplastic syndrome, thyroid cancer such as follicular thyroid cancer, fibrosarcoma, paraganglioma, melanoma, myeloproliferative neoplasms such as CML, or colorectal cancer. Metastases of the aforementioned cancers can also be treated or prevented in accordance with the methods described herein.

The methods described herein are useful in treating cancer in nervous system, e.g., brain tumor, e.g., glioma, e.g., glioblastoma multiforme (GBM), e.g., by inhibiting a neoactivity of a mutant enzyme, e.g., an enzyme in a metabolic pathway, e.g., a metabolic pathway leading to fatty acid biosynthesis, glycolysis, glutaminolysis, the pentose phosphate shunt, the nucleotide biosynthetic pathway, or the fatty acid biosynthetic pathway, e.g., IDH1 or IDH2.

Gliomas, a type of brain tumors, can be classified as grade I to grade IV on the basis of histopathological and clinical criteria established by the World Health Organization (WHO). WHO grade I gliomas are often considered benign. Gliomas of WHO grade II or III are invasive, progress to higher-grade lesions. WHO grade IV tumors (glioblastomas) are the most invasive form. Exemplary brain tumors include, e.g., astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. Exemplary cancers are described in Acta Neuropathol (2008) 116:597-602 and N Engl J Med. 2009 Feb. 19; 360(8):765-73, the contents of which are each incorporated herein by reference.

In embodiments the disorder is glioblastoma.

In an embodiment the disorder is prostate cancer, e.g., stage T1 (e.g., T1a, T1b and T1c), T2 (e.g., T2a, T2b and T2c), T3 (e.g., T3a and T3b) and T4, on the TNM staging system. In embodiments the prostate cancer is grade G1, G2, G3 or G4 (where a higher number indicates greater difference from normal tissue). Types of prostate cancer include, e.g., prostate adenocarcinoma, small cell carcinoma, squamous carcinoma, sarcomas, and transitional cell carcinoma.

In an embodiment, the disorder is a fibrosarcoma or paraganglioma. In an embodiment, the disorder is thyroid cancer. In an embodiment, the disorder is colon cancer. In an embodiment, the disorder is melanoma. In an example, the disorder is myeloma. In an embodiment, the disorder is myeloproliferative neoplasms (MPN) such as CML.

Methods and compositions of the invention can be combined with art-known treatment. Art-known treatment for prostate cancer can include, e.g., active surveillance, surgery (e.g., radical prostatectomy, transurethral resection of the prostate, orchiectomy, and cryosurgegry), radiation therapy including brachytherapy (prostate brachytherapy) and external beam radiation therapy, High-Intensity Focused Ultrasound (HIFU), chemotherapy, cryosurgery, hormonal therapy (e.g., antiandrogens (e.g., flutamide, bicalutamide, nilutamide and cyproterone acetate, ketoconazole, aminoglutethimide), GnRH antagonists (e.g., Abarelix)), or a combination thereof.

All references described herein are expressly incorporated herein by reference.

EXAMPLES

Example 1 IDH1 Cloning, Mutagenesis, Expression and Purification

1. Wild Type IDH1 was Cloned into pET41a, Creating His8 Tag at C-Terminus

The IDH1 gene coding region (cDNA) was purchased from Invitrogen in pENTR221 vector (www.invitrogen.com, Cat#B-068487_Ultimate_ORF). Oligo nucleotides were designed to PCR out the coding region of IDH1 with NdeI at the 5' end and XhoI at the 3'. (IDH1-f: TAATCATAT-GTCCAAAAAAATCAGT (SEQ ID NO:1), IDH1-r: TAATCTCGAGTGAAAGTTTGGCCTGAGCTAGTT (SEQ ID NO:2)). The PCR product is cloned into the NdeI/XhoI cleaved pET41a vector. NdeI/XhoI cleavage of the vector pET41a releases the GST portion of the plasmid, and creating a C-terminal His8 tag (SEQ ID NO:3) without the N-terminal GST fusion. The original stop codon of IDH1 is change to serine, so the junction sequence in final IDH1 protein is: Ser-Leu-Glu-His-His-His-His-His-His-His-His-Stop (SEQ ID NO:4).

The C-terminal His tag strategy instead of N-terminal His tag strategy was chosen, because C-terminal tag might not negatively impact IDH1 protein folding or activity. See, e.g., Xu X et al, J Biol Chem. 2004 Aug. 6; 279(32):33946-57.

Figure 1:
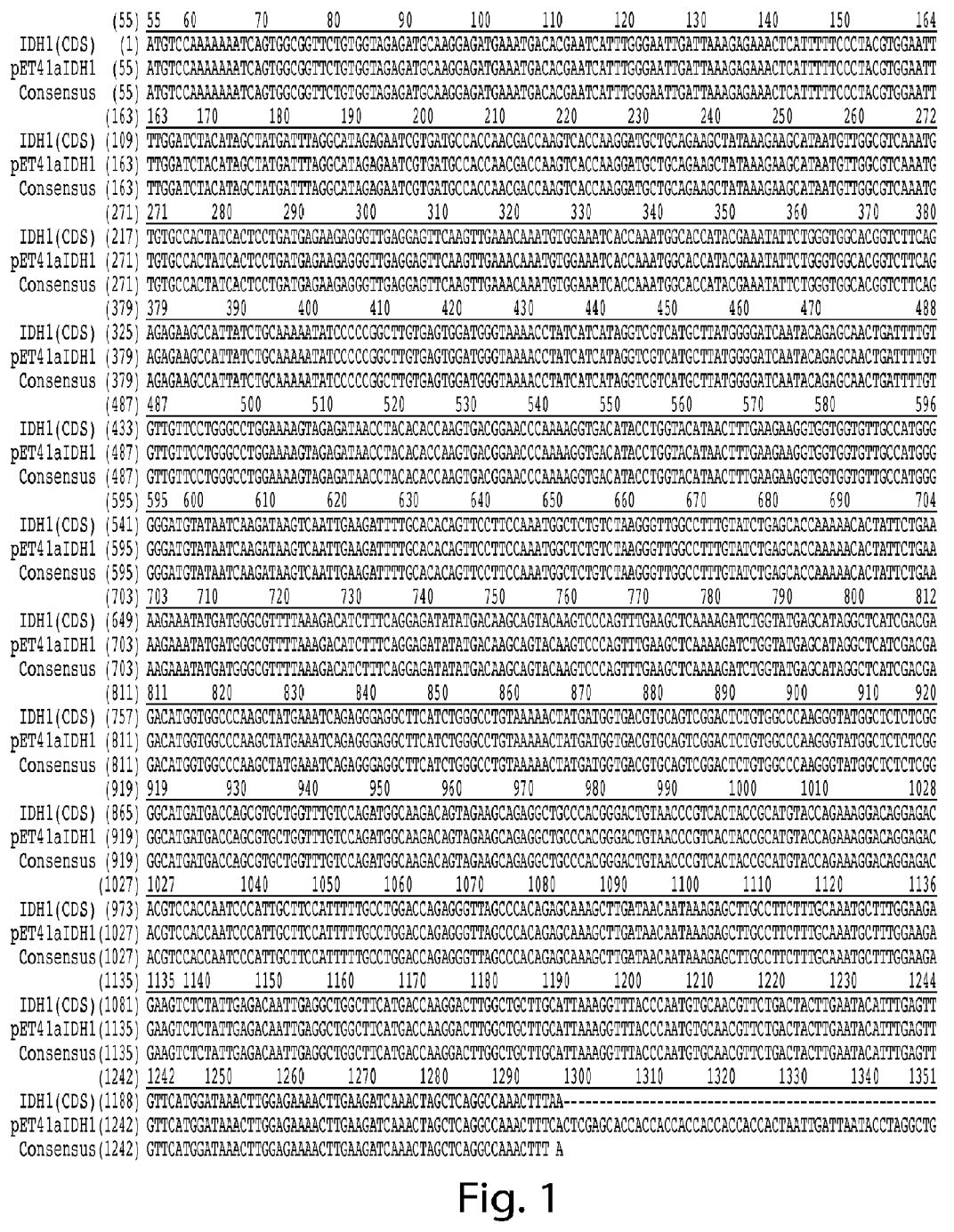

The sequence for pET41a-IDH1 plasmid is confirmed by DNA sequencing. FIG. 1 shows detailed sequence verification of pET41a-IDH1 and alignment against published IDH1 CDS below.

2. IDH1 Site Directed Mutagenesis to Create the IDHr132s and IDHr132h Mutants

Site directed mutagenesis was performed to convert R132 to S or H, DNA sequencing confirmed that G395 is mutated to A (creating Arg→His mutation in the IDH1 protein), and C394 is mutated to A (creating Arg→Ser in the IDH1 protein). Detailed method for site directed mutagenesis is described in the user manual for QuikChange® MultiSite-Directed Mutagenesis Kit (Stratagene, cat#200531). FIG. 2 shows DNA sequence verification of such mutations. Highlighted nucleotides were successfully changed in the mutagenesis: G395→A mutation allows amino acid Arg132→His; C394→A mutation allows amino acid Arg132→Ser.

3. IDH1 Protein Expression and Purification

IDHwt, IDHR132S, and IDHR132H proteins were expressed in the *E. coli* strain Rosetta and purified according to the detailed procedure below. Active IDH1 proteins are in dimer form, and SEC column fraction/peak that correspond to the dimer form were collected for enzymology analysis and cross comparison of catalytic activities of these proteins.

A. Cell Culturing:

Cells were grown in LB (20 µg/ml Kanamycin) at 37° C. with shaking until OD600 reaches 0.6. The temperature was changed to 18° C. and protein was induced by adding IPTG to final concentration of 1 mM. Cells were collected 12-16 hours after IPTG induction.

B. Buffer System:

Lysis buffer: 20 mM Tris, pH7.4, 0.1% Triton X-100, 500 mM NaCl, 1 mM PMSF, 5 mM β-mercaptoethanol, 10% glycerol.

Ni-Column Buffer A: 20 mM Tris, pH7.4, 500 mM NaCl, 5 mM β-mercaptoethanol, 10% glycerol.

Ni-column Buffer B: 20 mM Tris, pH7.4, 500 mM NaCl, 5 mM β-mercaptoethanol, 500 mM Imidazole, 10% glycerol Gel filtration Buffer C: 200 mM NaCl, 50 mM Tris 7.5, 5 mM β-mercaptoethanol, 2 mM $MnSO_4$, 10% glycerol.

C. Protein Purification Procedure

1. Cell pellet were resuspended in the lysis buffer (1 gram cell/5-10 ml buffer).
2. Cells were broken by passing the cell through Microfludizer with at a pressure of 15,000 psi for 3 times.
3. Soluble protein was collected from supernatant after centrifugation at 20,000 g (Beckman Avanti J-26XP) for 30 min at 4° C.
4. 5-10 ml of Ni-column was equilibrated by Buffer A until the A280 value reached baseline. The supernatant was loaded onto a 5-ml Ni-Sepharose column (2 ml/min). The column was washed by 10-20 CV of washing buffer (90% buffer A+10% buffer B) until A280 reach the baseline (2 ml/min).
5. The protein was eluted by liner gradient of 10-100% buffer B (20 CV) with the flow rate of 2 ml/min and the sample fractions were collected as 2 ml/tube.
6. The samples were analyzed on SDS-PAGE gel.
7. The samples were collected and dialyzed against 200× Gel filtration buffer for 2 times (1 hour and >4 hours).
8. The samples were concentrated to 10 ml.
9. 200 ml of S-200 Gel-filtration column was equilibrated by buffer C until the A280 value reached baseline. The samples were loaded onto Gel filtration column (0.5 ml/min).
10. The column was washed by 10 CV of buffer C, collect fractions as 2-4 ml/tube.
11. The samples were analyzed on SDS-PAGE gel and protein concentration was determined.

D. Protein Purification Results

The results for purification of wild type IDH1 are shown in FIGS. 3, 4, 5A and 5B.

The results for purification of mutant IDH1R132S are shown in FIGS. 6, 7, 8A and 8B.

The results for purification of wild type IDH1R132H are shown in FIGS. 9, 10, 11A and 11B.

Example 2 Enzymology Analysis of IDH1 Wild Type and Mutants

1. Analysis of IDH1 Wild-Type and Mutants R132H and R132S in the Oxidative Decarboxylation of Isocitrate to α-Ketoglutarate (α-KG)

A. Methods

To determine the catalytic efficiency of enzymes in the oxidative decarboxylation of isocitrate to α-Ketoglutarate (α-KG) direction, reactions were performed to determine Vmax and Km for isocitrate. In these reactions, the substrate was varied while the cofactor was held constant at 500 uM. All reactions were performed in 150 mM NaCl, 20 mM Tris-Cl, pH 7.5, 10% glycerol, and 0.03% (w/v) BSA). Reaction progress was followed by spectroscopy at 340 nM monitoring the change in oxidation state of the cofactor. Sufficient enzyme was added to give a linear change in absorbance for 10 minutes.

B. ICDH1 R132H and ICDH1 R132S are Impaired for Conversion of Isocitrate to α-KG.

Figure 12A:
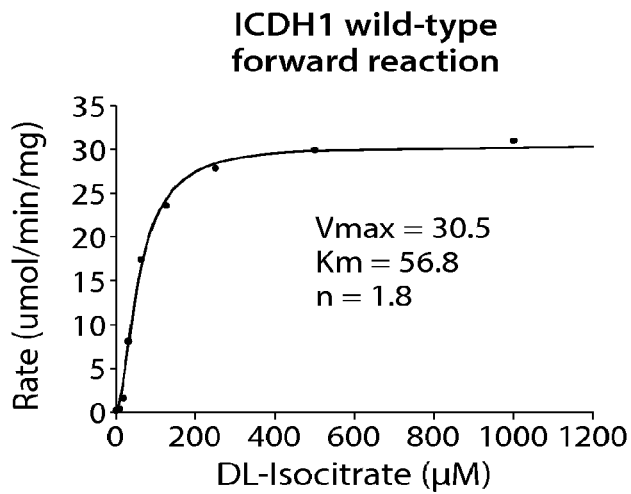
FIG. 12A depicts Michaelis-Menten plot of IDH1 wild-type in the oxidative decarboxylation of ioscitrate to α-ketoglutarate.
Figure 12B:
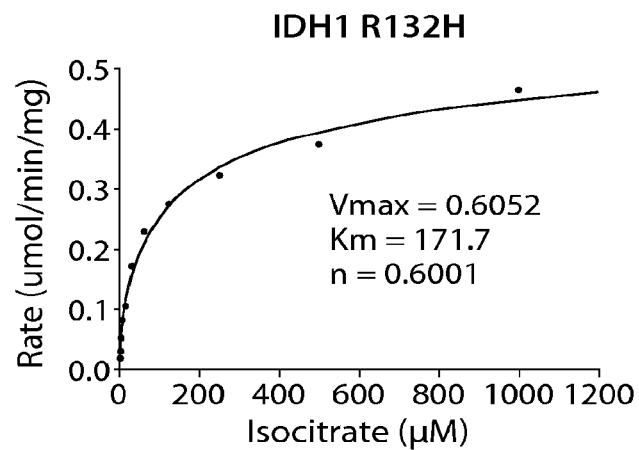
FIG. 12B depicts Michaelis-Menten plot of R132H mutant enzyme in the oxidative decarboxylation of ioscitrate to α-ketoglutarate.
Figure 12C:
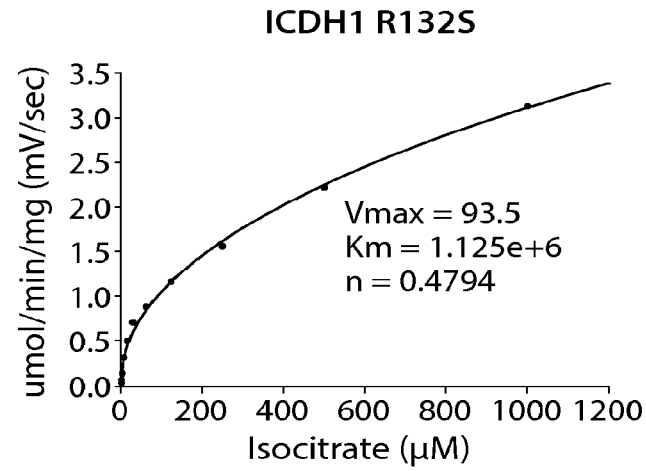
FIG. 12C depicts Michaelis-Menten plot of R132S mutant enzyme in the oxidative decarboxylation of ioscitrate to α-ketoglutarate.

Michaelis-Menten plots for the relationship of isocitrate concentration to reaction velocity are presented in FIGS. 12A-12C. Kinetic parameters are summarized in the Table 1. All data was fit to the Hill equation by least-squares regression analysis.

TABLE 1

| Enzyme | Vmax (umol/min/mg) | Km (uM) | Hill Constant | Vmax/Km | Relative Catalytic Efficiency |
|---|---|---|---|---|---|
| Wt | 30.5 | 56.8 | 1.8 | 0.537 | 100% |
| R132H | 0.605 | 171.7 | 0.6 | 0.0035 | 0.35% |
| R132S | 95 | >1e6 | 0.479 | <9.5e7 | <.001% |

Both mutant enzymes display a reduced Hill coefficient and an increase in Km for isocitrate, suggesting a loss of co-operativity in substrate binding and/or reduced affinity for substrate. R132H enzyme also displays a reduced Vmax, suggestive of a lower kcat. R132S displays an increase in Vmax, suggesting an increase in kcat, although this comes at the expense of a 20,000 fold increase in Km so that the overall effect on catalytic efficiency is a great decrease as compared to the wild-type enzyme. The relative catalytic efficiency, described as Vmax/Km, is dramatically lower for the mutants as compared to wild-type. The in vivo effect of these mutations would be to decrease the flux conversion of isocitrate to α-KG.

C. The ICDH1 R132H and R132S Mutants Display Reduced Product Inhibition in the Oxidative Decarboxylation of Isocitrate to α-Ketoglutarate (α-KG).

Figure 13A:
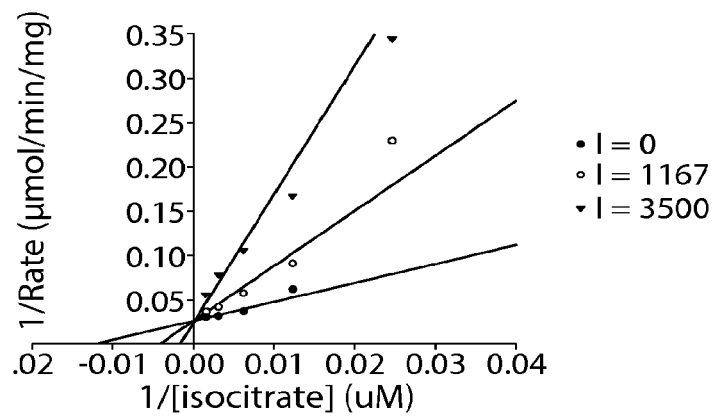
FIG. 13A depicts α-KG inhibition of IDH1 wild-type.
Figure 13B:
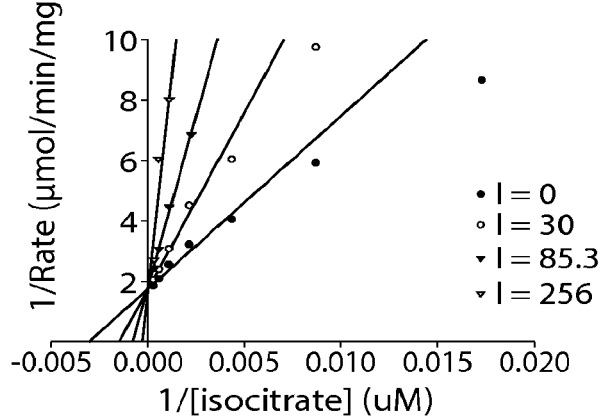
FIG. 13B depicts α-KG inhibition of R132H mutant enzyme.
Figure 13C:
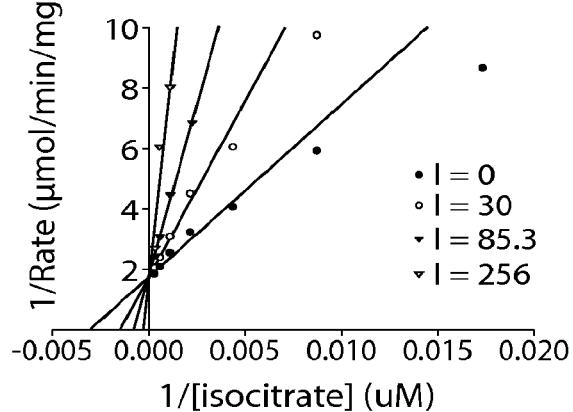
FIG. 13C depicts α-KG inhibition of R132S mutant enzyme.

A well-known regulatory mechanism for control of metabolic enzymes is feedback inhibition, in which the product of the reaction acts as a negative regulator for the generating enzyme. To examine whether the R132S or R132H mutants maintain this regulatory mechanism, the Ki for α-KG in the oxidative decarboxylation of ioscitrate to α-ketoglutarate was determined. Data is presented in FIGS. 13A-13C and summarized in Table 2. In all cases, α-KG acts as a competitive inhibitor of the isocitrate substrate. However, R132H and R132S display a 20-fold and 13-fold increase in sensitivity to feedback inhibition as compared to the wild-type enzyme.

TABLE 2

| Enzyme | Ki (uM) |
|---|---|
| Wt | 612.2 |
| R132H | 28.6 |
| R132S | 45.3 |

D. The Effect of MnCl$_2$ in Oxidative Decarboxylation of Isocitrate to α-Ketoglutarate (α-KG).

MnCl$_2$ can be substituted with MgCl$_2$ to examine if there is any difference in oxidative decarboxylation of isocitrate to α-Ketoglutarate (α-KG).

E. The Effect of R132 Mutations on the Inhibitory Effect of Oxalomalate on IDH1

The purpose of this example is to examine the susceptibility of IDH1R132S and IDH1R132H in oxidative decarboxylation of isocitrate to α-Ketoglutarate (α-KG) to the known IDH1 inhibitor oxalomalate. Experiments were performed to examine if R132 mutations circumvent the inhibition by oxalomalate.

Figure 17A:
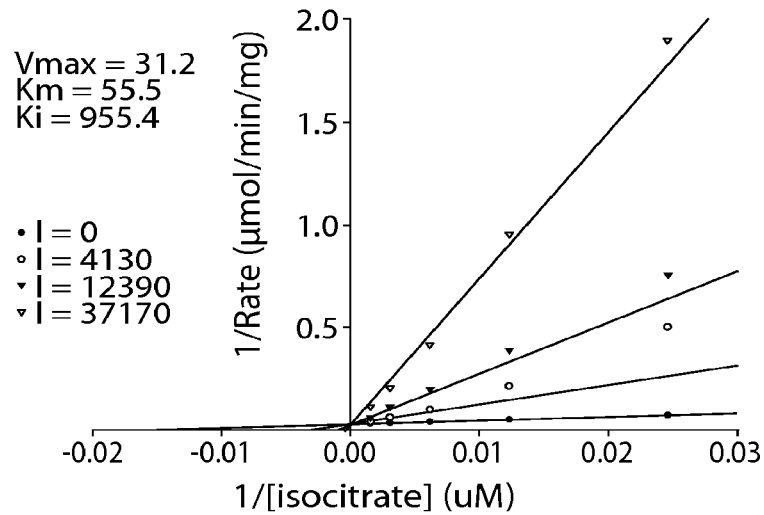
FIG. 17A depicts oxalomalate inhibition to IDH1 wt.
Figure 17B:
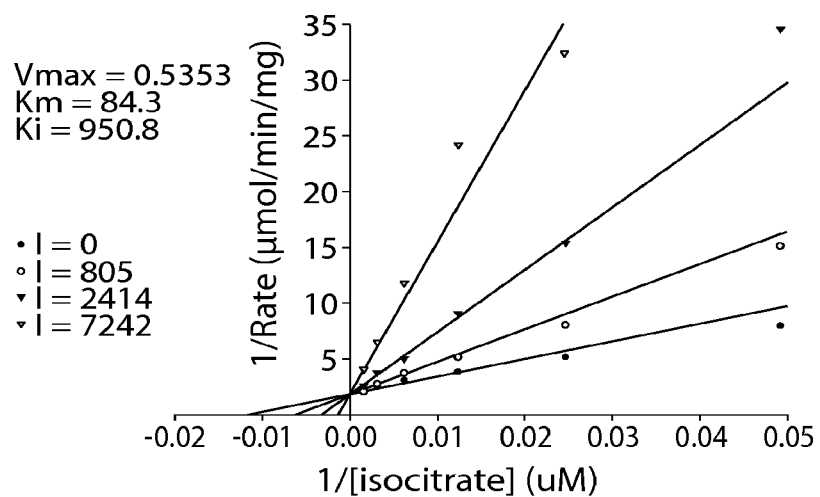
FIG. 17B depicts oxalomalate inhibition to R132H.
Figure 17C:
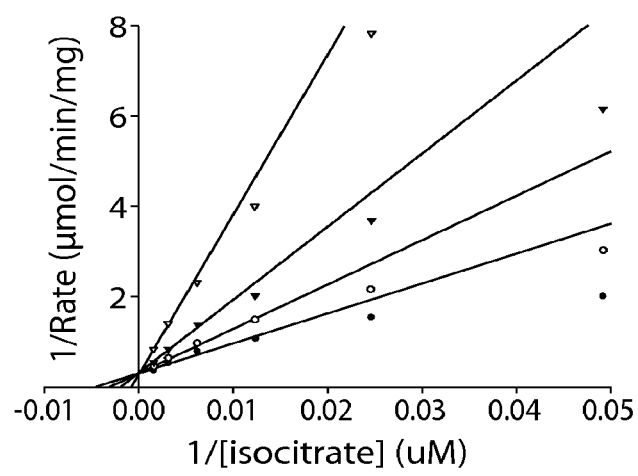
FIG. 17C depicts oxalomalate inhibition to R132S.

Final concentrations: Tris 7.5 20 mM, NaCl 150 mM, MnCl$_2$ 2 mM, Glycerol 10%, BSA 0.03%, NADP 0.5 mM, IDH1 wt 1.5 ug/ml, IDH1R132S 30 ug/ml, IDH1R132H 60 ug/ml, DL-isocitrate (5-650 uM). The results are summarized in FIG. 17 and Table 3. The R132S mutation displays approximately a two-fold increase in susceptibility to inhibition by oxalomalate, while the R132H mutation is essentially unaffected. In all three cases, the same fully competitive mode of inhibition with regards to isocitrate was observed.

TABLE 3

| Enzyme | Oxalomalate Ki (uM) |
|---|---|
| wt | 955.4 |
| R132S | 510 |
| R132H | 950.8 |

F. Forward Reactions (Isocitrate to α-KG) of Mutant Enzyme do not go to Completion.

Figure 23:
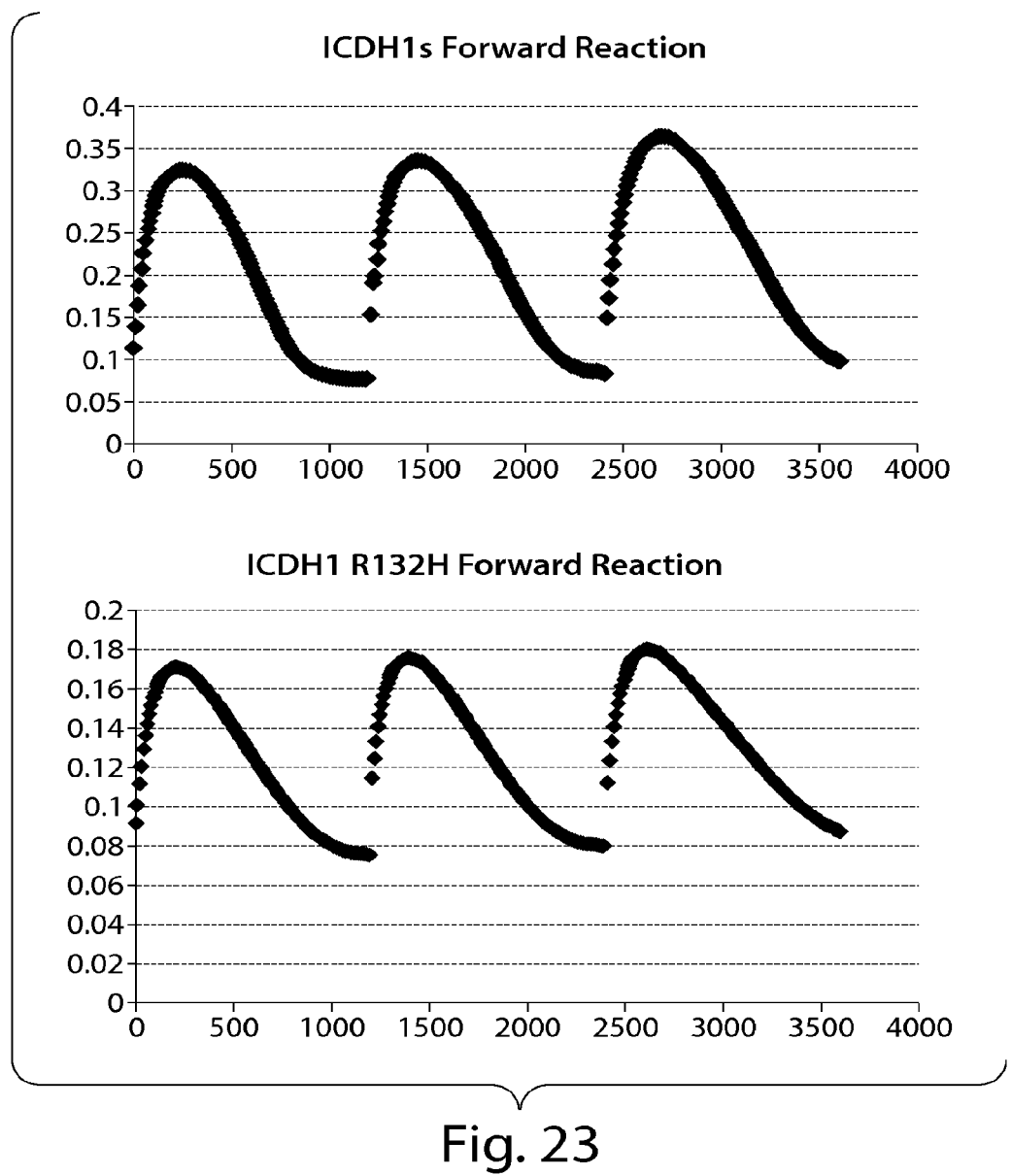
FIG. 23 depicts the progress of forward reactions (isocitrate to α-KG) for the mutant enzyme R132H and R132S.

Forward reactions containing ICDH1 R132S or ICDH1 R132H were assembled and reaction progress monitored by an increase in the OD340 of the reduced NADPH cofactor. It was observed (FIG. 23), that these reactions proceed in the forward direction for a period of time and then reverse direction and oxidize the cofactor reduced in the early stages of the reaction, essentially to the starting concentration present at the initiation of the experiment. Addition of further isocitrate re-initiated the forward reaction for a period of time, but again did not induce the reaction to proceed to completion. Rather, the system returned to initial concentrations of NADPH. This experiment suggested that the mutant enzymes were performing a reverse reaction other than the conversion of α-KG to isocitrate.

2. Analysis of IDH1 Wild-Type and Mutants R132H and R132S in the Reduction of α-Ketoglutarate (α-KG)

A. Methods

To determine the catalytic efficiency of enzymes in the reduction of α-Ketoglutarate (α-KG), reactions were performed to determine Vmax and Km for α-KG. In these reactions, substrate was varied while the cofactor was held constant at 500 uM. All reactions were performed in 50 mM potassium phosphate buffer, pH 6.5, 10% glycerol, 0.03% (w/v) BSA, 5 mM MgCl$_2$, and 40 mM sodium hydrocarbonate. Reaction progress was followed by spectroscopy at 340 nM monitoring the change in oxidation state of the cofactor. Sufficient enzyme was added to give a linear change in absorbance for 10 minutes.

B. The R132H and R132S Mutant Enzymes, but not the Wild-Type Enzyme, Support the Reduction of α-KG.

Figure 14:
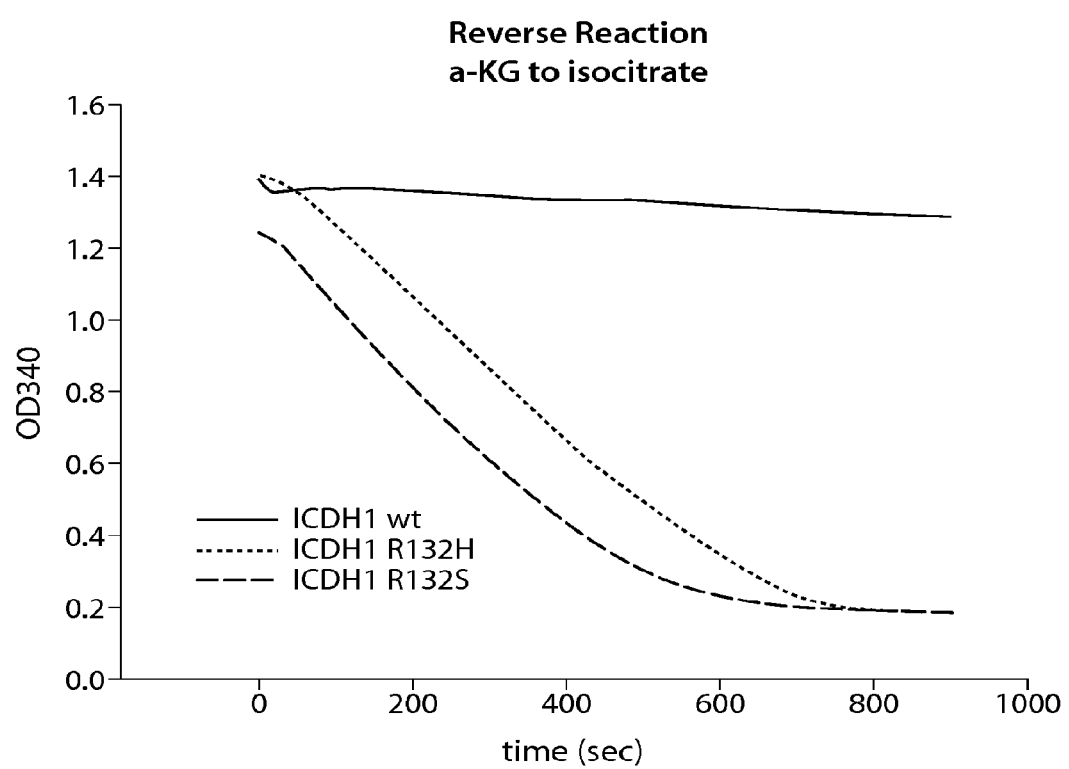
FIG. 14 depicts IDH1 wt, R132H, and R132S in the conversion α-ketoglutarate to 2-hydroxyglutarate.

To test the ability of the mutant and wild-type enzymes to perform the reduction of α-KG, 40 ug/ml of enzyme was incubated under the conditions for the reduction of α-Ketoglutarate (α-KG) as described above. Results are presented in FIG. 14. The wild-type enzyme was unable to consume NADPH, while R132S and R132H reduced α-KG and consumed NADPH.

C. The reduction of α-KG by the R132H and R132S mutants occurs in vitro at physiologically relevant concentrations of α-KG.

Figure 15A:
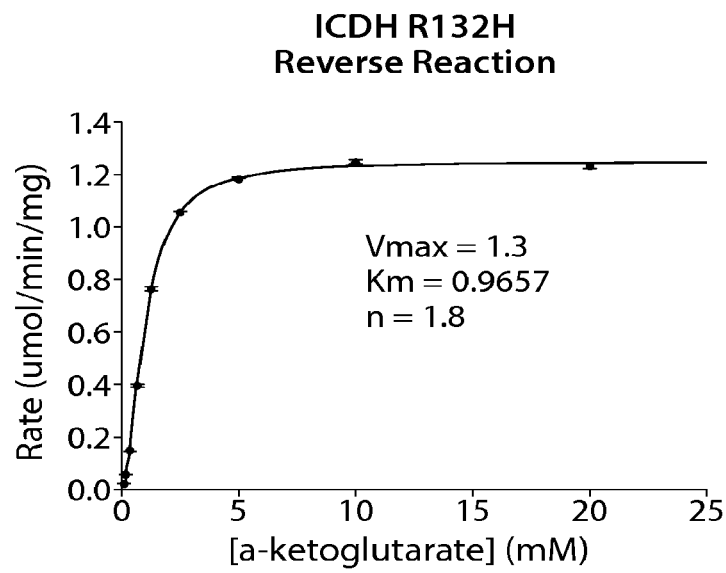
FIG. 15A depicts Substrate-Concentration velocity plot for R132H mutant enzyme.
Figure 15B:
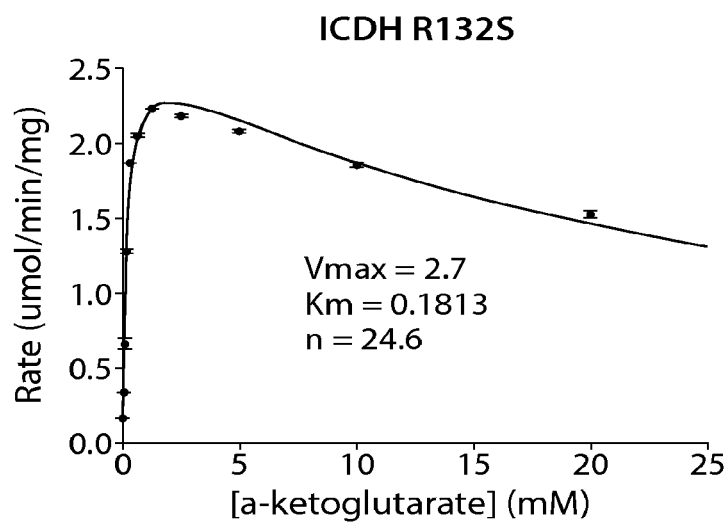
FIG. 15B depicts Substrate-Concentration velocity plot for R132S mutant enzyme.

To determine the kinetic parameters of the reduction of α-KG performed by the mutant enzymes, a substrate titration experiment was performed, as presented in FIGS. 15A-15B. R132H maintained the Hill-type substrate interaction as seen in the oxidative decarboxylation of isocitrate, but displayed positive substrate co-operative binding. R132S showed a conversion to Michaelis-Menten kinetics with the addition of uncompetitive substrate inhibition, as compared to wild-type enzyme in the oxidative decarboxylation of isocitrate. The enzymatic parameters of the mutant enzyme are presented in Table 4. Since the wild-type enzyme did not consume measurable NADPH in the experiment described above, a full kinetic workup was not performed.

TABLE 4

| Enzyme | Vmax (umol/min/mg) | Km (mM) | Hill Constant | Ki (mM) | Vmax/Km |
|---|---|---|---|---|---|
| R132H | 1.3 | 0.965 | 1.8 | | 1.35 |
| R132S | 2.7 | 0.181 | 0.479 | 24.6 | 14.92 |

The relative catalytic efficiency of reduction of α-KG is approximately ten-fold higher in the R132S mutant than in the R132H mutant. The biological consequence is that the rate of metabolic flux should be greater in cells expressing R132S as compared to R132H.

D. Analysis of IDH1 wild-type and mutants R132H and R132S in the reduction of alpha-ketoglutarate with NADH.

In order to evaluate the ability of the mutant enzymes to utilize NADH in the reduction of alpha-ketoglutarate, the following experiment was conducted. Final concentrations: NaHCO3 40 mM, MgCl2 5 mM, Glycerol 10%, K2HPO4 50 mM, BSA 0.03%, NADH 0.5 mM, IDH1 wt 5 ug/ml, R132S 30 ug/ml, R132H 60 ug/ml, alpha-Ketoglutarate 5 mM.

Figure 16:
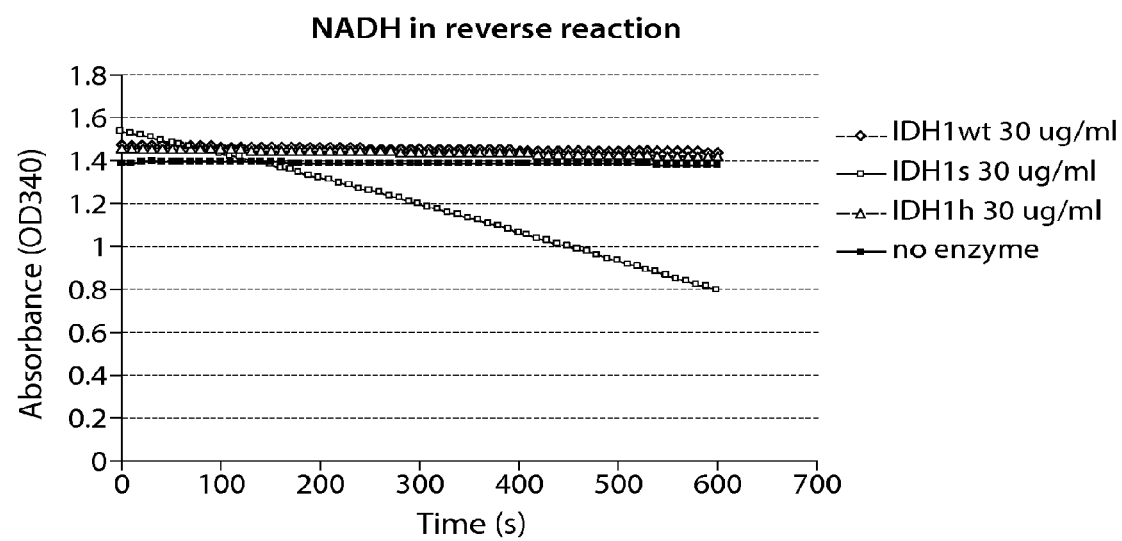
FIG. 16 depicts IDH1 wt, R132H, and R132S in the conversion α-ketoglutarate to 2-hydroxyglutarate with NADH.

The results are shown in FIG. 16 and Table 5. The R132S mutant demonstrated the ability to utilize NADH while the wild type and R132H show no measurable consumption of NADH in the presence of alpha-ketoglutarate.

TABLE 5

Consumption of NADH by R132S in the presence of alpha-ketoglutarate

| | R132S | | Mean | SD |
|---|---|---|---|---|
| Rate (ΔA/sec) | 0.001117 | 0.001088 | 0.001103 | 2.05E−05 |
| Umol/min/mg | 0.718328 | 0.699678 | 0.709003 | 0.013187 |

SUMMARY

Figure 30A:
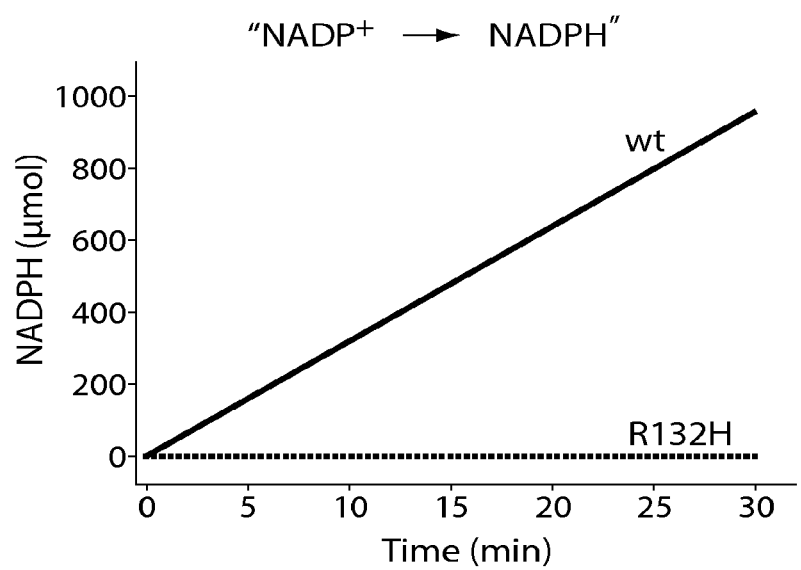
FIG. 30A depicts the enzymatic properties of IDH1 R132H mutants when ecombinant human wild-type (WT) and R132H mutant (R132H) IDH1 enzymes were assessed for oxidative decarboxylation of isocitrate to αKG with NADP$^+$ as cofactor. Different concentrations of enzyme were used to generate the curves.
Figure 30B:
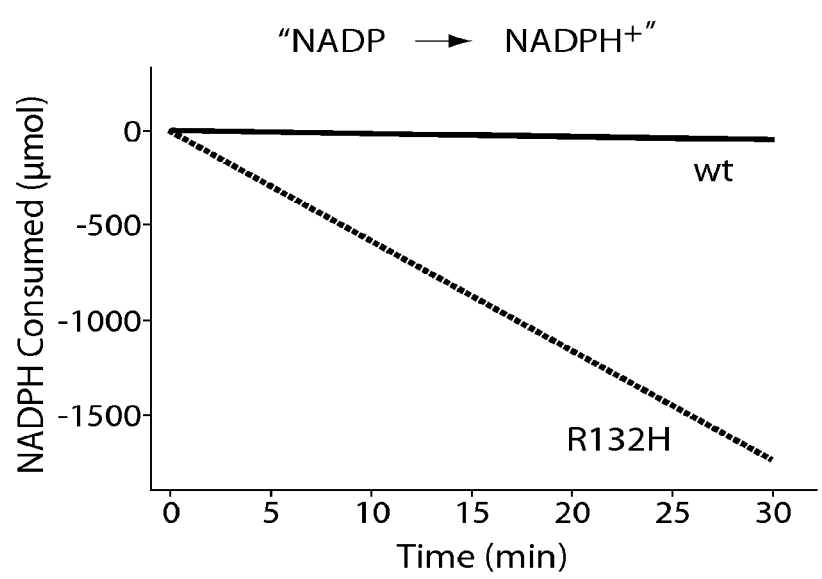
FIG. 30B depicts the enxymatic properties of IDH R132 mutants when WT and R132H mutant IDH1 enzymes were assessed for reduction of αKG with NADPH as cofactor. Different concentrations of enzyme were used to generate the curves.

To understand how R132 mutations alter the enzymatic properties of IDH1, wild-type and R132H mutant IDH1 proteins were produced and purified from E. coli. When NADP$^+$-dependent oxidative decarboxylation of isocitrate was measured using purified wild-type or R132H mutant IDH1 protein, it was confirmed that R132H mutation impairs the ability of IDH1 to catalyze this reaction (Yan, H. et al. N Engl J Med 360, 765-73 (2009); Zhao, S. et al. Science 324, 261-5 (2009)), as evident by the loss in binding affinity for both isocitrate and $MgCl_2$ along with a 1000-fold decrease in catalytic turnover (FIGS. 30A and 30C). In contrast, when NADPH-dependent reduction of αKG was assessed using either wild-type or R132H mutant IDH1 protein, only R132H mutant could catalyze this reaction at a measurable rate (FIGS. 30 and 30C). Part of this increased rate of αKG reduction results from an increase in binding affinity for both the cofactor NADPH and substrate αKG in the R132H mutant IDH1 (FIG. 30C). Taken together, these data demonstrate that while the R132H mutation leads to a loss of enzymatic function for oxidative decarboxylation of isocitrate, this mutation also results in a gain of enzyme function for the NADPH-dependent reduction of αKG.

2: Analysis of mutant IDH1

The R132H Mutant does not Result in the Conversion of α-KG to Isocitrate.

Using standard experimental methods, an API2000 mass spectrometer was configured for optimal detection of α-KG and isocitrate (Table 6). MRM transitions were selected and tuned such that each analyte was monitored by a unique transition. Then, an enzymatic reaction containing 1 mM α-KG, 1 mM NADPH, and ICDH1 R132H were assembled and run to completion as judged by the decrease to baseline of the optical absorbance at 340 nM. A control reaction was performed in parallel from which the enzyme was omitted. Reactions were quenched 1:1 with methanol, extracted, and subjected to analysis by LC-MS/MS.

Figure 18A:
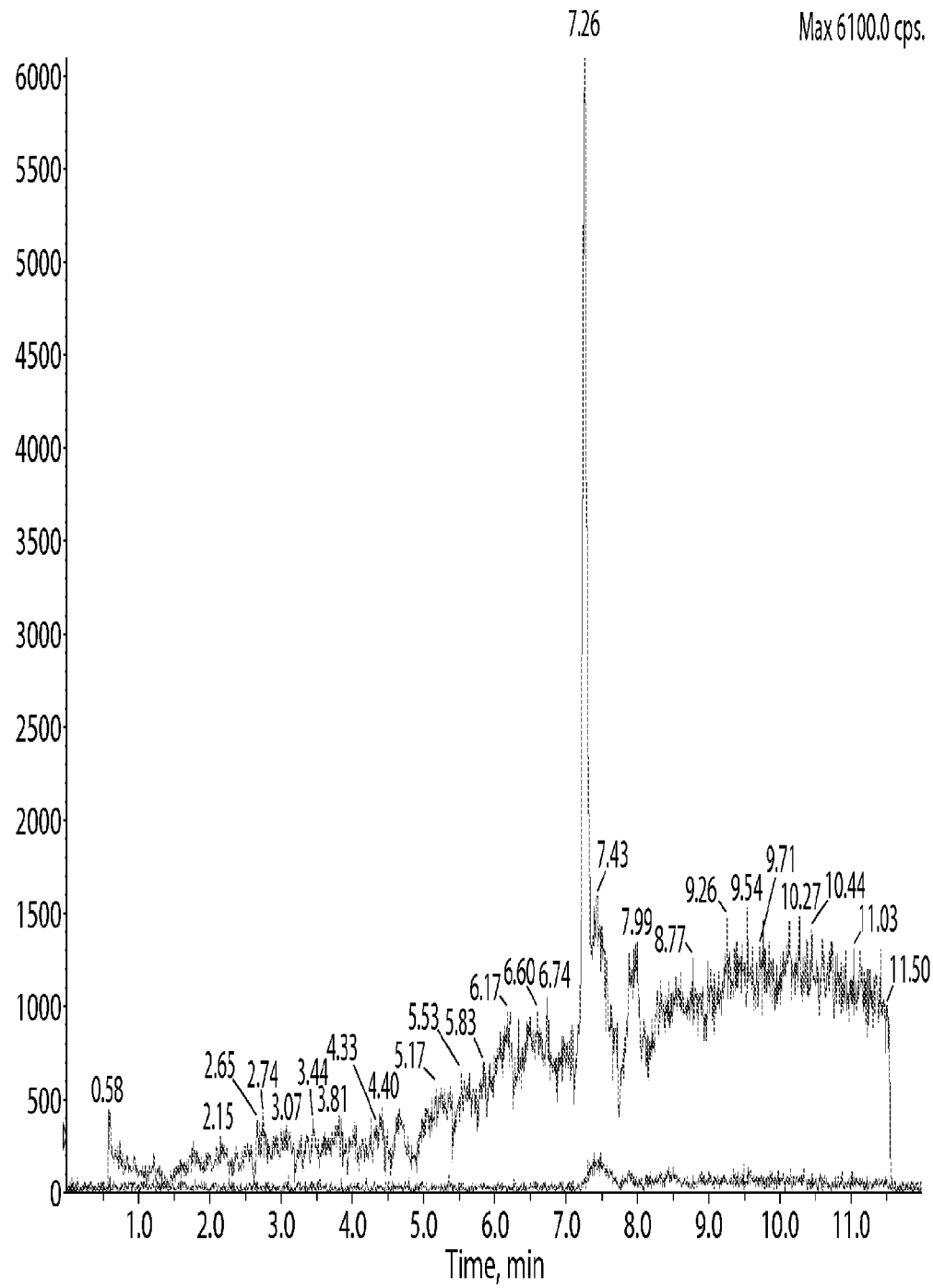
FIG. 18A depicts LC-MS/MS analysis of the control reaction.
Figure 18B:
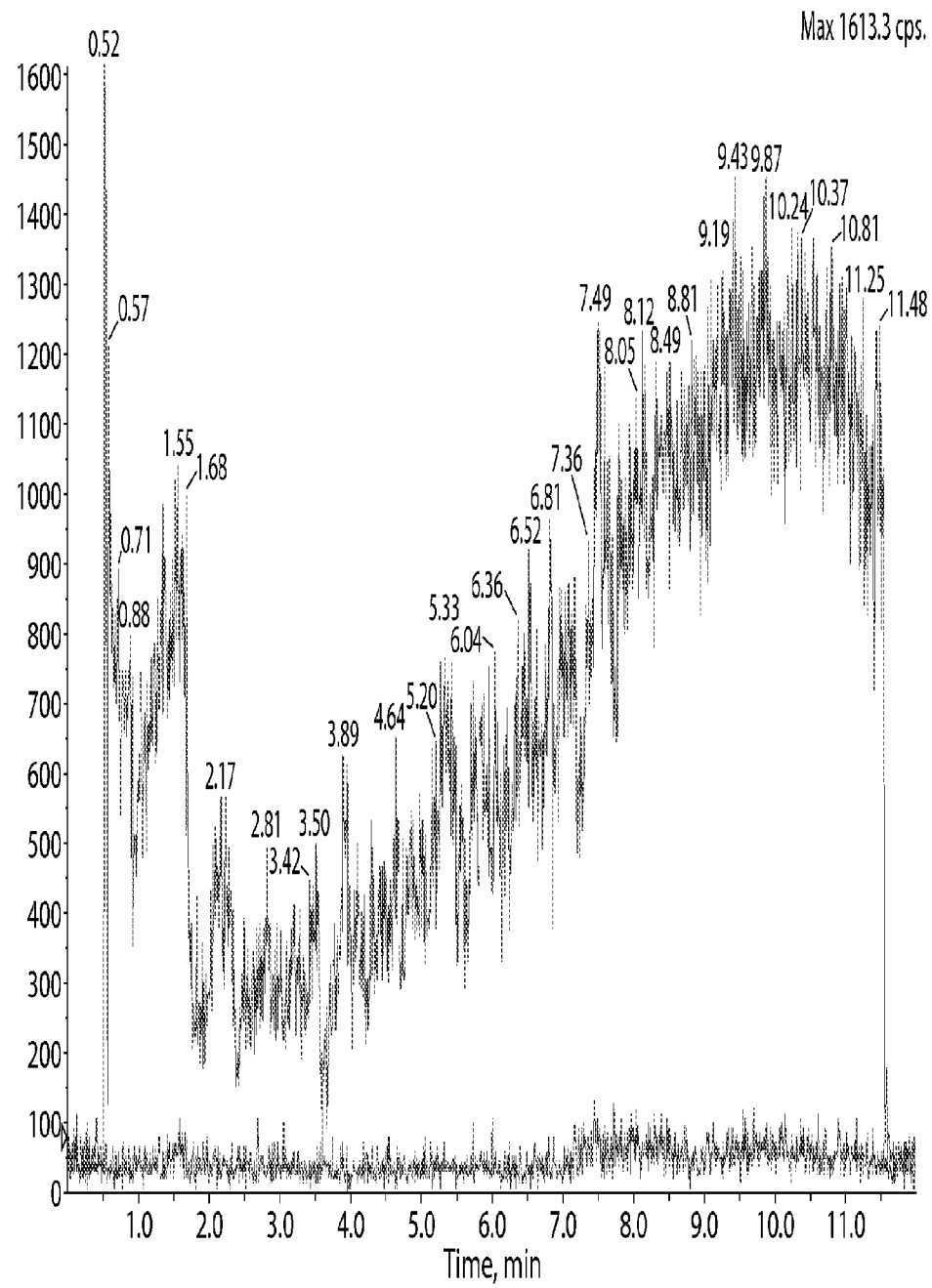
FIG. 18B depicts LC-MS/MS analysis of the reaction containing enzyme.
Figure 18C:
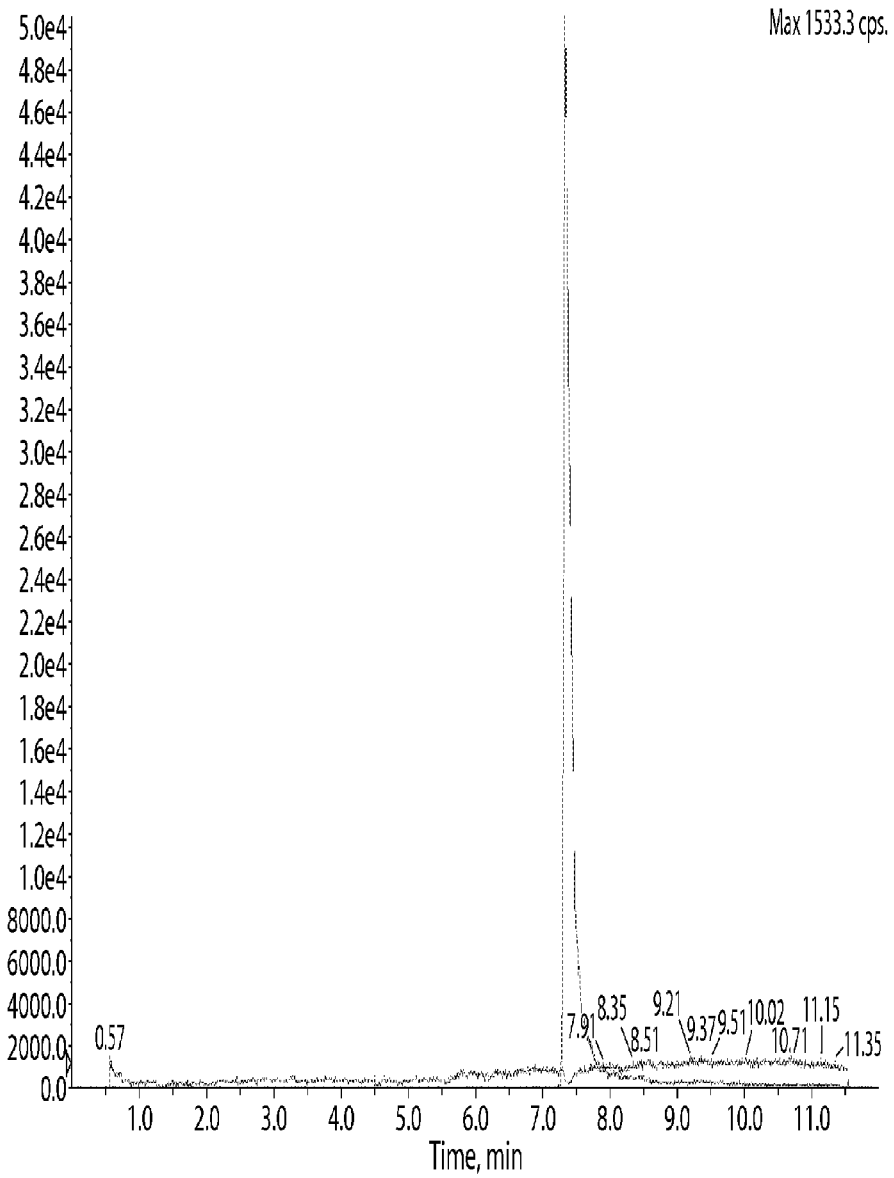
FIG. 18C depicts LC-MS/MS analysis of the spiked control reaction.

FIG. 18A presents the control reaction indicating that αKG was not consumed in the absence of enzyme, and no detectable isocitrate was present. FIG. 18B presents the reaction containing R132H enzyme, in which the α-KG has been consumed, but no isocitrate was detected. FIG. 18C presents a second analysis of the reaction containing enzyme in which isocitrate has been spiked to a final concentration of 1 mM, demonstrating that had α-KG been converted to isocitrate at any appreciable concentration greater than 0.01%, the configured analytical system would have been capable of detecting its presence in the reaction containing enzyme. The conclusion from this experiment is that while α-KG was consumed by R132H, isocitrate was not produced. This experiment indicates that one neoactivity of the R132H mutant is the reduction of α-KG to a compound other than isocitrate.

TABLE 6

Instrument settings for MRM detection of compounds

| Compound | Q1 | Q3 | DP | FP | EP | CEP | CE | CXP |
|---|---|---|---|---|---|---|---|---|
| α-KG | 144.975 | 100.6 | −6 | −220 | −10 | −16 | −10 | −22 |
| isocitrate | 191.235 | 110.9 | −11 | −230 | −4.5 | −14 | −16 | −24 |
| a-hydroxy-glutarate | 147.085 | 128.7 | −11 | −280 | −10 | −22 | −12 | −24 |

The R132H Mutant Reduces α-KG to 2-Hydroxyglutaric Acid.

Figure 19:
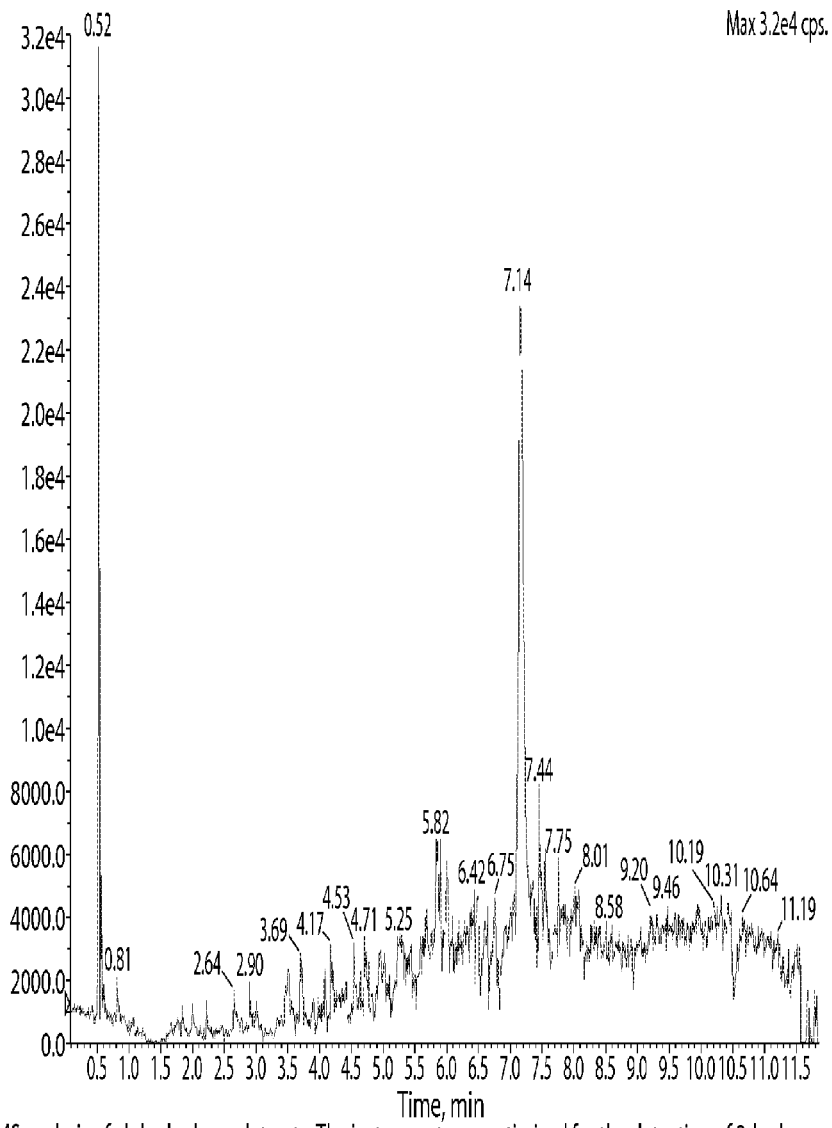
FIG. 19 depicts LC-MS/MS analysis of alpha-hydroxyglutarate.
Figure 20:
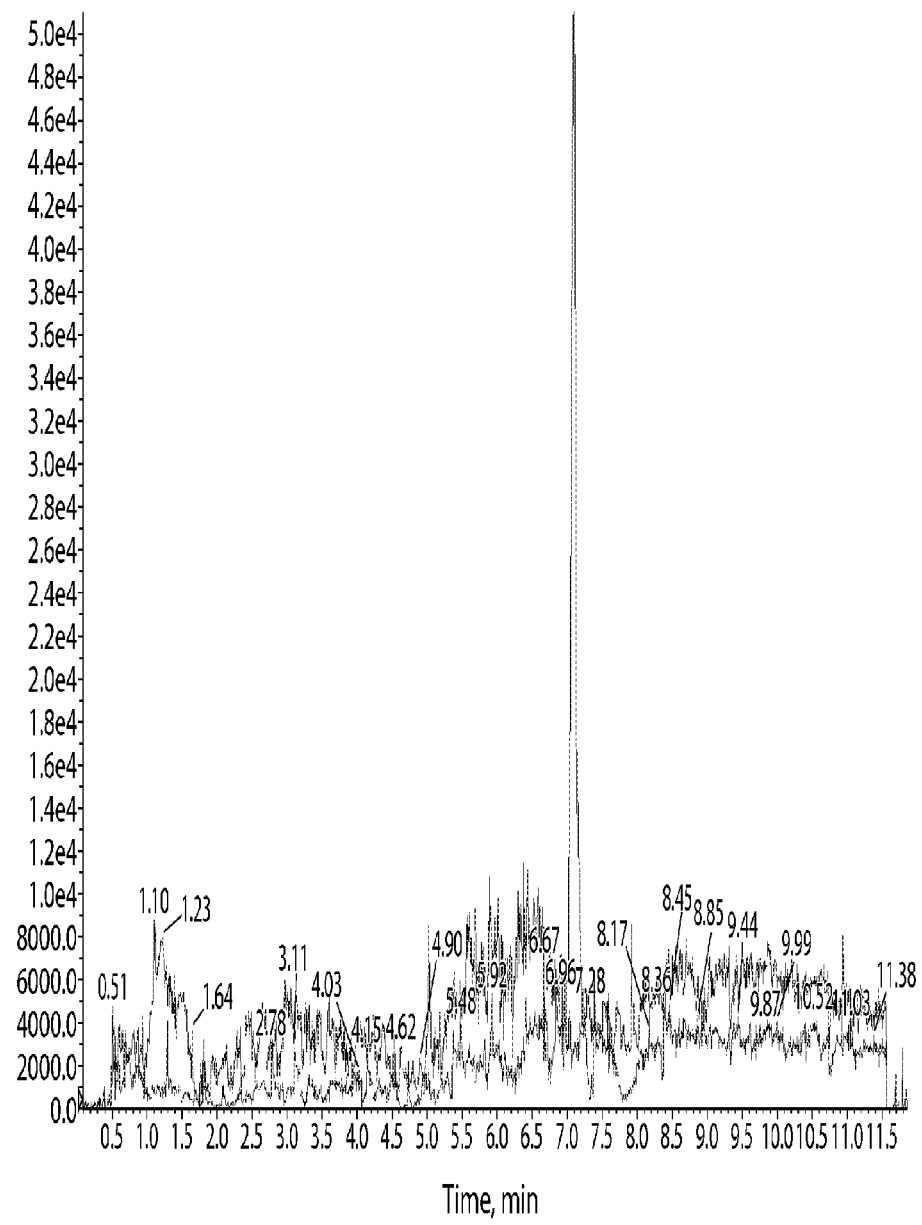
FIG. 20 depicts LC-MS/MS analysis showing that R132H consumes α-KG to produce 2-hydroxyglutaric acid.

Using standard experimental methods, an API2000 mass spectrometer was configured for optimal detection 2-hydroxyglutarate (Table 6 and FIG. 19). The reaction products of the control and enzyme-containing reactions from above were investigated for the presence of 2-hydroxyglutaric acid, FIG. 20. In the control reaction, no 2-hydroxyglutaric acid was detected, while in reaction containing R132H, 2-hydroxyglutaric acid was detected. This data confirms that one neoactivity of the R132H mutant is the reduction of α-KG to 2-hydroxyglutaric acid.

Figure 31A:
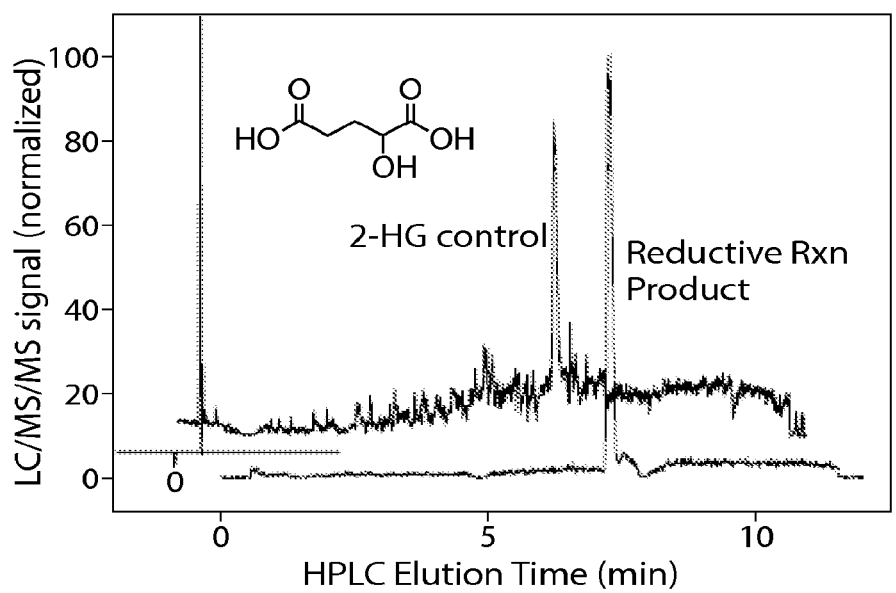
FIG. 31A depicts the LC-MS/MS analysis identifying 2HG as the reductive reaction product of recombinant human R132H mutant IDH1.

To determine whether R132H mutant protein directly produced 2HG from αKG, the product of the mutant IDH1 reaction was examined using negative ion mode triple quadrupole electrospray LC-MS. These experiments confirmed that 2HG was the direct product of NADPH-dependent αKG reduction by the purified R132H mutant protein through comparison with a known metabolite standards (FIG. 31A). Conversion of αKG to isocitrate was not observed.

One can determine the enantiomeric specificity of the reaction product through derivitazation with DATAN (di-acetyl-L-tartaric acid) and comparing the retention time to that of known R and S standards. This method is described in Struys et al. Clin Chem 50:1391-1395(2004). The stereo-specific production of either the R or S enantomer of alpha-hydroxyglutaric acid by ICDH1 R132H may modify the biological activity of other enzymes present in the cell. The racemic production may also occur.

For example, one can measure the inhibitory effect of alpha-hydroxyglutaric acid on the enzymatic activity of enzymes which utilize α-KG as a substrate. In one embodiment, alpha-hydroxyglutaric acid may be a substrate- or product-analogue inhibitor of wild-type ICDH1. In another embodiment alpha-hydroxyglutaric acid may be a substrate- or product-analogue inhibitor of HIF1 prolyl hydroxylase. In the former case, inhibition of wild type ICDH1 by the enzymatic product of R132H will reduce the circulating levels of αKG in the cell. In the latter case, inhibition of HIF1 prolyl hydroxylase will result in the stabilization of HIF1 and an induction of the hypoxic response cohort of cellular responses.

ICDH R132H Reduces αKG to the R-Enantiomer of 2-Hydroxyglutarate.

There are two possible enantiomers of the ICDHR132H reductive reaction product, converting alpha-ketoglutarate to 2-hydroxyglutarate, with the chiral center being located at the alpha-carbon position. Exemplary products are depicted below.

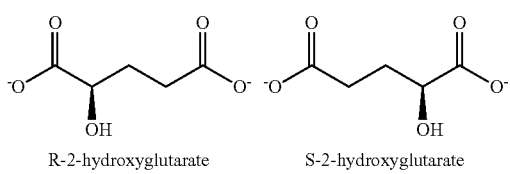

R-2-hydroxyglutarate    S-2-hydroxyglutarate

These are referred to by those with knowledge in the art as the R (or pro-R) and S (or pro-S) enantiomers, respectively. In order to determine which form or both is produced as a result of the ICDH1 neoactivity described above, the relative amount of each chiral form in the reaction product was determined in the procedure described below.

Reduction of α-KG to 2-HG was performed by ICDHR132H in the presence of NADPH as described above, and the reaction progress was monitored by a change in extinction coefficient of the nucleotide cofactor at 340 nM; once the reaction was judged to be complete, the reaction was extracted with methanol and dried down completely in a stream of nitrogen gas. In parallel, samples of chirally pure R-2-HG and a racemic mixture of R- and S-2-HG (produced by a purely chemical reduction of α-KG to 2-HG) were resuspended in ddH$_2$O, similarly extracted with methanol, and dried.

The reaction products or chiral standards were then resuspended in a solution of dichloromethane:acetic acid (4:1) containing 50 g/L DATAN and heated to 75° C. for 30 minutes to promote the derivitization of 2-HG in the scheme described below:

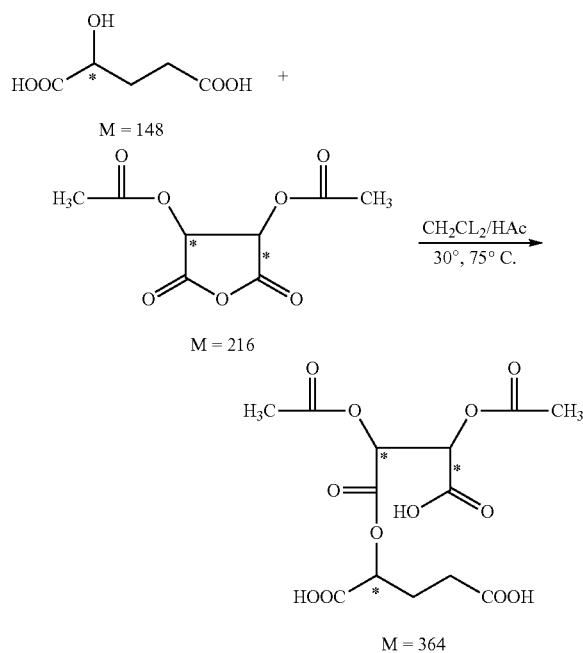

After cooling to room temperature, the derivitization reactions were dried to completion and resuspended in ddH$_2$O for analysis on an LC-MS/MS system. Analysis of reaction products and chiral standards was performed on an API2000 LC-MS/MS system using a 2×150 mM C18 column with an isocratic flow of 200 μl/min of 90:10 (ammonium formate, pH 3.6:methanol) and monitoring the retention times of the 2-HG-DATAN complex using XIC and the diagnostic MRM transition of 363/147 in the negative ion mode.

It should be noted that retention times in the experiments described below are approximate and accurate to within +/−1 minute; the highly reproducible peak seen at 4 minutes is an artefact of a column switching valve whose presence has no result on the conclusions drawn from the experiment.

Figure 24A:
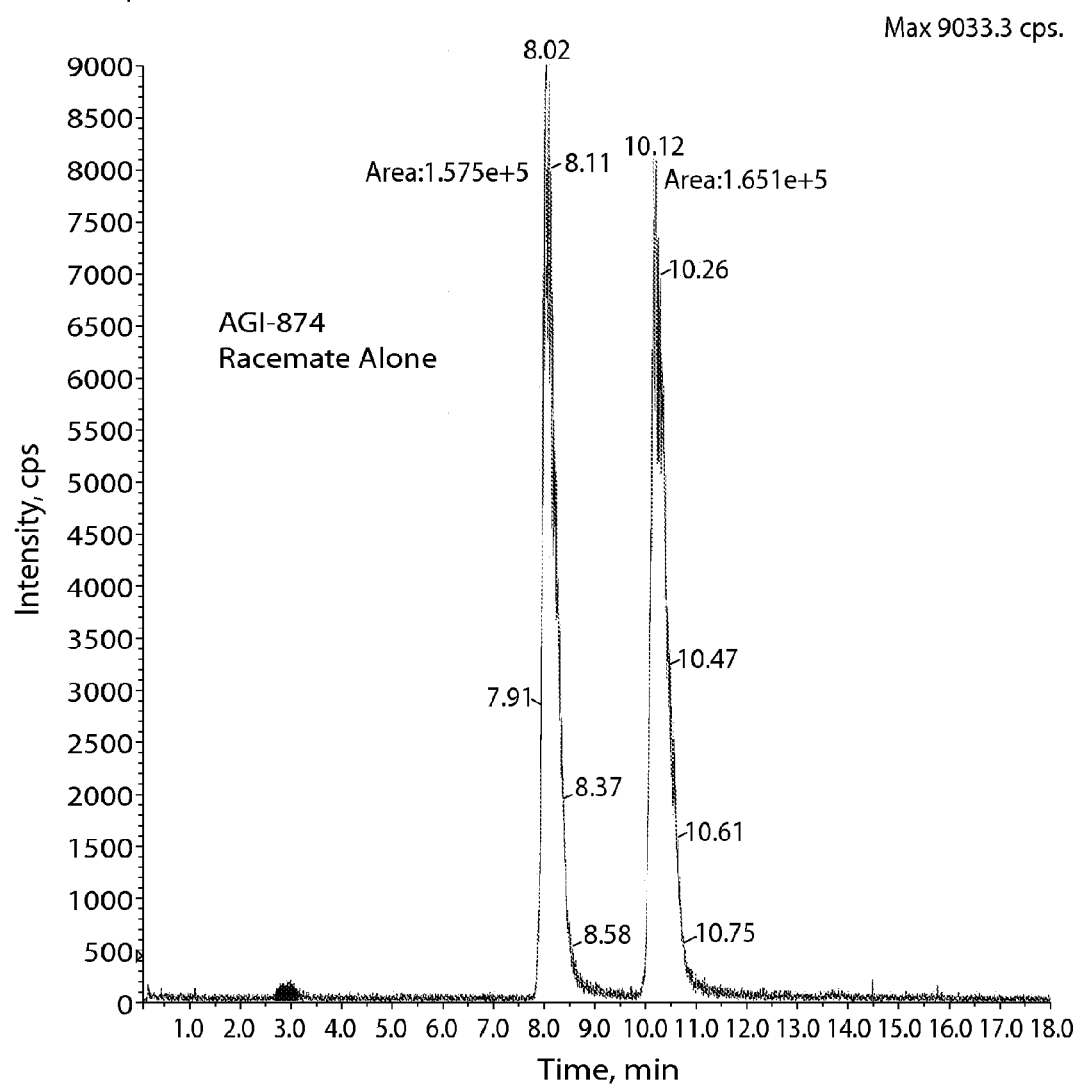
FIG. 24A depicts LC-MS/MS analysis of derivitized 2-HG racemic mixture.
Figure 24B:
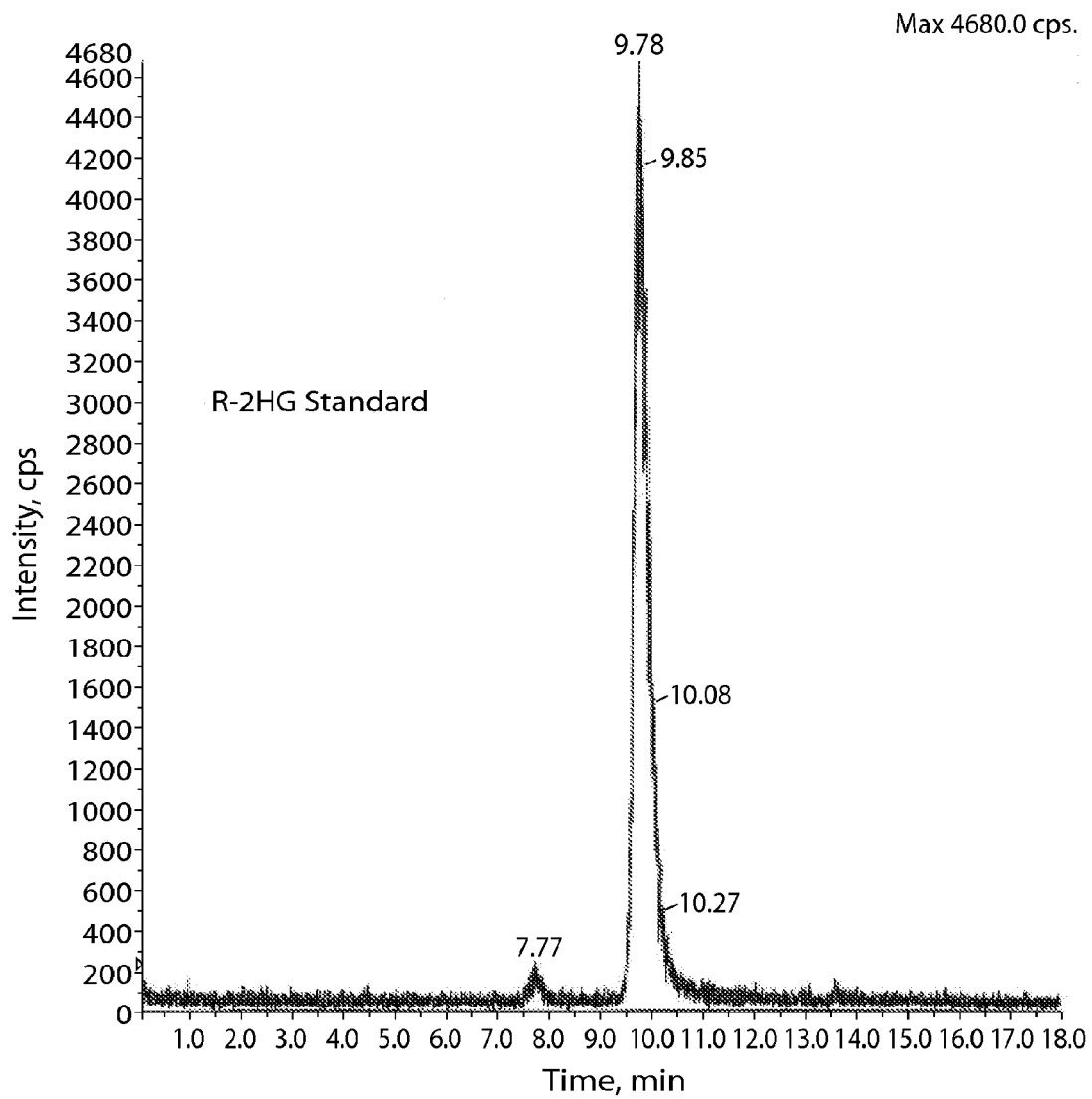
FIG. 24B depicts LC-MS/MS analysis of derivitized R-2HG standard.
Figure 24C:
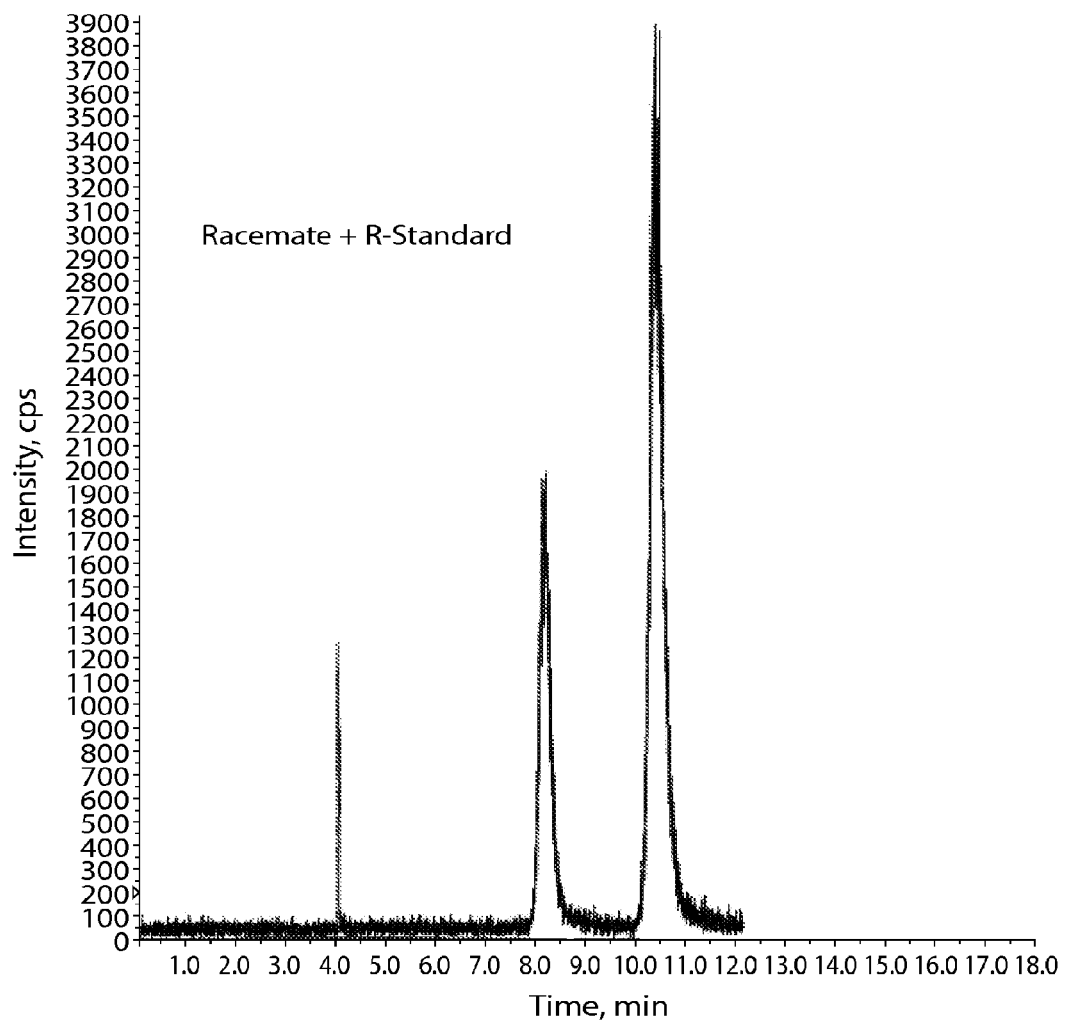
FIG. 24C depicts LC-MS/MS analysis of a coinjection of derivitized 2-HG racemate and R-2-HG standard.

Injection of the racemic mixture gave two peaks of equal area at retention times of 8 and 10 minutes (FIG. 24A), while injection of the R-2-HG standard resulted in a major peak of >95% area at 10 minutes and a minor peak <5% area at 8 minutes (FIG. 24B); indicating that the R-2-HG standard is approximately 95% R and 5% S. Thus, this method allows us to separate the R and S-2-HG chiral forms and to determine the relative amounts of each in a given sample. Coinjection of the racemic mixture and the R-2-HG standard resulted in two peaks at 8 and 10 minutes, with a larger peak at 10 minutes resulting from the addition of surplus pro-R-form (the standard) to a previously equal mixture of R- and S-2-HG (FIG. 24C). These experiments allow us to assign the 8 minute peak to the S-2-HG form and the 10 minute peak to the R-2-HG form.

Figure 24D:
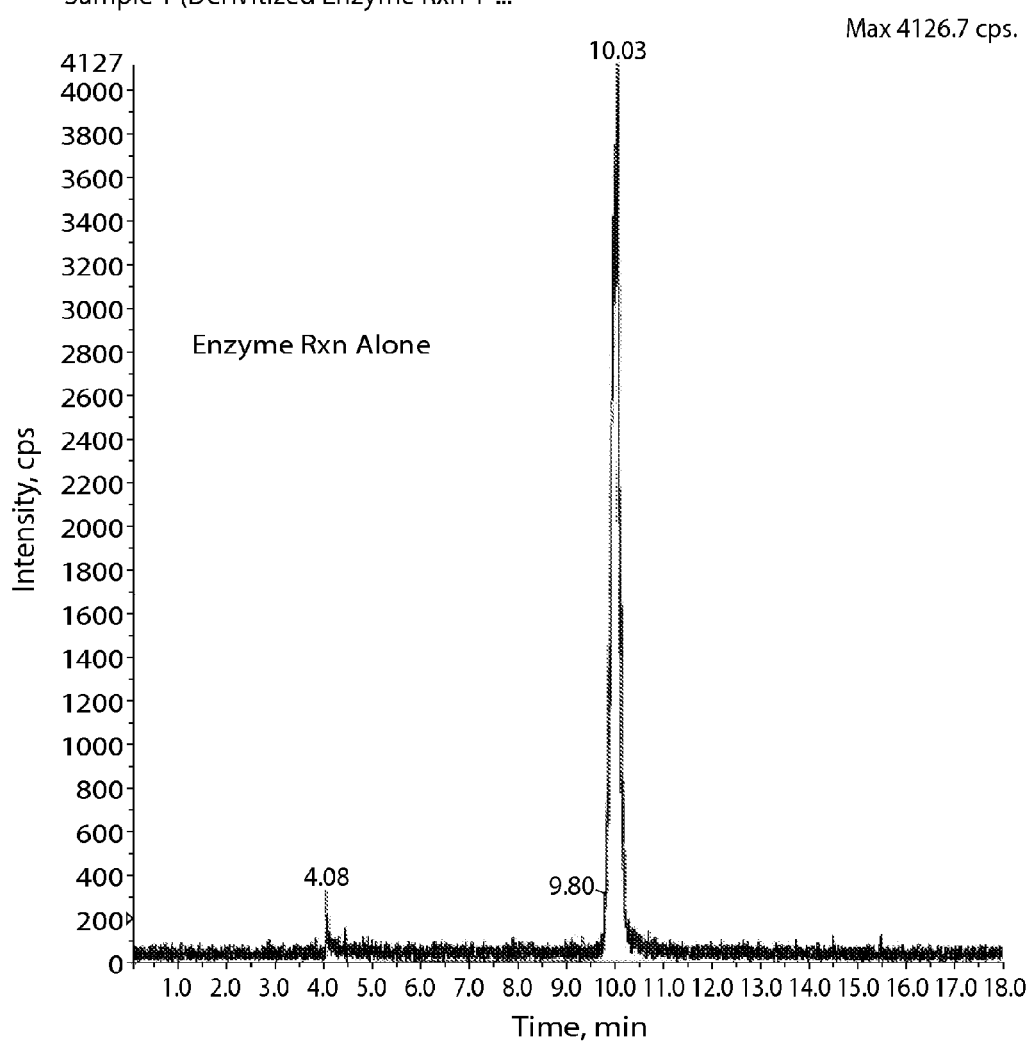
FIG. 24D depicts LC-MS/MS analysis of the derivatized neoactivity reaction product.
Figure 24E:
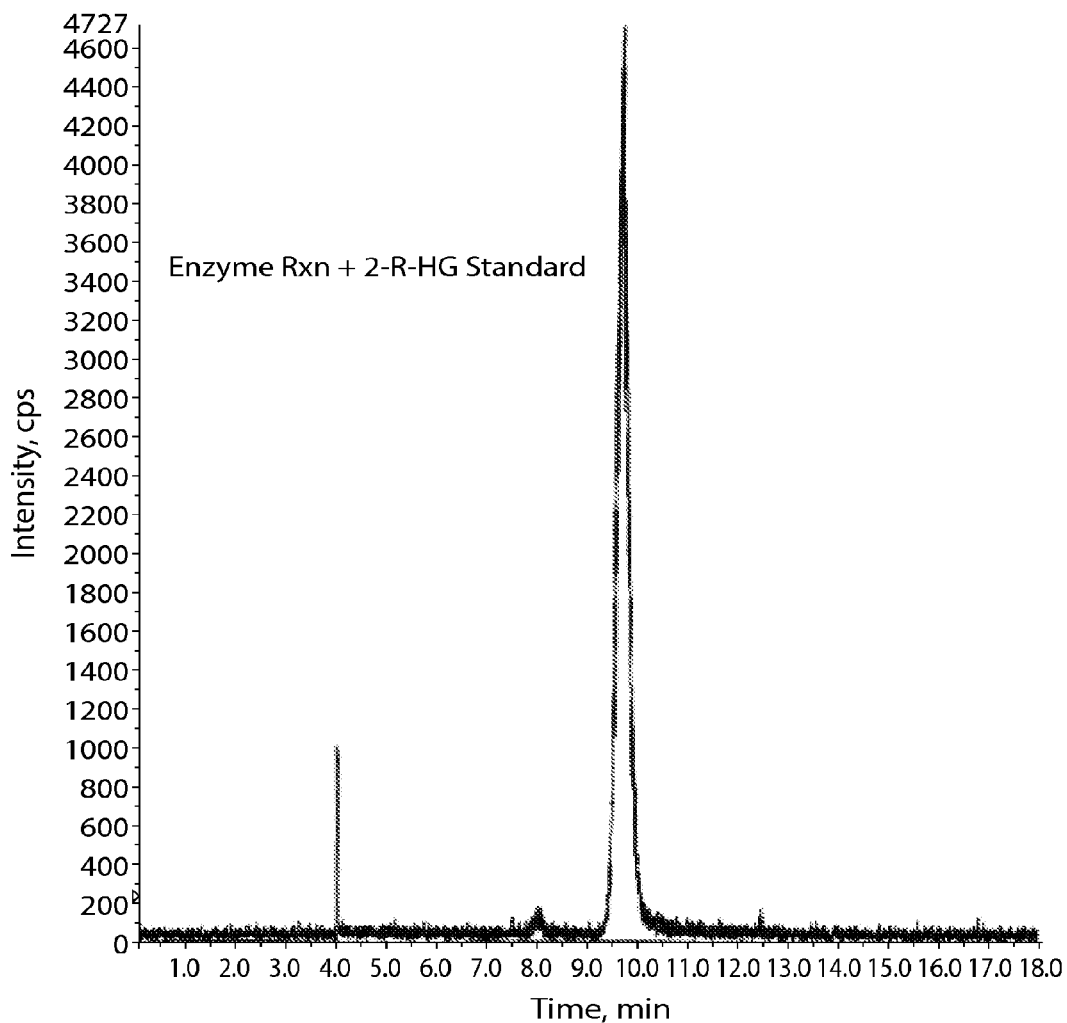
FIG. 24E depicts LC-MS/MS analysis of a coinjection of the neoactivty enzyme reaction product and the R-2-HG standard.
Figure 24F:
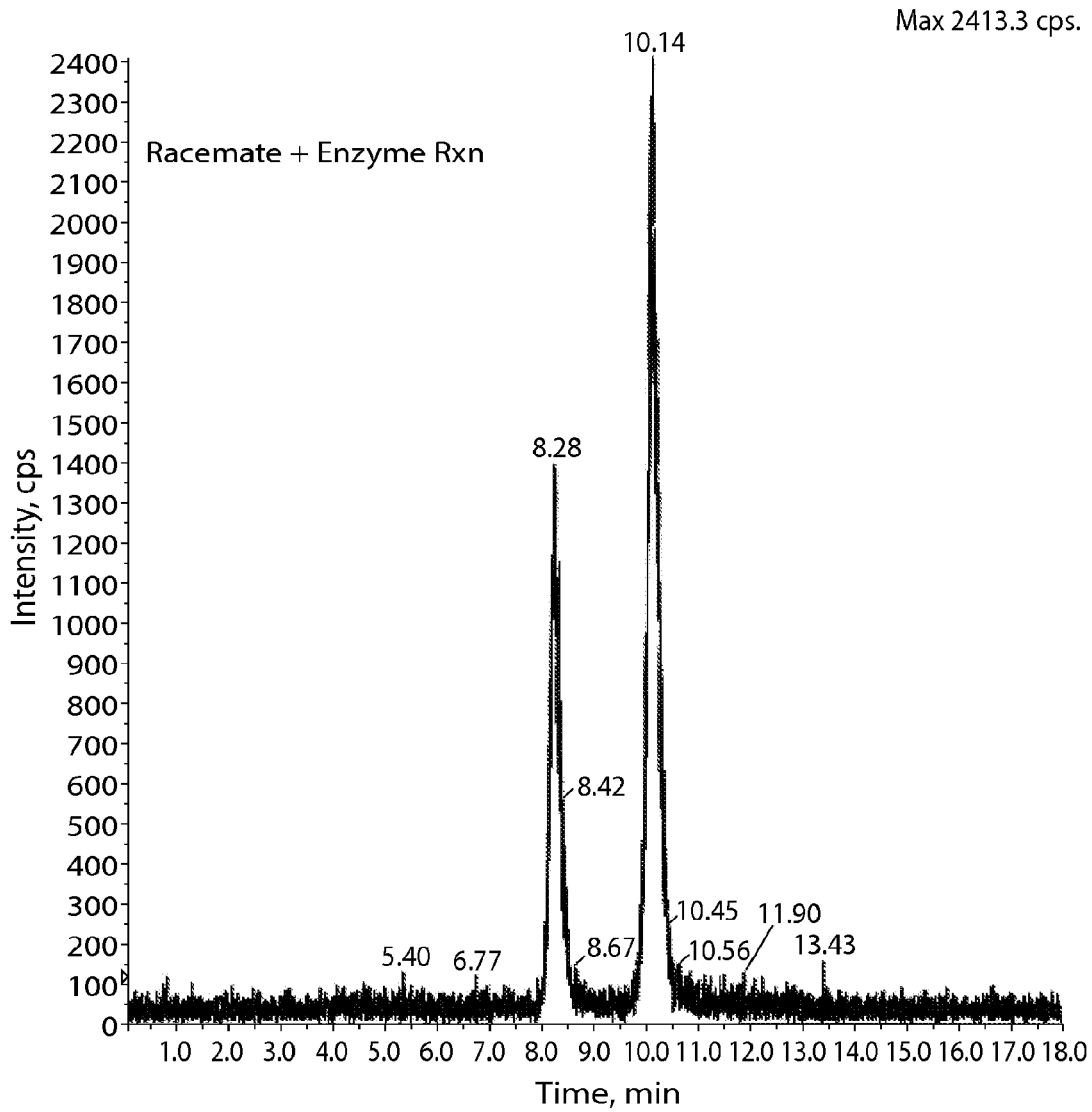
FIG. 24F depicts LC-MS/MS analysis of a coinjection of the neoactivity enzyme reaction product and the 2-HG racemic mixture.

Injection of the derivatized neoactivity enzyme reaction product alone yields a single peak at 10 minutes, suggesting that the neoactivity reaction product is chirally pure R-2-HG (FIG. 24D). Coinjection of the neoactivity reaction product with the R-2-HG standard results in a major peak of >95% area at 10 minutes (FIG. 24E) and a single minor peak of <5% area at 8 minutes (previously observed in injection of the R-2-HG standard alone) confirming the chirality of the neoactivity product as R. Coinjection of a racemic mixture and the neoactivity reaction product (FIG. 24F) results in a 60% area peak at 10 minutes and a 40% area peak at 8 minutes; this deviation from the previously symmetrical peak areas observed in the racemate sample being due to the excess presence of R-2-HG form contributed by the addition of the neoactivity reaction product. These experiments allow us to conclude that the ICDH1 neoactivity is a highly specific chiral reduction of α-KG to R-2-HG.

Enzyme Properties of Other IDH1 Mutations

To determine whether the altered enzyme properties resulting from R132H mutation were shared by other R132 mutations found in human gliomas, recombinant R132C, R132L and R132S mutant IDH1 proteins were generated and the enzymatic properties assessed. Similar to R132H mutant protein, R132C, R132L, and R132S mutations all result in a gain-of-function for NADPH-dependent reduction of αKG (data not shown). Thus, in addition to impaired oxidative decarboxylation of isocitrate, one common feature shared among the IDH1 mutations found in human gliomas is the ability to catalyze direct NADPH-dependent reduction of αKG.

Identification of 2-HG Production in Glioblastoma Cell Lines Containing the IDH-1 R132H Mutant Protein.

Generation of Genetic Engineered Glioblastoma Cell Lines Expressing Wildtype or Mutant IDH-1 Protein.

A carboxy-terminal Myc-DDK-tagged open reading frame (ORF) clone of human isocitrate dehydrogenase 1 (IDH1; Ref. ID: NM_005896) cloned in vector pCMV6 was obtained from commercial vendor Origen Inc. Vector pCMV6 contains both kanamycin and neomycin resistance cassettes for selection in both bacterial and mammalian cell systems. Standard molecular biology mutagenesis techniques were utilized to alter the DNA sequence at base pair 364 of the ORF to introduce base pair change from guanine to adenine resulting in a change in the amino acid code at position 132 from argentine (wt) to histidine (mutant; or R132H). Specific DNA sequence alteration was confirmed by standard methods for DNA sequence analysis. Parental vector pCMV6 (no insert), pCMV6-wt IDH1 or pCMV6-R132H were transfected into immortalized human glioblastoma cell lines ATCC® CRL-2610 (LN-18) or HTB-14 (U-87) in standard growth medium (DMEM; Dulbecco's modified Eagles Medium containing 10% fetal bovine serum). Approximately 24 hrs after transfection, the cell cultures were transitioned to DMEM containing G418 sodium salt at concentrations of either 750 ug/ml (CRL-2610) or 500 ug/ml (HTB-14) to select those cells in culture that expressed the integrated DNA cassette expressing both the neomycin selectable marker and the ORF for human wild type or R132H. Pooled populations of G418 resistant cells were generated and expression of either wild type IDH1 or R132 IDH1 was confirmed by standard Western blot analysis of cell lysates using commercial antibodies recognizing either human IDH1 antigen or the engineered carboxy-terminal MYC-DDK expression tag. These stable clonal pools were then utilized for metaobolite preparation and analysis.

Procedure for Metabolite Preparation and Analysis.

Glioblastoma cell lines (CRL-2610 and HTB-14) expressing wildtype or mutant IDH-1 protein were grown using standard mammalian tissue culture techniques on DMEM media containing 10% FCS, 25 mM glucose, 4 mM glutamine, and G418 antibiotic (CRL-2610 at 750 ug/mL; HTB-14 at 500 ug/mL) to insure ongoing selection to preserve the transfected mutant expression sequences. In preparation for metabolite extraction experiments, cells were passaged into 10 cm round culture dishes at a density of $1 \times 10^6$ cells. Approximately 12 hours prior to metabolite extraction, the culture media was changed (8 mL per plate) to DMEM containing 10% dialyzed FCS (10,000 mwco), 5 mM glucose, 4 mM glutamine, and G-418 antibiotic as before; the dialyzed FCS removes multiple small molecules form the culture media and enables cell culture-specific assessment of metabolite levels. The media was again changed 2 horrs prior to metabolite extraction. Metabolite extraction was accomplished by quickly aspirating the media from the culture dishes in a sterile hood, immediately placing the dishes in a tray containing dry ice to cool them to −80° C., and as quickly as possible, adding 2.6 mL of 80% MeOH/20% water, pre-chilled to −80° C. in a dry-ice/acetone bath. These chilled, methanol extracted cells were then physically separated from the culture dish by scraping with a sterile polyethylene cell lifter (Corning #3008), brought into suspension and transferred to a 15 mL conical vial, then chilled to −20° C. An additional 1.0 mL of 80% MeOH/20% water was applied to the chilled culture dish and the cell lifting procedure repeated, to give a final extraction volume of 3.6 mL. The extracts were centrifuged at 20,000×g for 30 minutes to sediment the cell debris, and 3.0 mL of the supernatants was transferred to a screw-cap freezer vial and stored at −80° C. until ready for analysis.

In preparation for analysis, the extracts were removed from the freezer and dried on a nitrogen blower to remove methanol. The 100% aqueous samples were analyzed by LCMS as follows. The extract (10 μL) was injected onto a reverse-phase HPLC column (Synergi 150 mm×2 mm, Phenomenex Inc.) and eluted using a linear gradient of LCMS-grade methanol (Buffer B) in Aq. 10 mM tributylamine, 15 mM Acetic acid (Buffer A), running from 3% Buffer B to 95% Buffer B over 45 minutes at 200 μL/min. Eluted metabolite ions were detected using a triple-quadrapole mass spectrometer, tuned to detect in negative mode with multiple-reaction-monitoring mode transition set (MRM's) according to the molecular weights and fragmentation patterns for 38 known central metabolites, including 2-hydroxyglutarate (MRM parameters were optimized by prior infusion of known compound standards). Data was processed using Analyst Software (Applied Biosystems, Inc.) and metabolite signal intensities were converted into absolute concentrations using signal build-up curves from injected mixtures of metabolite standards at known concentrations. Final metabolite concentrations were reported as mean of at least three replicates, +/− standard deviation.

Results.

Figure 26A:
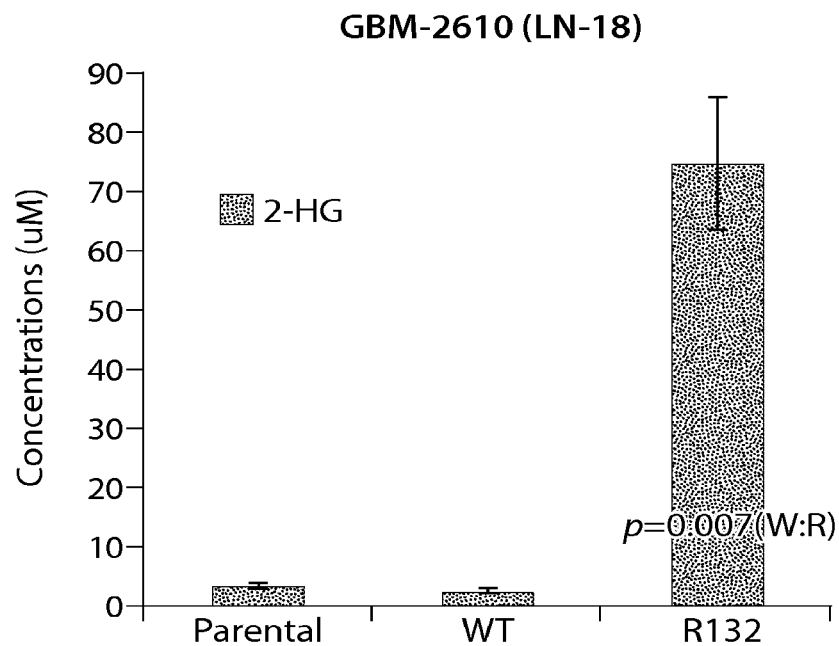
FIG. 26A depicts levels of 2-HG in CRL-2610 cell lines expressing wildtype or IDH-1 R132H mutant protein.
Figure 26B:
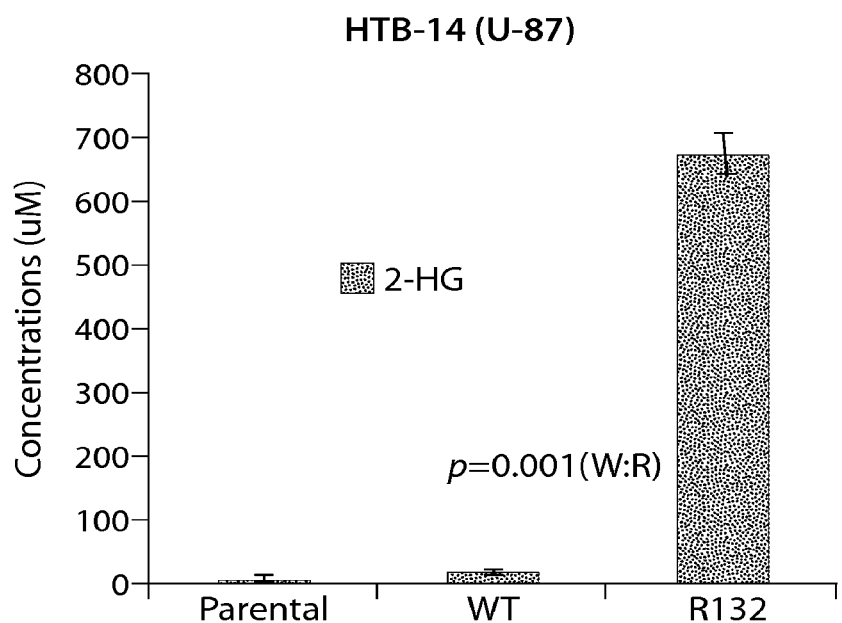
FIG. 26B depicts levels of 2-HG in HTB-14 cell lines expressing wildtype or IDH-1 R132H mutant protein.

Analyses reveal significantly higher levels of 2-HG in cells that express the IDH-1 R132H mutant protein. As shown in FIG. 26A, levels of 2-HG in CRL-2610 cell lines expressing the IDH-1 R132H mutant protein are approximately 28-fold higher than identical lines expressing the wild-type protein. Similarly, levels of 2-HG in HTB-14 cell lines expressing the IDH-1 R132H mutant protein are approximately 38-fold higher than identical lines expressing the wild-type protein, as shown in FIG. 26B.

Evaluation of 2-Hydroxyglutarate (2-HG) Production in Human Glioblastoma Tumors Containing Mutations in Isocitrate Dehydrogenase 1 (IDH1) at Amino Acid 132.

Heterozygous somatic mutations at nucleotide position 395 (amino acid codon 132) in the transcript encoding isocitrate dehydrogenase 1(IDH1) can occur in brain tumors.

Tissue Source:

Human brain tumors were obtained during surgical resection, flash frozen in liquid nitrogen and stored at −80° C. Clinical classification of the tissue as gliomas was performed using standard clinical pathology categorization and grading.

Genomic Sequence Analysis to Identify Brain Tumor Samples Containing Either Wild Type Isocitrate Dehydrogenase (IDH1) or Mutations Altering Amino Acid 132.

Genomic DNA was isolated from 50-100 mgs of brain tumor tissue using standard methods. A polymerase chain reaction (PCR) procedure was then performed on the isolated genomic DNA to amplify a 295 base pair fragment of the genomic DNA that contains both intron and $2^{nd}$ exon sequences of human IDH1 (FIG. 27). In FIG. 27, intron sequence is shown in lower case font; $2^{nd}$ exon IDH1 DNA sequence is shown in upper case font; forward (5') and reverse (3') primer sequences are shown in underlined font; guanine nucleotide mutated in a subset of human glioma tumors is shown in bold underlined font.

The amplified DNA fragment was then sequenced using standard protocols and sequence alignments were performed to classify the sequences as either wild type or mutant at the guanine nucleotide at base pair 170 of the amplified PCR fragment. Tumors were identified that contained genomic DNA having either two copies of guanine (wild type) or a mixed or monoalellic combination of one IDH1 allele containing guanine and the other an adenine (mutant) sequence at base pair 170 of the amplified product (Table 15). The nucleotide change results in a change at amino acid position 132 of human IDH1 protein from arginine (wild type) to histidine (mutant) as has been previously reported.

TABLE 15

Sequence variance at base pair 170 of the amplified genomic DNA from human glioma samples.

| Sample ID | Base 170 | IDH1 Amino Acid 132 | Genotype |
|---|---|---|---|
| 1102 | G | arginine | wild type |
| 1822 | A | histidine | mutant |
| 496 | G | arginine | wild type |
| 1874 | A | histidine | mutant |
| 816 | A | histidine | mutant |
| 534 | G | arginine | wild type |
| AP-1 | A | histidine | mutant |
| AP-2 | A | histidine | mutant |

Procedure for Metabolite Preparation and Analysis.

Metabolite extraction was accomplished by adding a 10× volume (m/v ratio) of −80 C methanol:water mix (80%:20%) to the brain tissue (approximately 100 mgs) followed by 30 s homogenization at 4 C. These chilled, methanol extracted homogenized tissues were then centrifuged at 14,000 rpm for 30 minutes to sediment the cellular and tissue debris and the cleared tissue supernatants were transferred to a screw-cap freezer vial and stored at −80° C. For analysis, a 2× volume of tributylamine (10 mM) acetic acid (10 mM) pH 5.5 was added to the samples and analyzed by LCMS as follows. Sample extracts were filtered using a Millex-FG 0.20 micron disk and 10 μL were injected onto a reverse-phase HPLC column (Synergi 150 mm×2 mm, Phenomenex Inc.) and eluted using a linear gradient LCMS-grade methanol (50%) with 10 mM tributylamine and 10 mM acetic acid) ramping to 80% methanol:10 mM tributylamine: 10 mM acetic acid over 6 minutes at 200 μL/min. Eluted metabolite ions were detected using a triple-quadrapole mass spectrometer, tuned to detect in negative mode with multiple-reaction-monitoring mode transition set (MRM's) according to the molecular weights and fragmentation patterns for 8 known central metabolites, including 2-hydroxyglutarate (MRM parameters were optimized by prior infusion of known compound standards). Data was processed using Analyst Software (Applied Biosystems, Inc.) and metabolite signal intensities were obtained by standard peak integration methods.

Results.

Figure 28:
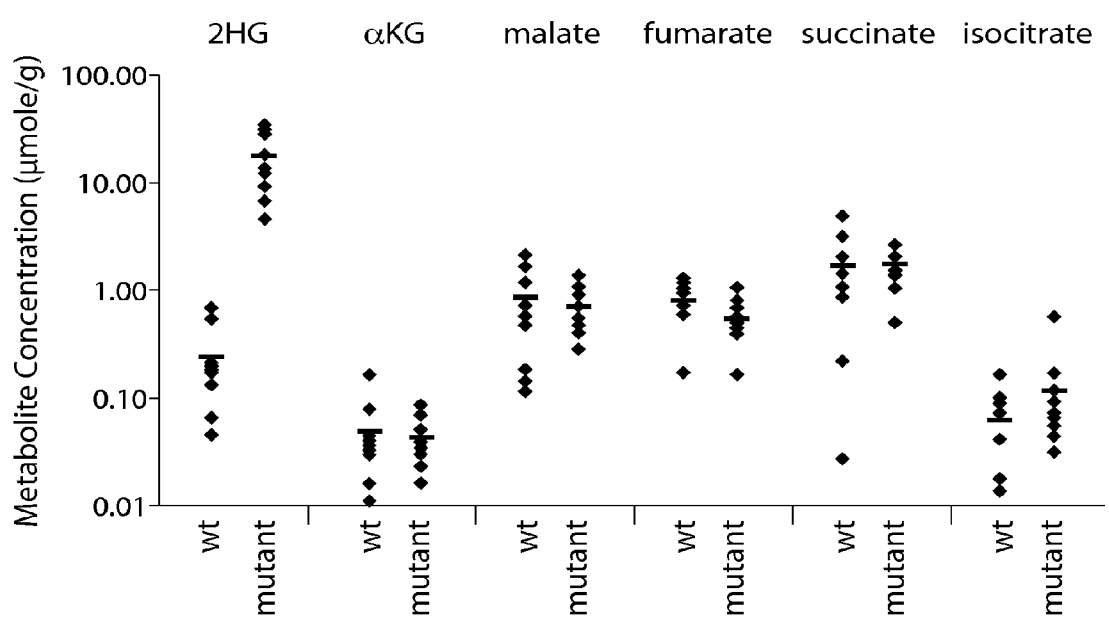
FIG. 28 depicts concentrations of 2HG in human malignant gliomas containing R132 mutations in IDH1. Human glioma samples obtained by surgical resection were snap frozen, genotyped to stratify as wild-type (WT) (N=10) or carrying an R132 mutant allele (Mutant) (n=12) and metabolites extracted for LC-MS analysis. Among the 12 mutant tumors, 10 carried a R132H mutation, one an R132S mutation, and one an R132G mutation. Each symbol represents the amount of the listed metabolite found in each tumor sample. Red lines indicate the group sample means. The difference in 2HG observed between WT and R132 mutant IDH1 mutant tumors was statistically significant by Student's t-test (p<0.0001). There were no statistically significant differences in αKG, malate, fumarate, succinate, or isocitrate levels between the WT and R132 mutant IDH1 tumors.

Analyses revealed dramatically higher levels of 2-HG in cells tumor samples that express the IDH-1 R132H mutant protein. Data is summarized in Table 16 and FIG. 28.

TABLE 16

| Sample ID | Primary Specimen Diagnosis | Grade | Tumor Cells in Tumor Foci (%) | Genotype | Nucleotide change | Codon | 2HG (μmole/g) | αKG (μmole/g) | Malate (μmole/g) | Fumarate (μmole/g) | Succinate (μmole/g) | Isocitrate (μmole/g) |
|---|---|---|---|---|---|---|---|---|---|---|---|---|
| 1 | Glioblastoma, residual/recurrent | WHO grade IV | n/a | wild type | wild type | R132 | 0.18 | 0.161 | 1.182 | 0.923 | 1.075 | 0.041 |
| 2 | Glioblastoma | WHO grade IV | n/a | wild type | wild type | R132 | 0.16 | 0.079 | 1.708 | 1.186 | 3.156 | 0.100 |
| 3 | Glioblastoma | WHO grade IV | n/a | wild type | wild type | R132 | 0.13 | 0.028 | 0.140 | 0.170 | 0.891 | 0.017 |
| 4 | Oligoastrocytoma | WHO grade II | n/a | wild type | wild type | R132 | 0.21 | 0.016 | 0.553 | 1.061 | 1.731 | 0.089 |
| 5 | Glioblastoma | WHO grade IV | n/a | mutant | G364A | R132H | 16.97 | 0.085 | 1.091 | 0.807 | 1.357 | 0.058 |
| 6 | Glioblastoma | WHO grade IV | n/a | mutant | G364A | R132H | 19.42 | 0.023 | 0.462 | 0.590 | 1.966 | 0.073 |
| 7 | Glioblastoma | WHO grade IV | n/a | mutant | G364A | R132H | 31.56 | 0.068 | 0.758 | 0.503 | 2.019 | 0.093 |
| 8 | Oligodendroglioma, anaplastic | WHO grade III | 75 | mutant | G364A | R132H | 12.49 | 0.033 | 0.556 | 0.439 | 0.507 | 0.091 |
| 9 | Oligodendroglioma, anaplastic | WHO grade III | 90 | mutant | G364A | R132H | 4.59 | 0.029 | 1.377 | 1.060 | 1.077 | 0.574 |
| 10 | Oligoastrocytoma | WHO grade II | n/a | mutant | G364A | R132H | 6.80 | 0.038 | 0.403 | 0.503 | 1.561 | 0.065 |
| 11 | Glioblastoma | WHO grade IV | n/a | wild type | wild type | R132 | 0.686 | 0.686 | 0.686 | 0.686 | 0.686 | 0.007 |
| 12 | Glioblastoma | WHO grade IV | n/a | mutant | G364A | R132H | 18.791 | 18.791 | 18.791 | 18.791 | 18.791 | 0.031 |
| 13 | Glioblastoma | WHO grade IV | n/a | mutant | G364A | R132H | 4.59 | 0.029 | 1.377 | 1.060 | 1.077 | 0.043 |
| 14 | Glioblastoma | WHO grade IV | n/a | wild type | wild type | R132 | 0.199 | 0.046 | 0.180 | 0.170 | 0.221 | 0.014 |
| 15 | Glioblastoma | WHO grade IV | n/a | mutant | C363G | R132G | 13.827 | 0.030 | 0.905 | 0.599 | 1.335 | 0.046 |
| 16 | Glioblastoma | WHO grade IV | n/a | mutant | G364A | R132H | 28.364 | 0.068 | 0.535 | 0.488 | 2.105 | 0.054 |
| 17 | Glioblastoma | WHO grade IV | n/a | mutant | C363A | R132S | 9.364 | 0.029 | 1.038 | 0.693 | 2.151 | 0.121 |
| 18 | Glioblastoma | WHO grade IV | n/a | wild type | wild type | R132 | 0.540 | 0.031 | 0.468 | 0.608 | 1.490 | 0.102 |
| 19 | Glioma, malignant, astrocytoma | WHO grade IV | 80 | mutant | G364A | R132H | 19.000 | 0.050 | 0.654 | 0.391 | 2.197 | 0.171 |
| 20 | Oligodendro glioma | WHO grade III | 80 | wild type | wild type | R132 | 0.045 | 0.037 | 1.576 | 0.998 | 1.420 | 0.018 |

TABLE 16-continued

| Sample ID | Primary Specimen Diagnosis | Grade | Tumor Cells in Tumor Foci (%) | Geno-type | Nucleo-tide change | Codon | 2HG (µmole/g) | αKG (µmole/g) | Malate (µmole/g) | Fumarate (µmole/g) | Succinate (µmole/g) | Isocitrate (µmole/g) |
|---|---|---|---|---|---|---|---|---|---|---|---|---|
| 21 | Glioma, malignant, astrocytoma | WHO grade IV | 95 | wild type | wild type | R132 | 0.064 | 0.034 | 0.711 | 0.710 | 2.105 | 0.165 |
| 22 | Glioblastoma | WHO grade IV | 70 | wild type | wild type | R132 | 0.171 | 0.041 | 2.066 | 1.323 | 0.027 | 0.072 |

To determine if 2HG production is characteristic of tumors harboring mutations in IDH1, metabolites were extracted from human malignant gliomas that were either wild-type or mutant for IDH1. It has been suggested that αKG levels are decreased in cells transfected with mutant IDH1 (Zhao, S. et al. Science 324, 261-5 (2009)). The average αKG level from 12 tumor samples harboring various R132 mutations was slightly less than the average αKG level observed in 10 tumors which are wild-type for IDH1. This difference in αKG was not statistically significant, and a range of αKG levels was observed in both wild-type and mutant tumors. In contrast, increased 2HG levels were found in all tumors that contained an R132 IDH1 mutation. All R132 mutant IDH1 tumors examined had between 5 and 35 µmol of 2HG per gram of tumor, while tumors with wild-type IDH1 had over 100 fold less 2HG. This increase in 2HG in R132 mutant tumors was statistically significant ($p<0.0001$). It was confirmed that (R)-2HG was the isomer present in tumor samples (data not shown). Together these data establish that the novel enzymatic activity associated with R132 mutations in IDH1 results in the production of 2HG in human brain tumors that harbor these mutations.

2HG is known to accumulate in the inherited metabolic disorder 2-hydroxyglutaric aciduria. This disease is caused by deficiency in the enzyme 2-hydroxyglutarate dehydrogenase, which converts 2HG to αKG (Struys, E. A. et al. Am J Hum Genet 76, 358-60 (2005)). Patients with 2-hydroxyglutarate dehydrogenase deficiencies accumulate 2HG in the brain as assessed by MRI and CSF analysis, develop leukoencephalopathy, and have an increased risk of developing brain tumors (Aghili, M., Zahedi, F. & Rafiee, J Neurooncol 91, 233-6 (2009); Kolker, S., Mayatepek, E. & Hoffmann, G. F. Neuropediatrics 33, 225-31 (2002); Wajner, M., Latini, A., Wyse, A. T. & Dutra-Filho, C. S. J Inherit Metab Dis 27, 427-48 (2004)). Furthermore, elevated brain levels of 2HG result in increased ROS levels (Kolker, S. et al. Eur J Neurosci 16, 21-8 (2002); Latini, A. et al. Eur J Neurosci 17, 2017-22 (2003)), potentially contributing to an increased risk of cancer. The ability of 2HG to act as an NMDA receptor agonist may contribute to this effect (Kolker, S. et al. Eur J Neurosci 16, 21-8 (2002)). 2HG may also be toxic to cells by competitively inhibiting glutamate and/or αKG utilizing enzymes. These include transaminases which allow utilization of glutamate nitrogen for amino and nucleic acid biosynthesis, and αKG-dependent prolyl hydroxylases such as those which regulate Hif1α levels. Alterations in Hif1α have been reported to result from mutant IDH1 protein expression (Zhao, S. et al. Science 324, 261-5 (2009)). Regardless of mechanism, it appears likely that the gain-of-function ability of cells to produce 2HG as a result of R132 mutations in IDH1 contributes to tumorigenesis. Patients with 2-hydroxyglutarate dehydrogenase deficiency have a high risk of CNS malignancy (Aghili, M., Zahedi, F. & Rafiee, E. J Neurooncol 91, 233-6 (2009)). The ability of mutant IDH1 to directly act on αKG may explain the prevalence of IDH1 mutations in tumors from CNS tissue, which are unique in their high level of glutamate uptake and its ready conversion to αKG in the cytosol (Tsacopoulos, M. J Physiol Paris 96, 283-8 (2002)), thereby providing high levels of substrate for 2HG production. The apparent co-dominance of the activity of mutant IDH1 with that of the wild-type enzyme is consistent with the genetics of the disease, in which only a single copy of the gene is mutated. As discussed above, the wild-type IDH1 could directly provide NADPH and αKG to the mutant enzyme. These data also demonstrate that mutation of R132 to histidine, serine, cysteine, glycine or leucine share a common ability to catalyze the NADPH-dependent conversion of αKG to 2HG. These findings help clarify why mutations at other amino acid residues of IDH1, including other residues essential for catalytic activity, are not found. Finally, these findings have clinical implications in that they suggest that 2HG production will identify patients with IDH1 mutant brain tumors. This will be important for prognosis as patients with IDH1 mutations live longer than patients with gliomas characterized by other mutations (Parsons, D. W. et al. Science 321, 1807-12 (2008)). In addition, patients with lower grade gliomas may benefit by the therapeutic inhibition of 2HG production. Inhibition of 2HG production by mutant IDH1 might slow or halt conversion of lower grade glioma into lethal secondary glioblastoma, changing the course of the disease.

The Reaction Product of ICDH1 R132H Reduction of α-KG Inhibits the Oxidative Decarboxylation of Isocitrate by Wild-Type ICDH1.

Figure 25:
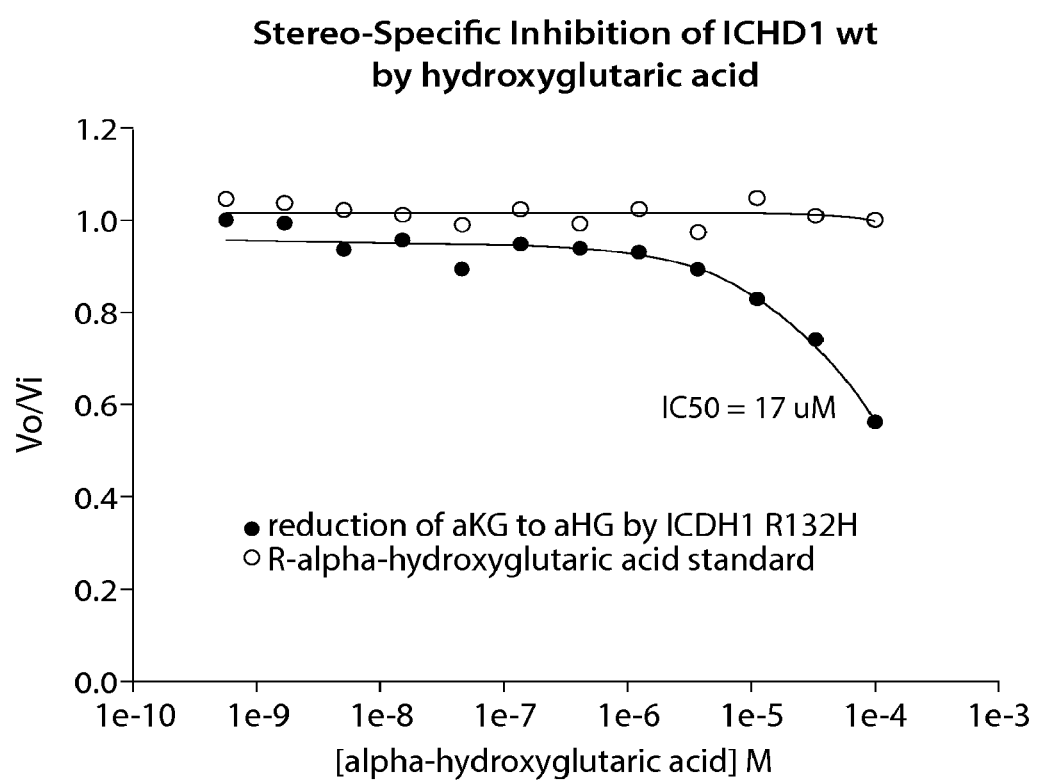
FIG. 25 depicts the inhibitory effect of 2-HG derived from the reduction of α-KG by ICDH1 R132H on the wild-type ICDH1 catalytic oxidative decarboxylation of isocitrate to α-KG.

A reaction containing the wild-type ICDH1, NADP, and α-KG was assembled (under conditions as described above) to which was added in a titration series either (R)-2-hydroxyglutarate or the reaction product of the ICDH1 R1321H mutant reduction of α-KG to 2-hydroxyglutarate. The reaction product 2-HG was shown to inhibit the oxidative decarboxylation of isocitrate by the wild-type ICDH1, while the (R)-2-hydroxyglutarate did not show any effect on the rate of the reaction. Since there are only two possible chiral products of the ICDH1 R132H mutant reduction of α-KG to 2-HG, and the (R)-2-HG did not show inhibition in this assay, it follows that the product of the mutant reaction is the (S)-2-HG form. This experiment is presented in FIG. 25.

Figure 31B:
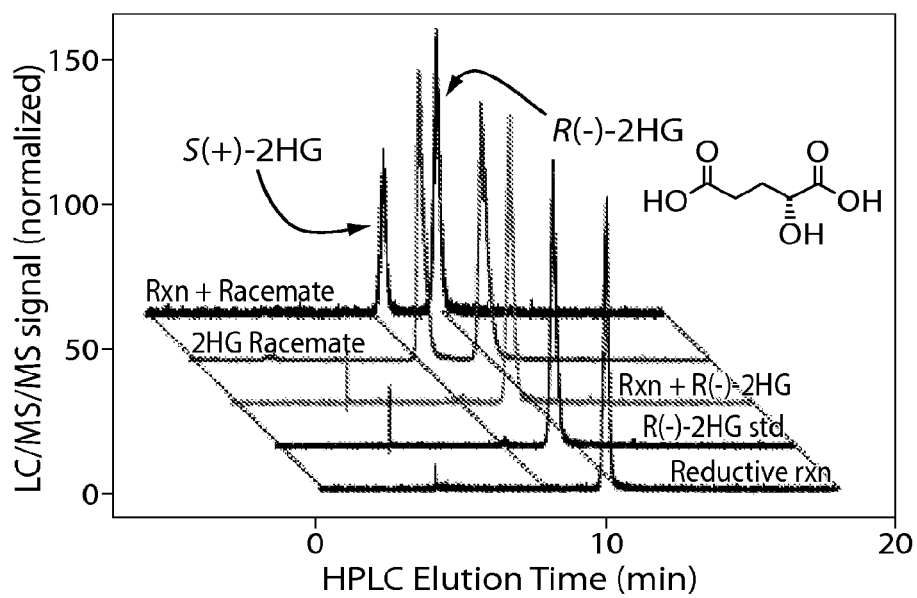
FIG. 31B depicts the diacetyl-L-tartaric anhydride derivatization and LC-MS/MS analysis of the chirality of 2HG produced by R132H mutant IDH1. Normalized LC-MS/MS signal for the reductive reaction (rxn) product alone, an R(−)-2HG standard alone, and the two together (Rxn+R(−)-2HG) are shown as is the signal for a racemic mixture of R(−) and S(+) forms (2HG Racemate) alone or with the reaction products (Rxn+Racemate).

To determine the chirality of the 2HG produced, the products of the R132H reaction was derivatized with diacetyl-L-tartaric anhydride, which allowed separating the (S) and (R) enantiomers of 2HG by simple reverse-phase LC and detecting the products by tandem mass spectrometry (Struys, E. A., Jansen, E. E., Verhoeven, N. M. & Jakobs, C. Clin Chem 50, 1391-5 (2004)) (FIG. 31B). The peaks corresponding to the (S) and (R) isomers of 2HG were confirmed using racemic and R(−)-2HG standards. The reaction product from R132H co-eluted with R(−)-2HG peak, demonstrating that the R(−) stereoisomer is the product produced from αKG by R132H mutant IDH1.

The observation that the reaction product of the mutant enzyme is capable of inhibiting a metabolic reaction known to occur in cells suggests that this reaction product might also inhibit other reactions which utilize α-KG, isocitrate, or citrate as substrates or produce them as products in vivo or in vitro.

Example 3 Metabolomics Analysis of IDH1 Wild Type and Mutants

Metabolomics research can provide mechanistic basis for why R132 mutations confer survival advantage for GBM patients carrying such mutations.
1. Metabolomics of GBM Tumor Cell Lines: Wild Type Vs R132 Mutants
Cell lines with R132 mutations can be identified and profiled. Experiments can be performed in proximal metabolite pool with a broad scope of metabolites.
2. Oxalomalate Treatment of GBM Cell Lines
Oxalomalate is a competitive inhibitor of IDH1. Change of NADPH (metabolomics) when IDH1 is inhibited by a small molecule can be examined.
3. Metabolomics of Primary GBM Tumors: Wild Type Vs R132 Mutations
Primary tumors with R132 mutations can be identified. Experiments can be performed in proximal metabolite pool with a broad scope of metabolites.
4. Detection of 2-Hydroxyglutarate in Cells that Overexpress IDH1 132 Mutants
Overexpression of an IDH1 132 mutant in cells may cause an elevated level of 2-hydroxyglutarate and/or a reduced level of alpha-ketoglutarate. One can perform a metabolomic experiment to demonstrate the consequence of this mutation on the cellular metabolite pool.

Example 4 Evaluation of IDH1 as a Cancer Target shRNAmir inducible knockdown can be performed to examine the cellular phenotype and metabolomics profiles. HTS grade IDH1 enzymes are available. The IDH mutations described herein can be used for patient selection.

Example 5 siRNAs

IDH1

Exemplary siRNAs are presented in the following tables. Art-known methods can be used to select other siRNAs. siRNAs can be evaluated, e.g., by determining the ability of an siRNA to silence an IDH, e.g., IDH1, e.g., in an in vitro system, e.g., in cultured cells, e.g., HeLa cells or cultured glioma cells. siRNAs known in the art for silencing the target can also be used, see, e.g., *Silencing of cytosolic NADP+ dependent isoccitrate dehydrogenase by small interfering RNA enhances the sensitivity of HeLa cells toward stauropine*, Lee et al., 2009, Free Radical Research, 43: 165-173.

The siRNAs in Table 7 (with the exception of entry 1356) were generated using the siRNA selection tool available on the worldwide web at jura.wi.mit.edu/bioc/siRNAext/. (Yuan et al. Nucl. Acids. Res. 2004 32:W130-W134.) Other selection tools can be used as well. Entry 1356 was adapted from *Silencing of cytosolic NADP+ dependent isoccitrate dehydrogenase by small interfering RNA enhances the sensitivity of HeLa cells toward stauropine*, Lee et al., 2009, Free Radical Research, 43: 165-173.

The siRNAs in Tables 7, 8, 9, 10, 11, 12, 13 and 14 represent candidates spanning the IDH1 mRNA at nucleotide positions 628 and 629 according to the sequence at GenBank Accession No. NM_005896.2 (SEQ ID NO:9, FIG. 22).

The RNAs in the tables can be modified, e.g., as described herein. Modifications include chemical modifications to enhance properties, e.g., resistance to degradation, or the use of overhangs. For example, either one or both of the sense and antisense strands in the tables can include an additional dinucleotide at the 3' end, e.g., TT, UU, dTdT.

TABLE 7

| siRNAs targeting wildtype IDH1 | | | | |
|---|---|---|---|---|
| Position on mRNA (FIG. 21B) | sense (5' to 3') | SEQ ID NO: | antisense (5' to 3') | SEQ ID NO: |
| 13 | GGUUUCUGCAGAGUCUACU | 14 | AGUAGACUCUGCAGAAACC | 15 |
| 118 | CUCUUCGCCAGCAUAUCAU | 16 | AUGAUAUGCUGGCGAAGAG | 17 |
| 140 | GGCAGGCGAUAAACUACAU | 18 | AUGUAGUUUAUCGCCUGCC | 19 |
| 145 | GCGAUAAACUACAUUCAGU | 20 | ACUGAAUGUAGUUUAUCGC | 21 |
| 199 | GAAAUCUAUUCACUGUCAA | 22 | UUGACAGUGAAUAGAUUUC | 23 |
| 257 | GUUCUGUGGUAGAGAUGCA | 24 | UGCAUCUCUACCACAGAAC | 25 |
| 272 | GCAAGGAGAUGAAAUGACA | 26 | UGUCAUUUCAUCUCCUUGC | 27 |
| 277 | GGAGAUGAAAUGACACGAA | 28 | UUCGUGUCAUUUCAUCUCC | 29 |
| 278 | GAGAUGAAAUGACACGAAU | 30 | AUUCGUGUCAUUUCAUCUC | 31 |
| 280 | GAUGAAAUGACACGAAUCA | 32 | UGAUUCGUGUCAUUUCAUC | 33 |
| 292 | CGAAUCAUUUGGGAAUUGA | 34 | UCAAUUCCCAAAUGAUUCG | 35 |
| 302 | GGGAAUUGAUUAAAGAGAA | 36 | UUCUCUUUAAUCAAUUCCC | 37 |

TABLE 7-continued siRNAs targeting wildtype IDH1

| Position on mRNA (FIG. 21B) | sense (5' to 3') | SEQ ID NO: | antisense (5' to 3') | SEQ ID NO: |
|---|---|---|---|---|
| 332 | CCUACGUGGAAUUGGAUCU | 38 | AGAUCCAAUUCCACGUAGG | 39 |
| 333 | CUACGUGGAAUUGGAUCUA | 40 | UAGAUCCAAUUCCACGUAG | 41 |
| 345 | GGAUCUACAUAGCUAUGAU | 42 | AUCAUAGCUAUGUAGAUCC | 43 |
| 356 | GCUAUGAUUUAGGCAUAGA | 44 | UCUAUGCCUAAAUCAUAGC | 45 |
| 408 | GGAUGCUGCAGAAGCUAUA | 46 | UAUAGCUUCUGCAGCAUCC | 47 |
| 416 | CAGAAGCUAUAAAGAAGCA | 48 | UGCUUCUUUAUAGCUUCUG | 49 |
| 418 | GAAGCUAUAAAGAAGCAUA | 50 | UAUGCUUCUUUAUAGCUUC | 51 |
| 432 | GCAUAAUGUUGGCGUCAAA | 52 | UUUGACGCCAACAUUAUGC | 53 |
| 467 | CUGAUGAGAAGAGGGUUGA | 54 | UCAACCCUCUUCUCAUCAG | 55 |
| 481 | GUUGAGGAGUUCAAGUUGA | 56 | UCAACUUGAACUCCUCAAC | 57 |
| 487 | GAGUUCAAGUUGAAACAAA | 58 | UUUGUUUCAACUUGAACUC | 59 |
| 495 | GUUGAAACAAAUGUGGAAA | 60 | UUUCCACAUUUGUUUCAAC | 61 |
| 502 | CAAAUGUGGAAAUCACCAA | 62 | UUGGUGAUUUCCACAUUUG | 63 |
| 517 | CCAAAUGGCACCAUACGAA | 64 | UUCGUAUGGUGCCAUUUGG | 65 |
| 528 | CAUACGAAAUAUUCUGGGU | 66 | ACCCAGAAUAUUUCGUAUG | 67 |
| 560 | GAGAAGCCAUUAUCUGCAA | 68 | UUGCAGAUAAUGGCUUCUC | 69 |
| 614 | CUAUCAUCAUAGGUCGUCA | 70 | UGACGACCUAUGAUGAUAG | 71 |
| 618 | CAUCAUAGGUCGUCAUGCU | 72 | AGCAUGACGACCUAUGAUG | 73 |
| 621 | CAUAGGUCGUCAUGCUUAU | 74 | AUAAGCAUGACGACCUAUG | 75 |
| 691 | GAGAUAACCUACACACCAA | 76 | UUGGUGUGUAGGUUAUCUC | 77 |
| 735 | CCUGGUACAUAACUUUGAA | 78 | UUCAAAGUUAUGUACCAGG | 79 |
| 747 | CUUUGAAGAAGGUGGUGGU | 80 | ACCACCACCUUCUUCAAAG | 81 |
| 775 | GGGAUGUAUAAUCAAGAUA | 82 | UAUCUUGAUUAUACAUCCC | 83 |
| 811 | GCACACAGUUCCUUCCAAA | 84 | UUUGGAAGGAACUGUGUGC | 85 |
| 818 | GUUCCUUCCAAAUGGCUCU | 86 | AGAGCCAUUUGGAAGGAAC | 87 |
| 844 | GGUUGGCCUUUGUAUCUGA | 88 | UCAGAUACAAAGGCCAACC | 89 |
| 851 | CUUUGUAUCUGAGCACCAA | 90 | UUGGUGCUCAGAUACAAAG | 91 |
| 882 | GAAGAAAUAUGAUGGGCGU | 92 | ACGCCCAUCAUAUUUCUUC | 93 |
| 942 | GUCCCAGUUUGAAGCUCAA | 94 | UUGAGCUUCAAACUGGGAC | 95 |
| 968 | GGUAUGAGCAUAGGCUCAU | 96 | AUGAGCCUAUGCUCAUACC | 97 |
| 998 | GGCCCAAGCUAUGAAAUCA | 98 | UGAUUUCAUAGCUUGGGCC | 99 |
| 1001 | CCCAAGCUAUGAAAUCAGA | 100 | UCUGAUUUCAUAGCUUGGG | 101 |
| 1127 | CAGAUGGCAAGACAGUAGA | 102 | UCUACUGUCUUGCCAUCUG | 103 |
| 1133 | GCAAGACAGUAGAAGCAGA | 104 | UCUGCUUCUACUGUCUUGC | 105 |
| 1184 | GCAUGUACCAGAAAGGACA | 106 | UGUCCUUUCUGGUACAUGC | 107 |
| 1214 | CCAAUCCCAUUGCUUCCAU | 108 | AUGGAAGCAAUGGGAUUGG | 109 |
| 1257 | CCACAGAGCAAAGCUUGAU | 110 | AUCAAGCUUUGCUCUGUGG | 111 |

TABLE 7-continued siRNAs targeting wildtype IDH1

| Position on mRNA (FIG. 21B) | sense (5' to 3') | SEQ ID NO: | antisense (5' to 3') | SEQ ID NO: |
|---|---|---|---|---|
| 1258 | CACAGAGCAAAGCUUGAUA | 112 | UAUCAAGCUUUGCUCUGUG | 113 |
| 1262 | GAGCAAAGCUUGAUAACAA | 114 | UUGUUAUCAAGCUUUGCUC | 115 |
| 1285 | GAGCUUGCCUUCUUUGCAA | 116 | UUGCAAAGAAGGCAAGCUC | 117 |
| 1296 | CUUUGCAAAUGCUUUGGAA | 118 | UUCCAAAGCAUUUGCAAAG | 119 |
| 1301 | CAAAUGCUUUGGAAGAAGU | 120 | ACUUCUUCCAAAGCAUUUG | 121 |
| 1307 | CUUUGGAAGAAGUCUCUAU | 122 | AUAGAGACUUCUUCCAAAG | 123 |
| 1312 | GAAGAAGUCUCUAUUGAGA | 124 | UCUCAAUAGAGACUUCUUC | 125 |
| 1315 | GAAGUCUCUAUUGAGACAA | 126 | UUGUCUCAAUAGAGACUUC | 127 |
| 1356 | GGACUUGGCUGCUUGCAUU | 128 | AAUGCAAGCAGCCAAGUCC | 129 |
| 1359 | CUUGGCUGCUUGCAUUAAA | 130 | UUUAAUGCAAGCAGCCAAG | 131 |
| 1371 | CAUUAAAGGUUUACCCAAU | 132 | AUUGGGUAAACCUUUAAUG | 133 |
| 1385 | CCAAUGUGCAACGUUCUGA | 134 | UCAGAACGUUGCACAUUGG | 135 |
| 1390 | GUGCAACGUUCUGACUACU | 136 | AGUAGUCAGAACGUUGCAC | 137 |
| 1396 | CGUUCUGACUACUUGAAUA | 138 | UAUUCAAGUAGUCAGAACG | 139 |
| 1415 | CAUUUGAGUUCAUGGAUAA | 140 | UUAUCCAUGAACUCAAAUG | 141 |
| 1422 | GUUCAUGGAUAAACUUGGA | 142 | UCCAAGUUUAUCCAUGAAC | 143 |
| 1425 | CAUGGAUAAACUUGGAGAA | 144 | UUCUCCAAGUUUAUCCAUG | 145 |
| 1455 | CAAACUAGCUCAGGCCAAA | 146 | UUUGGCCUGAGCUAGUUUG | 147 |
| 1487 | CCUGAGCUAAGAAGGAUAA | 148 | UUAUCCUUCUUAGCUCAGG | 149 |
| 1493 | CUAAGAAGGAUAAUUGUCU | 150 | AGACAAUUAUCCUUCUUAG | 151 |
| 1544 | CUGUGUUACACUCAAGGAU | 152 | AUCCUUGAGUGUAACACAG | 153 |
| 1546 | GUGUUACACUCAAGGAUAA | 154 | UUAUCCUUGAGUGUAACAC | 155 |
| 1552 | CACUCAAGGAUAAAGGCAA | 156 | UUGCCUUUAUCCUUGAGUG | 157 |
| 1581 | GUAAUUUGUUUAGAAGCCA | 158 | UGGCUUCUAAACAAAUUAC | 159 |

TABLE 8 siRNAs targeting wildtype IDH1

| Position on mRNA (FIG. 21B) | sense (5' to 3') | SEQ ID NO: | antisense (5' to 3') | SEQ ID NO: |
|---|---|---|---|---|
| 611 | AACCUAUCAUCAUAGGUCG | 240 | CGACCUAUGAUGAUAGGUU | 241 |
| 612 | ACCUAUCAUCAUAGGUCGU | 242 | ACGACCUAUGAUGAUAGGU | 243 |
| 613 | CCUAUCAUCAUAGGUCGUC | 244 | GACGACCUAUGAUGAUAGG | 245 |
| 614 | CUAUCAUCAUAGGUCGUCA | 246 | UGACGACCUAUGAUGAUAG | 247 |
| 615 | UAUCAUCAUAGGUCGUCAU | 248 | AUGACGACCUAUGAUGAUA | 249 |
| 616 | AUCAUCAUAGGUCGUCAUG | 250 | CAUGACGACCUAUGAUGAU | 251 |
| 617 | UCAUCAUAGGUCGUCAUGC | 252 | GCAUGACGACCUAUGAUGA | 253 |

TABLE 8-continued siRNAs targeting wildtype IDH1

| Position on mRNA (FIG. 21B) | sense (5' to 3') | SEQ ID NO: | antisense (5' to 3') | SEQ ID NO: |
|---|---|---|---|---|
| 618 | CAUCAUAGGUCGUCAUGCU | 254 | AGCAUGACGACCUAUGAUG | 255 |
| 619 | AUCAUAGGUCGUCAUGCUU | 256 | AAGCAUGACGACCUAUGAU | 257 |
| 620 | UCAUAGGUCGUCAUGCUUA | 258 | UAAGCAUGACGACCUAUGA | 259 |
| 621 | CAUAGGUCGUCAUGCUUAU | 260 | AUAAGCAUGACGACCUAUG | 261 |
| 622 | AUAGGUCGUCAUGCUUAUG | 262 | CAUAAGCAUGACGACCUAU | 263 |
| 623 | UAGGUCGUCAUGCUUAUGG | 264 | CCAUAAGCAUGACGACCUA | 265 |
| 624 | AGGUCGUCAUGCUUAUGGG | 266 | CCCAUAAGCAUGACGACCU | 267 |
| 625 | GGUCGUCAUGCUUAUGGGG | 268 | CCCCAUAAGCAUGACGACC | 269 |
| 626 | GUCGUCAUGCUUAUGGGGA | 270 | UCCCAUAAGCAUGACGACC | 271 |
| 627 | UCGUCAUGCUUAUGGGGAU | 272 | AUCCCAUAAGCAUGACGAC | 273 |

TABLE 9 siRNAs targeting G395A mutant IDH1 (SEQ ID NO: 5) (equivalent to G629A of SEQ ID NO: 9 (FIG. 21B))

| Position on mRNA (FIG. 21B) | sense (5' to 3') | SEQ ID NO: | antisense (5' to 3') | SEQ ID NO: |
|---|---|---|---|---|
| 611 | AACCUAUCAUCAUAGGUCA | 274 | UGACCUAUGAUGAUAGGUU | 275 |
| 612 | ACCUAUCAUCAUAGGUCAU | 276 | AUGACCUAUGAUGAUAGGU | 277 |
| 613 | CCUAUCAUCAUAGGUCAUC | 278 | GAUGACCUAUGAUGAUAGG | 279 |
| 614 | CUAUCAUCAUAGGUCAUCA | 280 | UGAUGACCUAUGAUGAUAG | 281 |
| 615 | UAUCAUCAUAGGUCAUCAU | 282 | AUGAUGACCUAUGAUGAUA | 283 |
| 616 | AUCAUCAUAGGUCAUCAUG | 284 | CAUGAUGACCUAUGAUGAU | 285 |
| 617 | UCAUCAUAGGUCAUCAUGC | 286 | GCAUGAUGACCUAUGAUGA | 287 |
| 618 | CAUCAUAGGUCAUCAUGCU | 288 | AGCAUGAUGACCUAUGAUG | 289 |
| 619 | AUCAUAGGUCAUCAUGCUU | 290 | AAGCAUGAUGACCUAUGAU | 291 |
| 620 | UCAUAGGUCAUCAUGCUUA | 292 | UAAGCAUGAUGACCUAUGA | 293 |
| 621 | CAUAGGUCAUCAUGCUUAU | 294 | AUAAGCAUGAUGACCUAUG | 295 |
| 622 | AUAGGUCAUCAUGCUUAUG | 296 | CAUAAGCAUGAUGACCUAU | 297 |
| 623 | UAGGUCAUCAUGCUUAUGG | 298 | CCAUAAGCAUGAUGACCUA | 299 |
| 624 | AGGUCAUCAUGCUUAUGGG | 300 | CCCAUAAGCAUGAUGACCU | 301 |
| 625 | GGUCAUCAUGCUUAUGGGG | 302 | CCCCAUAAGCAUGAUGACC | 303 |
| 626 | GUCAUCAUGCUUAUGGGGA | 304 | UCCCCAUAAGCAUGAUGAC | 305 |
| 627 | UCAUCAUGCUUAUGGGGAU | 306 | AUCCCCAUAAGCAUGAUGA | 307 |

TABLE 10 siRNAs targeting C394A mutant IDH1 (SEQ ID NO: 5)
(equivalent to C628A of SEQ ID NO:9 (FIG. 21B))
(Arg132Ser (SEQ ID NO:8))

| Position on mRNA (FIG. 21B) | sense (5' to 3') | SEQ ID NO: | antisense (5' to 3') | SEQ ID NO: |
|---|---|---|---|---|
| 611 | AACCUAUCAUCAUAGGUAG | 308 | CUACCUAUGAUGAUAGGUU | 309 |
| 612 | ACCUAUCAUCAUAGGUAGU | 310 | ACUACCUAUGAUGAUAGGU | 311 |
| 613 | CCUAUCAUCAUAGGUAGUC | 312 | GACUACCUAUGAUGAUAGG | 313 |
| 614 | CUAUCAUCAUAGGUAGUCA | 314 | UGACUACCUAUGAUGAUAG | 315 |
| 615 | UAUCAUCAUAGGUAGUCAU | 316 | AUGACUACCUAUGAUGAUA | 317 |
| 616 | AUCAUCAUAGGUAGUCAUG | 318 | CAUGACUACCUAUGAUGAU | 319 |
| 617 | UCAUCAUAGGUAGUCAUGC | 320 | GCAUGACUACCUAUGAUGA | 321 |
| 618 | CAUCAUAGGUAGUCAUGCU | 322 | AGCAUGACUACCUAUGAUG | 323 |
| 619 | AUCAUAGGUAGUCAUGCUU | 324 | AAGCAUGACUACCUAUGAU | 325 |
| 620 | UCAUAGGUAGUCAUGCUUA | 326 | UAAGCAUGACUACCUAUGA | 327 |
| 621 | CAUAGGUAGUCAUGCUUAU | 328 | AUAAGCAUGACUACCUAUG | 329 |
| 622 | AUAGGUAGUCAUGCUUAUG | 330 | CAUAAGCAUGACUACCUAU | 331 |
| 623 | UAGGUAGUCAUGCUUAUGG | 332 | CCAUAAGCAUGACUACCUA | 333 |
| 624 | AGGUAGUCAUGCUUAUGGG | 334 | CCCAUAAGCAUGACUACCU | 335 |
| 625 | GGUAGUCAUGCUUAUGGGG | 336 | CCCCAUAAGCAUGACUACC | 337 |
| 626 | GUAGUCAUGCUUAUGGGGA | 338 | UCCCCAUAAGCAUGACUAC | 339 |
| 627 | UAGUCAUGCUUAUGGGGAU | 340 | AUCCCCAUAAGCAUGACUA | 341 |

TABLE 11 siRNAs targeting C394U mutant IDH1 (SEQ ID NO: 5)
(equivalent to C628U of SEQ ID NO: 9 (FIG. 21B))
(Arg132Cys (SEQ ID NO: 8))

| Position on mRNA (FIG. 21B) | sense (5' to 3') | SEQ ID NO: | antisense (5' to 3') | SEQ ID NO: |
|---|---|---|---|---|
| 611 | AACCUAUCAUCAUAGGUUG | 342 | CAACCUAUGAUGAUAGGUU | 343 |
| 612 | ACCUAUCAUCAUAGGUUGU | 244 | ACAACCUAUGAUGAUAGGU | 345 |
| 613 | CCUAUCAUCAUAGGUUGUC | 246 | GACAACCUAUGAUGAUAGG | 347 |
| 614 | CUAUCAUCAUAGGUUGUCA | 248 | UGACAACCUAUGAUGAUAG | 349 |
| 615 | UAUCAUCAUAGGUUGUCAU | 350 | AUGACAACCUAUGAUGAUA | 351 |
| 616 | AUCAUCAUAGGUUGUCAUG | 352 | CAUGACAACCUAUGAUGAU | 353 |
| 617 | UCAUCAUAGGUUGUCAUGC | 354 | GCAUGACAACCUAUGAUGA | 355 |
| 618 | CAUCAUAGGUUGUCAUGCU | 256 | AGCAUGACAACCUAUGAUG | 357 |
| 619 | AUCAUAGGUUGUCAUGCUU | 358 | AAGCAUGACAACCUAUGAU | 359 |
| 620 | UCAUAGGUUGUCAUGCUUA | 360 | UAAGCAUGACAACCUAUGA | 361 |
| 621 | CAUAGGUUGUCAUGCUUAU | 362 | AUAAGCAUGACAACCUAUG | 363 |
| 622 | AUAGGUUGUCAUGCUUAUG | 364 | CAUAAGCAUGACAACCUAU | 365 |
| 623 | UAGGUUGUCAUGCUUAUGG | 366 | CCAUAAGCAUGACAACCUA | 367 |

TABLE 11-continued siRNAs targeting C394U mutant IDH1 (SEQ ID NO: 5)
(equivalent to C628U of SEQ ID NO: 9 (FIG. 21B))
(Arg132Cys (SEQ ID NO: 8))

| Position on mRNA (FIG. 21B) | sense (5' to 3') | SEQ ID NO: | antisense (5' to 3') | SEQ ID NO: |
|---|---|---|---|---|
| 624 | AGGUUGUCAUGCUUAUGGG | 368 | CCCAUAAGCAUGACAACCU | 369 |
| 625 | GGUUGUCAUGCUUAUGGGG | 370 | CCCCAUAAGCAUGACAACC | 371 |
| 626 | GUUGUCAUGCUUAUGGGGA | 372 | UCCCCAUAAGCAUGACAAC | 373 |
| 627 | UUGUCAUGCUUAUGGGGAU | 374 | AUCCCCAUAAGCAUGACAA | 375 |

TABLE 12 siRNAs targeting C394G mutant IDH1 (SEQ ID NO: 5)
(equivalent to C628G of SEQ ID NO: 9 (FIG. 21B))
(Arg132Gly (SEQ ID NO: 8))

| Position on mRNA (FIG. 21B) | sense (5' to 3') | SEQ ID NO: | antisense (5' to 3') | SEQ ID NO: |
|---|---|---|---|---|
| 611 | AACCUAUCAUCAUAGGUGG | 376 | CCACCUAUGAUGAUAGGUU | 377 |
| 612 | ACCUAUCAUCAUAGGUGGU | 378 | ACCACCUAUGAUGAUAGGU | 379 |
| 613 | CCUAUCAUCAUAGGUGGUC | 380 | GACCACCUAUGAUGAUAGG | 381 |
| 614 | CUAUCAUCAUAGGUGGUCA | 382 | UGACCACCUAUGAUGAUAG | 383 |
| 615 | UAUCAUCAUAGGUGGUCAU | 384 | AUGACCACCUAUGAUGAUA | 385 |
| 616 | AUCAUCAUAGGUGGUCAUG | 386 | CAUGACCACCUAUGAUGAU | 387 |
| 617 | UCAUCAUAGGUGGUCAUGC | 388 | GCAUGACCACCUAUGAUGA | 389 |
| 618 | CAUCAUAGGUGGUCAUGCU | 390 | AGCAUGACCACCUAUGAUG | 391 |
| 619 | AUCAUAGGUGGUCAUGCUU | 392 | AAGCAUGACCACCUAUGAU | 393 |
| 620 | UCAUAGGUGGUCAUGCUUA | 394 | UAAGCAUGACCACCUAUGA | 395 |
| 621 | CAUAGGUGGUCAUGCUUAU | 396 | AUAAGCAUGACCACCUAUG | 397 |
| 622 | AUAGGUGGUCAUGCUUAUG | 398 | CAUAAGCAUGACCACCUAU | 399 |
| 623 | UAGGUGGUCAUGCUUAUGG | 400 | CCAUAAGCAUGACCACCUA | 401 |
| 624 | AGGUUGUCAUGCUUAUGGG | 402 | CCCAUAAGCAUGACCACCU | 403 |
| 625 | GGUUGUCAUGCUUAUGGGG | 404 | CCCCAUAAGCAUGACCACC | 405 |
| 626 | GUUGUCAUGCUUAUGGGGA | 406 | UCCCCAUAAGCAUGACCAC | 407 |
| 627 | UUGUCAUGCUUAUGGGGAU | 408 | AUCCCCAUAAGCAUGACCA | 409 |

TABLE 13 siRNAs targeting G395C mutant IDH1 (SEQ ID NO: 5)
(equivalent to G629C of SEQ ID NO: 9 (FIG. 21B))
(Arg132Pro (SEQ ID NO: 8))

| Position on mRNA (FIG. 21B) | sense (5' to 3') | SEQ ID NO: | antisense (5' to 3') | SEQ ID NO: |
|---|---|---|---|---|
| 611 | AACCUAUCAUCAUAGGUCG | 410 | CGACCUAUGAUGAUAGGUU | 411 |
| 612 | ACCUAUCAUCAUAGGUCGU | 412 | ACGACCUAUGAUGAUAGGU | 413 |

TABLE 13-continued siRNAs targeting G395C mutant IDH1 (SEQ ID NO: 5)
(equivalent to G629C of SEQ ID NO: 9 (FIG. 21B))
(Arg132Pro (SEQ ID NO: 8))

| Position on mRNA (FIG. 21B) | sense (5' to 3') | SEQ ID NO: | antisense (5' to 3') | SEQ ID NO: |
|---|---|---|---|---|
| 613 | CCUAUCAUCAUAGGUCGUC | 414 | GACGACCUAUGAUGAUAGG | 415 |
| 614 | CUAUCAUCAUAGGUCGUCA | 416 | UGACGACCUAUGAUGAUAG | 417 |
| 615 | UAUCAUCAUAGGUCGUCAU | 418 | AUGACGACCUAUGAUGAUA | 419 |
| 616 | AUCAUCAUAGGUCGUCAUG | 420 | CAUGACGACCUAUGAUGAU | 421 |
| 617 | UCAUCAUAGGUCGUCAUGC | 422 | GCAUGACGACCUAUGAUGA | 423 |
| 618 | CAUCAUAGGUCGUCAUGCU | 424 | AGCAUGACGACCUAUGAUG | 425 |
| 619 | AUCAUAGGUCGUCAUGCUU | 426 | AAGCAUGACGACCUAUGAU | 427 |
| 620 | UCAUAGGUCGUCAUGCUUA | 428 | UAAGCAUGACGACCUAUGA | 429 |
| 621 | CAUAGGUCGUCAUGCUUAU | 430 | AUAAGCAUGACGACCUAUG | 431 |
| 622 | AUAGGUCGUCAUGCUUAUG | 432 | CAUAAGCAUGACGACCUAU | 433 |
| 623 | UAGGUCGUCAUGCUUAUGG | 434 | CCAUAAGCAUGACGACCUA | 435 |
| 624 | AGGUCGUCAUGCUUAUGGG | 436 | CCCAUAAGCAUGACGACCU | 437 |
| 625 | GGUCGUCAUGCUUAUGGGG | 438 | CCCCAUAAGCAUGACGACC | 439 |
| 626 | GUCGUCAUGCUUAUGGGGA | 440 | UCCCCAUAAGCAUGACGAC | 441 |
| 627 | UCGUCAUGCUUAUGGGGAU | 442 | AUCCCCAUAAGCAUGACGA | 443 |

TABLE 14 siRNAs targeting G395U mutant IDH1 (SEQ ID NO: 5)
(equivalent to G629U of SEQ ID NO: 9 (FIG. 21B))
(Arg132Leu (SEQ ID NO: 8))

| Position on mRNA (FIG. 21B) | sense (5' to 3') | SEQ ID NO: | antisense (5' to 3') | SEQ ID NO: |
|---|---|---|---|---|
| 611 | AACCUAUCAUCAUAGGUCU | 444 | AGACCUAUGAUGAUAGGUU | 445 |
| 612 | ACCUAUCAUCAUAGGUCUU | 446 | AAGACCUAUGAUGAUAGGU | 447 |
| 613 | CCUAUCAUCAUAGGUCUUC | 448 | GAAGACCUAUGAUGAUAGG | 449 |
| 614 | CUAUCAUCAUAGGUCUUCA | 450 | UGAAGACCUAUGAUGAUAG | 451 |
| 615 | UAUCAUCAUAGGUCUUCAU | 452 | AUGAAGACCUAUGAUGAUA | 453 |
| 616 | AUCAUCAUAGGUCUUCAUG | 454 | CAUGAAGACCUAUGAUGAU | 455 |
| 617 | UCAUCAUAGGUCUUCAUGC | 456 | GCAUGAAGACCUAUGAUGA | 457 |
| 618 | CAUCAUAGGUCUUCAUGCU | 458 | AGCAUGAAGACCUAUGAUG | 459 |
| 619 | AUCAUAGGUCUUCAUGCUU | 460 | AAGCAUGAAGACCUAUGAU | 461 |
| 620 | UCAUAGGUCUUCAUGCUUA | 462 | UAAGCAUGAAGACCUAUGA | 463 |
| 621 | CAUAGGUCUUCAUGCUUAU | 464 | AUAAGCAUGAAGACCUAUG | 465 |
| 622 | AUAGGUCUUCAUGCUUAUG | 466 | CAUAAGCAUGAAGACCUAU | 467 |
| 623 | UAGGUCUUCAUGCUUAUGG | 468 | CCAUAAGCAUGAAGACCUA | 469 |
| 624 | AGGUCUUCAUGCUUAUGGG | 470 | CCCAUAAGCAUGAAGACCU | 471 |

TABLE 14-continued siRNAs targeting G395U mutant IDH1 (SEQ ID NO: 5)
(equivalent to G629U of SEQ ID NO: 9 (FIG. 21B))
(Arg132Leu (SEQ ID NO: 8))

| Position on mRNA (FIG. 21B) | sense (5' to 3') | SEQ ID NO: | antisense (5' to 3') | SEQ ID NO: |
|---|---|---|---|---|
| 625 | GGUCUUCAUGCUUAUGGGG | 472 | CCCCAUAAGCAUGAAGACC | 473 |
| 626 | GUCUUCAUGCUUAUGGGGA | 474 | UCCCCAUAAGCAUGAAGAC | 475 |
| 627 | UCUUCAUGCUUAUGGGGAU | 476 | AUCCCCAUAAGCAUGAAGA | 477 |

IDH2

Exemplary siRNAs are presented in the following tables. Art-known methods can be used to select other siRNAs. siRNAs can be evaluated, e.g., by determining the ability of an siRNA to silence an e.g., IDH2, e.g., in an in vitro system, e.g., in cultured cells, e.g., HeLa cells or cultured glioma cells. e.g., The siRNAs in Table 15 were generated using the siRNA selection tool available on the worldwide web at jura.wi.mit.edu/bioc/siRNAext/. (Yuan et al. Nucl. Acids. Res. 2004 32:W130-W134.) Other selection tools can be used as well. Entry 1356 was adapted from *Silencing of cytosolic NADP+ dependent isoccitrate dehydrogenase by small interfering RNA enhances the sensitivity of HeLa cells toward stauropine*, Lee et al., 2009, Free Radical Research, 43: 165-173.

The siRNAs in Tables 16-23 represent candidates spanning the IDH2 mRNA at nucleotide positions 600, 601, and 602 according to the mRNA sequence presented at GenBank Accession No. NM_002168.2 (Record dated Aug. 16, 2009; GI28178831) (SEQ ID NO:12, FIG. 22B; equivalent to nucleotide positions 514, 515, and 516 of the cDNA sequence represented by SEQ ID NO:11, FIG. FIG. 22A).

The RNAs in the tables can be modified, e.g., as described herein. Modifications include chemical modifications to enhance properties, e.g., resistance to degradation, or the use of overhangs. For example, either one or both of the sense and antisense strands in the tables can include an additional dinucleotide at the 3' end, e.g., TT, UU, dTdT.

TABLE 15 siRNAs targeting wildtype IDH2

| Position on mRNA (FIG. 22B) | sense (5' to 3') | SEQ ID NO: | antisense (5' to 3') | SEQ ID NO: |
|---|---|---|---|---|
| 250 | GUGAUGAGAUGACCCGUAU | 478 | AUACGGGUCAUCUCAUCAC | 479 |
| 252 | GAUGAGAUGACCCGUAUUA | 480 | UAAUACGGGUCAUCUCAUC | 481 |
| 264 | CGUAUUAUCUGGCAGUUCA | 482 | UGAACUGCCAGAUAAUACG | 483 |
| 274 | GGCAGUUCAUCAAGGAGAA | 484 | UUCUCCUUGAUGAACUGCC | 485 |
| 451 | GUGUGGAAGAGUUCAAGCU | 486 | AGCUUGAACUCUUCCACAC | 487 |
| 453 | GUGGAAGAGUUCAAGCUGA | 488 | UCAGCUUGAACUCUUCCAC | 489 |
| 456 | GAAGAGUUCAAGCUGAAGA | 490 | UCUUCAGCUUGAACUCUUC | 491 |
| 795 | CAGUAUGCCAUCCAGAAGA | 492 | UCUUCUGGAUGGCAUACUG | 493 |
| 822 | CUGUACAUGAGCACCAAGA | 494 | UCUUGGUGCUCAUGUACAG | 495 |
| 832 | GCACCAAGAACACCAUACU | 496 | AGUAUGGUGUUCUUGGUGC | 497 |
| 844 | CCAUACUGAAAGCCUACGA | 498 | UCGUAGGCUUUCAGUAUGG | 499 |
| 845 | CAUACUGAAAGCCUACGAU | 500 | AUCGUAGGCUUUCAGUAUG | 501 |
| 868 | GUUUCAAGGACAUCUUCCA | 502 | UGGAAGAUGUCCUUGAAAC | 503 |
| 913 | CCGACUUCGACAAGAAUAA | 504 | UUAUUCUUGUCGAAGUCGG | 505 |
| 915 | GACUUCGACAAGAAUAAGA | 506 | UCUUAUUCUUGUCGAAGUC | 507 |
| 921 | GACAAGAAUAAGAUCUGGU | 508 | ACCAGAUCUUAUUCUUGUC | 509 |
| 949 | GGCUCAUUGAUGACAUGGU | 510 | ACCAUGUCAUCAAUGAGCC | 511 |
| 1009 | GCAAGAACUAUGACGGAGA | 512 | UCUCCGUCAUAGUUCUUGC | 513 |

TABLE 15-continued siRNAs targeting wildtype IDH2

| Position on mRNA (FIG. 22B) | sense (5' to 3') | SEQ ID NO: | antisense (5' to 3') | SEQ ID NO: |
|---|---|---|---|---|
| 1010 | CAAGAACUAUGACGGAGAU | 514 | AUCUCCGUCAUAGUUCUUG | 515 |
| 1024 | GAGAUGUGCAGUCAGACAU | 516 | AUGUCUGACUGCACAUCUC | 517 |
| 1096 | CUGAUGGGAAGACGAUUGA | 518 | UCAAUCGUCUUCCCAUCAG | 519 |
| 1354 | GCAAUGUGAAGCUGAACGA | 520 | UCGUUCAGCUUCACAUUGC | 521 |
| 1668 | CUGUAAUUUAUAUUGCCCU | 522 | AGGGCAAUAUAAAUUACAG | 523 |
| 1694 | CAUGGUGCCAUAUUUAGCU | 524 | AGCUAAAUAUGGCACCAUG | 525 |
| 1697 | GGUGCCAUAUUUAGCUACU | 526 | AGUAGCUAAAUAUGGCACC | 527 |
| 1698 | GUGCCAUAUUUAGCUACUA | 528 | UAGUAGCUAAAUAUGGCAC | 529 |
| 1700 | GCCAUAUUUAGCUACUAAA | 530 | UUUAGUAGCUAAAUAUGGC | 531 |

TABLE 16 siRNAs targeting wildtype IDH2

| Position on mRNA (FIG. 22B) | sense (5' to 3') | SEQ ID NO: | antisense (5' to 3') | SEQ ID NO: |
|---|---|---|---|---|
| 584 | GCCCAUCACCAUUGGCAGG | 532 | CCUGCCAAUGGUGAUGGGC | 533 |
| 585 | CCCAUCACCAUUGGCAGGC | 534 | GCCUGCCAAUGGUGAUGGG | 535 |
| 586 | CCAUCACCAUUGGCAGGCA | 536 | UGCCUGCCAAUGGUGAUGG | 537 |
| 587 | CAUCACCAUUGGCAGGCAC | 538 | GUGCCUGCCAAUGGUGAUG | 539 |
| 588 | AUCACCAUUGGCAGGCACG | 540 | CGUGCCUGCCAAUGGUGAU | 541 |
| 589 | UCACCAUUGGCAGGCACGC | 542 | GCGUGCCUGCCAAUGGUGA | 543 |
| 590 | CACCAUUGGCAGGCACGCC | 544 | GGCGUGCCUGCCAAUGGUG | 545 |
| 591 | ACCAUUGGCAGGCACGCCC | 546 | GGGCGUGCCUGCCAAUGGU | 547 |
| 592 | CCAUUGGCAGGCACGCCCA | 548 | UGGGCGUGCCUGCCAAUGG | 549 |
| 593 | CAUUGGCAGGCACGCCCAU | 550 | AUGGGCGUGCCUGCCAAUG | 551 |
| 594 | AUUGGCAGGCACGCCCAUG | 552 | CAUGGGCGUGCCUGCCAAU | 553 |
| 595 | UUGGCAGGCACGCCCAUGG | 554 | CCAUGGGCGUGCCUGCCAA | 555 |
| 596 | UGGCAGGCACGCCCAUGGC | 556 | GCCAUGGGCGUGCCUGCCA | 557 |
| 597 | GGCAGGCACGCCCAUGGCG | 558 | CGCCAUGGGCGUGCCUGCC | 559 |
| 598 | GCAGGCACGCCCAUGGCGA | 560 | UCGCCAUGGGCGUGCCUGC | 561 |
| 599 | CAGGCACGCCCAUGGCGAC | 562 | GUCGCCAUGGGCGUGCCUG | 563 |
| 600 | AGGCACGCCCAUGGCGACC | 564 | GGUCGCCAUGGGCGUGCCU | 565 |

TABLE 17 siRNAs targeting A514G mutant IDH2 (equivalent to A600G of SEQ ID NO: 12 (FIG. 22B)

| Position on mRNA (FIG. 22B) | sense (5' to 3') | SEQ ID NO: | antisense (5' to 3') | SEQ ID NO: |
|---|---|---|---|---|
| 584 | GCCCAUCACCAUUGGCGGG | 566 | CCCGCCAAUGGUGAUGGGC | 567 |
| 585 | CCCAUCACCAUUGGCGGGC | 568 | GCCCGCCAAUGGUGAUGGG | 569 |
| 586 | CCAUCACCAUUGGCGGGCA | 570 | UGCCCGCCAAUGGUGAUGG | 571 |
| 587 | CAUCACCAUUGGCGGGCAC | 572 | GUGCCCGCCAAUGGUGAUG | 573 |
| 588 | AUCACCAUUGGCGGGCACG | 574 | CGUGCCCGCCAAUGGUGAU | 575 |
| 589 | UCACCAUUGGCGGGCACGC | 576 | GCGUGCCCGCCAAUGGUGA | 577 |
| 590 | CACCAUUGGCGGGCACGCC | 578 | GGCGUGCCCGCCAAUGGUG | 579 |
| 591 | ACCAUUGGCGGGCACGCCC | 580 | GGGCGUGCCCGCCAAUGGU | 581 |
| 592 | CCAUUGGCGGGCACGCCCA | 582 | UGGGCGUGCCCGCCAAUGG | 583 |
| 593 | CAUUGGCGGGCACGCCCAU | 584 | AUGGGCGUGCCCGCCAAUG | 585 |
| 594 | AUUGGCGGGCACGCCCAUG | 586 | CAUGGGCGUGCCCGCCAAU | 587 |
| 595 | UUGGCGGGCACGCCCAUGG | 588 | CCAUGGGCGUGCCCGCCAA | 589 |
| 596 | UGGCGGGCACGCCCAUGGC | 590 | GCCAUGGGCGUGCCCGCCA | 591 |
| 597 | GGCGGGCACGCCCAUGGCG | 592 | CGCCAUGGGCGUGCCCGCC | 593 |
| 598 | GCGGGCACGCCCAUGGCGA | 594 | UCGCCAUGGGCGUGCCCGC | 595 |
| 599 | CGGGCACGCCCAUGGCGAC | 596 | GUCGCCAUGGGCGUGCCCG | 597 |
| 600 | GGGCACGCCCAUGGCGACC | 598 | GGUCGCCAUGGGCGUGCCC | 599 |

TABLE 18 siRNAs targeting A514U mutant IDH2 (equivalent to A600U of SEQ ID NO: 12 (FIG. 22B)

| Position on mRNA (FIG. 22B) | sense (5' to 3') | SEQ ID NO: | antisense (5' to 3') | SEQ ID NO: |
|---|---|---|---|---|
| 584 | GCCCAUCACCAUUGGCUGG | 600 | CCAGCCAAUGGUGAUGGGC | 601 |
| 585 | CCCAUCACCAUUGGCUGGC | 602 | GCCAGCCAAUGGUGAUGGG | 603 |
| 586 | CCAUCACCAUUGGCUGGCA | 604 | UGCCAGCCAAUGGUGAUGG | 605 |
| 587 | CAUCACCAUUGGCUGGCAC | 606 | GUGCCAGCCAAUGGUGAUG | 607 |
| 588 | AUCACCAUUGGCUGGCACG | 608 | CGUGCCAGCCAAUGGUGAU | 609 |
| 589 | UCACCAUUGGCUGGCACGC | 610 | GCGUGCCAGCCAAUGGUGA | 611 |
| 590 | CACCAUUGGCUGGCACGCC | 612 | GGCGUGCCAGCCAAUGGUG | 613 |
| 591 | ACCAUUGGCUGGCACGCCC | 614 | GGGCGUGCCAGCCAAUGGU | 6125 |
| 592 | CCAUUGGCUGGCACGCCCA | 616 | UGGGCGUGCCAGCCAAUGG | 617 |
| 593 | CAUUGGCUGGCACGCCCAU | 618 | AUGGGCGUGCCAGCCAAUG | 619 |
| 594 | AUUGGCUGGCACGCCCAUG | 620 | CAUGGGCGUGCCAGCCAAU | 621 |
| 595 | UUGGCUGGCACGCCCAUGG | 622 | CCAUGGGCGUGCCAGCCAA | 623 |
| 596 | UGGCUGGCACGCCCAUGGC | 624 | GCCAUGGGCGUGCCAGCCA | 625 |

TABLE 18-continued siRNAs targeting A514U mutant IDH2 (equivalent to A600U of SEQ ID NO: 12 (FIG. 22B)

| Position on mRNA (FIG. 22B) | sense (5' to 3') | SEQ ID NO: | antisense (5' to 3') | SEQ ID NO: |
|---|---|---|---|---|
| 597 | GGCUGGCACGCCCAUGGCG | 626 | CGCCAUGGGCGUGCCAGCC | 627 |
| 598 | GCUGGCACGCCCAUGGCGA | 628 | UCGCCAUGGGCGUGCCAGC | 629 |
| 599 | CUGGCACGCCCAUGGCGAC | 630 | GUCGCCAUGGGCGUGCCAG | 631 |
| 600 | UGGCACGCCCAUGGCGACC | 632 | GGUCGCCAUGGGCGUGCCA | 633 |

TABLE 19 siRNAs targeting G515A mutant IDH2 (equivalent to G601A of SEQ ID NO: 12 (FIG. 22B)

| Position on mRNA (FIG. 22B) | sense (5' to 3') | SEQ ID NO: | antisense (5' to 3') | SEQ ID NO: |
|---|---|---|---|---|
| 584 | GCCCAUCACCAUUGGCAAG | 634 | CUUGCCAAUGGUGAUGGGC | 635 |
| 585 | CCCAUCACCAUUGGCAAGC | 636 | GCUUGCCAAUGGUGAUGGG | 637 |
| 586 | CCAUCACCAUUGGCAAGCA | 638 | UGCUUGCCAAUGGUGAUGG | 639 |
| 587 | CAUCACCAUUGGCAAGCAC | 640 | GUGCUUGCCAAUGGUGAUG | 641 |
| 588 | AUCACCAUUGGCAAGCACG | 642 | CGUGCUUGCCAAUGGUGAU | 643 |
| 589 | UCACCAUUGGCAAGCACGC | 644 | GCGUGCUUGCCAAUGGUGA | 645 |
| 590 | CACCAUUGGCAAGCACGCC | 646 | GGCGUGCUUGCCAAUGGUG | 647 |
| 591 | ACCAUUGGCAAGCACGCCC | 648 | GGGCGUGCUUGCCAAUGGU | 649 |
| 592 | CCAUUGGCAAGCACGCCCA | 650 | UGGGCGUGCUUGCCAAUGG | 651 |
| 593 | CAUUGGCAAGCACGCCCAU | 652 | AUGGGCGUGCUUGCCAAUG | 653 |
| 594 | AUUGGCAAGCACGCCCAUG | 654 | CAUGGGCGUGCUUGCCAAU | 655 |
| 595 | UUGGCAAGCACGCCCAUGG | 656 | CCAUGGGCGUGCUUGCCAA | 657 |
| 596 | UGGCAAGCACGCCCAUGGC | 658 | GCCAUGGGCGUGCUUGCCA | 659 |
| 597 | GGCAAGCACGCCCAUGGCG | 660 | CGCCAUGGGCGUGCUUGCC | 661 |
| 598 | GCAAGCACGCCCAUGGCGA | 662 | UCGCCAUGGGCGUGCUUGC | 663 |
| 599 | CAAGCACGCCCAUGGCGAC | 664 | GUCGCCAUGGGCGUGCUUG | 665 |
| 600 | AAGCACGCCCAUGGCGACC | 666 | GGUCGCCAUGGGCGUGCUU | 667 |

TABLE 20 siRNAs targeting G515C mutant IDH2 (equivalent to G601C of SEQ ID NO: 12 (FIG. 22B)

| Position on mRNA (FIG. 22B) | sense (5' to 3') | SEQ ID NO: | antisense (5' to 3') | SEQ ID NO: |
|---|---|---|---|---|
| 584 | GCCCAUCACCAUUGGCACG | 668 | CGUGCCAAUGGUGAUGGGC | 669 |
| 585 | CCCAUCACCAUUGGCACGC | 670 | GCGUGCCAAUGGUGAUGGG | 671 |
| 586 | CCAUCACCAUUGGCACGCA | 672 | UGCGUGCCAAUGGUGAUGG | 673 |
| 587 | CAUCACCAUUGGCACGCAC | 674 | GUGCGUGCCAAUGGUGAUG | 675 |

TABLE 20-continued siRNAs targeting G515C mutant IDH2 (equivalent to G601C of SEQ ID NO: 12 (FIG. 22B)

| Position on mRNA (FIG. 22B) | sense (5' to 3') | SEQ ID NO: | antisense (5' to 3') | SEQ ID NO: |
| --- | --- | --- | --- | --- |
| 588 | AUCACCAUUGGCACGCACG | 676 | CGUGCGUGCCAAUGGUGAU | 677 |
| 589 | UCACCAUUGGCACGCACGC | 678 | GCGUGCGUGCCAAUGGUGA | 679 |
| 590 | CACCAUUGGCACGCACGCC | 680 | GGCGUGCGUGCCAAUGGUG | 681 |
| 591 | ACCAUUGGCACGCACGCCC | 682 | GGGCGUGCGUGCCAAUGGU | 683 |
| 592 | CCAUUGGCACGCACGCCCA | 684 | UGGGCGUGCGUGCCAAUGG | 685 |
| 593 | CAUUGGCACGCACGCCCAU | 686 | AUGGGCGUGCGUGCCAAUG | 687 |
| 594 | AUUGGCACGCACGCCCAUG | 688 | CAUGGGCGUGCGUGCCAAU | 689 |
| 595 | UUGGCACGCACGCCCAUGG | 690 | CCAUGGGCGUGCGUGCCAA | 691 |
| 596 | UGGCACGCACGCCCAUGGC | 692 | GCCAUGGGCGUGCGUGCCA | 693 |
| 597 | GGCACGCACGCCCAUGGCG | 694 | CGCCAUGGGCGUGCGUGCC | 695 |
| 598 | GCACGCACGCCCAUGGCGA | 696 | UCGCCAUGGGCGUGCGUGC | 697 |
| 599 | CACGCACGCCCAUGGCGAC | 698 | GUCGCCAUGGGCGUGCGUG | 699 |
| 600 | ACGCACGCCCAUGGCGACC | 700 | GGUCGCCAUGGGCGUGCGU | 701 |

TABLE 21 siRNAs targeting G515U mutant IDH2 (equivalent to G601U of SEQ ID NO: 12 (FIG. 22B)

| Position on mRNA (FIG. 22B) | sense (5' to 3') | SEQ ID NO: | antisense (5' to 3') | SEQ ID NO: |
| --- | --- | --- | --- | --- |
| 584 | GCCCAUCACCAUUGGCAUG | 702 | CAUGCCAAUGGUGAUGGGC | 703 |
| 585 | CCCAUCACCAUUGGCAUGC | 704 | GCAUGCCAAUGGUGAUGGG | 705 |
| 586 | CCAUCACCAUUGGCAUGCA | 706 | UGCAUGCCAAUGGUGAUGG | 707 |
| 587 | CAUCACCAUUGGCAUGCAC | 708 | GUGCAUGCCAAUGGUGAUG | 709 |
| 588 | AUCACCAUUGGCAUGCACG | 710 | CGUGCAUGCCAAUGGUGAU | 711 |
| 589 | UCACCAUUGGCAUGCACGC | 712 | GCGUGCAUGCCAAUGGUGA | 713 |
| 590 | CACCAUUGGCAUGCACGCC | 714 | GGCGUGCAUGCCAAUGGUG | 715 |
| 591 | ACCAUUGGCAUGCACGCCC | 716 | GGGCGUGCAUGCCAAUGGU | 717 |
| 592 | CCAUUGGCAUGCACGCCCA | 718 | UGGGCGUGCAUGCCAAUGG | 719 |
| 593 | CAUUGGCAUGCACGCCCAU | 720 | AUGGGCGUGCAUGCCAAUG | 721 |
| 594 | AUUGGCAUGCACGCCCAUG | 722 | CAUGGGCGUGCAUGCCAAU | 723 |
| 595 | UUGGCAUGCACGCCCAUGG | 724 | CCAUGGGCGUGCAUGCCAA | 725 |
| 596 | UGGCAUGCACGCCCAUGGC | 726 | GCCAUGGGCGUGCAUGCCA | 727 |
| 597 | GGCAUGCACGCCCAUGGCG | 728 | CGCCAUGGGCGUGCAUGCC | 729 |
| 598 | GCAUGCACGCCCAUGGCGA | 730 | UCGCCAUGGGCGUGCAUGC | 731 |
| 599 | CAUGCACGCCCAUGGCGAC | 732 | GUCGCCAUGGGCGUGCAUG | 733 |
| 600 | AUGCACGCCCAUGGCGACC | 734 | GGUCGCCAUGGGCGUGCAU | 735 |

TABLE 22 siRNAs targeting G516C mutant IDH2 (equivalent to G602C of SEQ ID NO: 12 (FIG. 22B)

| Position on mRNA (FIG. 22B) | sense (5' to 3') | SEQ ID NO: | antisense (5' to 3') | SEQ ID NO: |
|---|---|---|---|---|
| 584 | GCCCAUCACCAUUGGCAGC | 736 | GCUGCCAAUGGUGAUGGGC | 737 |
| 585 | CCCAUCACCAUUGGCAGCC | 738 | GGCUGCCAAUGGUGAUGGG | 739 |
| 586 | CCAUCACCAUUGGCAGCCA | 740 | UGGCUGCCAAUGGUGAUGG | 741 |
| 587 | CAUCACCAUUGGCAGCCAC | 742 | GUGGCUGCCAAUGGUGAUG | 743 |
| 588 | AUCACCAUUGGCAGCCACG | 744 | CGUGGCUGCCAAUGGUGAU | 745 |
| 589 | UCACCAUUGGCAGCCACGC | 746 | GCGUGGCUGCCAAUGGUGA | 747 |
| 590 | CACCAUUGGCAGCCACGCC | 748 | GGCGUGGCUGCCAAUGGUG | 749 |
| 591 | ACCAUUGGCAGCCACGCCC | 750 | GGGCGUGGCUGCCAAUGGU | 751 |
| 592 | CCAUUGGCAGCCACGCCCA | 752 | UGGGCGUGGCUGCCAAUGG | 753 |
| 593 | CAUUGGCAGCCACGCCCAU | 754 | AUGGGCGUGGCUGCCAAUG | 755 |
| 594 | AUUGGCAGCCACGCCCAUG | 756 | CAUGGGCGUGGCUGCCAAU | 757 |
| 595 | UUGGCAGCCACGCCCAUGG | 758 | CCAUGGGCGUGGCUGCCAA | 759 |
| 596 | UGGCAGCCACGCCCAUGGC | 760 | GCCAUGGGCGUGGCUGCCA | 761 |
| 597 | GGCAGCCACGCCCAUGGCG | 762 | CGCCAUGGGCGUGGCUGCC | 763 |
| 598 | GCAGCCACGCCCAUGGCGA | 764 | UCGCCAUGGGCGUGGCUGC | 765 |
| 599 | CAGCCACGCCCAUGGCGAC | 766 | GUCGCCAUGGGCGUGGCUG | 767 |
| 600 | AGCCACGCCCAUGGCGACC | 768 | GGUCGCCAUGGGCGUGGCU | 769 |

TABLE 23 siRNAs targeting G516U mutant IDH2 (equivalent to G602U of SEQ ID NO: 12 (FIG. 22B)

| Position on mRNA (FIG. 22B) | sense (5' to 3') | SEQ ID NO: | antisense (5' to 3') | SEQ ID NO: |
|---|---|---|---|---|
| 584 | GCCCAUCACCAUUGGCAGU | 770 | ACUGCCAAUGGUGAUGGGC | 771 |
| 585 | CCCAUCACCAUUGGCAGUC | 772 | GACUGCCAAUGGUGAUGGG | 773 |
| 586 | CCAUCACCAUUGGCAGUCA | 774 | UGACUGCCAAUGGUGAUGG | 775 |
| 587 | CAUCACCAUUGGCAGUCAC | 776 | GUGACUGCCAAUGGUGAUG | 777 |
| 588 | AUCACCAUUGGCAGUCACG | 778 | CGUGACUGCCAAUGGUGAU | 779 |
| 589 | UCACCAUUGGCAGUCACGC | 780 | GCGUGACUGCCAAUGGUGA | 781 |
| 590 | CACCAUUGGCAGUCACGCC | 782 | GGCGUGACUGCCAAUGGUG | 783 |
| 591 | ACCAUUGGCAGUCACGCCC | 784 | GGGCGUGACUGCCAAUGGU | 785 |
| 592 | CCAUUGGCAGUCACGCCCA | 786 | UGGGCGUGACUGCCAAUGG | 787 |
| 593 | CAUUGGCAGUCACGCCCAU | 788 | AUGGGCGUGACUGCCAAUG | 789 |
| 594 | AUUGGCAGUCACGCCCAUG | 790 | CAUGGGCGUGACUGCCAAU | 791 |
| 595 | UUGGCAGUCACGCCCAUGG | 792 | CCAUGGGCGUGACUGCCAA | 793 |

TABLE 23-continued siRNAs targeting G516U mutant IDH2 (equivalent to G602U of SEQ ID NO: 12 (FIG. 22B)

| Position on mRNA (FIG. 22B) | sense (5' to 3') | SEQ ID NO: | antisense (5' to 3') | SEQ ID NO: |
|---|---|---|---|---|
| 596 | UGGCAGUCACGCCCAUGGC | 794 | GCCAUGGGCGUGACUGCCA | 795 |
| 597 | GGCAGUCACGCCCAUGGCG | 796 | CGCCAUGGGCGUGACUGCC | 797 |
| 598 | GCAGUCACGCCCAUGGCGA | 798 | UCGCCAUGGGCGUGACUGC | 799 |
| 599 | CAGUCACGCCCAUGGCGAC | 800 | GUCGCCAUGGGCGUGACUG | 801 |
| 600 | AGUCACGCCCAUGGCGACC | 802 | GGUCGCCAUGGGCGUGACU | 803 |

Example 6 Structural Analysis of R132H Mutant IDH1

To define how R132 mutations alter the enzymatic properties of IDH1, the crystal structure of R132H mutant IDH1 bound to αKG, NADPH, and $Ca^{2+}$ was solved at 2.1 Å resolution.

Figure 29A:
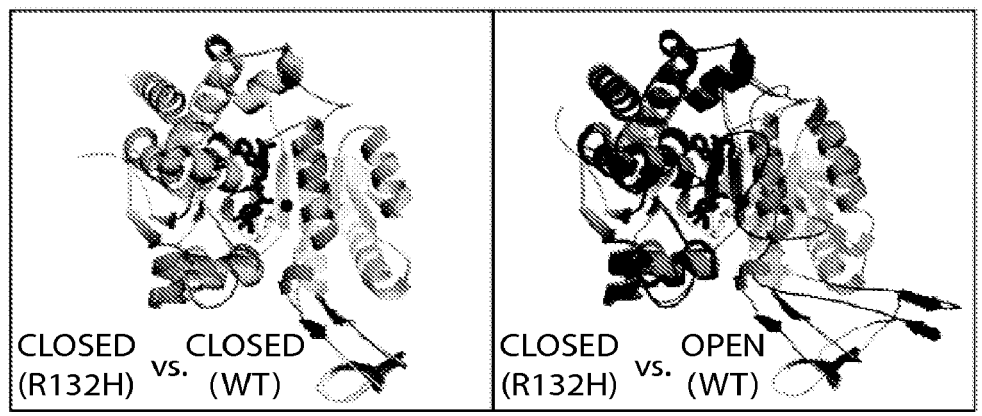
FIG. 29A depicts the structural analysis of R132H mutant IDH1. On left is shown an overlay structure of R132H mutant IDH1 and WT IDH1 in the 'closed' conformation. On the right is shown an overlay structure of WT IDH1 in the 'open' conformation with mutant IDH1 for comparison.

The overall quaternary structure of the homodimeric R132H mutant enzyme adopts the same closed catalytically competent conformation (shown as a monomer in FIG. 29A) that has been previously described for the wild-type enzyme (Xu, X. et al. J Biol Chem 279, 33946-57 (2004)). NADPH is positioned as expected for hydride transfer to αKG in an orientation that would produce R(–)-2HG, consistent with our chiral determination of the 2HG product.

Figure 29B:
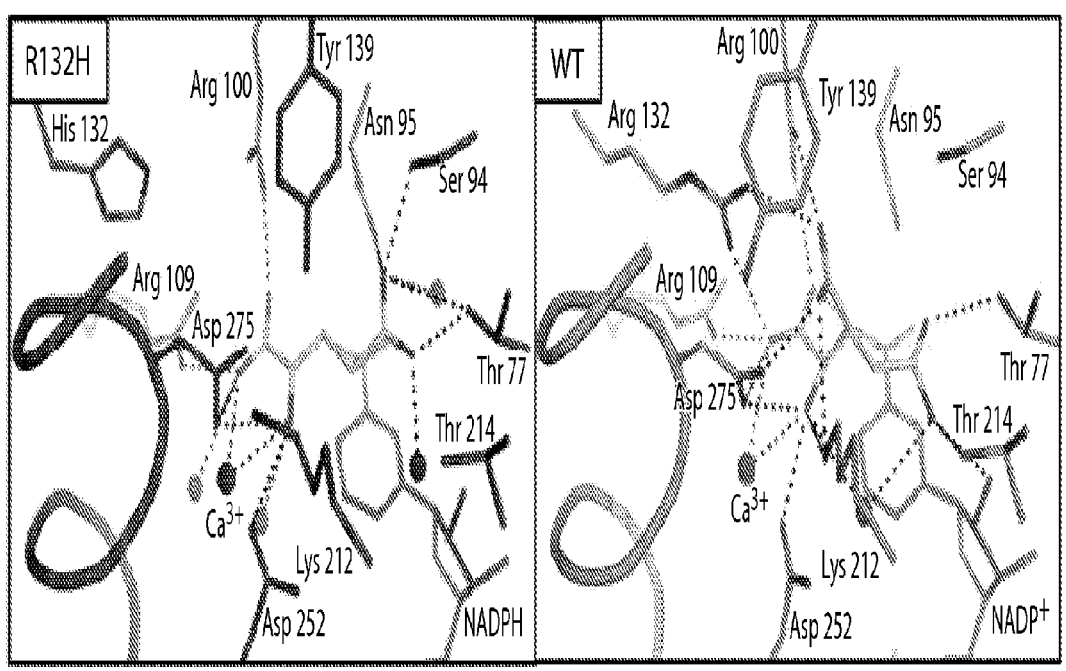
FIG. 29B depicts the close-up structural comparison of the R132H IDH1 (left) and wild-type (WT) IDH1 (right) active-site containing both αKG and NADPH. In addition to changes at residue 132, the position of the catalytic residues Tyr 139 and Lys 212 are different and αKG is oriented differently relative to NADPH for catalytic hydride transfer in the WT versus R132H mutant enzymes.

Two important features were noted by the change of R132 to histidine: the effect on catalytic conformation equilibrium and the reorganization of the active-site. Locating atop a β-sheet in the relatively rigid small domain, R132 acts as a gate-keeper residue and appears to orchestrate the hinge movement between the open and closed conformations. The guanidinium moiety of R132 swings from the open to the closed conformation with a distance of nearly 8 Å. Substitution of histidine for arginine is likely to change the equilibrium in favor of the closed conformation that forms the catalytic cleft for cofactor and substrate to bind efficiently, which partly explains the high-affinity for NADPH exhibited by the R132H mutant enzyme. This feature may be advantageous for the NADPH-dependent reduction of αKG to R(–)-2HG in an environment where NADPH concentrations are low. Secondly, closer examination of the catalytic pocket of the mutant IDH1 structure in comparison to the wild-type enzyme showed not only the expected loss of key salt-bridge interactions between the guanidinium of R132 and the α/β carboxylates of isocitrate, as well as changes in the network that coordinates the metal ion, but also an unexpected reorganization of the active-site. Mutation to histidine resulted in a significant shift in position of the highly conserved residues Y139 from the A subunit and K212' from the B subunit (FIG. 29B), both of which are thought to be critical for catalysis of this enzyme family (Aktas, D. F. & Cook, P. F. Biochemistry 48, 3565-77 (2009)). In particular, the hydroxyl moiety of Y139 now occupies the space of the β-carboxylate of isocitrate. In addition, a significant repositioning of αKG compared to isocitrate where the distal carboxylate of αKG now points upward to make new contacts with N96 and S94 was observed. Overall, this single R132 mutation results in formation of a distinct active site compared to wild-type IDH1.

Example 7 Materials and Methods

Summary

R132H, R132C, R132L and R132S mutations were introduced into human IDH1 by standard molecular biology techniques. 293T and the human glioblastoma cell lines U87MG and LN-18 were cultured in DMEM, 10% fetal bovine serum. Cells were transfected and selected using standard techniques. Protein expression levels were determined by Western blot analysis using IDHc antibody (Santa Cruz Biotechnology), IDH1 antibody (proteintech), MYC tag antibody (Cell Signaling Technology), and IDH2 antibody (Abcam). Metabolites were extracted from cultured cells and from tissue samples according to close variants of a previously reported method (Lu, W., Kimball, E. & Rabinowitz, J. D. J Am Soc Mass Spectrom 17, 37-50 (2006)), using 80% aqueous methanol (–80° C.) and either tissue scraping or homogenization to disrupt cells. Enzymatic activity in cell lysates was assessed by following a change in NADPH fluorescence over time in the presence of isocitrate and NADP, or αKG and NADPH. For enzyme assays using recombinant IDH1 enzyme, proteins were produced in E. coli and purified using Ni affinity chromatography followed by Sephacryl S-200 size-exclusion chromatography. Enzymatic activity for recombinant IDH1 protein was assessed by following a change in NADPH UV absorbance at 340 nm using a stop-flow spectrophotometer in the presence of isocitrate and NADP or αKG and NADPH. Chirality of 2HG was determined as described previously (Struys, E. A., Jansen, E. E., Verhoeven, N. M. & Jakobs, C. Clin Chem 50, 1391-5 (2004)). For crystallography studies, purified recombinant IDH1 (R132H) at 10 mg/mL in 20 mM Tris pH 7.4, 100 mM NaCl was pre-incubated for 60 min with 10 mM NADPH, 10 mM calcium chloride, and 75 mM αKG. Crystals were obtained at 20° C. by vapor diffusion equilibration using 3 μL drops mixed 2:1 (protein:precipitant) against a well-solution of 100 mM MES pH 6.5, 20% PEG 6000. Patient tumor samples were obtained after informed consent as part of a UCLA IRB-approved research protocol. Brain tumor samples were obtained after surgical resection, snap frozen in isopentane cooled by liquid nitrogen and stored at –80 C. The IDH1 mutation status of each sample was determined using standard molecular biology techniques as described previously (Yan, H. et al. N Engl J Med 360, 765-73 (2009)). Metabolites were extracted and analyzed by LC-MS/MS as described above. Full methods are available in the supplementary material.

Supplementary Methods

Cloning, Expression, and Purification of ICDH1 wt and Mutants in E. Coli.

The open reading frame (ORF) clone of human isocitrate dehydrogenase 1 (cDNA) (IDH1; ref. ID NM_005896) was purchased from Invitrogen in pENTR221 (Carlsbad, Calif.) and Origene Inc. in pCMV6 (Rockville, Md.). To transfect cells with wild-type or mutant IDH1, standard molecular biology mutagenesis techniques were utilized to alter the DNA sequence at base pair 395 of the ORF in pCMV6 to introduce base pair change from guanine to adenine, which resulted in a change in the amino acid code at position 132 from arginine (wt) to histidine (mutant; or R132H), and confirmed by standard DNA sequencing methods. For 293T cell transfection, wild-type and R132H mutant IDH1 were subcloned into pCMV-Sport6 with or without a carboxy-terminal Myc-DDK-tag. For stable cell line generation, constructs in pCMV6 were used. For expression in E. coli, the coding region was amplified from pENTR221 by PCR using primers designed to add NDEI and XHO1 restrictions sites at the 5' and 3' ends respectively. The resultant fragment was cloned into vector pET41a (EMD Biosciences, Madison, Wis.) to enable the E. coli expression of C-terminus His8-tagged protein. Site directed mutagenesis was performed on the pET41a-ICHD1 plasmid using the QuikChange® MultiSite-Directed Mutagenesis Kit (Stratagene, La Jolla, Calif.) to change G395 to A, resulting in the Arg to His mutation. R132C, R132L and R132S mutants were introduced into pET41a-ICHD1 in an analogous way.

Wild-type and mutant proteins were expressed in and purified from the E. coli Rosetta™ strain (Invitrogen, Carlsbad, Calif.) as follows. Cells were grown in LB (20 µg/ml Kanamycin) at 37° C. with shaking until OD600 reaches 0.6. The temperature was changed to 18° C. and protein expression was induced by adding IPTG to final concentration of 1 mM. After 12-16 hours of IPTG induction, cells were resuspended in Lysis Buffer (20 mM Tris, pH7.4, 0.1% Triton X-100, 500 mM NaCl, 1 mM PMSF, 5 mM β-mercaptoethanol, 10% glycerol) and disrupted by microfluidation. The 20,000 g supernatant was loaded on metal chelate affinity resin (MCAC) equilibrated with Nickel Column Buffer A (20 mM Tris, pH7.4, 500 mM NaCl, 5 mM β-mercaptoethanol, 10% glycerol) and washed for 20 column volumes. Elution from the column was effected by a 20 column-volume linear gradient of 10% to 100% Nickel Column Buffer B (20 mM Tris, pH7.4, 500 mM NaCl, 5 mM β-mercaptoethanol, 500 mM Imidazole, 10% glycerol) in Nickel Column Buffer A). Fractions containing the protein of interest were identified by SDS-PAGE, pooled, and dialyzed twice against a 200-volume excess of Gel Filtration Buffer (200 mM NaCl, 50 mM Tris 7.5, 5 mM β-mercaptoethanol, 2 mM $MnSO_4$, 10% glycerol), then concentrated to 10 ml using Centricon (Millipore, Billerica, Mass.) centrifugal concentrators. Purification of active dimers was achieved by applying the concentrated eluent from the MCAC column to a Sephacryl S-200 (GE Life Sciences, Piscataway, N.J.) column equilibrated with Gel Filtration Buffer and eluting the column with 20 column volumes of the same buffer. Fractions corresponding to the retention time of the dimeric protein were identified by SDS-PAGE and pooled for storage at −80° C.

Cell Lines and Cell Culture.

293T cells were cultured in DMEM (Dulbecco's modified Eagles Medium) with 10% fetal bovine serum and were transfected using pCMV-6-based IDH-1 constructs in six-well plates with Fugene 6 (Roche) or Lipofectamine 2000 (Invitrogen) according to manufacturer's instructions. Parental vector pCMV6 (no insert), pCMV6-wt IDH1 or pCMV6-R132H were transfected into human glioblastoma cell lines (U87MG; LN-18 (ATCC, HTB-14 and CRL-2610; respectively) cultured in DMEM with 10% fetal bovine serum. Approximately 24 hrs after transfection, the cell cultures were transitioned to medium containing G418 sodium salt at concentrations of either 500 ug/ml (U87MG) or 750 ug/ml (LN-18) to select stable transfectants. Pooled populations of G418 resistant cells were generated and expression of either wild-type IDH1 or R132 IDH1 was confirmed by standard Western blot analysis.

Western Blot.

For transient transfection experiments in 293 cells, cells were lysed 72 hours after transfection with standard R1PA buffer. Lysates were separated by SDS-PAGE, transferred to nitrocellulose and probed with goat-anti-IDHc antibody (Santa Cruz Biotechnology sc49996) or rabbit-anti-MYC tag antibody (Cell Signaling Technology #2278) and then detected with HRP-conjugated donkey anti-goat or HRP-conjugated goat-anti-rabbit antibody (Santa Cruz Biotechnology sc2004). IDH1 antibody to confirm expression of both wild-type and R132H IDH1 was obtained from Proteintech. The IDH2 mouse monoclonal antibody used was obtained from Abcam.

Detection of Isocitrate, αKG, and 2HG in Purified Enzyme Reactions by LC-MS/MS.

Enzyme reactions performed as described in the text were run to completion as judged by measurement of the oxidation state of NADPH at 340 nm. Reactions were extracted with eight volumes of methanol, and centrifuged to remove precipitated protein. The supernatant was dried under a stream of nitrogen and resuspended in $H_2O$. Analysis was conducted on an API2000 LC-MS/MS (Applied Biosystems, Foster City, Calif.). Sample separation and analysis was performed on a 150×2 mm, 4 uM Synergi Hydro-RP 80 A column, using a gradient of Buffer A (10 mM tributylamine, 15 mM acetic acid, 3% (v/v) methanol, in water) and Buffer B (methanol) using MRM transitions.

Cell Lysates Based Enzyme Assays.

293T cell lysates for measuring enzymatic activity were obtained 48 hours after transfection with M-PER lysis buffer supplemented with protease and phosphatase inhibitors. After lysates were sonicated and centrifuged at 12,000 g, supernatants were collected and normalized for total protein concentration. To measure IDH oxidative activity, 3 µg of lysate protein was added to 200 µl of an assay solution containing 33 mM Tris-acetate buffer (pH 7.4), 1.3 mM $MgCl_2$, 0.33 mM EDTA, 100 µM β-NADP, and varying concentrations of D-(+)-threo-isocitrate. Absorbance at 340 nm, reflecting NADPH production, was measured every 20 seconds for 30 min on a SpectraMax 190 spectrophotometer (Molecular Devices). Data points represent the mean activity of 3 replicates per lysate, averaged among 5 time points centered at every 5 min. To measure IDH reductive activity, 3 µg of lysate protein was added to 200 µl of an assay solution which contained 33 mM Tris-acetate (pH 7.4), 1.3 mM $MgCl_2$, 25 µM β-NADPH, 40 mM $NaHCO_3$, and 0.6 mM αKG. The decrease in 340 nm absorbance over time was measured to assess NADPH consumption, with 3 replicates per lysate.

Recombinant IDH1 Enzyme Assays.

All reactions were performed in standard enzyme reaction buffer (150 mM NaCl, 20 mM Tris-Cl, pH 7.5, 10% glycerol, 5 mM $MgCl_2$ and 0.03% (w/v) bovine serum albumin). For determination of kinetic parameters, sufficient enzyme was added to give a linear reaction for 1 to 5 seconds. Reaction progress was monitored by observation of the reduction state of the cofactor at 340 nm in an SFM-400 stopped-flow spectrophotometer (BioLogic, Knoxville, Tenn.). Enzymatic constants were determined using curve fitting algorithms to standard kinetic models with the Sigmaplot software package (Systat Software, San Jose, Calif.). Determination of Chirality of Reaction Products from Enzyme Reactions and Tumors.

Enzyme reactions were run to completion and extracted with methanol as described above, then derivatized with enantiomerically pure tartaric acid before resolution and analysis by LC-MS/MS. After being thoroughly dried, samples were resuspended in freshly prepared 50 mg/ml (2R,3R)-(+)-Tartaric acid in dichloromethane:acetic acid (4:1) and incubated for 30 minutes at 75° C. After cooling to room temperature, samples were briefly centrifuged at 14,000 g, dried under a stream of nitrogen, and resuspended in $H_2O$. Analysis was conducted on an API200 LC-MS/MS (Applied Biosystems, Foster City, Calif.), using an isocratic flow of 90:10 (2 mM ammonium formate, pH 3.6:MeOH) on a Luna C18(2) 150×2 mm, 5 uM column. Tartaric-acid derivatized 2HG was detected using the 362.9/146.6 MRM transition and the following instrument settings: DP-1, FP-310, EP-4, CE-12, CXP-26. Analysis of the (R)-2HG standard, 2HG racemic mixture, and methanol-extracted tumor biomass (q.v.) was similarly performed.

Crystallography Conditions.

Crystals were obtained at 20° C. by vapor diffusion equilibration using 3 µL drops mixed 2:1 (protein:precipitant) against a well-solution of 100 mM MES pH 6.5, 20% PEG 6000.

Protein Characterization.

Figure 32A:
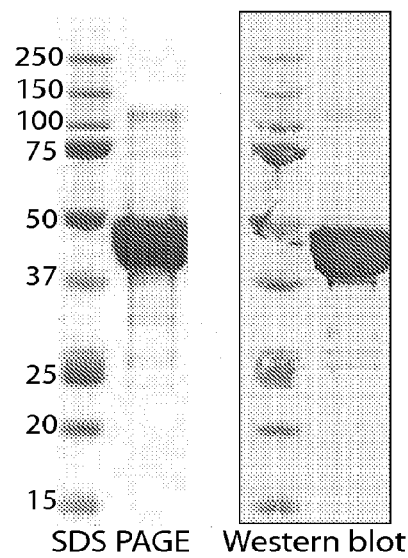
FIG. 32A depicts SDS-PAGE and Western blot analyses of C-terminal affinity-purification tagged IDH1 R132S protein used for crystallization.
Figure 32B:
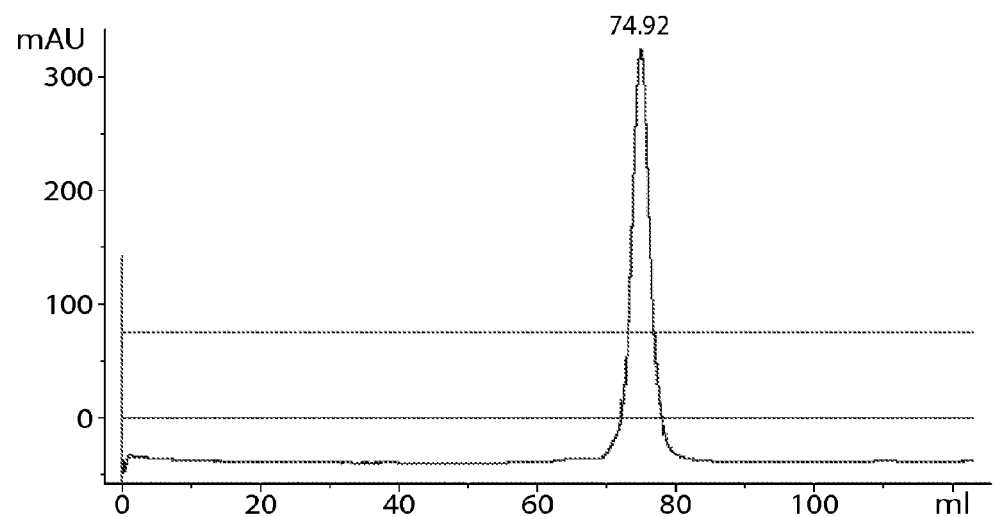
FIG. 32B depicts the chromatogram of FPLC analysis of the IDH1 R132S protein sample.

Approximately 90 mg of human cytosolic isocitrate dehydrogenase (HcIDH) was supplied to Xtal BioStructures by Agios. This protein was an engineered mutant form, R132S, with an 11-residue C-terminal affinity-purification tag (sequence SLEHHHHHHHH). The calculated monomeric molecular weight was 48.0 kDa and the oretical pI was 6.50. The protein, at about 6 mg/mL concentration, was stored in 1-mL aliquots in 50 mM Tris-HCl (pH 7.4), 500 mM NaCl, 5 mM β-mercaptoethanol and 10% glycerol at −80° C. As shown in FIG. 32A, SDS-PAGE was performed to test protein purity and an anti-histidine Western blot was done to demonstrate the protein was indeed his-tagged. A sample of the protein was injected into an FPLC size-exclusion column to evaluate the sample purity and to determine the polymeric state in solution. FIG. 32B is a chromatogram of this run showing a single peak running at an estimated 87.6 kDa, suggesting IDH exists as a dimer at pH 7.4. Prior to crystallization, the protein was exchanged into 20 mM Tris-HCl (pH 7.4) and 100 mM NaCl using Amicon centrifugal concentrators. At this time, the protein was also concentrated to approximately 15 mg/mL. At this protein concentration and ionic strength, the protein tended to form a detectable level of precipitate. After spinning out the precipitate, the solution was stable at ~10 mg/mL at 4° C.

Initial Attempts at Crystallization.

The strategy for obtaining diffraction-quality crystals was derived from literature conditions, specifically "Structures of Human Cytosolic NADP-dependent Isocitrate Dehydrogenase Reveal a Novel Self-regulatory Mechanism of Activity," Xu, et al. (2005) *J. Biol. Chem.* 279: 33946-56. In this study, two crystal forms of HcIDH wildtype protein were produced. One contained their "binary complex", IDH-NADP, which crystallized from hanging drops in the tetragonal space group $P4_32_12$. The drops were formed from equal parts of protein solution (15 mg/mL IDH, 10 mM NADP) and precipitant consisting of 100 mM MES (pH 6.5) and 12% PEG 20000. The other crystal form contained their "quaternary complex", IDH-NADP/isocitrate/$Ca^{2+}$, which crystallized in the monoclinic space group $P2_1$ using 100 mM MES (pH 5.9) and 20% PEG 6000 as the precipitant. Here they had added 10 mM DL-isocitrate and 10 mM calcium chloride to the protein solution. First attempts at crystallizing the R132S mutant in this study centered around these two reported conditions with little variation. The following lists the components of the crystallization that could be varied; several different combinations of these components were tried in the screening process.

In the protein solution:

| | |
|---|---|
| HcIDH(R132S) | always ~10 mg/mL or ~0.2 mM |
| Tris-HCl (pH 7.4) | always 20 mM |
| NaCl | always 100 mM |
| $NADP^+$/NADPH | absent or 5 mM $NADP^+$ (did not try NADPH) |
| DL-isocitic acid, trisodium salt | absent or 5 mM |
| calcium chloride | absent or 10 mM |
| In the precipitant: | 100 mM MES (pH 6.5) and 12% PEG 20000 OR 100 mM MES (pH 6.0) and 20% PEG 6000 |
| Drop size: | always 3 µL |
| Drop ratios: | 2:1, 1:1 or 1:2 (protein:precipitant) |

Figure 33:
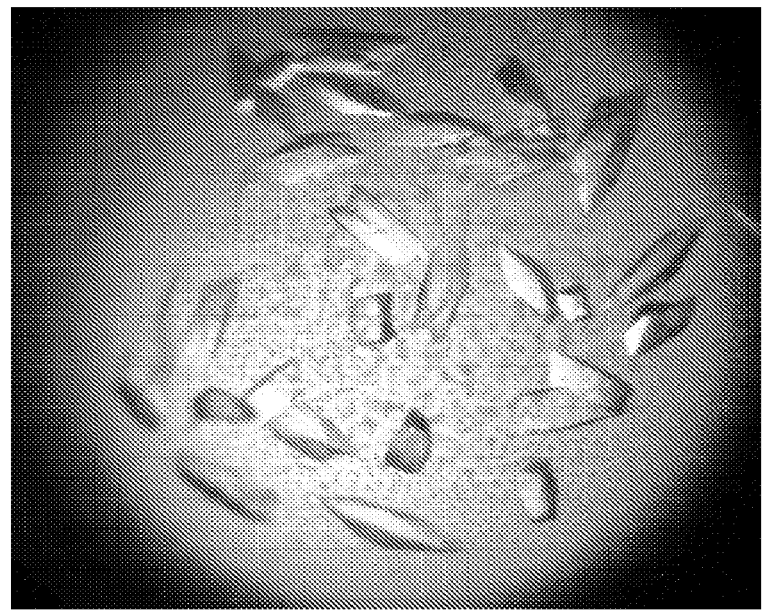
FIG. 33 depicts crystals obtained from a protein solution contained 5 mM NADP, 5 mM isocitrate, 10 mM Ca2+. Precipitant solution contained 100 mM MES (pH 6.0) and 20% PEG 6000 using a hanging drop method of crystallization.

Upon forming the hanging drops, a milky precipitate was always observed. On inspection after 2-4 days at 20° C. most drops showed dense precipitation or phase separation. In some cases, the precipitate subsided and it was from these types of drops small crystals had grown, for example, as shown in FIG. 33.

Crystal Optimization.

Once bonafide crystals were achieved, the next step was to optimize the conditions to obtain larger and more regularly-shaped crystals of IDH-NADP/isocitrate/$Ca^{2+}$ in a timely and consistent manner. The optimal screen focused on varying the pH from 5.7 to 6.2, the MES concentration from 50 to 200 mM and the PEG 6000 concentration from 20 to 25%. Also, bigger drops were set up (5-6 µl) and the drop ratios were again varied. These attempts failed to produce larger, diffraction-quality crystals but did reproduce the results reported above. Either a dense precipitate, oily phase separation or small crystals were observed.

Using α-Ketoglutarate.

Figure 34:
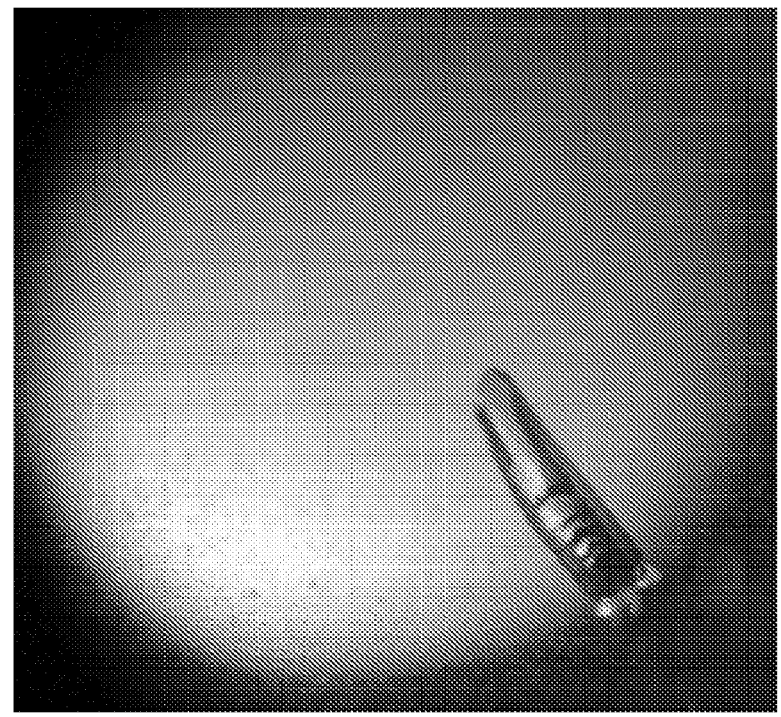
FIG. 34 depicts crystal obtained from a protein solution contained 5 mM NADP, 5 mM α-ketoglutarate, 10 mM Ca2+. Precipitant contained 100 mM MES (pH 6.5) and 12% PEG 20000.

Concurrent to the optimization of the isocitrate crystals, other screens were performed to obtain crystals of IDH (R132S) complexed with α-ketoglutarate instead. The protein solution was consistently 10 mg/mL IDH in 20 mM Tris-HCl (pH 7.4) and 100 mM NaCl. The following were added in this order: 5 mM NADP, 5 mM α-ketoglutaric acid (free acid, pH balanced with NaOH) and 10 mM calcium chloride. The protein was allowed to incubate with these compounds for at least an hour before the drops were set up. The precipitant was either 100 mM MES (pH 6.5) and 12% PEG 20000 or 100 mM MES (pH 6.5) and 20% PEG 6000. Again, precipitation or phase separation was primarily seen, but in some drops small crystals did form. At the edge of one of the drops, a single large crystal formed, pictured below. This was the single crystal used in the following structure determination. FIG. 34 shows crystal obtained from a protein solution contained 5 mM NADP, 5 mM α-ketoglutarate, 10 mM Ca2+. Precipitant contained 100 mM MES (pH 6.5) and 12% PEG 20000.

Cryo Conditions.

In order to ship the crystal to the X-ray source and protect it during cryo-crystallography, a suitable cryo-protectant was needed. Glycerol is quite widely used and was the first choice. A cryo solution was made, basically as a mixture of the protein buffer and precipitant solution plus glycerol: 20 mM Tris-HCl (pH 7.5), 100 mM NaCl, 5 mM NADP, 5 mM α-ketoglutaric acid, 10 mM calcium chloride, 100 mM MES (pH 6.5), 12% PEG 20000 and either 12.5% glycerol or 25% glycerol. The crystal was transferred to the cryo solution in two steps. First, 5 µL of the 12.5% glycerol solution was added directly to the drop and incubated for 10 minutes, watching for possible cracking of the crystal. The liquid was removed from the drop and 10 µL of the 25% glycerol solution was added on top of the crystal. Again, this incubated for 10 minutes, harvested into a nylon loop and plunged into liquid nitrogen. The crystal was stored submerged in a liquid nitrogen dewar for transport.

Data Collection and Processing.

The frozen crystal was mounted on a Rigaku RAXIS IV X-ray instrument under a stream of nitrogen gas at temperatures near −170° C. A 200° dataset was collected with the image plate detector using 1.54 Å wavelength radiation from a rotating copper anode home source, 1° oscillations and 10 minute exposures. The presence of 25% glycerol as a cryoprotectant was sufficient for proper freezing, as no signs of crystal cracking (split spots or superimposed lattices) were observed. A diffuse ring was observed at 3.6 Å resolution, most likely caused by icing. The X-ray diffraction pattern showed clear lattice planes and reasonable spot separation, although the spacing along one reciprocal axis was rather small (b=275.3). The data was indexed to 2.7 Å resolution into space group P2$_1$2$_1$2 with HKL2000 (Otwinowski and Minor, 1997). Three structures for HcIDH are known, designated the closed form (1T0L), the open form (1T09 subunit A) and semi-open form (1T09 subunit B). Molecular replacement was performed with the CCP4 program PHASER (Bailey, 1994) using only the protein atoms from these three forms. Only the closed form yielded a successful molecular replacement result with 6 protein subunits in the asymmetric unit. The unit cell contains approximately 53.8% solvent.

Model Refinement.

Using the CCP4 program REFMAC5, rigid-body refinement was performed to fit each of the 6 IDH subunits in the asymmetric unit. This was followed by rigid-body refinement of the three domains in each protein subunit. Restrained refinement utilizing non-crystallographic symmetry averaging of related pairs of subunits yielded an initial structure with R$_{cryst}$ of 33% and R$_{free}$ of 42%. Model building and real-space refinement were performed using the graphics program COOT (Emsley and Cowtan, 2004). A difference map was calculated and this showed strong electron density into which six individual copies of the NADP ligand and calcium ion were manually fit with COOT. Density for the α-ketoglutarate structure was less defined and was fit after the binding-site protein residues were fit using a 2F$_o$-F$_c$ composite omit map. Automated Ramachandran-plot optimization coupled with manual real-space density fitting was applied to improve the overall geometry and fit. A final round of restrained refinement with NCS yielded an R$_{cryst}$ of 30.1% and R$_{free}$ of 35.2%.

| a, Å | b, Å | c, Å | α | β | γ | Unit cell volume, Å$^3$ | Z |
|---|---|---|---|---|---|---|---|
| 116.14 | 275.30 | 96.28 | 90° | 90° | 90° | 3.08 × 10$^6$ | 24 |

| | |
|---|---|
| Reflections in working set/test set | 68,755/3,608 (5.0%) |
| R$_{cryst}$ | 30.1% |
| R$_{free}$ | 35.2% |

X-ray data and refinement statistics for IDH(R132S)-NADP/α-ketoglurate/Ca$^{2+}$

| | |
|---|---|
| Crystal parameters | |
| Space group | P2$_1$2$_1$2 |
| Unit cell dimensions | |
| a, b, c, Å | 116.139, 275.297, 96.283 |
| α, β, γ, ° | 90.0, 90.0, 90.0 |
| Volume, Å$^3$ | 3,078,440 |
| No. protein molecules in asymmetric unit | 6 |
| No. protein molecules in unit cell, Z | 24 |
| Data collection | |
| Beam line | |
| Date of collection | Apr. 25, 2009 |
| λ, Å | 1.5418 |
| Detector | Rigaku Raxis IV |
| Data set (phi), ° | 200 |
| Resolution, Å | 25-2.7 (2.8-2.7) |
| Unique reflections (N, F > 0) | 73,587 |
| Completeness, % | 85.4 (48.4) |
| <I>/σI | 9.88 (1.83) |
| R-merge | 0.109 (0.33) |
| Redundancy | 4.3 (1.8) |
| Mosaicity | 0.666 |
| Wilson B factor | 57.9 |
| Anisotropy B factor, Å$^2$ | −1.96 |
| Refinement Statistics | |
| Resolution limit, Å | 20.02-2.70 |
| No. of reflections used for R-work$^a$/R-free$^b$ | 68,755/3608 |
| Protein atoms | 19788 |
| Ligand atoms | 348 |
| No. of waters | 357 |
| Ions etc. | 6 |
| Matthews coeff. Å$^3$/Dalton | 2.68 |
| Solvent, % | 53.8 |
| R-work$^a$/R-free$^b$, (%) | 30.1/35.2 |
| Figure-of-merit$^c$ | 0.80 (0.74) |
| Average B factors | 31.0 |
| Coordinates error (Luzzati plot), Å | 0.484 |
| R.M.S. deviations | |
| Bond lengths, Å | 0.026 |
| Bond angles, ° | 2.86 |

Completeness and R-merge are given for all data and for data in the highest resolution shell. Highest shell values are in parentheses.
$^a$R factor = $\Sigma_{hkl} |F_o - F_c|/\Sigma_{hkl} F_o$, where $F_o$ and $F_c$ are the observed and calculated structure factor amplitudes, respectively for all reflections hkl used in refinement.
$^b$R-free is calculated for 5% of the data that were not used in refinement.

$^c$Figure of merit = $\sqrt{x^2 + y^2}$, where x = ($\Sigma_0^{2\pi}$ P(α)cos α)/($\Sigma_0^{2\pi}$ P(α)), y = ($\Sigma_0^{2\pi}$ P(α)sin α)/($\Sigma_0^{2\pi}$ P(α)), and the phase probability P(α) = exp(A cos α + B sin α + C cos(2α) + D sin(2α)), where A, B, C, and D are the Hendrickson-Lattman coefficients and α is the phase.

Stereochemistry of IDH(R132S)-NADP/α-ketoglurate/Ca$^{2+}$

| Ramachandran plot statistics | No. of amino acids | % of Residues |
|---|---|---|
| Residues in most favored regions [A, B, L] | 1824 | 82.2 |
| Residues in additional allowed regions [a, b, l, p] | 341 | 15.4 |
| Residues in generously allowed regions [−a, −b, −l, −p] | 38 | 1.7 |

-continued

Stereochemistry of IDH(R132S)-NADP/α-ketoglurate/Ca²⁺

| Ramachandran plot statistics | No. of amino acids | % of Residues |
|---|---|---|
| Residues in disallowed regions | 17 | 0.8 |
| Number of non-glycine and non-proline residues | 2220 | 100 |
| Number of end-residues (excl. Gly and Pro) | 387 | |
| Number of glycine residues | 198 | |
| Number of proline residues | 72 | |
| Total number of residues | 2877 | |
| Overall <G> -factor[d] score (>−1.0) | −0.65 | |

Generated by PROCHECK (Laskowski R A, MacArthur M W, Moss D S, Thornton J M (1993) J Appl Crystallogr 26: 283-291.)
[d]G-factors for main-chain and side-chain dihedral angles, and main-chain covalent forces (bond lengths and bond angles). Values should be ideally −0.5 or above −1.0.

| | |
|---|---|
| Radiation wavelength, Å | 1.54 |
| Resolution, Å (outer shell) | 20-2.70 (2.80-2.70) |
| Unique reflections | 73,587 |
| Completeness (outer shell) | 85.4% (48.4%) |
| Redundancy (outer shell) | 4.3 (1.8) |
| $R_{merge}$ (outer shell) | 10.9% (33%) |
| <I>/<σ(I)> (outer shell) | 9.88 (1.83) |

Clinical Specimens, Metabolite Extraction and Analysis.

Human brain tumors were obtained during surgical resection, snap frozen in isopentane cooled by liquid nitrogen and stored at −80 C. Clinical classification of the tissue was performed using standard clinical pathology categorization and grading as established by the WHO. Genomic sequence analysis was deployed to identify brain tumor samples containing either wild-type isocitrate dehydrogenase (IDH1) or mutations altering amino acid 132. Genomic DNA was isolated from 50-100 mgs of brain tumor tissue using standard methods. A polymerase chain reaction on the isolated genomic DNA was used to amplify a 295 base pair fragment of the genomic DNA that contains both the intron and $2^{nd}$ exon sequences of human IDH1 and mutation status assessed by standard molecular biology techniques. Metabolite extraction was accomplished by adding a 10× volume (m/v ratio) of −80° C. methanol:water mix (80%:20%) to the brain tissue (approximately 100 mgs) followed by 30 s homogenization at 4 C. These chilled, methanol extracted homogenized tissues were then centrifuged at 14,000 rpm for 30 minutes to sediment the cellular and tissue debris and the cleared tissue supernatants were transferred to a screw-cap freezer vial and stored at −80° C. For analysis, a 2× volume of tributylamine (10 mM) acetic acid (10 mM) pH 5.5 was added to the samples and analyzed by LCMS as follows. Sample extracts were filtered using a Millex-FG 0.20 micron disk and 10 μL were injected onto a reverse-phase HPLC column (Synergi 150 mm×2 mm, Phenomenex Inc.) and eluted using a linear gradient LCMS-grade methanol (50%) with 10 mM tributylamine and 10 mM acetic acid) ramping to 80% methanol:10 mM tributylamine: 10 mM acetic acid over 6 minutes at 200 μL/min. Eluted metabolite ions were detected using a triple-quadrupole mass spectrometer, tuned to detect in negative mode with multiple-reaction-monitoring mode transition set (MRM's) according to the molecular weights and fragmentation patterns for 8 known central metabolites, including 2-hydroxy-glutarate as described above. Data was processed using Analyst Software (Applied Biosystems, Inc.) and metabolite signal intensities were obtained by standard peak integration methods.

Example 9 High Throughput Screening (HTS) for IDH1 R132H Inhibitors

Assays were conducted in a volume of 76 ul assay buffer (150 mM NaCl, 10 mM MgCl2, 20 mM Tris pH 7.5, 0.03% bovine serum albumin) as follows in a standard 384-well plate: To 25 ul of substrate mix (8 uM NADPH, 2 mM αKG), 1 ul of test compound was added in DMSO. The plate was centrifuged briefly, and then 25 ul of enzyme mix was added (0.2 ug/ml ICDH1 R132H) followed by a brief centrifugation and shake at 100 RPM. The reaction was incubated for 50 minutes at room temperature, then 25 ul of detection mix (30 uM resazurin, 36 ug/ml) was added and the mixture further incubated for 5 minutes at room temperature. The conversion of resazurin to resorufin was detected by fluorescent spectroscopy at Ex544 Em590 c/o 590.

Table 24a shows the wild type vs mutant selectivity profile of the top 5 examples of IDH1R132H inhibitors. The IDH1 wt assay was performed at 1× Km of NADPH as opposed to IDHR132H at 10× or 100× Km of NADPH. The second example showed no inhibition, even at 100 uM. Also, the first example has IC50=5.74 uM but is shifted significantly when assayed at 100× Km, indicating direct NADPH-competitive inhibitor. The selectivity between wild type vs mutant could be >20-fold.

TABLE 24a

| STRUCTURE | LDHa IC50 | LDHb IC50 | ICDH IC50 (uM) @ 4 uM (10× Km) NADPH | ICDH IC50 (uM) @ 40 uM NADPH | IC50 Ratio (40/4) | IDH1 wt IC50 @ 1× Km (uM) |
|---|---|---|---|---|---|---|
| 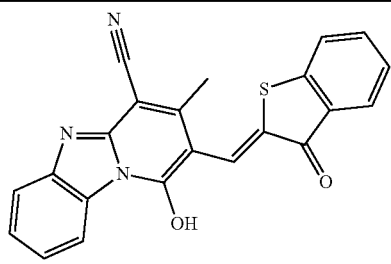 | 25.43 | 64.07 | 5.74 | >100 | 17.42 | 16.22 |

TABLE 24a-continued
| STRUCTURE | LDHa IC50 | LDHb IC50 | ICDH IC50 (uM) @ 4 uM (10x Km) NADPH | ICDH IC50 (uM) @ 40 uM NADPH | IC50 Ratio (40/4) | IDH1 wt IC50 @ 1x Km (uM) |
|---|---|---|---|---|---|---|
| 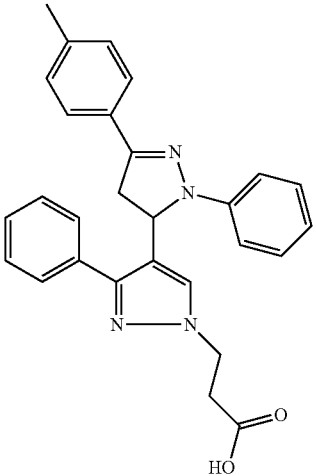 [SMILES: Cc1ccc(C2=NN(c3ccccc3)C(c3cn(CCC(=O)O)nc3-c3ccccc3)C2)cc1] | 5.92 | 17.40 | 12.26 | 41.40 | 3.38 | No inhibition |
| 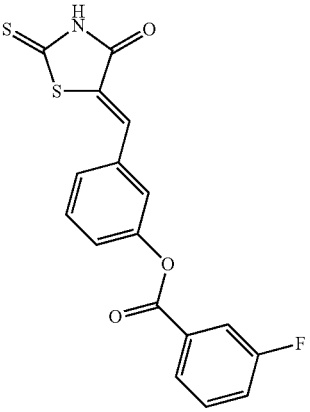 [SMILES: O=C1NC(=S)S/C1=C\c1cccc(OC(=O)c2cccc(F)c2)c1] | 8.61 | >100 | 12.79 | 14.70 | 1.15 | 19.23 |
| 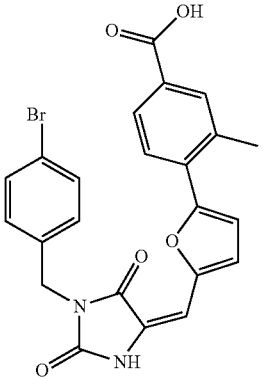 [SMILES: Cc1cc(C(=O)O)ccc1-c1ccc(/C=C2/NC(=O)N(Cc3ccc(Br)cc3)C2=O)o1] | 33.75 | >100 | 14.98 | 19.17 | 1.28 | 46.83 |
| 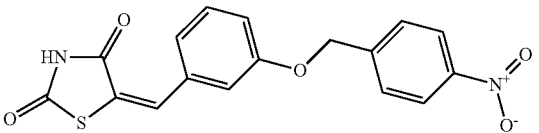 [SMILES: O=C1NC(=O)/C(=C\c2cccc(OCc3ccc([N+](=O)[O-])cc3)c2)S1] | 12.76 | >100 | 23.80 | 33.16 | 1.39 | 69.33 |

Additional exemplary compounds that inhibit IDH1R132H are provided below in Table 24b.
| Compound | No. |
|---|---|
| 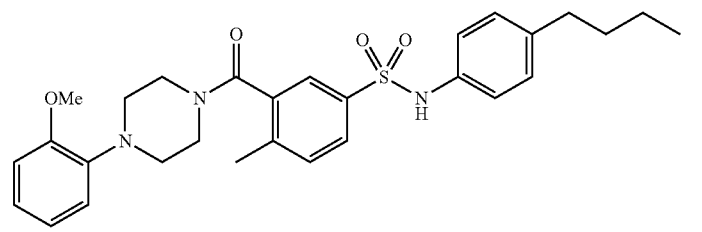 [SMILES: CCCCc1ccc(NS(=O)(=O)c2ccc(C)c(C(=O)N3CCN(c4ccccc4OC)CC3)c2)cc1] | 1 |
| 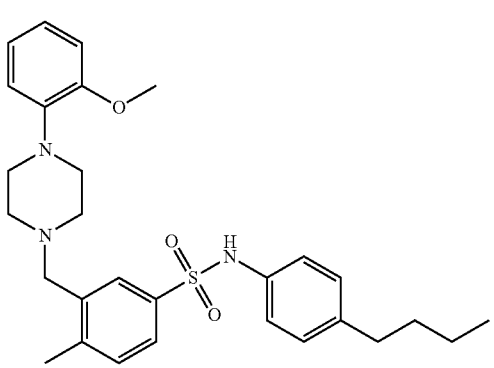 [SMILES: CCCCc1ccc(NS(=O)(=O)c2ccc(C)c(CN3CCN(c4ccccc4OC)CC3)c2)cc1] | 2 |
| 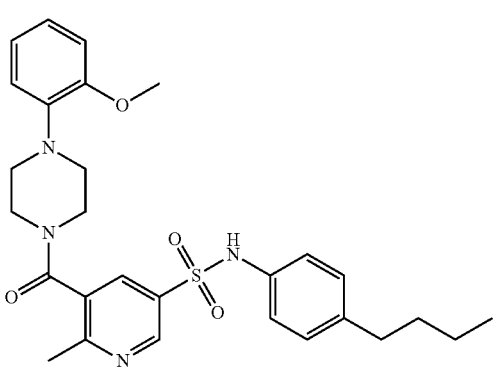 [SMILES: CCCCc1ccc(NS(=O)(=O)c2cnc(C)c(C(=O)N3CCN(c4ccccc4OC)CC3)c2)cc1] | 3 |
| 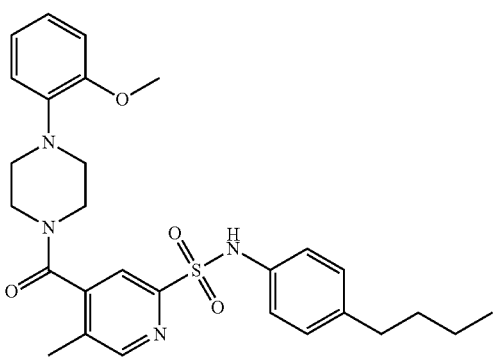 | 4 |

-continued
| Compound | No. |
|---|---|
| 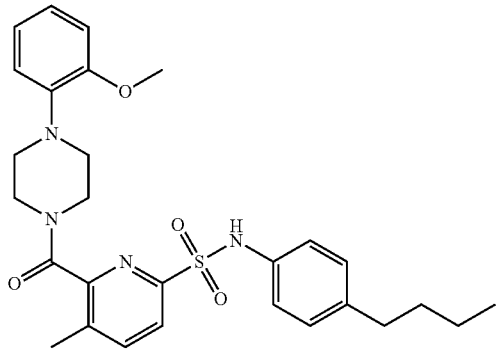 [SMILES: CCCCc1ccc(NS(=O)(=O)c2ccc(C)c(C(=O)N3CCN(c4ccccc4OC)CC3)n2)cc1] | 5 |
| 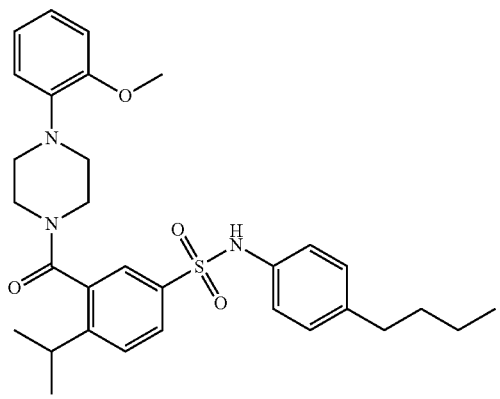 [SMILES: CCCCc1ccc(NS(=O)(=O)c2ccc(C(C)C)c(C(=O)N3CCN(c4ccccc4OC)CC3)c2)cc1] | 6 |
| 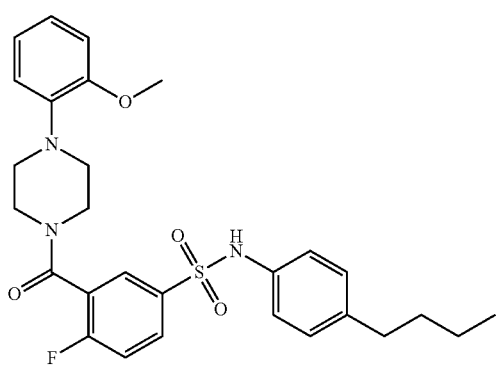 [SMILES: CCCCc1ccc(NS(=O)(=O)c2ccc(F)c(C(=O)N3CCN(c4ccccc4OC)CC3)c2)cc1] | 7 |
| 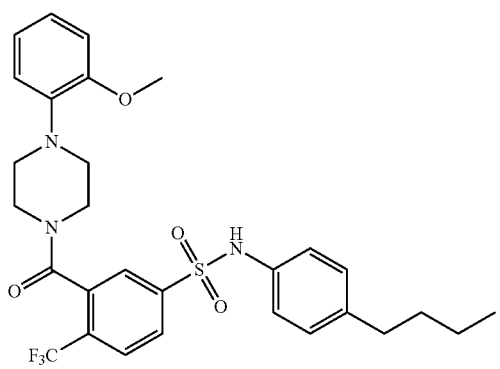 [SMILES: CCCCc1ccc(NS(=O)(=O)c2ccc(C(F)(F)F)c(C(=O)N3CCN(c4ccccc4OC)CC3)c2)cc1] | 8 |

| Compound | No. |
|---|---|
| 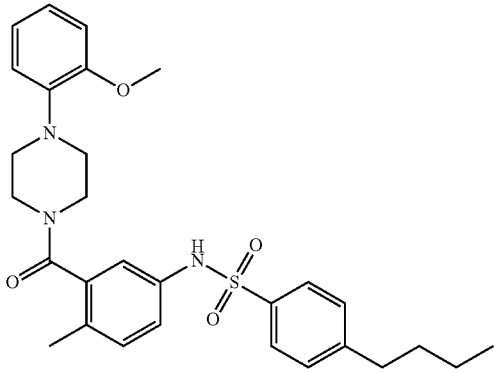 [SMILES: CCCCc1ccc(S(=O)(=O)Nc2ccc(C)c(C(=O)N3CCN(c4ccccc4OC)CC3)c2)cc1] | 9 |
| 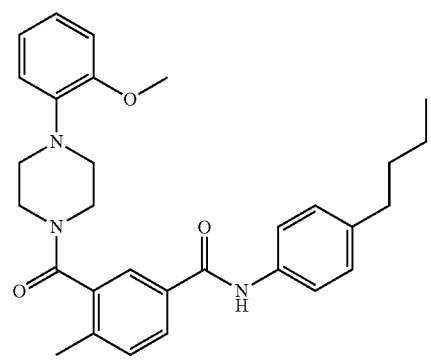 [SMILES: CCCCc1ccc(NC(=O)c2ccc(C)c(C(=O)N3CCN(c4ccccc4OC)CC3)c2)cc1] | 10 |
| 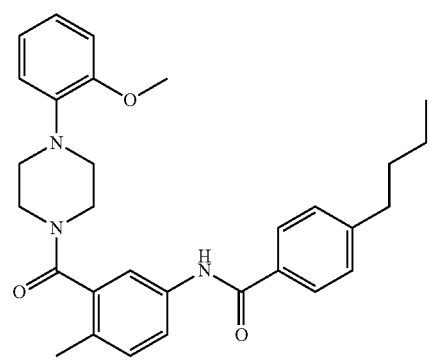 [SMILES: CCCCc1ccc(C(=O)Nc2ccc(C)c(C(=O)N3CCN(c4ccccc4OC)CC3)c2)cc1] | 11 |
| 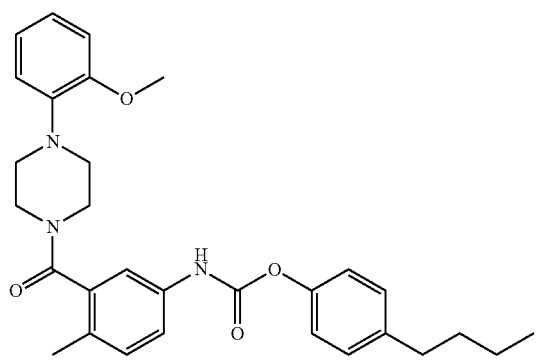 [SMILES: CCCCc1ccc(OC(=O)Nc2ccc(C)c(C(=O)N3CCN(c4ccccc4OC)CC3)c2)cc1] | 12 |

| Compound | No. |
|---|---|
| 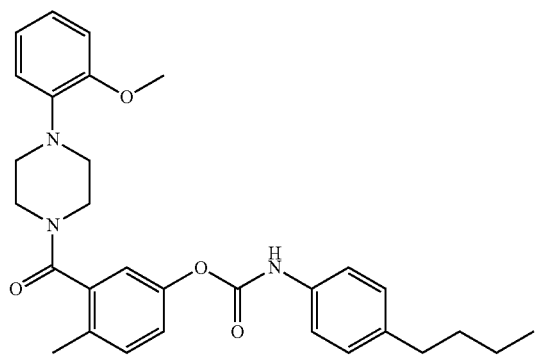 [SMILES: CCCCc1ccc(NC(=O)Oc2ccc(C)c(C(=O)N3CCN(c4ccccc4OC)CC3)c2)cc1] | 13 |
| 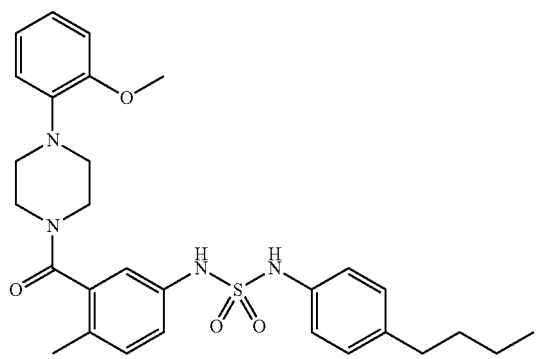 [SMILES: CCCCc1ccc(NS(=O)(=O)Nc2ccc(C)c(C(=O)N3CCN(c4ccccc4OC)CC3)c2)cc1] | 14 |
| 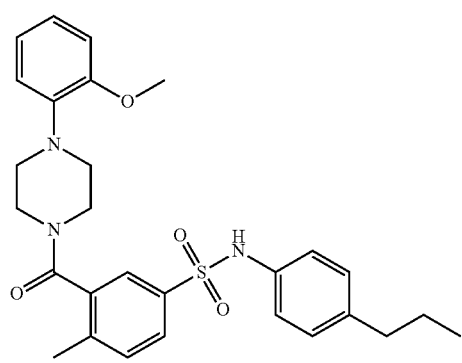 [SMILES: CCCc1ccc(NS(=O)(=O)c2ccc(C)c(C(=O)N3CCN(c4ccccc4OC)CC3)c2)cc1] | 15 |
| 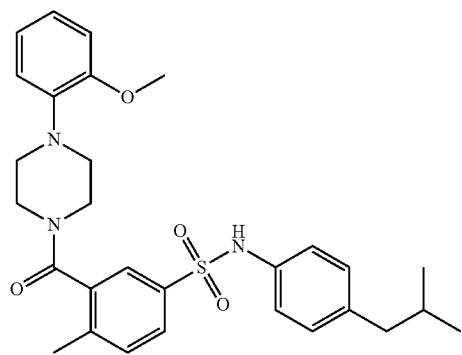 [SMILES: COc1ccccc1N1CCN(C(=O)c2cc(S(=O)(=O)Nc3ccc(CC(C)C)cc3)ccc2C)CC1] | 16 |

| Compound | No. |
|---|---|
| 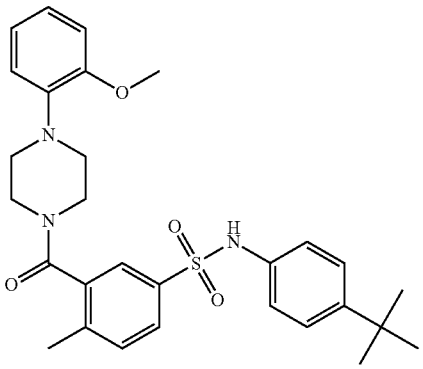 [SMILES: COc1ccccc1N1CCN(C(=O)c2cc(S(=O)(=O)Nc3ccc(C(C)(C)C)cc3)ccc2C)CC1] | 17 |
| 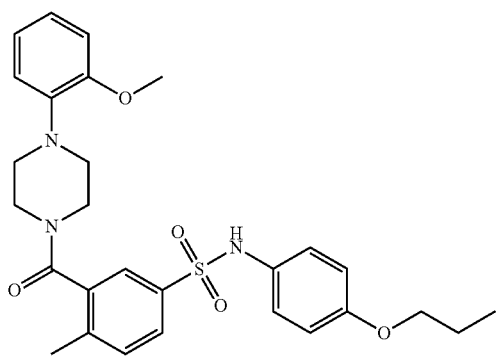 [SMILES: CCCOc1ccc(NS(=O)(=O)c2ccc(C)c(C(=O)N3CCN(c4ccccc4OC)CC3)c2)cc1] | 18 |
| 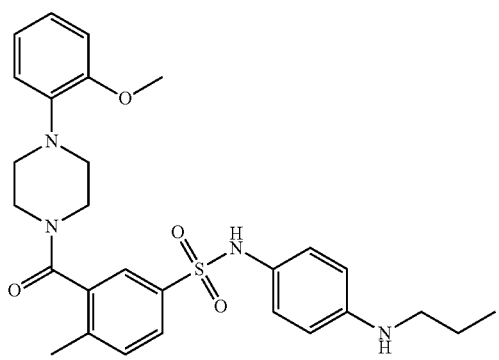 [SMILES: CCCNc1ccc(NS(=O)(=O)c2ccc(C)c(C(=O)N3CCN(c4ccccc4OC)CC3)c2)cc1] | 19 |
| 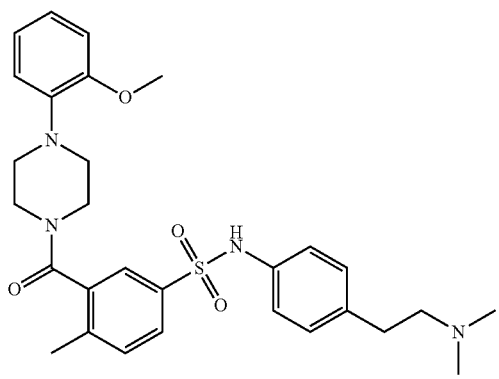 [SMILES: COc1ccccc1N1CCN(C(=O)c2cc(S(=O)(=O)Nc3ccc(CCN(C)C)cc3)ccc2C)CC1] | 20 |

| Compound | No. |
|---|---|
| 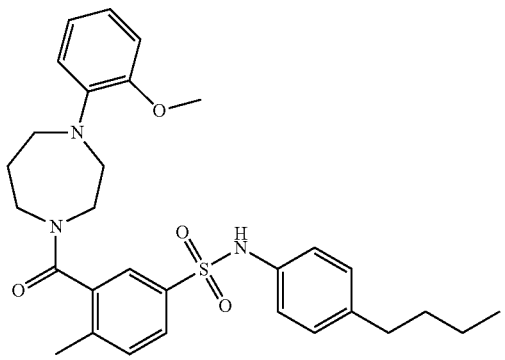 [SMILES: CCCCc1ccc(NS(=O)(=O)c2ccc(C)c(C(=O)N3CCCN(c4ccccc4OC)CC3)c2)cc1] | 21 |
| 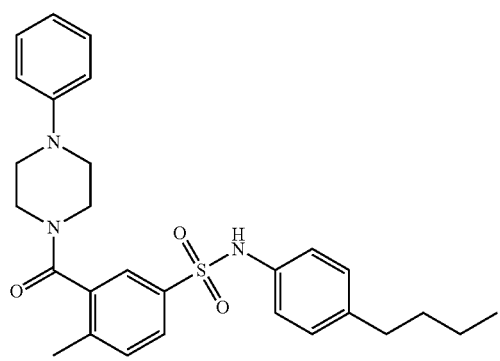 [SMILES: CCCCc1ccc(NS(=O)(=O)c2ccc(C)c(C(=O)N3CCN(c4ccccc4)CC3)c2)cc1] | 22 |
| 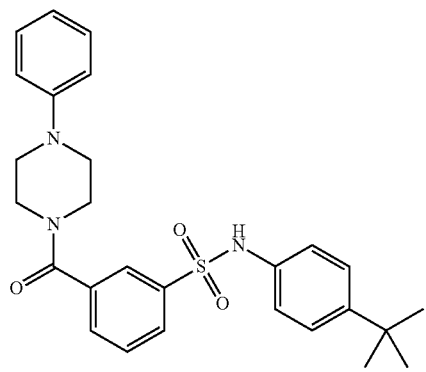 [SMILES: CC(C)(C)c1ccc(NS(=O)(=O)c2cccc(C(=O)N3CCN(c4ccccc4)CC3)c2)cc1] | 23 |
| 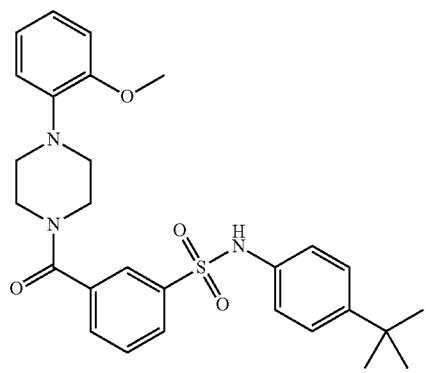 [SMILES: COc1ccccc1N1CCN(C(=O)c2cccc(S(=O)(=O)Nc3ccc(C(C)(C)C)cc3)c2)CC1] | 24 |

| Compound | No. |
|---|---|
| 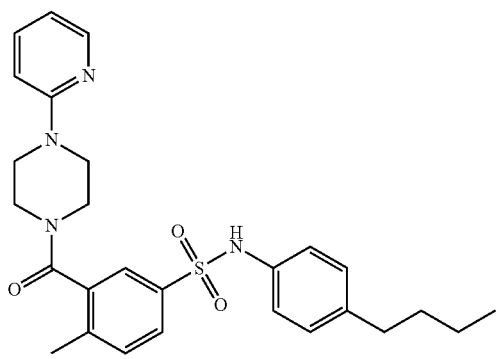 [SMILES: CCCCc1ccc(NS(=O)(=O)c2ccc(C)c(C(=O)N3CCN(c4ccccn4)CC3)c2)cc1] | 25 |
| 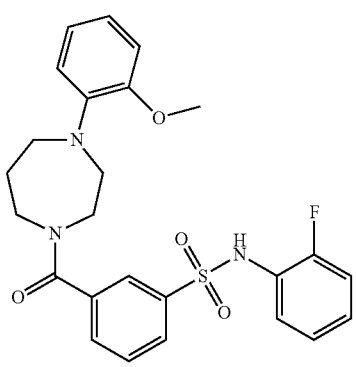 [SMILES: COc1ccccc1N1CCCN(C(=O)c2cccc(S(=O)(=O)Nc3ccccc3F)c2)CC1] | 26 |
| 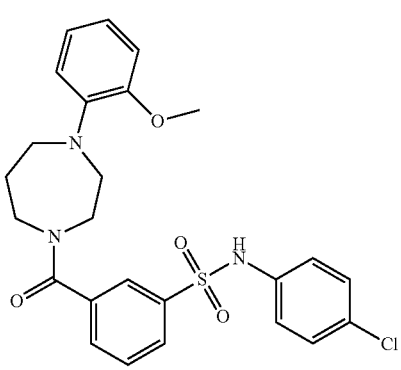 [SMILES: COc1ccccc1N1CCCN(C(=O)c2cccc(S(=O)(=O)Nc3ccc(Cl)cc3)c2)CC1] | 27 |
| 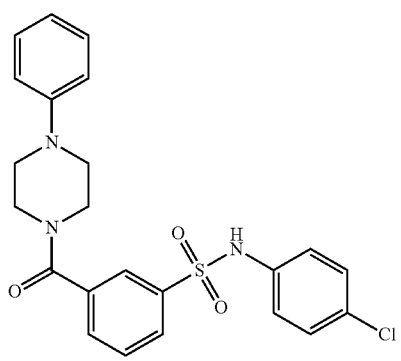 [SMILES: O=C(c1cccc(S(=O)(=O)Nc2ccc(Cl)cc2)c1)N1CCN(c2ccccc2)CC1] | 28 |

| Compound | No. |
|---|---|
| 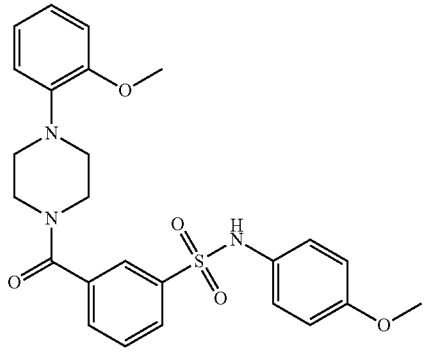 [SMILES: COc1ccc(NS(=O)(=O)c2cccc(C(=O)N3CCN(c4ccccc4OC)CC3)c2)cc1] | 29 |
| 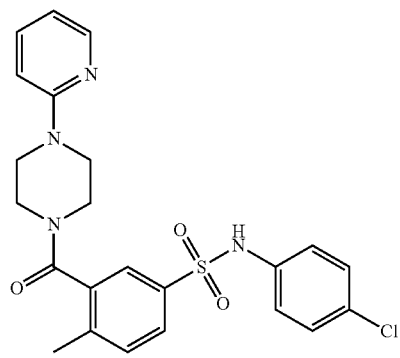 [SMILES: Cc1ccc(S(=O)(=O)Nc2ccc(Cl)cc2)cc1C(=O)N1CCN(c2ccccn2)CC1] | 30 |
| 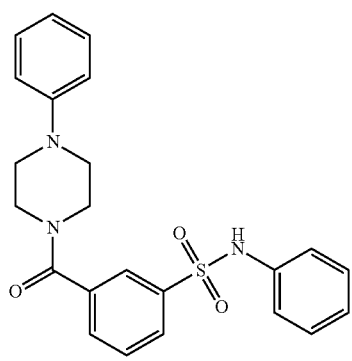 [SMILES: O=C(c1cccc(S(=O)(=O)Nc2ccccc2)c1)N1CCN(c2ccccc2)CC1] | 31 |
| 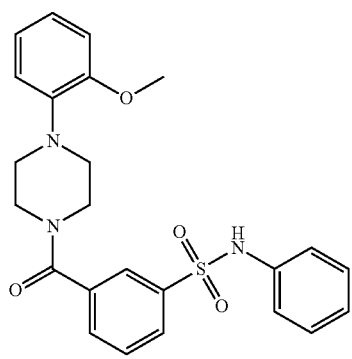 [SMILES: COc1ccccc1N1CCN(C(=O)c2cccc(S(=O)(=O)Nc3ccccc3)c2)CC1] | 32 |

-continued

| Compound | No. |
|---|---|
| | 33 |
| | 34 |
| | 35 |
| | 36 |

-continued
| Compound | No. |
|---|---|
| 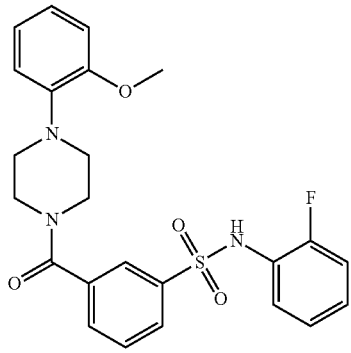 [SMILES: COc1ccccc1N1CCN(C(=O)c2cccc(S(=O)(=O)Nc3ccccc3F)c2)CC1] | 37 |
| 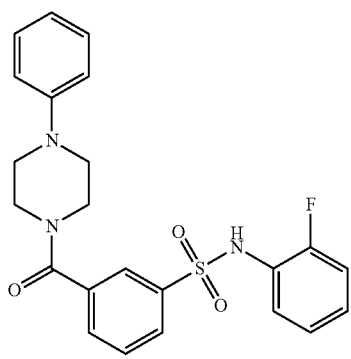 [SMILES: O=C(c1cccc(S(=O)(=O)Nc2ccccc2F)c1)N1CCN(c2ccccc2)CC1] | 38 |
| 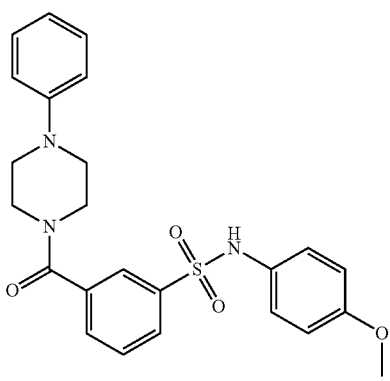 [SMILES: COc1ccc(NS(=O)(=O)c2cccc(C(=O)N3CCN(c4ccccc4)CC3)c2)cc1] | 39 |
| 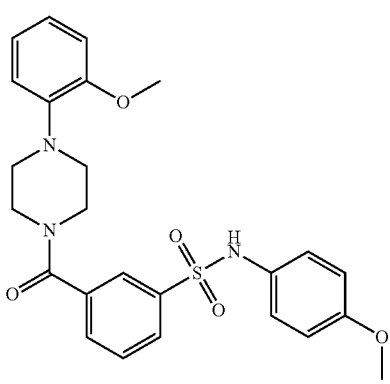 [SMILES: COc1ccc(NS(=O)(=O)c2cccc(C(=O)N3CCN(c4ccccc4OC)CC3)c2)cc1] | 40 |

-continued
| Compound | No. |
|---|---|
| 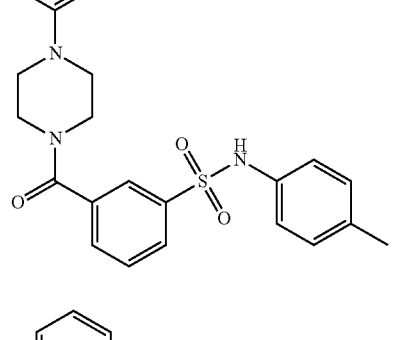 | 41 |
| 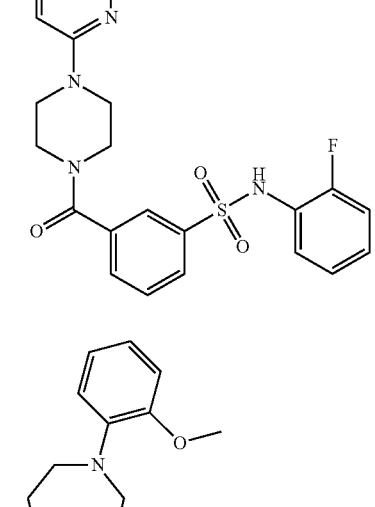 | 42 |
| 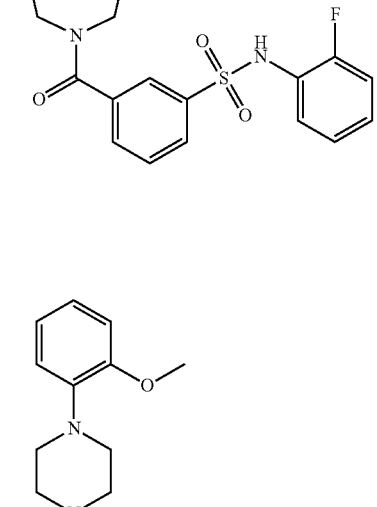 | 43 |
| 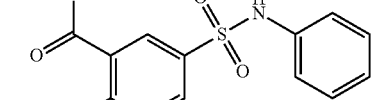 | 44 |

| Compound | No. |
|---|---|
| 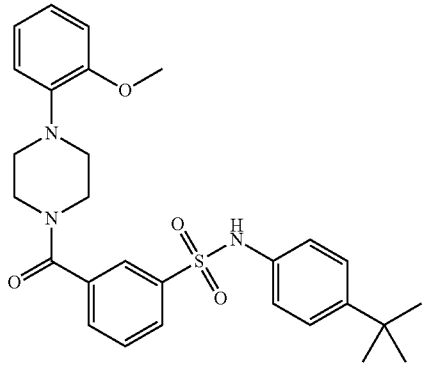 [SMILES: COc1ccccc1N1CCN(C(=O)c2cccc(S(=O)(=O)Nc3ccc(C(C)(C)C)cc3)c2)CC1] | 45 |
| 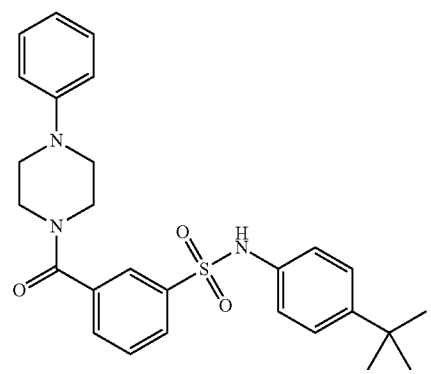 [SMILES: CC(C)(C)c1ccc(NS(=O)(=O)c2cccc(C(=O)N3CCN(c4ccccc4)CC3)c2)cc1] | 46 |
| 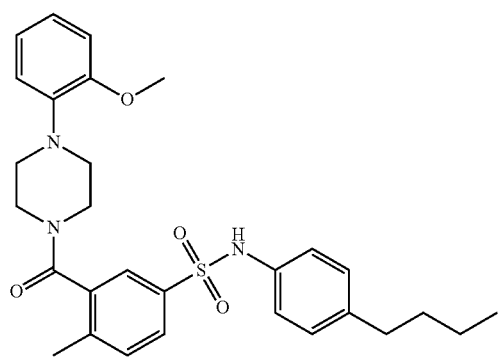 [SMILES: CCCCc1ccc(NS(=O)(=O)c2ccc(C)c(C(=O)N3CCN(c4ccccc4OC)CC3)c2)cc1] | 47 |
| 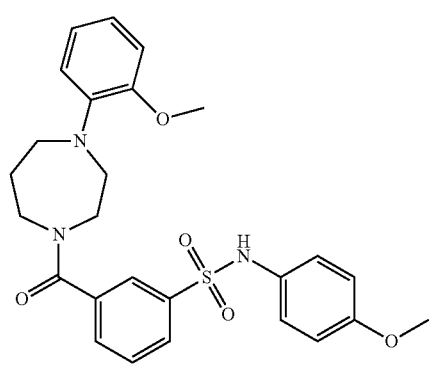 [SMILES: COc1ccc(NS(=O)(=O)c2cccc(C(=O)N3CCCN(c4ccccc4OC)CC3)c2)cc1] | 48 |

-continued
| Compound | No. |
|---|---|
| 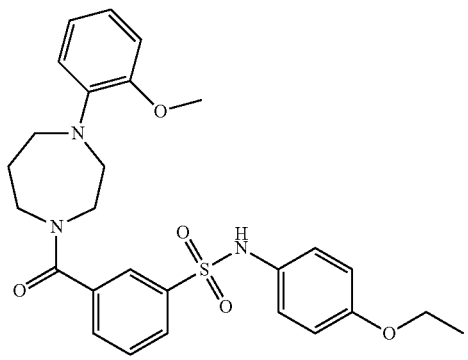 [SMILES: CCOc1ccc(NS(=O)(=O)c2cccc(C(=O)N3CCCN(c4ccccc4OC)CC3)c2)cc1] | 49 |
| 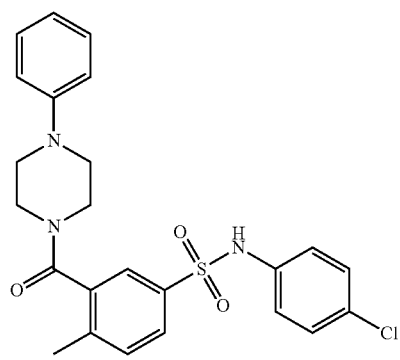 [SMILES: Cc1ccc(S(=O)(=O)Nc2ccc(Cl)cc2)cc1C(=O)N1CCN(c2ccccc2)CC1] | 50 |
| 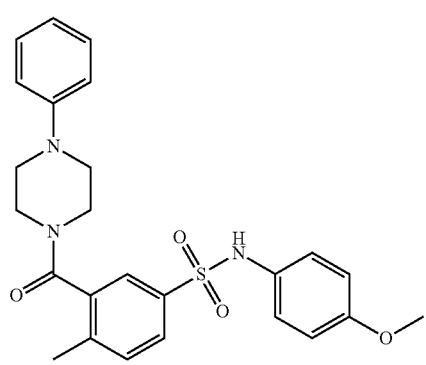 [SMILES: COc1ccc(NS(=O)(=O)c2ccc(C)c(C(=O)N3CCN(c4ccccc4)CC3)c2)cc1] | 51 |
| 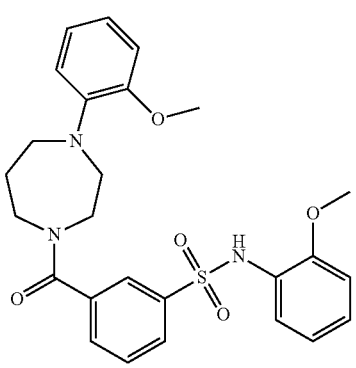 [SMILES: COc1ccccc1NS(=O)(=O)c1cccc(C(=O)N2CCCN(c3ccccc3OC)CC2)c1] | 52 |

-continued

| Compound | No. |
|---|---|
| (structure) | 53 |
| (structure) | 54 |
| (structure) | 55 |
| (structure) | 56 |

-continued
| Compound | No. |
|---|---|
| 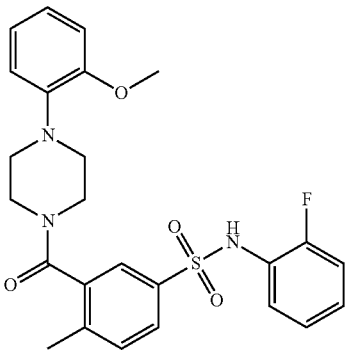 [SMILES: COc1ccccc1N1CCN(C(=O)c2cc(S(=O)(=O)Nc3ccccc3F)ccc2C)CC1] | 57 |
| 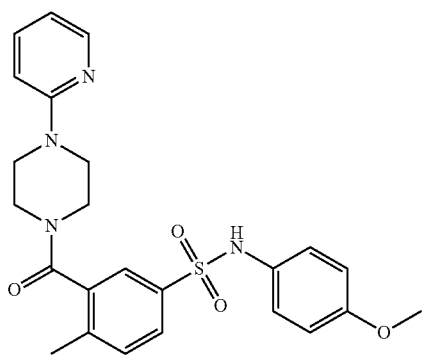 [SMILES: COc1ccc(NS(=O)(=O)c2ccc(C)c(C(=O)N3CCN(c4ccccn4)CC3)c2)cc1] | 58 |
| 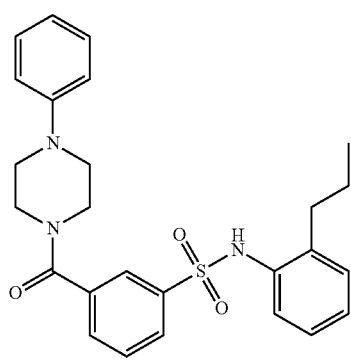 [SMILES: CCCc1ccccc1NS(=O)(=O)c1cccc(C(=O)N2CCN(c3ccccc3)CC2)c1] | 59 |
| 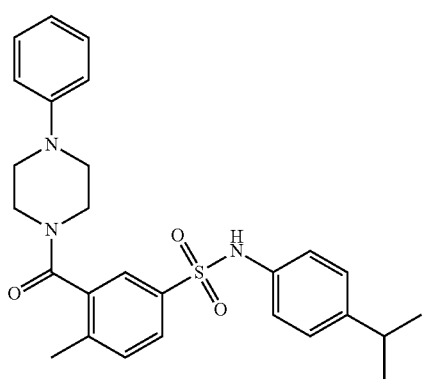 [SMILES: Cc1ccc(S(=O)(=O)Nc2ccc(C(C)C)cc2)cc1C(=O)N1CCN(c2ccccc2)CC1] | 60 |

| Compound | No. |
|---|---|
| (structure: 4-(pyridin-2-yl)piperazine-1-carbonyl attached to 4-methylbenzene with sulfonamide N-H linked to 4-ethoxyphenyl) | 61 |
| (structure: 4-(2-methoxyphenyl)-1,4-diazepane-1-carbonyl attached to benzene with sulfonamide N-H linked to 4-isopropylphenyl) | 62 |
| (structure: 4-(pyrimidin-2-yl)piperazine-1-carbonyl attached to benzene with sulfonamide N-H linked to 4-butylphenyl) | 63 |
| (structure: 4-(3-chloro-5-methylpyridin-2-yl)piperazine-1-carbonyl attached to benzene with sulfonamide N-H linked to 4-butylphenyl) | 64 |

| Compound | No. |
|---|---|
| (structure) | 65 |
| (structure) | 66 |
| (structure) | 67 |
| (structure) | 68 |

| Compound | No. |
|---|---|
| 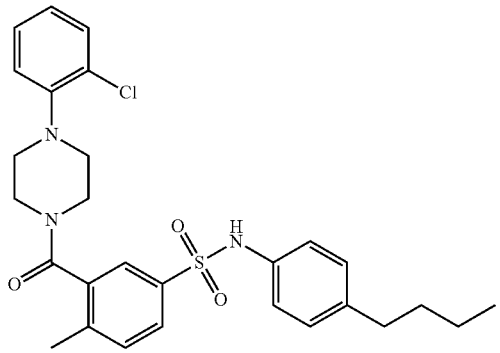 | 69 |
| 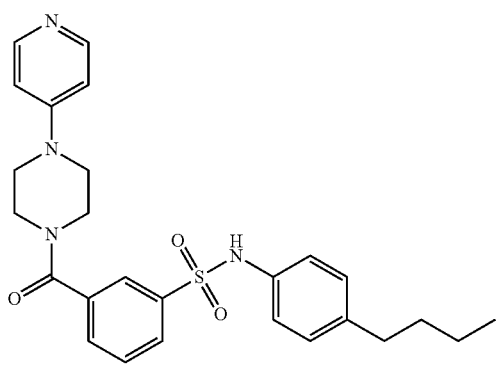 [SMILES: CCCCc1ccc(NS(=O)(=O)c2cccc(C(=O)N3CCN(c4ccncc4)CC3)c2)cc1] | 70 |
| 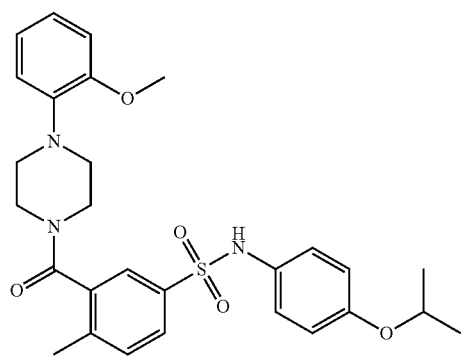 [SMILES: COc1ccccc1N1CCN(C(=O)c2cc(S(=O)(=O)Nc3ccc(OC(C)C)cc3)ccc2C)CC1] | 71 |
| 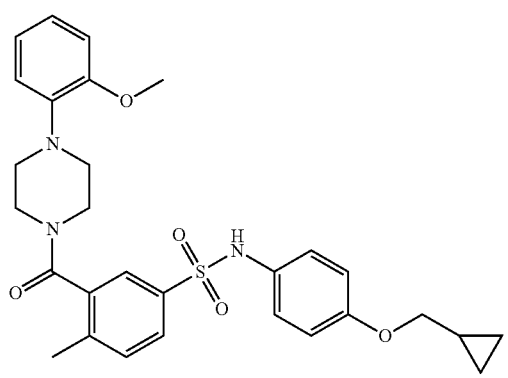 [SMILES: COc1ccccc1N1CCN(C(=O)c2cc(S(=O)(=O)Nc3ccc(OCC4CC4)cc3)ccc2C)CC1] | 72 |

| Compound | No. |
|---|---|
| 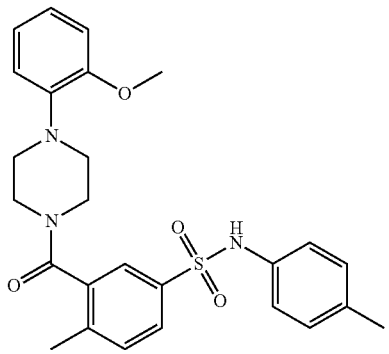 [SMILES: COc1ccccc1N1CCN(C(=O)c2cc(S(=O)(=O)Nc3ccc(C)cc3)ccc2C)CC1] | 73 |
| 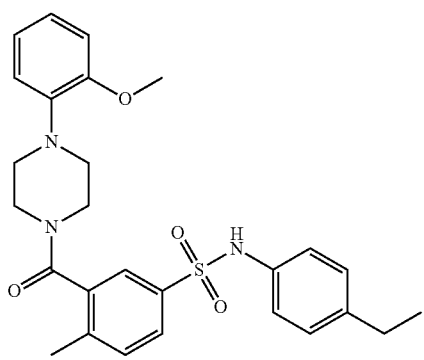 [SMILES: CCc1ccc(NS(=O)(=O)c2ccc(C)c(C(=O)N3CCN(c4ccccc4OC)CC3)c2)cc1] | 74 |
| 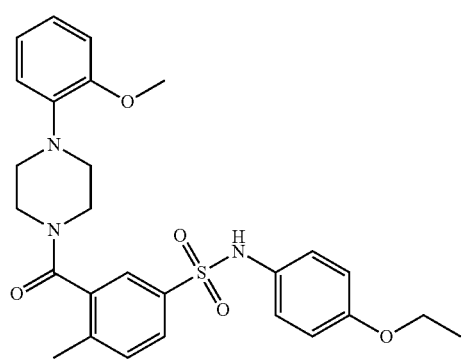 [SMILES: CCOc1ccc(NS(=O)(=O)c2ccc(C)c(C(=O)N3CCN(c4ccccc4OC)CC3)c2)cc1] | 75 |
| 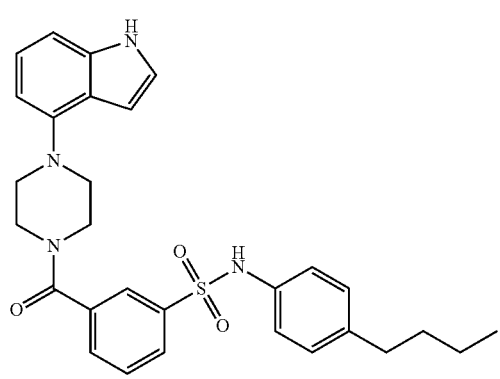 [SMILES: CCCCc1ccc(NS(=O)(=O)c2cccc(C(=O)N3CCN(c4cccc5[nH]ccc45)CC3)c2)cc1] | 76 |

| Compound | No. |
|---|---|
| 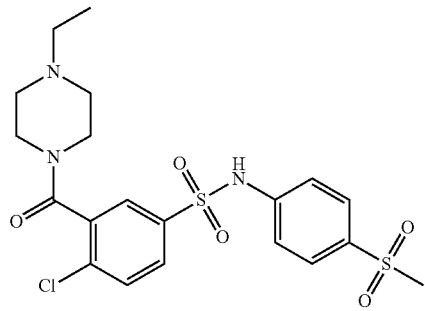 [SMILES: CCN1CCN(C(=O)c2cc(S(=O)(=O)Nc3ccc(S(C)(=O)=O)cc3)ccc2Cl)CC1] | 77 |
| 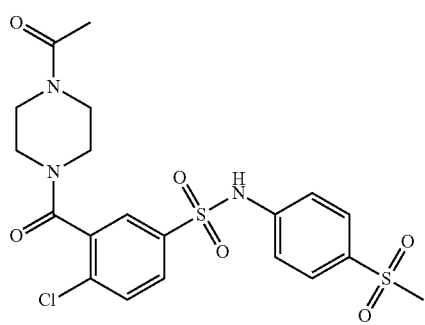 [SMILES: CC(=O)N1CCN(C(=O)c2cc(S(=O)(=O)Nc3ccc(S(C)(=O)=O)cc3)ccc2Cl)CC1] | 78 |
| 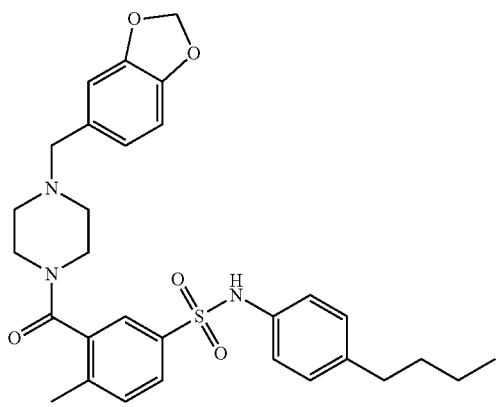 [SMILES: CCCCc1ccc(NS(=O)(=O)c2ccc(C)c(C(=O)N3CCN(Cc4ccc5c(c4)OCO5)CC3)c2)cc1] | 79 |
| 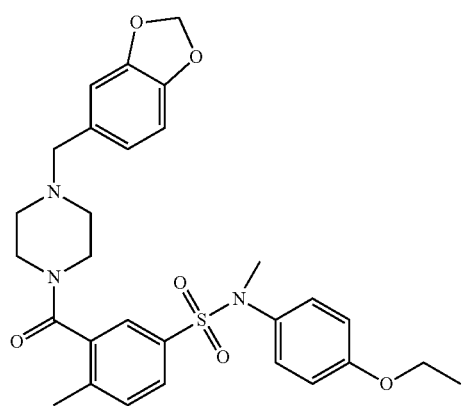 [SMILES: CCOc1ccc(N(C)S(=O)(=O)c2ccc(C)c(C(=O)N3CCN(Cc4ccc5c(c4)OCO5)CC3)c2)cc1] | 80 |

| Compound | No. |
|---|---|
| 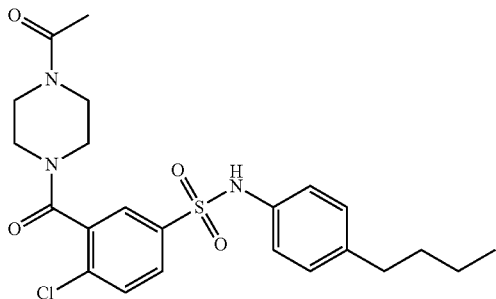 [SMILES: CCCCc1ccc(NS(=O)(=O)c2ccc(Cl)c(C(=O)N3CCN(C(C)=O)CC3)c2)cc1] | 81 |
| 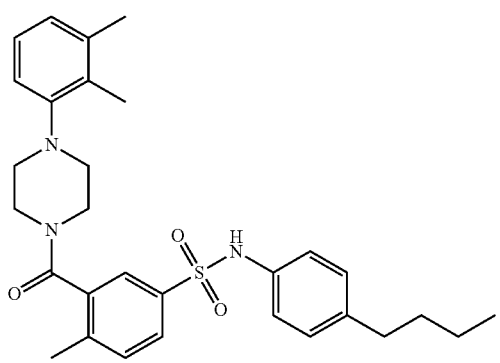 [SMILES: CCCCc1ccc(NS(=O)(=O)c2ccc(C)c(C(=O)N3CCN(c4cccc(C)c4C)CC3)c2)cc1] | 82 |
| 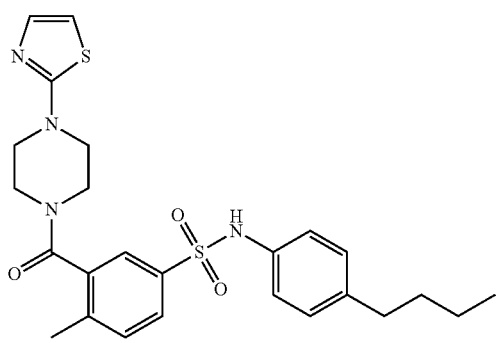 [SMILES: CCCCc1ccc(NS(=O)(=O)c2ccc(C)c(C(=O)N3CCN(c4nccs4)CC3)c2)cc1] | 83 |
| 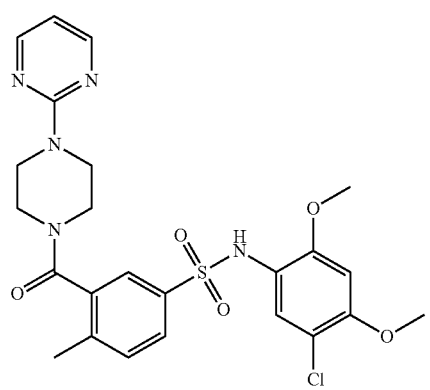 [SMILES: COc1cc(OC)c(NS(=O)(=O)c2ccc(C)c(C(=O)N3CCN(c4ncccn4)CC3)c2)cc1Cl] | 84 |

-continued
| Compound | No. |
|---|---|
| 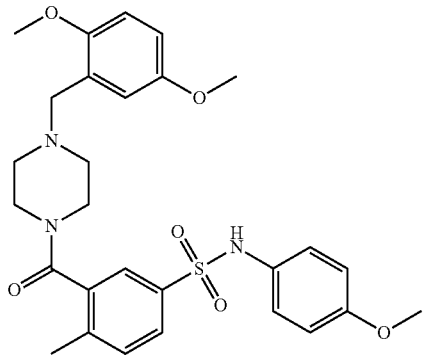 [SMILES: COc1ccc(NS(=O)(=O)c2ccc(C)c(C(=O)N3CCN(Cc4cc(OC)ccc4OC)CC3)c2)cc1] | 85 |
| 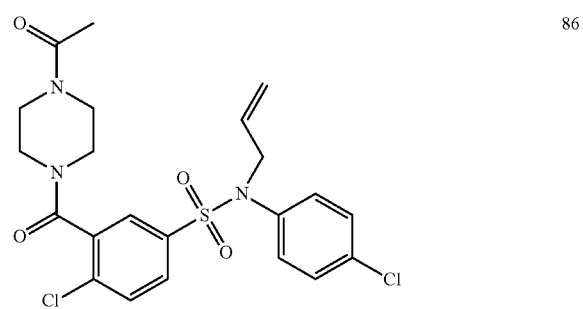 | 86 |
| 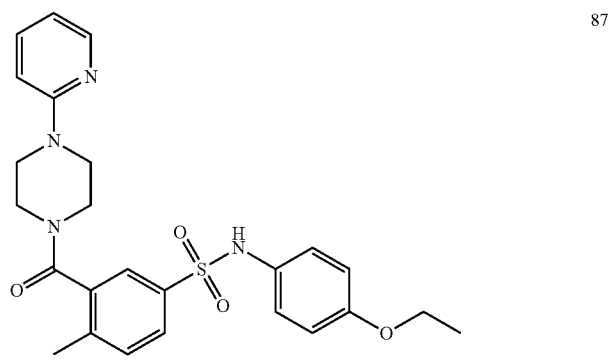 | 87 |
| 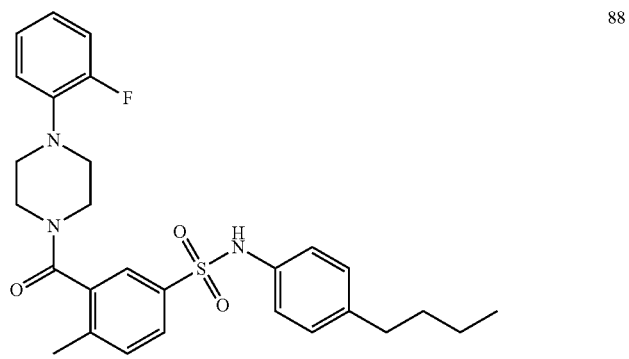 | 88 |

| Compound | No. |
|---|---|
| 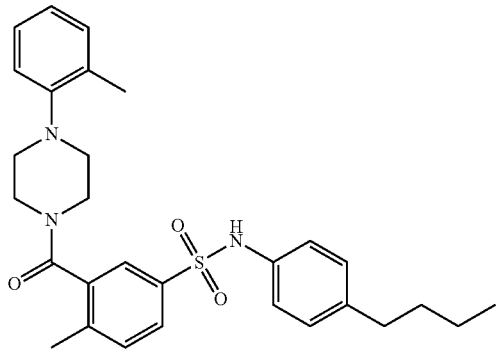 [SMILES: CCCCc1ccc(NS(=O)(=O)c2ccc(C)c(C(=O)N3CCN(c4ccccc4C)CC3)c2)cc1] | 89 |
| 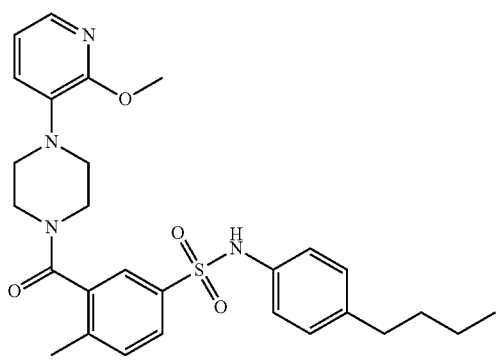 [SMILES: CCCCc1ccc(NS(=O)(=O)c2ccc(C)c(C(=O)N3CCN(c4cccnc4OC)CC3)c2)cc1] | 90 |
| 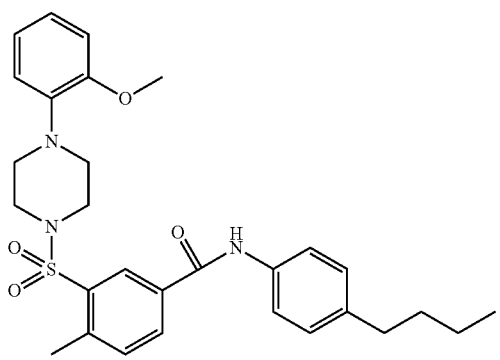 [SMILES: CCCCc1ccc(NC(=O)c2ccc(C)c(S(=O)(=O)N3CCN(c4ccccc4OC)CC3)c2)cc1] | 91 |

| Compound | No. |
|---|---|
| 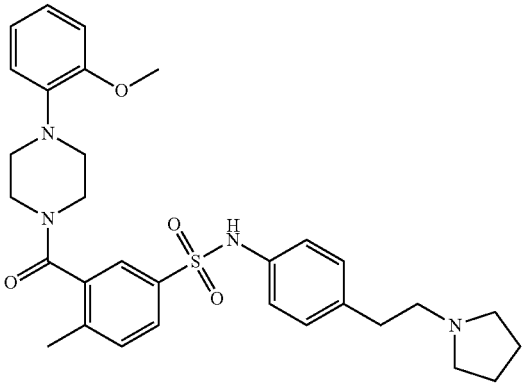 [SMILES: COc1ccccc1N1CCN(C(=O)c2cc(S(=O)(=O)Nc3ccc(CCN4CCCC4)cc3)ccc2C)CC1] | 92 |

Example 10

The Mutant Enzyme IDH2-R172K has Elevated NADPH reductive catalysis activity as compared to wildtype IDH2 enzyme.

Figure 35:
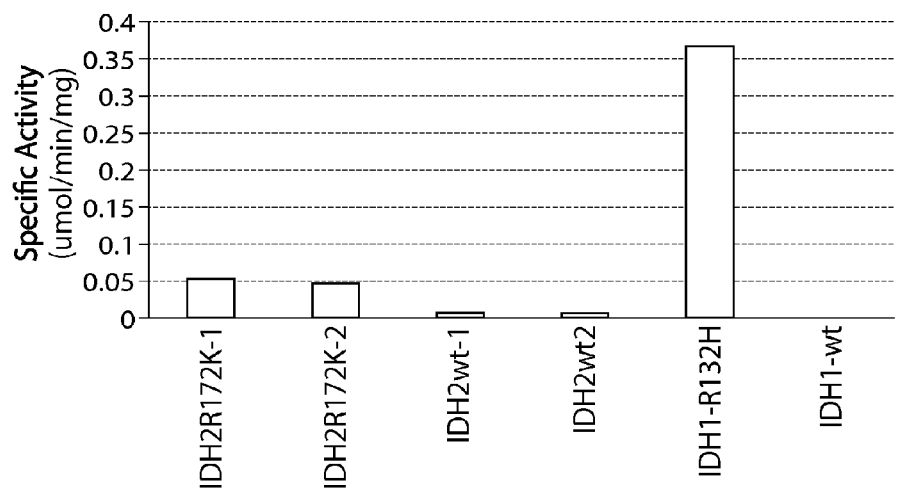
FIG. 35 is a bar graph depicting elevated NADPH reductive catalysis activity in IDH2-R172K mutant enzyme as compared to wildtype IDH2.

NADPH reduction activity was measured for the enzymes IDH2-R172K, IDH2-wildtype, IDH1-R132H and IDH1-wildtype. The final reactant concentrations for each reaction were as follows: 20 mM Tris 7.5, 150 mM NaCl, 2 mM $MnCl_2$, 10% glycerol, 0.03% BSA, enzyme (1-120 µg/mL), 1 mM NADPH, and 5 mM αKG (alpha ketoglutarate). The resulting specific activities (µmol/min/mg) are presented in the graph in FIG. 35. The results indicate that the mutant IDH2 has elevated reductive activity as compared to wild-type IDH2, even though both the mutant and wildtype IDH2 enzymes were able to make 2HG (2-hydroxyglutarate) at saturating levels of reactants αKG and NADPH.

Example 11 2-HG Accumulates in AML with IDH1/2 Mutations

Patients and Clinical Data

Peripheral blood and bone marrow were collected from AML patients at the time of diagnosis and at relapse, following REB approved informed consent. The cells were separated by ficol hypaque centrifugation, and stored at −150° C. in 10% DMSO, 40% FCS and 50% alpha-MEM medium. Patient sera were stored at −80° C. Cytogenetics and molecular testing were performed in the diagnostic laboratory of the University Health Network (Toronto, Canada). A subgroup of patients (n=132) was given consistent initial treatment using a standard induction and consolidation chemotherapy regimen consisting of daunorubicin and cytarabine.

IDH1 and IDH2 Genotyping

DNA was extracted from leukemic cells and cell lines using the Qiagen Puregene kit (Valencia Calif.). For a subset of samples (n=96), RNA was extracted from leukemic cells using a Qiagen RNeasy kit, and reverse transcribed into cDNA for IDH1 and IDH2 genotyping. IDH1 and IDH2 genotype was determined at the Analytical Genetics Technology Centre at the University Health Network (Toronto, Canada) using a Sequenom MassARRAY™ platform (Sequenom, San Diego, Calif.). Positive results were confirmed by direct sequencing on an ABI PRISM 3130XL genetic analyzer (Applied Biosystems, Foster City, Calif.).

Cell Lines

AML cell lines (OCI/AML-1, OCI/AML-2, OCI/AML-3, OCI/AML-4, OCI/AML-5, HL-60, MV-4-11, THP-1, K562, and KG1A) and 5637 cells were obtained from the laboratory of Mark Minden (Ontario Cancer Institute, Toronto, Canada). Primary AML cells were cultured in alpha-MEM media supplemented with 20% fetal bovine serum, and 10% 5637 cell conditioned media as previously described[13]. Growth curves were generated by counting viable cells as assessed by trypan blue exclusion on a Vi-CELL automated cell counter (Beckman Coulter, Fullarton, Calif.).

Expression/Purification of IDH1 and IDH2 Proteins

The human IDH1 cDNA (ref. ID NM_005896) and IDH2 cDNA (ref. ID NM_002168) were purchased from OriGene Technologies (Rockville, Md.). For expression in *E. coli*, the coding region was amplified by PCR using primers designed to add NDEI and XHO1 restrictions sites at the 5' and 3' ends respectively. The resultant fragments for IDH1 (full length) and IDH2 (residues 40-452) were cloned into vector pET41a (EMD Biosciences, Madison, Wis.) to enable the *E. coli* expression of C-terminal His8-tagged protein. Site directed mutagenesis was performed on the pET41a-IDH1 and pET41a-IDH2 plasmid using the QuikChange® Lightning Site-Directed Mutagenesis Kit (Stratagene, La Jolla, Calif.) to change C394 to T in the IDH1 cDNA, resulting in the R132C mutation, and to change G515 to A in the IDH2 cDNA, resulting in the R172K mutation. Wild-type and mutant IDH1 proteins were expressed in and purified from the *E. coli* Rosetta™ (DE3) strain according to manufacturer's instructions (Invitrogen, Carlsbad, Calif.). Overexpression of IDH2 protein was accomplished by co-transfection of expression plasmids encoding respective IDH2 clones and pG-KJE8 expressing chaperone proteins.

IDH1/2 Activity Assays

Enzymatic activity was assessed by following the change in NADPH absorbance at 340 nm over time in an SFM-400 stopped-flow spectrophotometer (BioLogic, Knoxville, Tenn.) in the presence of isocitrate and NADP+ (forward reaction), or α-KG and NADPH (reverse reaction). All reactions were performed in standard enzyme reaction buffer (150 mM NaCl, 20 mM Tris-Cl, pH 7.5, 10 mM $MgCl_2$ and 0.03% (w/v) bovine serum albumin). For determination of kinetic parameters, sufficient enzyme was added to give a linear reaction for 1 to 5 seconds. Enzymatic binding constants were determined using curve fitting algorithms to standard kinetic models with the Sigmaplot software package (Systat Software, San Jose, Calif.). For determination of kcat, enzyme was incubated with 5× Km of substrate and cofactor; consumption of NADPH or NADP was determined by a change in the $OD_{340}$ over time. In both cases an extinction coefficient of 6200 $M^{-1}$ $cm^{-1}$ was used for NADPH.

2-HG and Metabolite Analysis

Metabolites were extracted from cultured cells, primary leukemic cells, and sera using 80% aqueous methanol (−80° C.) as previously described. For cell extraction, frozen biopsies were thawed quickly at 37° C., and an aliquot of 2 million cells was spun down at 4° C. The pellet was resuspended in −80° C. 80% methanol. For serum extraction, 1 ml of serum was thawed quickly and mixed with 4 ml −80° C. methanol. All extracts were spun at 13000 rpm at 4° C. to remove precipitate, dried at room temperature, and stored at −80° C. until analysis by LC-MS. Metabolite levels (2-HG, α-KG, succinate, fumarate, and malate) were determined by ion paired reverse phase LC coupled to negative mode electrospray triple-quadropole MS using multiple reaction monitoring, and integrated elution peaks were compared with metabolite standard curves for absolute quantification as described.

Statistical Analysis

Fisher's exact test was used to test for differences in categorical variables between IDH1/2 wt and IDH1/2 mutant patients. One way ANOVA followed by a student's t-test with correction for multiple comparisons was used to test for differences in IDH1 activity and metabolite concentrations. Differences with p<0.05 were considered significant.

Results

In order to investigate the role of IDH1 R132 mutations in AML, leukemic cells obtained at initial presentation, from a series of 145 AML patients treated at the Princess Margaret Hospital with the aim of identifying mutant samples in our viable cell tissue bank were genotyped. Heterozygous IDH1 R132 mutations were found in 11 (8%) of these patients (Table 25). The spectrum of IDH1 mutations observed in AML appears to differ from that seen in CNS tumors. In the CNS, the majority of mutations (80-90%) are IDH1 R132H substitutions, whereas 5, 4, and 2 patients with IDH1 R132H, R132C, and R132G mutations, respectively (Table 25), were observed. In four cases, leukemic cells were also available from samples taken at the time of relapse. The IDH1 mutation was retained in 4/4 of these samples (Table 25). One of the patients harboring an IDH1 mutation had progressed to AML from an earlier myelodysplastic syndrome (MDS). When cells from the prior MDS in this patient were analyzed, IDH1 was found to be wild-type. An additional 14 patients with MDS were genotyped, and all patients were found to be wild-type for IDH1, suggesting that IDH1 mutations are not a common feature of this disease. In samples from a subset of IDH1 mutant patients (n=8), reverse transcribed RNA was used for genotyping in order to assess the relative expression of mutant and wild-type alleles. Seqenom genotyping showed balanced allele peaks for these samples, indicating that both the wild-type and mutant genes are expressed. Ten established AML cell lines were also genotyped (OCI/AML-1, OCI/AML-2, OCI/AML-3, OCI/AML-4, OCI/AML-5, HL-60, MV-4-11, THP-1, K562, and KG1A) and none carried an IDH1 R132 mutation.

Figure 36A:
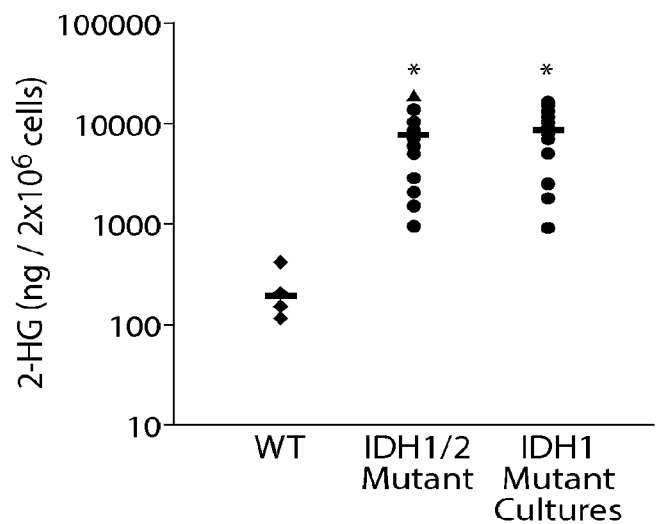
FIGS. 36A-C are graphs depicting the following: (A) Extracts from IDH1/2 wt (n=10), and IDH1/2 mutant (n=16) patient leukemia cells obtained at presentation and relapse, and IDH1 R132 mutant leukemia cells grown in culture for 14 days (n=14) analyzed by LC-MS to measure levels of 2-HG; and (B) 2-HG measured in serum of patients with IDH1 wt or IDH1 R132 mutant leukemia. In (A) and (B), each point represents an individual patient sample. Diamonds represent wildtype, circles represent IDH1 mutants, and triangles represent IDH2 mutants. Horizontal bars indicate the mean. (*) indicates a statistically significant difference relative to wild-type patient cells (p<0.05). (C) depicts In vitro growth curves of IDH1 R132 mutant and IDH1 wild-type AML cells.
Figure 36B:
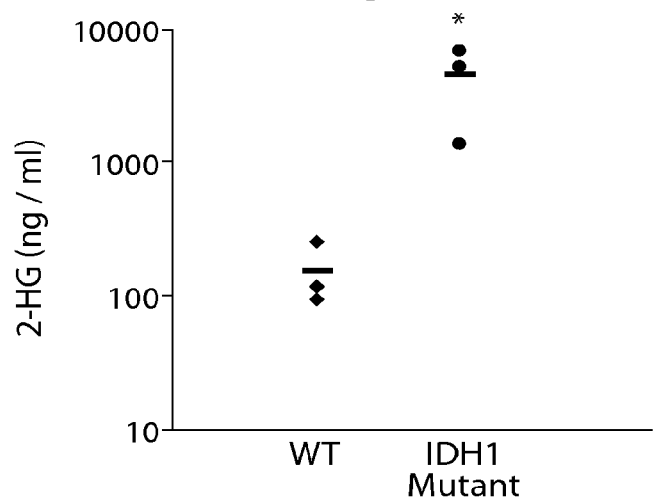

A metabolite screening assay to measure 2-HG in this set of AML samples was set up. Levels of 2-HG were approximately 50-fold higher in samples harboring an IDH1 R132 mutation (Table 25, FIG. 36A, Table 26). 2-HG was also elevated in the sera of patients with IDH1 R132 mutant AML (FIG. 36B). There was no relationship between the specific amino acid substitution at residue 132 of IDH1 and the level of 2-HG in this group of patients.

TABLE 25

Identification of 13 AML patients bearing an IDH1 R132 or IDH2 R172 mutation*

| Patient ID | Mutation | Amino acid change | FAB subtype | NPM1 and FLT3 status | Cytogenetic profile | Genotype at relapse | 2-HG level (ng/2 × $10^6$ cells) |
|---|---|---|---|---|---|---|---|
| IDH1 mutations | | | | | | | |
| 090108 | G/A | R132H | M4 | na | Normal | na | 2090 |
| 090356 | G/A | R132H | na | na | a | na | 1529 |
| 0034 | C/T | R132C | M5a | Normal | Normal | na | 10285 |
| 0086 | C/G | R132G | M2 | Normal | Normal | na | 10470 |
| 0488 | C/T | R132C | M0 | Normal | Normal | R132C | 13822 |
| 8587 | G/A | R132H | na | Normal | Normal | na | 5742 |
| 8665 | C/T | R132C | M1 | na | Normal | na | 7217 |
| 8741 | G/A | R132H | M4 | NPM1 | Normal | R132H | 6419 |
| 9544 | C/G | R132G | na | na | Normal | R132G | 4962 |
| 0174268 | G/A | R132H | M1 | NPM1 | Normal | R132H | 8464 |
| 090148 | C/T | R132C | M1 | na | 46, xx, i(7) (p10) [20] | na | na |
| IDH2 mutations | | | | | | | |
| 9382 | G/A | R172K | M0 | Normal | Normal | na | 19247 |
| 0831 | G/A | R172K | M1 | Normal | Normal | na | 15877 |

*NPM1 denotes nucleophosmin 1, and FLT FMS-related tyrosine kinase 3. na indicates that some data was not available for some patients.

TABLE 26

Metabolite concentrations in individual IDH½ mutant and wild-type AML cells*

| Sample | IDH½ Genotype | 2-HG (ng/2 × 10⁶ cells) | α-KG (ng/2 × 10⁶ cells) | Malate (ng/2 × 10⁶ cells) | Fumarate (ng/2 × 10⁶ cells) | Succinate (ng/2 × 10⁶ cells) |
|---|---|---|---|---|---|---|
| 0034 | R132 | 10285 | 125 | 192 | 239 | 2651 |
| 0086 | R132G | 10470 | 124 | 258 | 229 | 3043 |
| 0488 | R132 | 13822 | 95 | 184 | 193 | 2671 |
| 8587 | R132H | 5742 | 108 | 97 | 95 | 1409 |
| 8665 | R132 | 7217 | 137 | 118 | 120 | 1648 |
| 8741 | R132H | 6419 | 87 | 66 | 61 | 938 |
| 9544 | R132 | 4962 | 95 | 76 | 72 | 1199 |
| 0174268 | R132H | 8464 | 213 | 323 | 318 | 2287 |
| 090356 | R132 | 1529 | 138 | 657 | 366 | 1462 |
| 090108 | R132H | 2090 | Na | 246 | 941 | 3560 |
| 090148† | R132 | na | Na | na | na | Na |
| 8741‡ | R132H | 2890 | 131 | 113 | 106 | 1509 |
| 9554‡ | R132 | 7448 | 115 | 208 | 227 | 2658 |
| 0174268‡ | R132H | 964 | 72 | 134 | 138 | 2242 |
| 0488‡ | R132 | 7511 | 85 | 289 | 310 | 3448 |
| 9382 | R172K | 19247 | 790 | 821 | 766 | 5481 |
| 0831 | R172K | 15877 | 350 | 721 | 708 | 5144 |
| 157 | Wild type | 212 | 121 | 484 | 437 | 3057 |
| 202 | Wid type | 121 | 57 | 161 | 136 | 1443 |
| 205 | Wild type | 147 | 39 | 162 | 153 | 1011 |
| 209 | Wild type | 124 | 111 | 167 | 168 | 1610 |
| 239 | Wild type | 112 | 106 | 305 | 361 | 1436 |
| 277 | Wild type | 157 | 61 | 257 | 257 | 2029 |
| 291 | Wild type | 113 | 118 | 124 | 128 | 1240 |
| 313 | Wild type | 116 | 75 | 151 | 181 | 1541 |
| 090158 | Wild type | 411 | 217 | 658 | 647 | 3202 |
| 090156 | Wild type | 407 | 500 | 1276 | 1275 | 6091 |

* IDH½ denotes isocitrate dehydrogenase 1 and 2, 2-HG 2-hydroxy glutarate, and α-KG alpha-ketogluatarate. Metabolite measurements were not available for all patients.
†metabolic measurements were not made due to limited patient sample
‡indicates samples obtained at relapse.

Two samples harboring wild-type IDH1 also showed high levels of 2-HG (Table 25). The high 2-HG concentration prompted sequencing of the IDH2 gene in these two AML samples, which established the presence of IDH2 R172K mutations in both samples (Table 25).

Evaluation of the clinical characteristics of patients with or without IDH1/2 mutations revealed a significant correlation between IDH1/2 mutations and normal karyotype (p=0.05), but no other differences between these two groups (Table 27). Notably, there was no difference in treatment response for a subgroup of patients who received consistent treatment (n=136). These findings are consistent with the initial report identifying IDH1 mutations in AML.

TABLE 27

Characteristics of IDH1/2 mutant and wild-type patients*

| Variable | IDH1/2 Wild-type (N = 132) | IDH1/2 Mutant (N = 13) | P Value |
|---|---|---|---|
| Age (yr) | 58.8 ± 16.2 | 52.6 ± 7.0 | 0.17† |
| Sex (% male) | 53 (70/132) | 62 (8/13) | 0.77‡ |
| WBC at diagnosis (10⁹ cells/L) | 40.7 ± 50.6 | 28.7 ± 34.1 | 0.38† |
| Initial treatment response (% complete remission) | 70 (85/122) | 62 (8/13) | 0.54‡ |
| Cytogenetic profile (% normal) | 62 (72/117) | 92 (11/12) | 0.05‡ |
| Additional mutations | | | |
| FLT3 (%) | 17 (8/47) | 0 (0/8) | 0.58‡ |
| NPM1 (%) | 30 (14/47) | 25 (2/8) | 1.0‡ |

*For plus-minus values, the value indicates the mean, and ± indicates the standard deviation. IDH1/2 denotes isocitrate dehydrogenase 1 and 2, WBC white blood cell count, FLT3 FMS-related tyrosine kinase 3, and NPM1 nucleophosmin 1.
†P-value was calculated using the student's t-test.
‡P-value was calculated using Fisher's exact test.

Figure 36C:
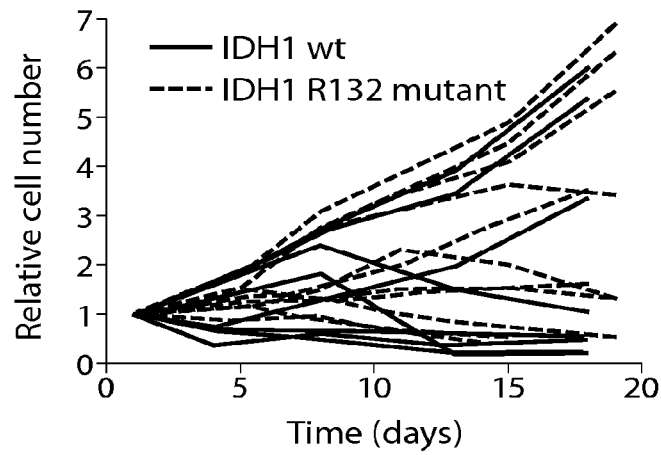
Figure 37:
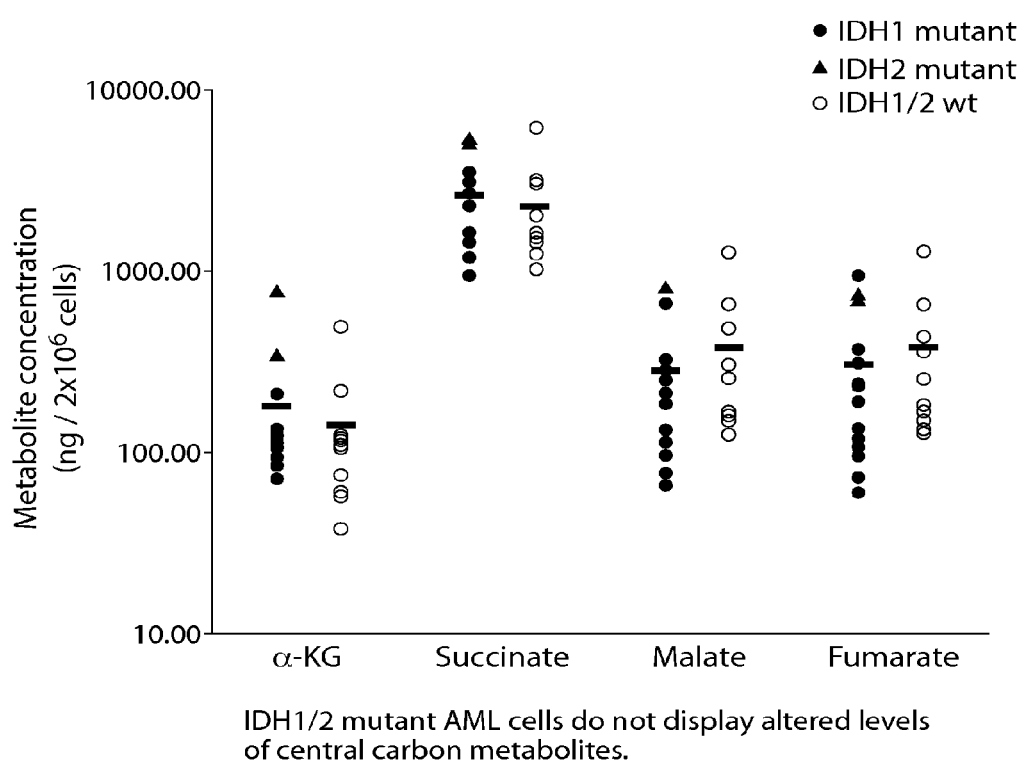
FIG. 37 is a graph depicting the results of extracts from leukemia cells of AML patients carrying an IDH1/2 mutant (n=16) or wild-type (n=10) allele obtained at initial presentation and relapse assayed by LC-MS for levels of α-KG, succinate, malate, and fumarate. Each point represents an individual patient sample. Open circles represent wild-types, closed circles represent IDH1 mutants, and triangles represent IDH2 mutants. Horizontal bars represent the mean. There were no statistically significant differences between the wild-type and IDH1/2 mutant AML samples.

Panels of AML cells from wild-type and IDH1 mutant patients were cultured in vitro. There was no difference in the growth rates or viability of the IDH1 R132 mutant and wild-type cells, with both groups showing high variability in their ability to proliferate in culture, as is characteristic of primary AML cells (FIG. 36C). There was no relationship between 2-HG levels in the IDH1 R132 mutant cells and their growth rate or viability in culture. After 14 days in culture, the mutant AML cells retained their IDH1 R132 mutations (11/11), and continued to accumulate high levels of 2-HG (FIG. 36A), further confirming that IDH1 R132 mutations lead to the production and accumulation of 2-HG in AML cells.

To investigate the effect of IDH1/2 mutations on the concentration of cellular metabolites proximal to the IDH reaction, α-KG, succinate, malate, and fumarate levels were measured in AML cells with IDH1/2 mutations and in a set of wild-type AML cells matched for AML subtype and cytogenetic profile. None of the metabolites were found to be greatly altered in the IDH1 mutants compared to the IDH1 wild-type cells (FIG. 27, Supplementary Table 26). The mean level of α-KG was not altered in the IDH1/2 mutant AML cells, suggesting that the mutation does not decrease the concentration of this metabolite as has been previously hypothesized.

Figure 38:
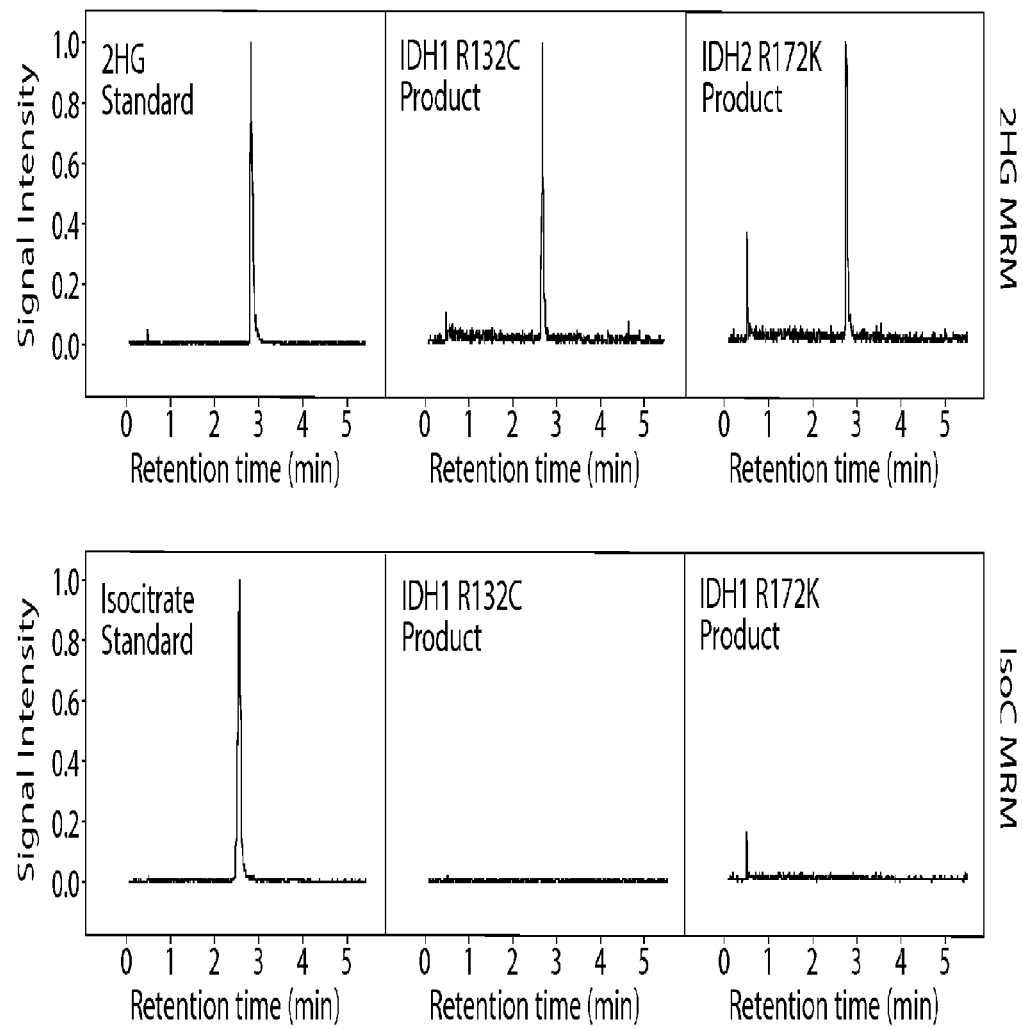
FIG. 38 depicts graphical representations of LC-MS analysis of in vitro reactions using recombinant IDH1 R132C and IDH2 R172K confirming that 2-HG and not isocitrate is the end product of the mutant enzyme reactions.

To confirm that the R132C mutation of IDH1, and the R172K mutation of IDH2 confer a novel enzymatic activity that produces 2-HG, recombinant mutant enzymes were assayed for the NADPH-dependent reduction of α-KG. When samples were analyzed by LC-MS upon completion of the enzyme assay, 2-HG was identified as the end product for both the IDH1 R132C and IDH2 R172K mutant enzymes (FIG. 38). No isocitrate was detectable by LC-MS, indicating that 2-HG is the sole product of this reaction (FIG. 38).

This observation held true even when the reductive reaction was performed in buffer containing $NaHCO_3$ saturated with $CO_2$.

Figure 39A:
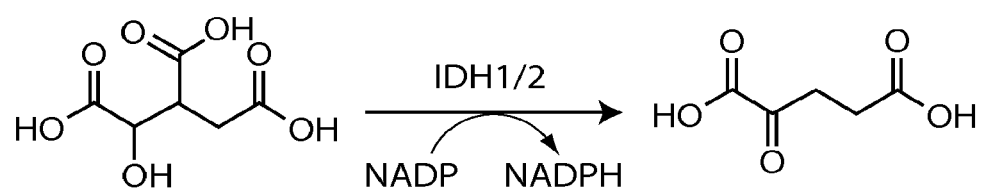
FIGS. 39A and B depict (A) the wild-type IDH1 enzyme catalysis of the oxidative decarboxylation of isocitrate to alpha-ketoglutarate with the concomitant reduction of NADP to NADPH; and (B) the IDH1 R132C mutant reduction of alpha-ketoglutarate to 2-hydroxyglutarate while oxidizing NADPH to NADP. These are referred to as the "forward" and "partial reverse" reactions, respectively.
Figure 39B:
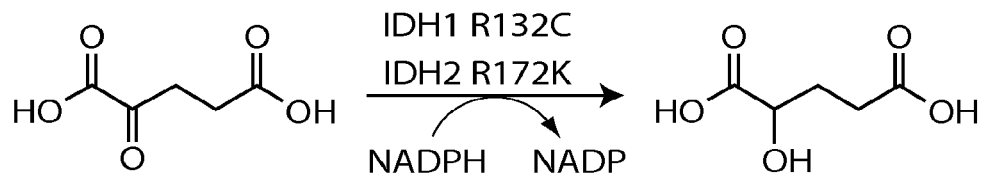

A large proportion of IDH1 mutant patients in AML have an IDH1 R132C mutation (Table 25). In order to biochemically characterize mutant IDH1 R132C, the enzymatic properties of recombinant R132C protein were assessed in vitro. Kinetic analyses showed that the R132C substitution severely impairs the oxidative decarboxylation of isocitrate to α-KG, with a significant decrease in $k_{cat}$, even though the affinity for the co-factor $NADP^+$ remains essentially unchanged (Table 28). However, unlike the R132H mutant enzyme described previously the R132C mutation leads to a dramatic loss of affinity for isocitrate ($K_M$), and a drop in net isocitrate metabolism efficiency ($k_{cat}/K_M$) of more than six orders of magnitude (Table 28). This suggests a potential difference in the substrate-level regulation of enzyme activity in the context of AML. While substitution of cysteine at R132 inactivates the canonical conversion of isocitrate to α-KG, the IDH1 R132C mutant enzyme acquires the ability to catalyze the reduction of α-KG to 2-HG in an NADPH dependent manner (FIG. 39). This reductive reaction of mutant IDH1 R132C is highly efficient ($k_{cat}/K_M$) compared to the wild-type enzyme, due to the considerable increase in binding affinity of both the NADPH and α-KG substrates ($K_M$) (Table 28).

TABLE 28

Kinetic parameters of the IDH1 R132C mutant enzyme

|  | WT | R132C |
|---|---|---|
| Oxidative (→ NADPH) | | |
| $K_{M,\ NADP+}$ (µM) | 49 | 21 |
| $K_{M,\ isocitrate}$ (µM) | 57 | $8.7 \times 10^4$ |
| $K_{M,\ MgCl2}$ (µM) | 29 | $4.5 \times 10^2$ |
| $K_{i,\ \alpha KG}$ (µM) | $6.1 \times 10^2$ | 61 |
| $k_{cat}$ (s$^{-1}$) | $1.3 \times 10^5$ | $7.1 \times 10^2$ |
| $k_{cat}/K_{M,\ isoc}$ (M$^{-1} \cdot$ s$^{-1}$) | $2.3 \times 10^9$ | $8.2 \times 10^3$ |
| Reductive (→ NADP$^+$) | | |
| $K_{M,\ NADPH}$ (µM) | n/a* | 0.3 |
| $K_{M,\ \alpha KG}$ (µM) | n/a | 295 |
| $k_{cat}$ (s$^{-1}$) | ~7 (est.) | $5.5 \times 10^2$ |

*n/a indicates no measureable activity

The invention claimed is:

1. A method of treating a subject having a cell proliferation-related disorder characterized by the presence of a mutant isocitrate dehydrogenase 2 enzyme having a mutation at residue 140 (IDH2R140X), the method comprising administering to the subject a therapeutically effective amount of an inhibitor of said mutant isocitrate dehydrogenase 2 enzyme or a pharmaceutically acceptable salt thereof having the formula (XI) wherein:

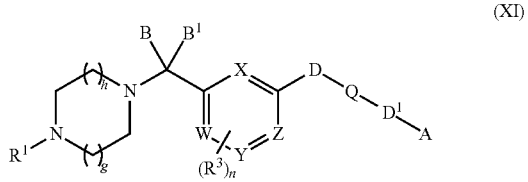

(XI)

W, X, Y and Z are each independently selected from CH or N;
B and $B^1$ are independently selected from hydrogen, alkyl or when taken together with the carbon to which they are attached form a carbonyl group;
Q is C=O or $SO_2$;
D and $D^1$ are independently selected from a bond, oxygen or $NR^c$;
A is optionally substituted aryl or optionally substituted heteroaryl;
$R^1$ is independently selected from alkyl, cycloalkyl, aryl, heteroaryl, heterocyclyl, heterocyclylalkyl, cycloalkylalkyl, aralkyl, and heteroaralkyl; each of which may be optionally substituted with 0-3 occurrences of $R^d$;
each $R^3$ is independently selected from halo, haloalkyl, alkyl and —$OR^a$;
each $R^a$ is independently selected from alkyl, and haloalkyl;
each $R^b$ is independently alkyl;
each $R^c$ is independently selected from hydrogen and alkyl;
each $R^d$ is independently selected from halo, haloalkyl, alkyl, nitro, cyano, and $OR^a$, or two $R^d$ taken together with the carbon atoms to which they are attached form an optionally substituted heterocyclyl;
n is 0, 1, or 2;
h is 0, 1, 2; and
g is 0, 1 or 2.

2. The method of claim 1, wherein the inhibitor binds to IDH2R140X and inhibits neoactivity, wherein the neoactivity is the ability to convert alpha-ketoglutarate to 2-hydroxyglutarate (2HG).

3. The method of claim 1, wherein IDH2R140X is detected in a sample obtained from the subject.

4. The method of claim 3, wherein the sample comprises tissue, product or bodily fluid.

5. The method of claim 1, wherein IDH2R140X is detected by sequencing a nucleic acid from an affected cell that encodes the relevant amino acid(s) from IDH2R140X.

6. The method of claim 5, wherein the sequencing is performed by polymerase chain reaction (PCR).

7. The method of claim 1, wherein IDH2R140X is selected from IDH2R140Q, IDH2R140W, and IDH2R140L.

8. The method of claim 1, wherein IDH2R140X is IDH2R140Q.

9. The method of claim 1, wherein the cell proliferation-related disorder is selected from the group consisting of a tumor of the CNS, a leukemia, prostate cancer, fibrosarcoma, paraganglioma, follicular thyroid cancer, myeloma, thyroid cancer, sarcoma, osteosarcoma, myeloproliferative neoplasms, and myelodysplastic syndrome (myelodysplasia).

10. The method of claim 9, wherein the cell proliferation-related disorder is myelodysplastic syndrome.

11. The method of claim 9, wherein the leukemia is acute myelogenous lymphoplastic leukemia (AML) or acute lymphoblastic leukemia (ALL).

12. The method of claim 9, wherein the cell proliferation-related disorder is acute myelogenous leukemia (AML).

13. The method of claim 11, wherein the ALL is B-cell ALL or T-cell ALL.

14. The method of claim 9, wherein the myeloproliferative neoplasm is chronic myelogenous leukemia (CML).

* * * * *